US012674134B2

(12) United States Patent
Wang et al.

(10) Patent No.: US 12,674,134 B2
(45) **Date of Patent: *Jul. 7, 2026**

(54) METHOD OF INHIBITING TAU PHOSPHORYLATION

(71) Applicant: Filana Therapeutics, Inc., Austin, TX (US)

(72) Inventors: Hoau-Yan Wang, Philadelphia, PA (US); Lindsay Burns Barbier, Austin, TX (US)

(73) Assignee: Filana Therapeutics, Inc., Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 18/955,937

(22) Filed: Nov. 21, 2024

(65) Prior Publication Data

US 2025/0092361 A1 Mar. 20, 2025

Related U.S. Application Data

(60) Continuation of application No. 18/323,075, filed on May 24, 2023, now abandoned, which is a continuation of application No. 17/006,338, filed on Aug. 28, 2020, now Pat. No. 11,661,580, which is a continuation of application No. 16/030,494, filed on Jul. 9, 2018, now Pat. No. 10,760,052, which is a division of application No. 13/940,016, filed on Jul. 11, 2013, now Pat. No. 10,017,736.

(60) Provisional application No. 61/789,180, filed on Mar. 15, 2013, provisional application No. 61/671,235, filed on Jul. 13, 2012.

(51) Int. Cl.

| | |
|---|---|
| ***C12N 5/079*** | (2010.01) |
| ***C07D 205/04*** | (2006.01) |
| ***C07D 207/08*** | (2006.01) |
| ***C07D 211/14*** | (2006.01) |
| ***C07D 211/74*** | (2006.01) |
| ***C07D 217/04*** | (2006.01) |
| ***C07D 265/30*** | (2006.01) |
| ***C07D 265/36*** | (2006.01) |
| ***C07D 277/02*** | (2006.01) |
| ***C07D 277/04*** | (2006.01) |
| ***C07D 279/12*** | (2006.01) |
| ***C07D 295/08*** | (2006.01) |
| ***C07D 295/088*** | (2006.01) |
| ***C07D 471/10*** | (2006.01) |
| ***C07D 491/04*** | (2006.01) |
| ***C07D 491/056*** | (2006.01) |
| ***C07D 498/10*** | (2006.01) |
| ***G01N 33/50*** | (2006.01) |
| ***G01N 33/68*** | (2006.01) |
| ***G01N 33/94*** | (2006.01) |

(52) U.S. Cl.

CPC ......... *C12N 5/0622* (2013.01); *C07D 205/04* (2013.01); *C07D 207/08* (2013.01); *C07D 211/14* (2013.01); *C07D 211/74* (2013.01); *C07D 217/04* (2013.01); *C07D 265/30* (2013.01); *C07D 265/36* (2013.01); *C07D 277/02* (2013.01); *C07D 277/04* (2013.01); *C07D 279/12* (2013.01); *C07D 295/08* (2013.01); *C07D 295/088* (2013.01); *C07D 471/10* (2013.01); *C07D 491/04* (2013.01); *C07D 491/056* (2013.01); *C07D 498/10* (2013.01); *G01N 33/50* (2013.01); *G01N 33/6896* (2013.01); *G01N 33/94* (2013.01); *G01N 2333/70571* (2013.01); *G01N 2800/2821* (2013.01); *G01N 2800/52* (2013.01)

(58) Field of Classification Search

CPC ......... A61P 25/00; A61P 29/00; A61P 37/02; A61P 43/00; C07D 205/04; C07D 207/08; C07D 211/14; C07D 211/74; C07D 217/04; C07D 265/36; C07D 471/10

See application file for complete search history.

(56) References Cited

U.S. PATENT DOCUMENTS

| | | | |
|---|---|---|---|
| 3,203,992 | A | 8/1965 | Kunz et al. |
| 3,723,442 | A | 3/1973 | Nakanishi et al. |
| 4,981,858 | A | 1/1991 | Fisher et al. |
| 4,996,210 | A | 2/1991 | Tsukamoto et al. |
| 5,534,520 | A | 7/1996 | Fisher et al. |
| 5,593,846 | A | 1/1997 | Schenk et al. |
| 5,852,029 | A | 12/1998 | Fisher et al. |
| 5,869,496 | A | 2/1999 | Hale et al. |

(Continued)

FOREIGN PATENT DOCUMENTS

| | | | |
|---|---|---|---|
| WO | WO 2001040261 | A1 | 6/2001 |
| WO | WO 2005095398 | A1 | 10/2005 |
| WO | WO 2010051497 | A1 | 5/2010 |

OTHER PUBLICATIONS

Wang et al. (Alzheimer's & Dementia, 8, 45, 7, 259-260, Jul. 1, 2012) (Year: 2012).*

(Continued)

*Primary Examiner* — Umamaheswari Ramachandran
(74) *Attorney, Agent, or Firm* — Jones Day

(57) ABSTRACT

A method of inhibiting phosphorylation of the tau protein and/or a TLR4-mediated immune response is disclosed. The method contemplates administering to cells in recognized need thereof such as cells of the central nervous system an effective amount of a of a compound or a pharmaceutically acceptable salt thereof that binds to a pentapeptide of filamin A (FLNA) of SEQ ID NO: 1, and contains at least four of the six pharmacophores of FIGS. 35-40.

20 Claims, 81 Drawing Sheets

Specification includes a Sequence Listing.

(56) References Cited

U.S. PATENT DOCUMENTS

| | | | |
|---|---|---|---|
| 6,060,469 | A | 5/2000 | Baker et al. |
| 6,441,049 | B2 | 8/2002 | Reitz et al. |
| 6,630,492 | B1 | 10/2003 | Bauer et al. |
| 7,049,321 | B2 | 5/2006 | Fisher et al. |
| 7,192,964 | B2 | 3/2007 | Hashimoto et al. |
| 7,544,695 | B2 | 6/2009 | Berk et al. |
| 7,557,117 | B2 | 7/2009 | Hashimoto et al. |
| 7,560,468 | B2 | 7/2009 | Sundermann et al. |
| 7,951,815 | B2 | 5/2011 | Sundermann et al. |
| 8,048,890 | B2 | 11/2011 | Buschmann et al. |
| 8,088,787 | B2 | 1/2012 | Hong et al. |
| 8,153,795 | B2 | 4/2012 | Sundermann et al. |
| 8,273,731 | B2 | 9/2012 | Heldman |
| 8,492,349 | B2 | 7/2013 | Wang et al. |
| 8,580,808 | B2 | 11/2013 | Barbier et al. |
| 8,580,809 | B2 | 11/2013 | Barbier et al. |
| 8,614,324 | B2 | 12/2013 | Barbier et al. |
| 8,653,068 | B2 | 2/2014 | Barbier et al. |
| 9,500,640 | B2 | 11/2016 | Wang et al. |
| 10,017,736 | B2 | 7/2018 | Wang et al. |
| 10,222,368 | B2 | 3/2019 | Wang et al. |
| 11,370,791 | B2 | 6/2022 | Zamloot et al. |
| 11,385,221 | B2 | 7/2022 | Wang et al. |
| 11,661,580 | B2 | 5/2023 | Wang |
| 12,065,440 | B2 | 8/2024 | Zamloot et al. |
| 2002/0013374 | A1 | 1/2002 | Reitz et al. |
| 2005/0075505 | A1 | 4/2005 | Gandhi et al. |
| 2007/0111970 | A1 | 5/2007 | Cruz et al. |
| 2007/0117824 | A1 | 5/2007 | Berk et al. |
| 2007/0149543 | A1 | 6/2007 | Stockwell et al. |
| 2008/0038199 | A1 | 2/2008 | Hong et al. |
| 2010/0197740 | A1 | 8/2010 | Wang et al. |
| 2010/0279997 | A1 | 11/2010 | Barbier et al. |
| 2010/0280061 | A1 | 11/2010 | Barbier et al. |
| 2011/0105481 | A1 | 5/2011 | Burns Barbier et al. |
| 2011/0105487 | A1 | 5/2011 | Burns Barbier et al. |
| 2011/0312894 | A1 | 12/2011 | Wu |
| 2014/0018341 | A1 | 1/2014 | Wang et al. |
| 2021/0389298 | A1 | 12/2021 | Wang et al. |
| 2024/0117306 | A1 | 4/2024 | Wang et al. |
| 2024/0400566 | A1 | 12/2024 | Zamloot et al. |
| 2025/0084083 | A1 | 3/2025 | Zamloot et al. |

OTHER PUBLICATIONS

CAS (CAS Registry, PTI-125, 2010). (Year: 2010).*
Conejero-Goldberg et al. (Neuroscience and Biobehavioral Reviews 32 (2008) 693-706 (Year: 2008).*
"Guideline for Alzheimer's Disease Management" the State of California Department of Public Health (2008).
"Guideline Watch (2014): Practice Guideline for the Treatment of Patients With Alzheimer's Disease and Other Dementias", approved for publication by the American Psychiatric Association's (APA's) Executive Committee on Practice Guidelines as an interim up-date of the APA's 2007.
"Standards of Medical Care in Diabetes-2012", American Diabetes Association, Diabetes Care 35(Supp.1):S11-S63 (Jan. 2012), S21.
"Treatment Guidelines for Alzheimer's Disease: Redefining Perceptions in Primary Care", American Psychiatric Association (2007).
Abstract—Haffner, J. Cardiol .92(4A): 18J-26J (Aug. 18, 2003).
Aizen et al., Front Endocrinol 9:Article 105 (Mar. 2018).
Akdeniz et al., Niche, 1:24-30 (2012).
American Academy of Neurology, Neurology, 2013, 80:2250-2257.
American Diabetes Association, Diabetes Care 2021;44(Suppl. 1):S111-S124.
Anderson et al., Am Health Drug Benefits 7(4):231-235 (2014).
Anderson, Chem and Biol 10:787-797(2003).
Arun et al., Neurosci Lett 609:152-158 (2015).
Bendlin et al., Front Aging Neurosci, 2:Article 35 (2010).
Boelsterli et al., Toxicol Sci 131(2):654-667, 660-661 (2013).
Burns et al., Recent Patents on CNS Drug Discovery 5:210-220 (2010).
CAS RN 1070805-65-0 Nov. 4, 2008.
Cheng et al. (Pharmacology and Therapeutics, 2013, 139, 334-340). (Year: 2013).
Cho et al., J. Neurochem, 88:349-358 (2004).
Dale et al., J Neural Neurosurg Ps 54:116-118 (1991).
De Ycaza et al., Diabetes 71:381-391 (Mar. 2022);.
Ding et al., J. Biol. Chem. 281(28):19107-19114 (2006).
Dorwald, "Side Reactions in Organic Synthesis: A Guide to Successful Synthesis Design" 2005 Wiley-VCH Verlag GmbH & Co. KGaA, Weinheim.
Duka et al., Plosone, 8, 9, p. 1-11 (Sep. 2013).
Filiou et al., Neurogenetics 15:201-212 (2014).
Fulmer, SciBx, Jun. 7, 2012.
Gao et al., Acta Pharmacol Sin 33:182-188 (2012).
Gao et al., Front Physiol, 8:Article 508 (Jul. 2017).
Geerts et al., "Sabeluzole Stabilizes the Neuronal Cytoskeleton", Neurobiology of Aging, vol. 17, No. 4, pp. 573-581, 1996 Elsevier Science Inc. S0197-4580(96)00067-X.
Goedert et al., Neuron. 3:519-526 (1989).
Goedert et al., Proc. Natl. Acad. Sci. USA 85:4051-4055 (1988).
Goedert et al., Trends Neurosci. 33:317-325 (2010).
Goldfine et al., Ann Intern Med. 159(1):1-12 (Jul. 2, 2013).
Goldstein et al., Alzheimer's Research & Therapy 2014, 6:64.
Hally et al., Platelets, 30(5):599-607 (2019).
Harada et al., Biomolecules 6(1):7 (2016).
Hardy et al., Science 297:353-356 (2002).
He et al., J Biol Chem 278(29):27096-27104 (2003).
Henderson et al., Ann Neural 25(4):404-406 (Apr. 1989).
Hof et al., Acta Neuropathol 85(1):23-30 (Dec. 1992).
Hong-Qi et al., Transl Neurodegener 1:21 (2012).
Hyman et al., J Neural Neurosur Ps 48:1169-1171 (1985).
Iqbal et al. Curr Alzheimer Res, 7(8):656-664 (Dec. 2010).
Johnson et al., J. Cell Sci. 117:5721-5729 (2004).
Kandimalla, Biology Open, 1-6 (2013).
Kellett et al., Subcell Biochem 76:364-374 (2015).
Kickstein et al., Proc. Natl. Acad. Sci. USA 105(50):21830-21835 (2010).
Kimura, Frontiers in Molecular Neuroscience, 1-10 (Jul. 15, 2014).
Koyama et al., J Gerontol A Biol Sci Med Sci (2012).
McGeer et al., Lancet, 335:1037 (1995).
McKee et al., J Neuropathol Exp Neural 68(7):709-735 (Jul. 2009).
Metcalfe et al., Mount Sinai J of Medicine, 77:50-58 (2010).
Mohr et al., "Treatment of Alzheimer's Disease With Sabeluzone: Functional and Structural Correlates", Clinical Neuropharmacology, 20(4):338-345 (1997) Lippincott- Raven Publishers, Philadelphia.
Montenigro et al., Brain Pathol, 25 (2015) 304-315.
Nakamura et al., Cell Adhes Migr, 5:2, 160-169 (Mar./Apr. 2011), and Supplemental Information Table 1.
Noller, Chemistry of Organic Compounds, W.B. Saunders Company, Philadelphia, 1951, p. 35.
Olefsky et al. (Annual. Rev. Physiol. 2010, 72:219-46) (Year:2010).
Oxford Dictionary of Biochemistry and Molecular Biology, Oxford University Press, Inc., New York, NY, p. 22 (1997).
Package insert—AVANDIA (rosiglitazone maleate), GlaxoSmithKline, (Research Triangle Park, NC (2007).
Package Insert-Salsalsate, Acella Pharmaceuticals, LLC, Alpharetta, GA (Aug. 18, 2001).
Parachikova et al., J Alzheimer's Dis 21(2):527-542 (2010).
Patel et al., Cardiol Resd Pract 2012(7):121237—(Feb. 2012).
Patterson et al., Front Cell Neurosci, Dec. 2012, 6:Article 58.
Pradhan et al., JAMA 302(11):1186-1194 (Sep. 16, 2009).
Rajeshwar Narlawar, Modulation and Characterization of Alzheimer's Disease Associateed y-Secretase, Technischen Universitat Darmstadt, Thesis 2007.
Rametti et al., J. Biol. Chem. 279(52):54518-54528 (2004).
Remington the Science and Practice of Pharmacy, 22 ed, Pharmaceutical Press, Philadelphia, PA, p. 1101 (2013).
Rimadyl (carprofen) FDA Marketing Status.
Rimadyl (carprofen) Label.
Sancesario, Clinical Reviews in Clinical Laboratory Sciences, 1-13 (2015).
Saulle et al., Rehabil Res Pract vol. 2012:Article ID 816069:1-9.

(56) References Cited

OTHER PUBLICATIONS

Scorza et al., Am Fam Physician, Jan. 15, 2012, 85(2):123-132.
Serrano-Pozo et al., Cold Spring Harb Perspect Med 1:a006189 (2011).
Shoelson et al., J. Clin. Invest. 116:1793-1801 (2006).
Solito et al., Front Pharmacol, vol. 3, Article 14:1-10 (Feb. 2012).
Stedman's Medical Dictionary, Houghton Mifflin Co., Boston, MA, p. 25 (2002).
Streit et al., J Neuroinflamm 1:14 (2004).
Streit, Front Aging Neurosci 2:Article 22 (2010).
Supplementary Partial European Search Report for EP 13816713.5, mailed May 3, 2016.
Tariot et al., Arch Gen Psychiatry 43:727-732 (1986).
Tartaglia et al., Front Human Neurosci 8:Article 30 (Jan. 2014).
Teva-Loperamide, Monograph, Teva Canada Limited Toronto Ontario, Canada (2017).
Thau-Zuchman et al., J of Neurotrauma, 29:375-284.
Thiel, Nature Biotechnol 2:513-519 (2004).
Tsai et al., Diabetic Med 32(3):382-390 (Mar. 2015).
Van der Harg et al., Front. Neurosci. 9:432. doi: 10.3389/fnins. 2015.00432.
Vardy et al., Neurodegener Dis 9(1):31-37 (2012).
Walter et al., Cell Physiol Biochem 20:947-956 (2007).
Wang CV (2016).
Wang et al., "Reducing Amyloid-Related Alzheimer's Disease Pathogenesis by a Small Molecule Targeting Filamin A", J Neuroscience, 32(29):9773-9784 (Jul. 18, 2012).
Wang et al., J Alzheimer's Assn 8(4):259-260 (Jul. 19, 2012).
Wang et al., J Alzheimers Dis 44(2):385-396 (2015).
Wang et al., J Biol Chem 278:31547-31553 (2003).
Wang et al., Neurobiol Aging 55:99-114 (2017).
Wang et al., PLoS One 3(2):e1554 (2008).
Wang et al., PT1-125 Reduces Amyloid-Related Alzheimer's Pathogenesis by Targeting Filamin A, Feb. 12, 2003, Oral Sessions: Feb. 12: Therapeutics/Therapeutic Strategies: Beta-Amyloid Directed Therapy, p. 259-260.
Wang, Alzheimer's Disease: Advances for a New Century, 123-139 (2013).
Wang, Neurosci Bull, 359-366 (Apr. 1, 2014).
Watanabe et al., Gut 57(2):181-187 (2008).
Webster's Medical Desk Dictionary, Revised Ed., Merriam-Webster, Inc., p. 20 (2002).
Willer et al., Curr Treat Option N, 2006, 8:415-426.
Wolf, C&EN, Sep. 2014 (Jul. 21, 2014).
Wolfe, J Biol Chem 284(10):6021-6025 (2009).
Wu et al., Cire Res 126:1549-1564 (2020).
Wyss-Coray et al., Cold Spring Harb Perspect Med 2012; 2:a006346.
Zhang et al., J Am Soc Nephrol 19:923-932 (2008).
ZINC12342403 Compound Summary—NCBI PubChem Chemical Database, (Nov. 2007).
Wang et al., 2012, "O2-12-03: PTI-125 reduces amyloid-related Alzheimer's pathogenesis by targeting filamin A," Alzheimer's & Dementia, 8, Jul. 1, 2012, p. 259-p. 260 (2 pages), https://doi.org/10.1016/j.jalz.2012.05.692.
U.S. Appl. No. 18/955,938, filed Nov. 21, 2024, Wang et al.
Barkhoudarian et al., 2011, "The molecular pathophysiology of concussive brain injury," Clin Sports Med. 30(1):33-48 (16 pages).
Gavett et al., 2010, "Mild traumatic brain injury: a risk factor for neurodegeneration," Alzheimers Res Ther. 2(3):18 (3 pages).
Aboukhatwa et al., 2010, "Antidepressants are a rational complementary therapy for the treatment of Alzheimer's disease," Mol Neurodegener. 5:10 (17 pages).
Arnold et al., 2010, "Olfactory epithelium amyloid-beta and paired helical filament-tau pathology in Alzheimer disease," Ann Neurol 67(4).:462-469 (14 pages).
Beaney, 2025, "Cassava ends simufilam Alzheimer's programme after second Phase III failure," Clinical Trials Arena, Mar. 26, 2025 (4 pages).
Borgmann-Winter et al., 2009, "Human olfactory epithelial cells generated in vitro express diverse neuronal characteristics," Neuroscience 158:642-653 (24 pages).
Bui, 2012, "Antidepressants for Agitation and Psychosis in Patients with Dementia," Am Fam Physician 85(1):20-22 (3 pages).
Caccamo et al., 2006, "M1 Receptors Play a Central Role in Modulating AD-like Pathology in Transgenic Mice," Neuron 49:671-682 (12 pages).
Cassava Sciences, 2025, "Cassava Sciences Reports Topline Phase 3 REFOCUS-ALZ Data," Mar. 25, 2025 (3 pages).
Huang et al., 2012, "Alzheimer mechanisms and therapeutic strategies," Cell. 148(6):1204-22 (19 pages).
Liu et al., 2001, "β-Amyloid peptide blocks the response of a7-containing nicotinic receptors on hippocampal neurons," Proc Natl Acad Sci 98(8):4734-4739 (6 pages).
Oral Simufilam Slowed Cognitive Decline in a Randomized Withdrawal Trial of Mild-toModerate Alzheimer's Disease, Cassava Sciences, Inc., Jul. 5, 2023 (6 pages).
Petersen et al., 1999, "Mild cognitive impairment: clinical characterization and outcome," Arch Neurol 56:303-308 (8 pages).
Reuters, 2025, "Cassava Sciences' controversial Alzheimer's drug fails in second late-stage study," Reuters, Mar. 25, 2025 (2 pages).
Sarasa et al., 2009, "Natural Non-Trasgenic Animal Models for Research in Alzheimer's Disease," Current Alzheimer Res., 6:171-178 (8 pages).
Taylor, 2025, "Cassava stops Alzheimer's program as simufilam fails another phase 3," Biotech, Mar. 25, 2025 (3 pages).
Wang et al., 2000, "β-Amyloid1-42 Binds to α7 Nicotinic Acetylcholine Receptor with High Affinity, " J Biol Chem 275, 5626-5632 (7 pages).
Wang et al., 2009, "Dissociating β-Amyloid from α7 Nicotinic Acetylcholine Receptor by a Novel Therapeutic Agent, S 24795, Normalizes α7 Nicotinic Acetylcholine and NMDA Receptor Function in Alzheimer's Disease Brain," J Neurosci 29(35):10961-10973 (13 pages).
Wang et al., 2012, "Reducing Amyloid-Related Alzheimer's Disease Pathogenesis by a Small Molecule Targeting Filamin A," J Neurosci 32(29):9773-9784 (12 pages).
Wang et al., 2020, "PTI-125 Reduces Biomarkers of Alzheimer's Disease in Patients," J Prev Alz Dis 7(4):256-264 (9 pages).
Weintraub et al., 2010, "Sertraline for the treatment of depression in Alzheimer's disease: Week-24 outcomes," Am J Geriatric Psychiatry, 18(4):332-340 (14 pages).

* cited by examiner

Simultaneous treatment of C0105 or C0114 with $A\beta_{42}$ for 16 hr reverse $A\beta_{42}$-induced reduction in $K^+$-induced $Ca^{2+}$ influx in organotypic culture of frontal cortical slices.

Fig. 12A $A\beta_{42}$

Fig. 12B $A\beta_{42}$ + C0105

Fig. 12C Vehicle

Fig. 13A $A\beta_{42}$

Fig. 13B $A\beta_{42}$ + C0105

Fig. 13C Vehicle

Fig. 25
Fig. 25A
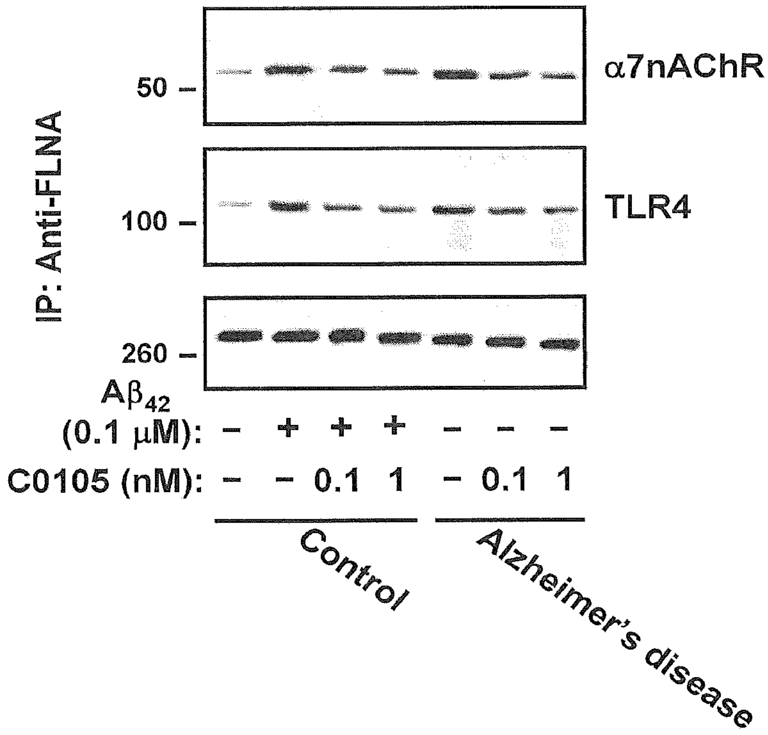
Fig. 25B
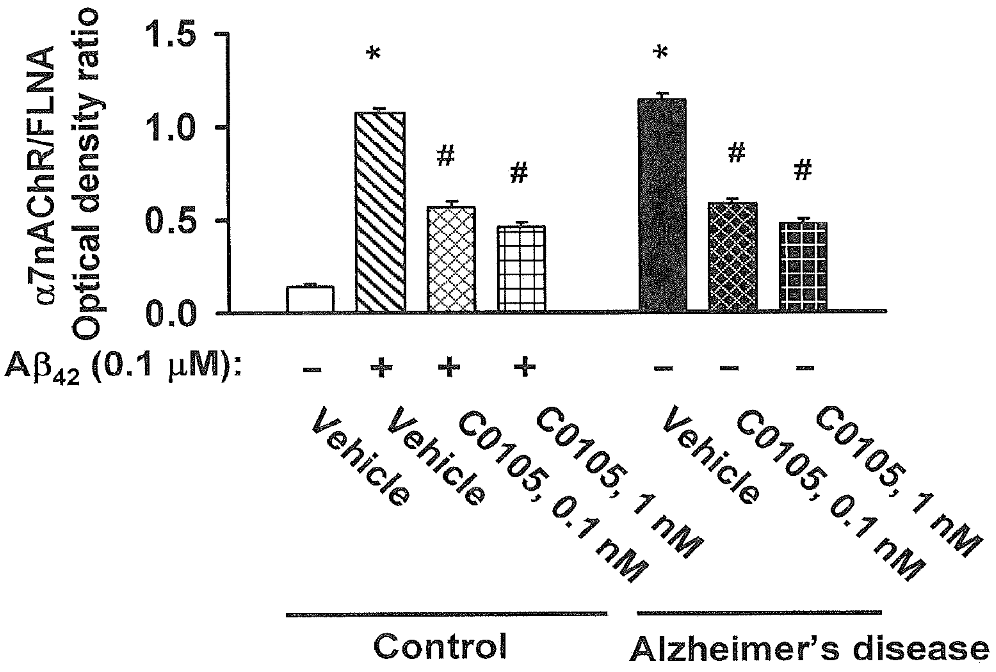

Fig. 26
Fig. 26A
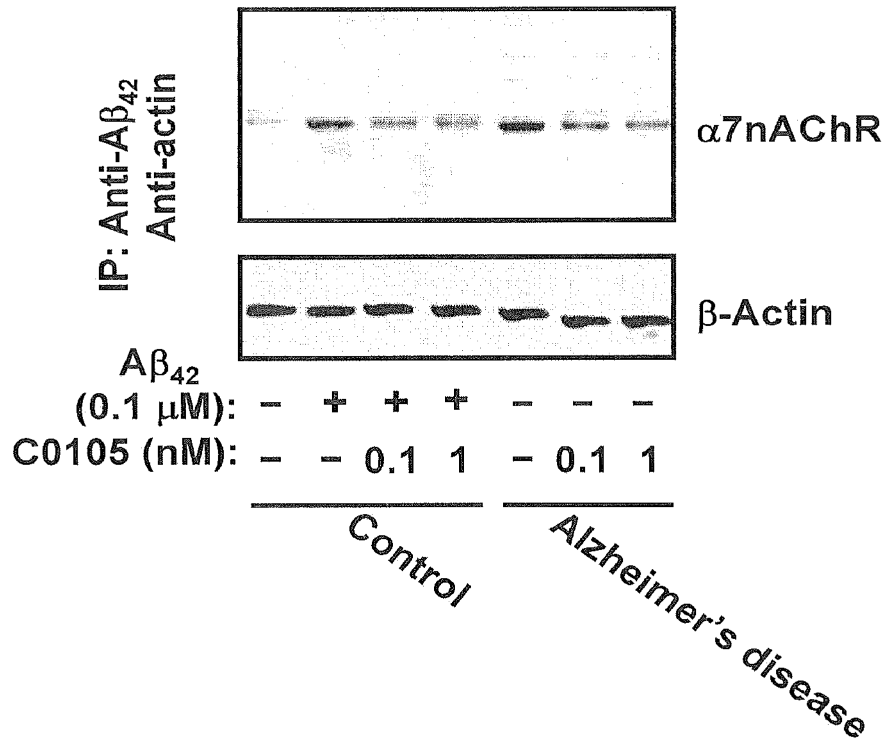
Fig. 26B
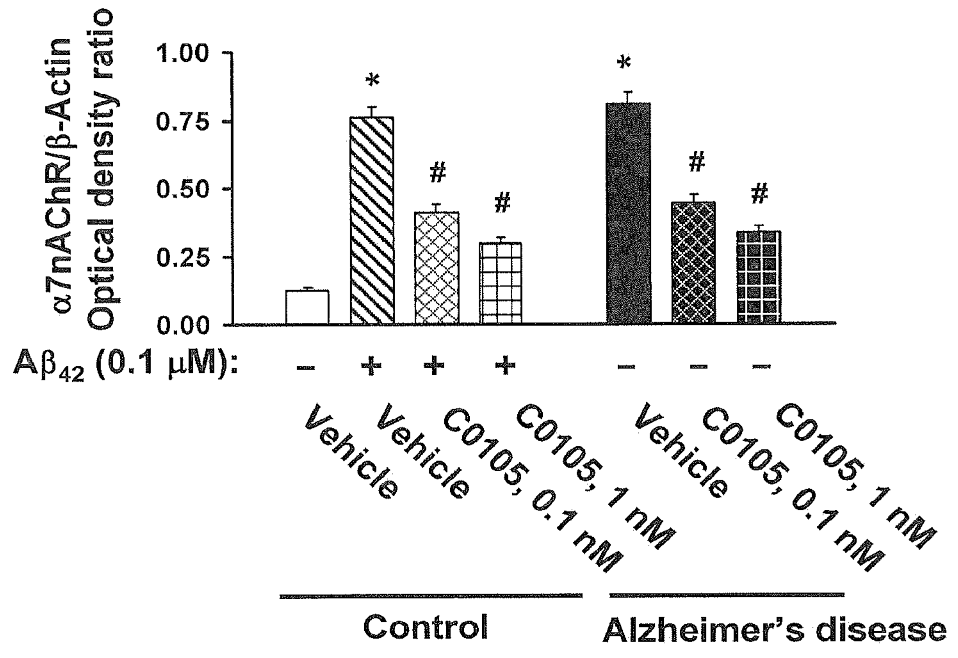

Fig. 27
Fig. 27A
| | K-R | C0105 |
|---|---|---|
| EC50_1 | 1.0350e-013 | 1.6250e-010 |
| EC50_2 | 9.2530e-010 | 3.0920e-007 |
| | K-R | C0105 |
|---|---|---|
| $R^2$ | 0.9006 | 0.9406 |
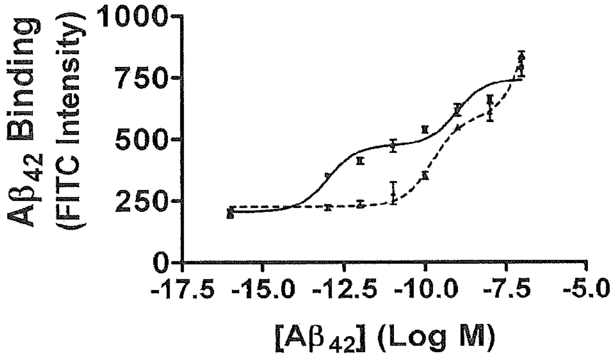
Fig. 27B
| | K-R | C0105 |
|---|---|---|
| EC50_1 | 7.7760e-013 | 1.4450e-009 |
| EC50_2 | 4.9650e-009 | 7.0010e-008 |
| | K-R | C0105 |
|---|---|---|
| $R^2$ | 0.9575 | 0.9814 |
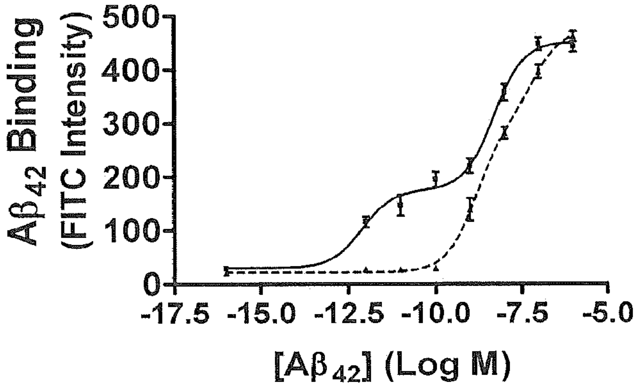

Fig. 32
Fig. 32A
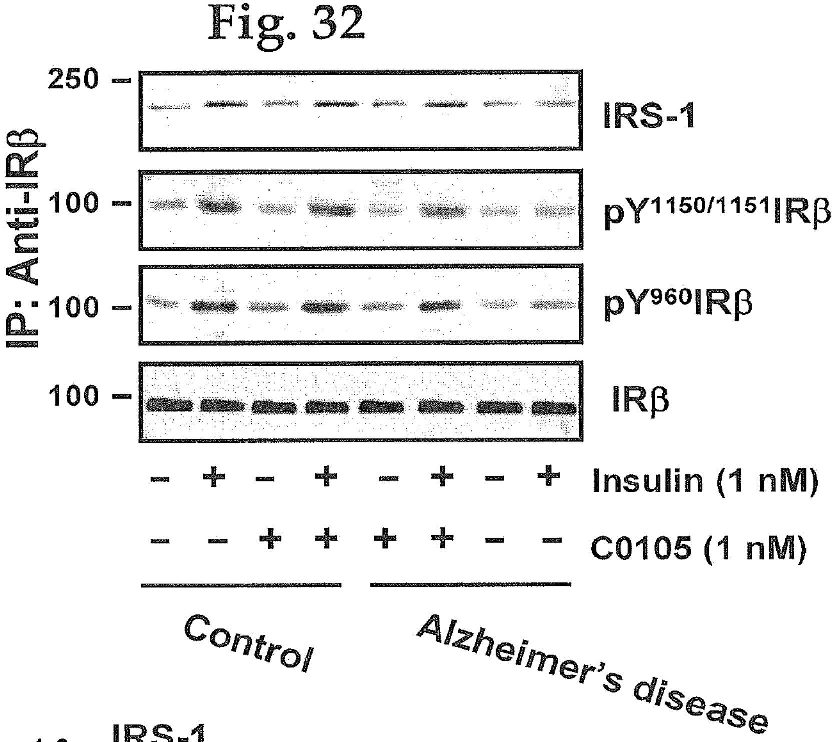
Fig. 32B
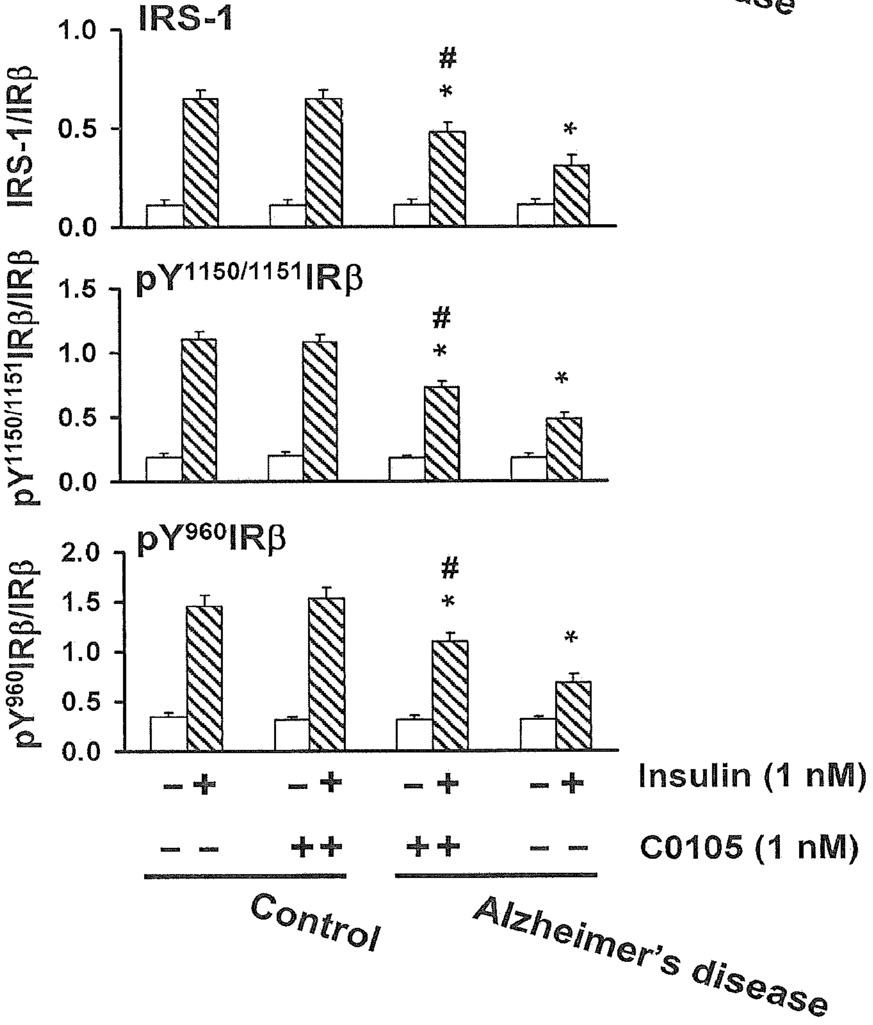

Fig. 33
Fig. 33A
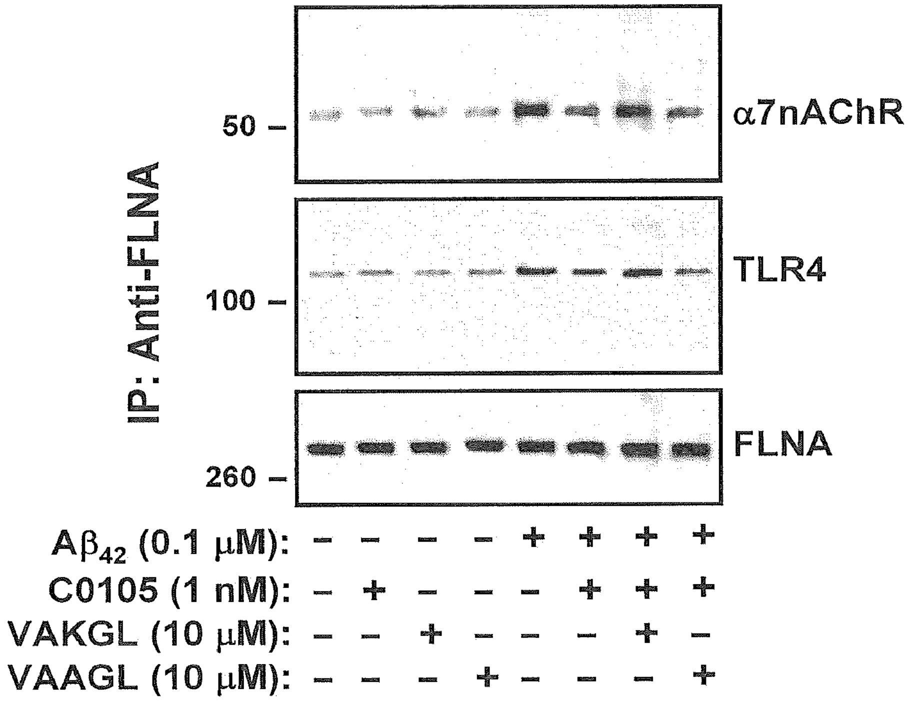
Fig. 33B
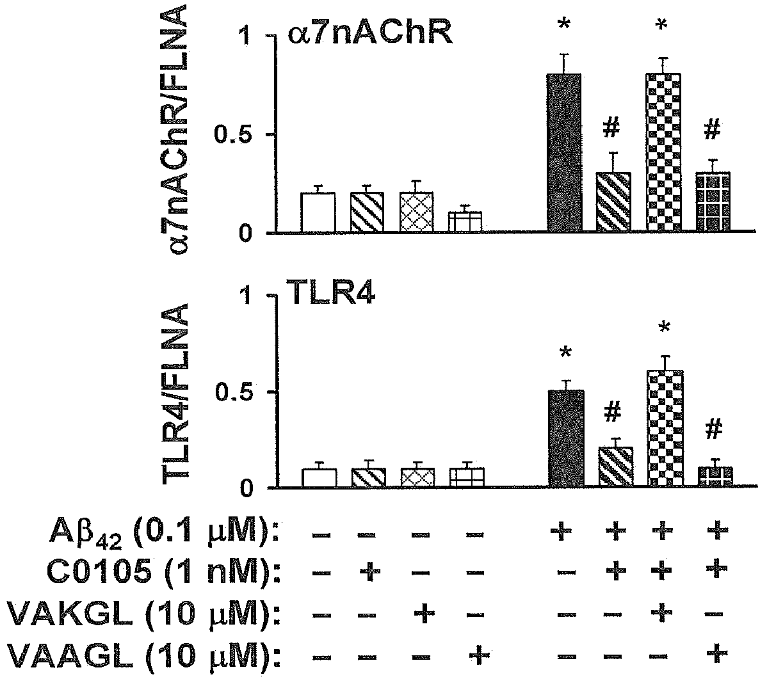

Fig. 34
Fig. 34A
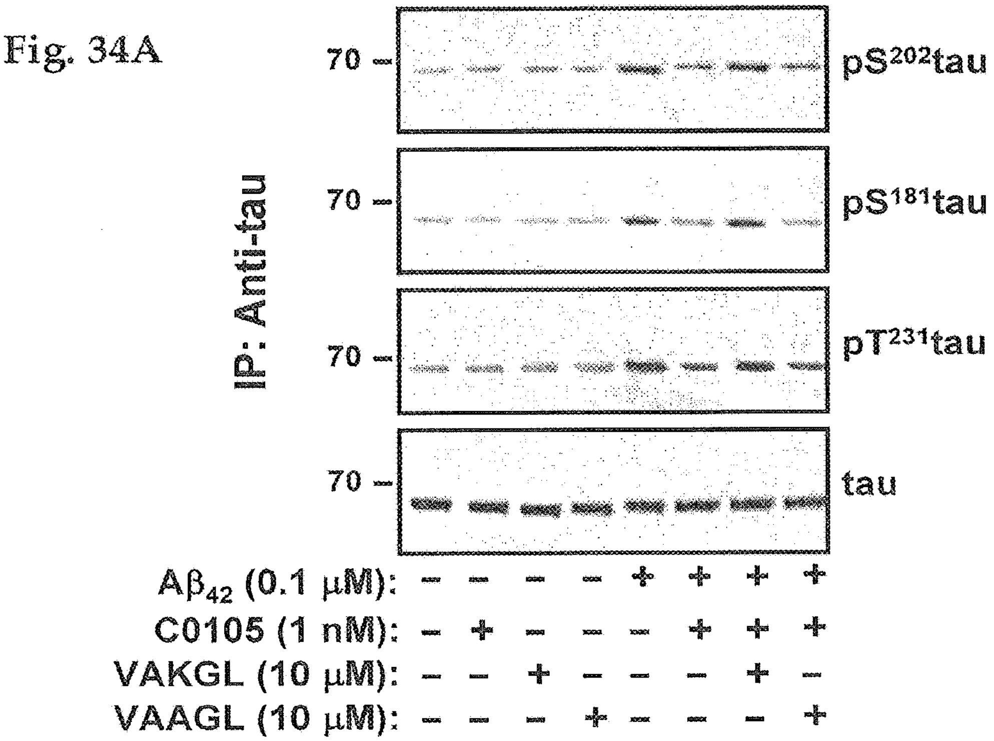
Fig. 34B
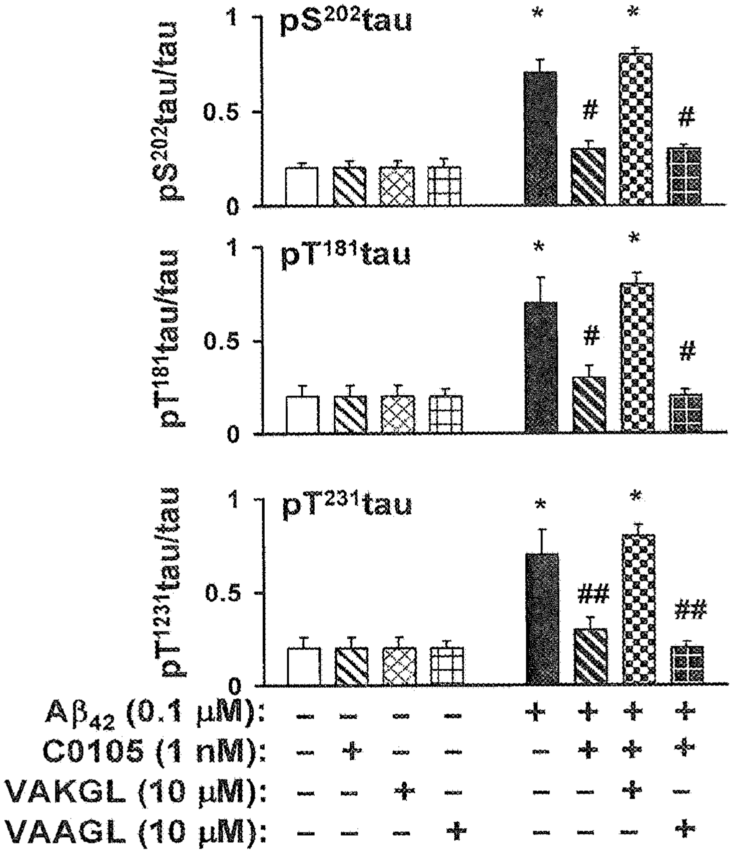

Pharmacophore 2

Pharmacophore 3

Pharmacophore 4

Pharmacophore 5

Pharmacophore 6

| | |
|---|---|
| EC50_1 | 4.3480e-013 |
| EC50_2 | 2.2550e-010 |
| $R^2$ | 0.9930 |

| | |
|---|---|
| EC50_1 | 2.0140e-013 |
| EC50_2 | 1.1140e-010 |
| $R^2$ | 0.9806 |

| | |
|---|---|
| EC50 | 2.7640e-012 |
| $R^2$ | 0.9463 |

SEQUENCE LISTING

```
Sequence total quantity: 2
SEQ ID NO: 1           moltype = AA  length = 5
FEATURE                Location/Qualifiers
REGION                 1..5
                       note = synthetic sequence
```

-continued

```
source                1..5
                      mol_type = protein
                      organism = synthetic construct
SEQUENCE: 1
VAKGL                                                               5

SEQ ID NO: 2          moltype = AA  length = 441
FEATURE               Location/Qualifiers
REGION                1..441
                      note = synthetic sequence
source                1..441
                      mol_type = protein
                      organism = synthetic construct
SEQUENCE: 2
MAEPRQEFEV MEDHAGTYGL GDRKDQGGYT MHQDQEGDTD AGLKESPLQT PTEDGSEEPG  60
SETSDAKSTP TAEDVTAPLV DEGAPGKQAA AQPHTEIPEG TTAEEAGIGD TPSLEDEAAG  120
HVTQARMVSK SKDGTGSDDK KAKGADGKTK IATPRGAAPP GQKGQANATR IPAKTPPAPK  180
TPPSSGEPPK SGDRSGYSSP GSPGTPGSRS RTPSLPTPPT REPKKVAVVR TPPKSPSSAK  240
SRLQTAPVPM PDLKNVKSKI GSTENLKHQP GGGKVQIINK KLDLSNVQSK CGSKDNIKHV  300
PGGGSVQIVY KPVDLSKVTS KCGSLGNIHH KPGGGQVEVK SEKLDFKDRV QSKIGSLDNI  360
THVPGGGNKK IETHKLTFRE NAKAKTDHGA EIVYKSPVVS GDTSPRHLSN VSSTGSIDMV  420
DSPQLATLAD EVSASLAKQG L                                             441
```

METHOD OF INHIBITING TAU PHOSPHORYLATION

CROSS-REFERENCE TO RELATED APPLICATIONS

This application is a continuation of U.S. patent application Ser. No. 18/323,075, filed May 24, 2023, which is a continuation of U.S. patent application Ser. No. 17/006,338, filed Aug. 28, 2020, now U.S. Pat. No. 11,661,580, which is a continuation of U.S. patent application Ser. No. 16/030,494, filed Jul. 9, 2018, now U.S. Pat. No. 10,760,052, which is a division of U.S. patent application Ser. No. 13/940,016, filed Jul. 11, 2013, now U.S. Pat. No. 10,017,736, which claims the benefit of Provisional Application No. 61/789,180, filed Mar. 15, 2013, and Provisional Application No. 61/671,235, filed Jul. 13, 2012, the disclosure of each of which is incorporated by reference herein in its entirety.

SEQUENCE LISTING

This application contains a computer readable Sequence Listing which has been submitted in XML file format via Patent Center, the entire content of which is incorporated by reference herein in its entirety. The Sequence Listing XML file submitted via Patent Center is entitled "14856-006-999_SL.xml", was created on Oct. 9, 2024, and is 3,781 bytes in size.

TECHNICAL FIELD

The present invention contemplates a method of central nervous system (CNS) treatment to inhibit the formation of hyperphosphorylated tau protein and the use of a contemplated compound in the manufacture of a medicament for inhibiting tau protein hyperphosphorylation that can lead to pathological formation of neurofibrillary tangles (NFTs). The method and use also lead to the enhancement of function of one or more of the alpha-7 nicotinic acetylcholine receptor (α7nAchR), the insulin receptor and the N-methyl-D-aspartate receptor.

BACKGROUND ART

The microtubule-associated protein tau (MAPT) occurs mostly in axons and in lesser amounts in astrocytes and oligodendrocytes, and stabilizes neuronal microtubules for their role in the development of cell processes, establishing cell polarity and intracellular transport. A single gene encodes a tau protein with an open reading frame that can encode 758 amino acid residues. Tau is listed in the UniProtKB/Swiss-Prot data base under the designation P10636. At least nine alternative splicing isoforms are recognized in the UniProtKB/Swiss-Prot data base.

Early work by Goedert and co-workers identified six isoforms that contain 352 to 441 amino acid residues [Mandelkow et al., *Trends in Cell Biology,* 8:425-427 (1998); see also, Johnson et al., *J. Cell Sci,* 117(24):5721-5729 (2004)]. The numbering of the amino acid residue sequence and the phosphorylation positions referred to herein is done in line with the human tau isoform referred to as "htau 40" in Goedert et al., *Neuron* 3:519-526 (1989). That 441 residue tau isoform is also referred to as Tau-4 or Tau-F in the UniProtKB/Swiss-Prot data base in which it is given the designation P10636-8. The amino acid residue sequence of TAU-4 (P10636-8, htau 40) is shown in SEQ ID NO: 2.

Tau is a substrate for a number of kinase enzymes [Johnson et al., *J Cell Sci,* 117(24):5721-5729 (2004)]. Phosphorylation at serine and threonine residues in S-P or T-P motifs by proline-directed protein kinases (PDPK1: CDK1, CDK5, GSK3, MAPK) and at serine residues in K-X-G-S motifs by MAP/microtubule affinity-regulating kinase (MARK1 or MARK2) are frequently found.

An enzyme of that group, glycogen synthase kinase 3β (GSK3β), can be a predominant tau kinase [Cho et al., *J. Neurochem,* 88:349-358 (2004)]. GSK3β can phosphorylate unprimed sites that are in proline-rich regions (Thr-181, Ser-184, Ser-262, Ser-356 and Ser-400) or unprimed sites (Ser-195, Ser-198, Ser-199, Ser-202, Thr-205, Thr-231, Ser-235, Ser-262, Ser-356 and Ser-404) where a serine or threonine is prephosphorylated by another protein kinase (e.g., A-kinase) at a site that is located four amino acid residues C-terminal to the GSK3β site [Cho et al., *J. Neurochem,* 88:349-358 (2004); Wang et al., *FEBS Lett,* 436:28-34 (1998)].

The normophosphorylated form of the protein is a microtublule-associated protein that stimulates and stabilizes microtubule assembly. That normophosphorylated form typically contains two-three moles of phosphate per mole of protein [Kickstein et al., *Proc Natl Acad Sci, USA,* 107(50):21830-21835 (2010)].

Multiply phosphorylated (hyper-phosphorylated) tau proteins; i.e., tau proteins that contain more than the normophosphorylated number of phosphate groups, can result in the formation of neurofibrillary tangles that are associated with several pathological conditions that are referred to collectively as tauopathies. For example, tau phosphorylation levels in Alzheimer's disease patients are three- to four-fold higher than the number of phosphate groups present in the normophosphorylated molecule [Kickstein et al., *Proc Natl Acad Sci, USA,* 107(50):21830-21835 (2010)].

Increasing evidence suggests that neuroinflammation is a common feature of tauopathies. Thus, activated microglia are found in the postmortem brain tissues of various human tauopathies including Alzheimer's disease (AD), frontotemporal dementia (FTD), progressive supranuclear palsy and corticobasal degeneration [Gebicke-Haerter, *Microsc Res Tech,* 54:47-58 (2001); Gerhard et al., *Mov Disord,* 21:89-93 (2006); Ishizawa et al., *J Neuropathol Exp Neurol,* 60:647-657 (2001)].

Induction of systemic inflammation via administration of the Toll-like receptor 4 (TLR4) ligand, lipopolysaccharide (LPS), significantly induces MAPT (tau) hyperphosphorylation in a triple transgenic mouse model of AD [Kitazawa et al., *J Neurosci,* 25:8843-8853 (2005)]. The immunosuppressant drug FK506 (tacrolimus) attenuated microglial activation and extended the life span of P301S transgenic mouse model of FTD [Yoshiyama et al., *Neuron* 53:337-351 (2007)]. Further, a growing number of studies suggest that proinflammatory cytokines, such as interleukin-1 (IL-1), interleukin-6 (IL-6), and nitric oxide released from astrocytes can accelerate MAPT pathology and formation of neurofibrillary tangles (NFTs) in vitro [Li et al., *J Neurosci,* 23:1605-1611 (2003); Quintanilla et al., *Exp Cell Res,* 295:245-257 (2004); Saez et al., *In Vivo,* 18:275-280 (2004)].

The toll-like receptors (TLRs) are a group of transmembrane receptors whose cytoplasmic portions are highly similar, having a high similarity to the interleukin-1 (IL-1) receptor. That cytoplasmic portion is now referred to as the Toll/IL-1 receptor (T1R) domain. The extracellular portions are structurally unrelated. The TLRs recognize pathogen components. [Takeda et al., *Seminars in Immunology,* 16:3-9 (2004).]

TLR4 plays a fundamental role in pathogen recognition in recognizing lipopolysaccharide (LPS) found in most gram-negative bacteria as well as other molecules. This receptor also plays a role in activation of innate immunity. TLR4 pathway activation can be an indicator of an infection.

TLR4 typically associates with the adapter molecule, MD2, CD14 and the lipopolysaccharide binding molecule (LPB) when associating with LPS. Signaling occurs through a series of cytoplasmic molecules in what are referred to as the myeloid differentiation factor 88- (MyD88-)dependent pathway common to all TLRs, and the MyD88-independent pathway shared by TLR3 and TLR4. TLR3 recognizes double-stranded RNA and its activation occurs under different conditions from TLR4 activation.

Signaling induced by LPS via the MyD88-independent pathway leads to activation of the transcription factor IRF-3, and thereby induces IFN-β. IFN-β, in turn, activates Stat1, leading to the induction of several IFN-inducible genes. LPS-induced activation of NF-κB and JNK appears to be independent of the presence of MyD88. [Takeda et al., *Seminars in Immunology,* 16:3-9 (2004).]

TLR4 is present in cells of the immune system such as B cells, T cells and macrophages, as well as cells of the CNS. TLR4 is an important mediator of the innate immune response, and significantly contributes to neuroinflammation induced by brain injury. The TLR4-mediated neuroinflammation typically proceeds through the above TLR4/adapter protein MyD88 signaling pathway.

Mao et al., *J Neurotrauma, May* 14 (2012) reported the potential neuroprotective mechanisms of pituitary adenylate cyclase-activating polypeptide- (PACAP-)pretreatment in a rat model of traumatic brain injury (TBI). It was found that TBI induced significant upregulation of TLR4 with peak expression occurring 24 hours post-trauma.

Pretreatment with PACAP significantly improved motor and cognitive dysfunction, attenuated neuronal apoptosis, and decreased brain edema. That pretreatment inhibited TLR4 upregulation as well as that of its downstream signaling molecules, MyD88, p-IκB, and NF-κB, and suppressed increases in levels of the downstream inflammatory agents, interleukin-1β (IL-1β) and tumor necrosis factor-α (TNF-α), in the brain tissue around the injured cortex and in the hippocampus. PACAP treatment thus exerted a neuroprotective effect in this rat model of TBI, potentially via inhibiting a secondary inflammatory response mediated by the TLR4/MyD88/NF-κB signaling pathway in microglia and neurons, thereby reducing neuronal death and improving the outcome following TBI.

Traumatic brain injury (TBI) is a "signature" injury of recent military conflicts and is associated with psychiatric symptoms and long-term cognitive disability. Chronic traumatic encephalopathy (CTE), a hyperphosphorylated tau protein-linked neurodegenerative disorder (tauopathy) reported in athletes with multiple concussions, shares clinical features with TBI in military personnel exposed to explosive blast. CTE also shares pathology found in boxers that was previously known as dementia pugilistica. [Gandy et al., *Sci. Transl. Med.* 4:1341-1343 (May 12, 2012).]

Goldstein et al., *Sci. Transl. Med.* 4:134ra60 (2012), investigated the connection between TBI and CTE in a series of postmortem brains from U.S. military veterans with blast exposure and/or concussive injury. Those authors reported evidence for CTE neuropathology in the military veteran brains that is similar to that observed in the brains of young amateur American football players and a professional wrestler. The investigators developed a mouse model of blast neurotrauma that mimics typical blast conditions associated with military blast injury and discovered that blast-exposed mice also demonstrate CTE neuropathology, including tau protein hyperphosphorylation, myelinated axonopathy, microvascular damage, chronic neuroinflammation, and neurodegeneration.

The mouse neuropathology was reported to be accompanied by functional deficits, including slowed axonal conduction, reduced activity-dependent long-term synaptic plasticity, and impaired spatial learning and memory that persisted for 1 month after exposure to a single blast. The investigators then showed that blast-induced learning and memory deficits in the mice were reduced by immobilizing the head during blast exposure.

Neuropathological findings in the military veterans with blast exposure and/or concussive injury and young-adult athletes with repetitive concussive injury were consistent with those authors' previous CTE case studies [McKee et al., *J Neuropathol Exp Neurol* 68:709-735 (2009); McKee et al., *J Neuropathol Exp Neurol* 69:918-929 (2010)], and were reported to be readily differentiated from neuropathology associated with Alzheimer's disease, frontotemporal dementia, and other age-related neurodegenerative disorders.

Apolipoprotein E (ApoE) is a class of apolipoprotein found in the chylomicron and intermediate-density lipoprotein (IDLs) that binds to a specific receptor on liver cells and peripheral cells. ApoE has been studied for its role in several biological processes not directly related to lipoprotein transport, its more-studied function, including Alzheimer's disease, immunoregulation, and cognition.

ApoE is 299 amino acids long and transports lipoproteins, fat-soluble vitamins, and cholesterol into the lymph system and then into the blood. It is synthesized principally in the liver, but has also been found in other tissues such as the brain. In the nervous system, non-neuronal cell types, most notably astroglia and microglia, are the primary producers of ApoE, whereas neurons preferentially express the receptors for ApoE.

There are seven currently identified mammalian receptors for ApoE that belong to the evolutionarily conserved low density lipoprotein receptor gene family. ApoE is a polymorphic gene with three major isoforms, ApoE2, ApoE3, ApoE4, which translate from three alleles of the gene, of which ApoE-F3 is the "normal" allele, and ApoE-F2 and ApoE-F4 are dysfunctional alleles.

ApoE4 has been implicated in atherosclerosis and Alzheimer's disease, impaired cognitive function, and reduced neurite outgrowth. The ApoE4 variant is the largest known genetic risk factor for late-onset sporadic Alzheimer's Disease (AD) in a variety of ethnic groups. Caucasian and Japanese carriers of two E4 alleles have between 10 and 30 times the risk of developing AD by 75 years of age, as compared to those not carrying any E4 alleles.

Although 40-65% of AD patients have at least one copy of the 4 allele, ApoE4 is not a determinant of the disease. At least one-third of patients with AD are ApoE4 negative and some ApoE4 homozygotes never develop the disease. However, those with two E4 alleles have up to 20 times the risk of developing AD.

In addition, ApoE4 overexpression in mouse neurons resulted in hyperphosphorylation of tau and the development of motor problems, accompanied by muscle wasting, loss of body weight and premature death. [Tesseur et al., *Am J Pathol,* 156(3):951-964 (2000).]On the other hand, treatment of neurons with exogenously supplied ApoE isoforms (E2 or E4) affects several downstream signaling cascades in neurons: decreased tau kinase phosphorylation and inhibition of tau phosphorylation at Thr171 and Ser202/Thr205 epitopes in the primary neuronal culture. ApoE can alter levels of tau kinases and phospho-tau epitopes, potentially affecting tau neuropathological changes seen in AD brains. [Hoe et al., *Molecular Degeneration,* 1:8 (2006).]

Eisenberg and co-workers have studied the formation of beta-sheet fibrils from self-aggregating tau protein, and found that a particular hexapeptide can inhibit their formation by interfering with the 'steric zipper' of the beta-sheet fibril. However, the inhibiting peptide is too large to penetrate deeply into the brain nor does it appear to penetrate the brain cells in which the tau fibrils form. See, Sawaya et al., *Nature,* 447:453-457 (2007); Landau et al., *PLoS Biology,* 9(6): e1001080 (2011); and Sievers et al., *Nature,* 475:96-100 (July 2011). It would therefore be beneficial if an inhibitor of the formation of tau-containing NFTs could be found that penetrates the brain and other CNS structures, as well as the cells of those structures.

Alzheimer's disease (AD) poses a huge unmet medical need, with an estimated 35 million current patients worldwide and no disease-modifying treatment available. The two classes of drugs currently used for AD, cholinesterase inhibitors and memantine, only transiently enhance cognitive function in these patients.

The causative agent in AD pathology is generally accepted to be amyloid-β (Aβ), $Aβ_{42}$. Aβ is a 39-42-residue proteolysis product of amyloid precursor protein (APP) that is an integral membrane protein expressed in many tissues and concentrated in the synapses of neurons.

Transgenic animals with increased levels of Aβ can model AD, and Aβ levels in postmortem AD brains are correlated with the degree of cognitive impairment and neuropathology [Tanzi et al., *Cell* 120:545-555 (2005)]. This correlation is higher for soluble Aβ than for Aβ-rich plaques, implicating soluble Aβ in AD pathogenesis [Naslund et al., *J Am Med Assoc,* 283:1571-1577 (2000).]

It is believed that the critical pathogenic role of soluble Aβ is toxic signaling via the α-7 nicotinic acetylcholine receptor (α7nAChR), as demonstrated a decade ago. Aβ binds this receptor with high affinity [Wang et al., *J Biol Chem* 275:5626-5632 (2000); Wang et al., *J Neurochem* 75:1155-1161 (2000)], activating ERK2, which phosphorylates the tau protein [Wang et al., *J Biol Chem* 278:31547-31553 (2003)]. ERK2 is also known as mitogen-activated protein kinase 1 (MAPK1) noted earlier.

Persistent abnormal hyperphosphorylation of tau proteins results in neurofibrillary tangles (NFTs), a prominent neuropathological feature in AD brain, and the magnitude of these lesions correlates with the severity of AD symptoms [Delacourte et al., *Neurology* 52:158-1165 (1999); Delacourte et al., *Neurology* 43:93-204 (1998).] The NFTs are initially intracellular, and become extracellular ghost tangles after death of the neuron [Mandelkow et al., *Trends in Cell Biology,* 8:425-427 (1998)].

Aβ peptide has been shown to induce tau phosphorylation in several in vitro experimental systems [Johnson et al., *J Alzheimers Dis* 1:29-351 (1999)], and Aβ-induced tau phosphorylation has been demonstrated to be dependent on α7nAChR, because pretreatment of tissues with α7nAChR antagonists or with $Aβ_{12-28}$, which inhibit the $Aβ_{42}$-α7nAChR interaction, reduces $Aβ_{42}$-induced tau phosphorylation [Wang et al., *J Biol Chem* 278:31547-31553 (2003)].

Phosphorylation of some sites appears to regulate microtubule-binding properties (e.g., Ser262 and Ser356) [Mandelkow et al., *Trends in Cell Biology,* 8:425-427 (1998)]. On the other hand, phosphorylation at one or more of 202Ser, 231Thr and 181Thr is found in tau-containing NFTs [Wang et al., *J Biol Chem* 278:31547-31553 (2003); Wang et al., *Biol Psychiatry* 67:522-530 (2010)].

The critical role of the α7nAChR in mediating neurofibrillary pathology is further supported by at least two findings: 1) protracted incubation of $Aβ_{42}$ with SK-N-MC cells that over-express (α7nAChRs promotes NFTs, and 2) antisense-α7nAChR oligonucleotides that reduce α7nAChR levels abolish $Aβ_{42}$-induced neurofibrillary lesions [Wang et al., *J Biol Chem* 278:31547-31553 (2003)]. These data suggest that chronic perturbation of the α7nAChRs with $Aβ_{42}$ in AD brains leads to neurofibrillary phosphorylated tau-containing lesions.

As discussed in detail hereinafter, the present invention provides a method to inhibit $Aβ_{42}$-induced hyperphosphorylation of tau proteins by inhibiting one or more signaling pathways that utilize the signaling scaffold, filamin A (FLNA). In one pathway, AR and α7nAChR interact leading to the recruitment of FLNA. In another pathway, TLR4 is activated by $Aβ_{42}$ or its cognate ligand, LPS for example, and the TLR4-mediated signaling is activated through the recruitment of FLNA to the TLR4 receptor. $Aβ_{42}$ induces FLNA recruitment to α7nAChR or TLR4 as well as tau phosphorylation can be observed by incubating 250,000 cells in 250 μl of oxygenated Kreb's-Ringer with 1 nM $Aβ_{42}$. This $Aβ_{42}$-mediated effect was found to be plateaued at 100 nM.

The treatment approach disclosed below is targeted at inhibiting hyperphosphorylation of tau proteins mediated by FLNA using a compound that binds FLNA with high affinity. This binding is believed to alter the conformation of FLNA and prevent it from interacting with other signaling molecules such as α7nAChRs, thereby inhibiting the hyperphosphorylation of the tau protein.

BRIEF SUMMARY OF THE INVENTION

The present invention contemplates a method of inhibiting hyperphosphorylation [phosphorylation at one or more of serine-202 (also 202Ser and $S^{202}$), threonine-231 (also 231Thr and $T^{231}$) and threonine-181 (also 181Thr and $T^{181}$) in addition to phosphorylation that may be present at any other site] of the tau protein that comprises the steps of administering to central nervous system cells in recognized (diagnosed) need thereof an effective amount of a compound or a pharmaceutically acceptable salt thereof that binds to filamin A (FLNA) or binds to a pentapeptide of filamin A of SEQ ID NO: 1 as described in Example 1, e.g., inhibits at least about 60 percent and more preferably about 70 percent of the FITC-labeled naloxone binding when present at a 10 μM concentration and using unlabeled naloxone as the control inhibitor at the same concentration. The compound is preferably of Series A, B, C-1, C-2, D or E as described hereinafter, and preferably contains at least four of the six pharmacophores of FIGS. 35-40. The administration is carried out in the absence of a mu opioid receptor (MOR)-binding effective amount of a separate MOR agonist or antagonist molecule.

The use of a single stereoisomer or mixture of stereoisomers, or a pharmaceutically acceptable salt of a contemplated compound is also contemplated. The contemplated administration can take place in vivo or in vitro, and is typically repeated over a period of days or months when administered in vivo.

Another aspect of the invention contemplates a method of inhibiting a TLR4-mediated immune response such as inflammation of cells of the CNS. A contemplated method comprises administering to TLR4-containing cells in recognized (diagnosed) need thereof an effective amount of a compound or a pharmaceutically acceptable salt thereof that binds to filamin A or binds to a pentapeptide of filamin A (FLNA) of SEQ ID NO: 1 as described in Example 1, inhibits at least about 60 percent and more preferably about 70 percent of the FITC-labeled naloxone binding when present at a 10 μM concentration and using unlabeled naloxone as the control inhibitor at the same concentration. A contemplated compound is preferably of Series A, B, C-1, C-2, D or E as described herein, and preferably contains at least four of the six pharmacophores of FIGS. 35-40. The administration is preferably carried out in the absence of a mu opioid receptor (MOR)-binding effective amount of a separate MOR agonist or antagonist molecule.

The use of a single stereoisomer or mixture of stereoisomers, or a pharmaceutically acceptable salt of a contemplated compound is also contemplated. The contemplated administration can take place in vivo or in vitro, and is typically repeated over a period of days or months when administered in vivo to the cells of a host animal such as a human.

In one aspect of an above method, tau hyperphosphorylation of one or more of $S^{202}$, $T^{231}$ and $T^{181}$ occurs through the interaction of AR and α7nAChR via the scaffolding protein filamin A (FLNA). In another aspect of a contemplated method, such tau hyperphosphorylation occurs via a TLR4-mediated immune response in a presently unknown mechanism that also involves the intermediacy of FNLA.

It is presently believed that each of the above pathways, Aβ-α7nAChR and TLR4, can operate at the same time and also independently. Illustrative CNS conditions that exhibit one or both of Aβ-α7nAChR-mediated and/or TLR4-mediated tau phosphorylations of one or more of $S^{202}$, $T^{231}$ and $T^{181}$ include those of persons and other animals whose CNS cells exhibit an immune response such as inflammation induced by brain injury such as traumatic brain injury (e.g., concussion), chronic traumatic encephalopathy, those having Alzheimer's disease (AD) symptoms, frontotemporal dementia (FTD), progressive supranuclear palsy, dementia pugilistica and corticobasal degeneration and also infection by one or both of Gram positive and Gram negative bacteria.

The binding inhibition to a SEQ ID NO: 1 pentapeptide by a contemplated compound is determined as discussed in Example 1. A contemplated compound is substantially free from binding with any other portion of FLNA at the concentration of contemplated compound used. Substantial freedom from binding with any other portion of FLNA can be determined using a titration assay such as that shown in FIG. 48A herein [FIG. 3 of Wang et al., *PLoS One.* 3(2): e1554 (2008)], which in that figure indicates the presence of two binding site regions by the two inflection points shown in the plot, whereas the presence of a single binding site is indicated by the presence of a single inflection point in such a plot (FIG. 48D). Substantial freedom from binding with any other portion of FLNA can also be inferred from functional data such as a cytokine release assay illustrated hereinafter that indicate contemplated compounds do not bind the second site on FLNA because the compounds are effective over a wide range of concentrations, unlike those compounds such as naloxone and naltrexone that bind to two binding sites on FLNA.

In presently preferred embodiments, the present invention contemplates a method of inhibiting phosphorylation of the tau protein at one or more of $S^{202}$, $T^{231}$ and $T^{181}$ that comprises the step of administering to cells of the central nervous system in recognized (diagnosed) need such as brain cells an effective amount of a compound of one or more of Series A, Series B, Series C-1 and Series C-2, Series D and Series E, a stereoisomer or a pharmaceutically acceptable salt thereof. The cells, in vivo or in vitro, such as brain cells in recognized need (diagnosed) are cells in those tissues or organs of a mammalian subject that exhibit an immune response such as inflammation induced by brain injury like traumatic brain injury, chronic traumatic encephalopathy, those having Alzheimer's disease (AD) symptoms, frontotemporal dementia (FTD), progressive supranuclear palsy, dementia pugilistica and corticobasal degeneration and also infection by one or both of Gram positive and Gram negative bacteria.

The administration is preferably carried out in the absence of a MOR-binding effective amount of a separate MOR agonist or antagonist molecule, and is often carried out a plurality of times over a period of days or months.

Also contemplated is the use of a compound or a pharmaceutically acceptable salt thereof in the manufacture of a medicament for inhibiting phosphorylation of the tau protein in cells of the central nervous system that are in recognized need of treatment. Such a compound or its salt binds to a pentapeptide of filamin A of SEQ ID NO: 1, inhibits at least about 60 percent and more preferably about 70 percent of the FITC-labeled naloxone binding when present at a 10 μM concentration and using unlabeled naloxone as the control inhibitor at the same concentration. This use contemplates manufacture of a medicament that inhibits tau hyperphosphorylation (phosphorylation) through the interaction of AR and α7nAChR via the scaffolding protein filamin A (FLNA), as well as such tau hyperphosphorylation that occurs via a TLR4-mediated immune response that is also believed to involve the intermediacy of FNLA as are noted above.

The general structures of the compounds of each series are shown below, followed by more specific disclosures for the various letters and R-groups.

Series A

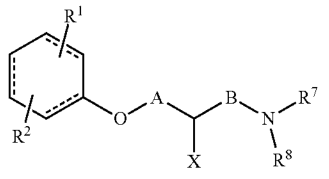

Series B

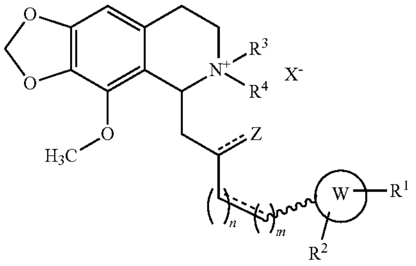

-continued

Series C-1

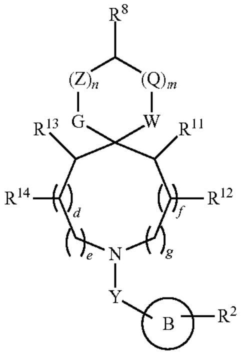

Series C-2

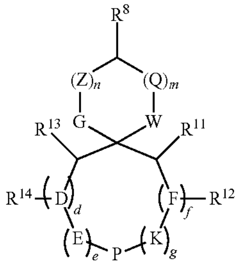

Series D

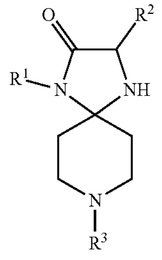

Series E

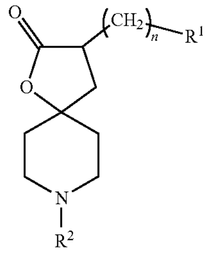

Individual optical isomers and mixtures of optical isomers of those compounds of the above Formulas are also contemplated, as are pharmaceutically acceptable salts of those compounds.

A contemplated compound described above or its pharmaceutically acceptable salt is typically administered in an effective amount dissolved or dispersed in a pharmaceutical composition. That pharmaceutical composition can be in solid or liquid form.

The invention also contemplates a method of:

a) inhibiting (α7nAChR-FLNA association (Complex formation);

b) inhibiting Aβ-induced α7nAChR-mediated signaling of extracellular signal-regulated kinase 2 [ERK2; also known as mitogen-activated protein kinase 1 (MAPK1)];

c) inhibiting $Aβ_{42}$-induced association of TLR4 with FLNA;

d) inhibiting $Aβ_{42}$-induced impairment in α7nAChR function, e.g., calcium influx, after α7nAChR stimulation;

e) restoring $Aβ_{42}$-induced impairment in N-methyl-D-aspartate (NMDA) receptor (NMDAR) function, e.g., calcium influx after stimulation of NMDAR with co-agonists NMDA and glycine;

f) restoring the $Aβ_{42}$-induced impairment in insulin receptor (IR) function as measured by one or both of phosphorylation of the subunit IRP and association with the IRS-1 signaling molecule;

g) inhibiting $Aβ_{42}$-induced impairment of $K^+$-evoked cellular calcium influx;

h) reducing the formation of tau-containing NFTs and also $Aβ_{42}$ aggregates (neuritic plaques) in the presence of $Aβ_{42}$; and i) inhibiting $Aβ_{42}$-induced inflammatory cytokine production. Each of those methods is carried out by administering to cells of the central nervous system such as brain cells an effective amount of a before-described compound that binds to the FLNA pentapeptide of SEQ ID NO: 1. The administration is carried out in the absence of a MOR-binding effective amount of a separate MOR agonist or antagonist molecule.

A still further aspect of this invention contemplates a method of promoting cartilage repair in a mammal having osteoarthritis, such as that induced by collagenase and/or surgery or other causes. This method comprises the steps of administering to multipotent mesenchymal stem cells in a mammal in recognized need (diagnosed) thereof an effective amount of a compound or a pharmaceutically acceptable salt thereof that binds to filamin A or binds to a pentapeptide of filamin A (FLNA) of SEQ ID NO: 1 as described in Example 1, e.g., inhibits at least about 60 percent and more preferably about 70 percent of the FITC-labeled naloxone binding when present at a 1 μM concentration and using unlabeled naloxone as the control inhibitor at the same concentration. The compound is preferably of Series A, B, C-1, C-2, D or E as described herein, and preferably contains at least four of the six pharmacophores of FIGS. 35-40. The administration is carried out in the absence of a mu opioid receptor (MOR)-binding effective amount of a separate MOR agonist or antagonist molecule.

The use of a single stereoisomer or mixture of stereoisomers, or a pharmaceutically acceptable salt of a contemplated stereoisometric compound is also contemplated. The contemplated administration can take place in vivo or in vitro, and is typically repeated when administered in vivo.

The present invention has several benefits and advantages.

One benefit is that a contemplated method inhibits AR signaling through α7nAChR that is believed superior to targeting the receptor itself. Disabling the Aβ-induced α7nAChR signaling without directly affecting the α7nAChRs avoids altering the sensitivity or cell surface level of the receptors, an insidious problem with using chronic receptor agonists or antagonists.

An advantage of this invention is that this approach appears to selectively affect the robust increase in filamin recruitment by AR while preserving basal coupling, suggesting that the compounds used in the method reduce the pathological signaling by Aβ, while retaining physiological α7nAChR signaling.

Another benefit of the invention is that administration of a contemplated compound inhibits the in vitro and in vivo phosphorylation of the tau protein.

Another advantage of the invention is that when a contemplated compound is administered in vivo, the administration inhibits the formation of NFTs in the brain of a subject mammal to which a contemplated compound is administered.

Yet another benefit of the invention is that administration of a contemplated compound can provide the benefits of one or more of the methods enumerated above by binding of that compound to the FLNA pentapeptide of SEQ ID NO: 1 disrupting one or more of the newly-found interactions of FLNA.

Yet another advantage of the invention is that its use can lessen the effects of tau phosphorylation in persons or other animals with head injuries and resultant TLR4-mediated inflammation.

Still further benefits and advantages will be apparent to those skilled in the art from the disclosures that follow.

BRIEF DESCRIPTION OF THE DRAWINGS

In the drawings forming a part of this disclosure,

FIG. 26 in two panels illustrates that Compound C0105 reduces $A\beta_{42}$-α7nAChR complexes in AD and $A\beta_{42}$-treated control. Solubilized synaptosomes from the same treated AD and control brain slices used in FIG. 25 were immunoprecipitated with anti-$A\beta_{42}$ and Western blots (FIG. 26A) of immunoprecipitates were probed with anti-α7nAChR and analyzed by densitometric quantitation (FIG. 26B). $A\beta_{42}$-α7nAChR complexes were elevated in both $A\beta_{42}$-treated control tissue and AD tissue, and Compound C0105 (0.1 and 1 nM) reduced this interaction. n=11. Data are means±SEM. *p<0.01 vs. vehicle-treated control, #p<0.01 vs. $A\beta_{42}$-treated control or vehicle-treated AD.

FIG. 27 in two panels illustrates that Compound C0105 reduces affinity of the $A\beta_{42}$-α7nAChR interaction. In postmortem control tissue, Compound C0105 incubation reduces $A\beta_{42}$ binding affinity for α7nAChR 1000-fold from 100 femtomolar to 16 nanomolar in biotinylated synaptic membranes from postmortem frontal cortices of non-demented controls (FIG. 27A). In fresh, SK-N-MC cells, Compound C0105 reduces this binding affinity 10,000-fold from 770 femtomolar to 1 nanomolar (FIG. 27B). Data are means SEM. n=11 for postmortem control tissue; n=6 for SK-N-MC cells.

FIG. 32 in two panels illustrates that Compound C0105 normalizes IR signaling impairments. IR signaling is impaired in AD and $A\beta_{42}$-treated control brain slices, as measured by phosphorylation of IPP and its association with the signaling molecule IRS-1. Incubation with Compound C0105 (1 nM) normalizes these impairments. Western blots (FIG. 32A), in which numerals outside of and to the left of the blots are as discussed before, were analyzed by densitometric quantitation (FIG. 32B). Data are means±SEM. n=11. *p<0.01 compared to insulin-stimulated level in control vehicle group; #p<0.01 vs. insulin-stimulated level in AD vehicle group.

FIG. 33 in two panels illustrates that VAKGL (SEQ ID NO: 1) pentapeptide (1 μM) blocks C0105's prevention of FLNA-α7nAChR or TLR4 association. Acting as a decoy for the FLNA protein, the pentapeptide binding site of Compound C0105 on FLNA blocks Compound C0105's reduction in $A\beta_{42}$-induced FLNA-α7nAChR/TLR4 association in postmortem frontal cortical synaptosomes. Western blots (FIG. 33A), in which numerals outside of and to the left of the blots are as discussed before, were analyzed by densitometric quantitation (FIG. 33B). Data are means±SEM. n=3. *p<0.01 vs. the respective basal level; #p<0.01 vs. $A\beta_{42}$-exposed tissues.

FIG. 34 VAKGL (SEQ ID NO: 1) pentapeptide (1 μM) blocks Compound C0105's prevention of tau phosphorylation. Again using postmortem frontal cortical synaptosomes, the VAKGL pentapeptide blocks C0105's reduction in tau phosphorylation at all three phosphorylation sites found in neurofibrillary tangles. Western blots (FIG. 34A), in which numerals outside of and to the left of the blots are as discussed before, were analyzed by densitometric quantitation (FIG. 34B). Data are means±SEM. n=3. *p<0.01 vs. the respective basal level; #p<0.01 vs. $A\beta_{42}$-exposed tissues.

FIGS. 41 and 41B, illustrates further high-affinity FLNA-binding compounds that reduce α7nAChR-FLNA association assayed as in FIG. 2. Frontal cortical synaptosomes from 2-month-old rats were treated with 1 or 10 nM concentrations of Compounds A, B, or C, using Compounds C0134 and C0105 as controls, either simultaneously (Sim) with or 10 minutes prior (10' pr) to $A\beta_{42}$ (0. μM) and were immunoprecipitated with immobilized anti-FLNA. The complexes in the solubilized synaptosomes, and α7nAChR, TLR4 and FLNA levels in the anti-FLNA immunoprecipitates were determined by Western blotting (FIG. 41A) in which numerals outside of and to the left of the blots are as discussed before. Amounts present in the blots were quantified by densitometry (FIG. 41B). Ratios of α7nAChR/FLNA were statistically different from $A\beta_{42}$ alone with p<0.01 for all compounds examined Dunnett's test. Ratios of TLR4/FLNA were statistically different from $A\beta_{42}$ alone for most of the compounds and conditions at *p<0.01 or **p<0.05. Structural formulas of the compounds used in this and the other figures are provided hereinafter.

ABBREVIATIONS AND SHORT FORMS

Figure 1:
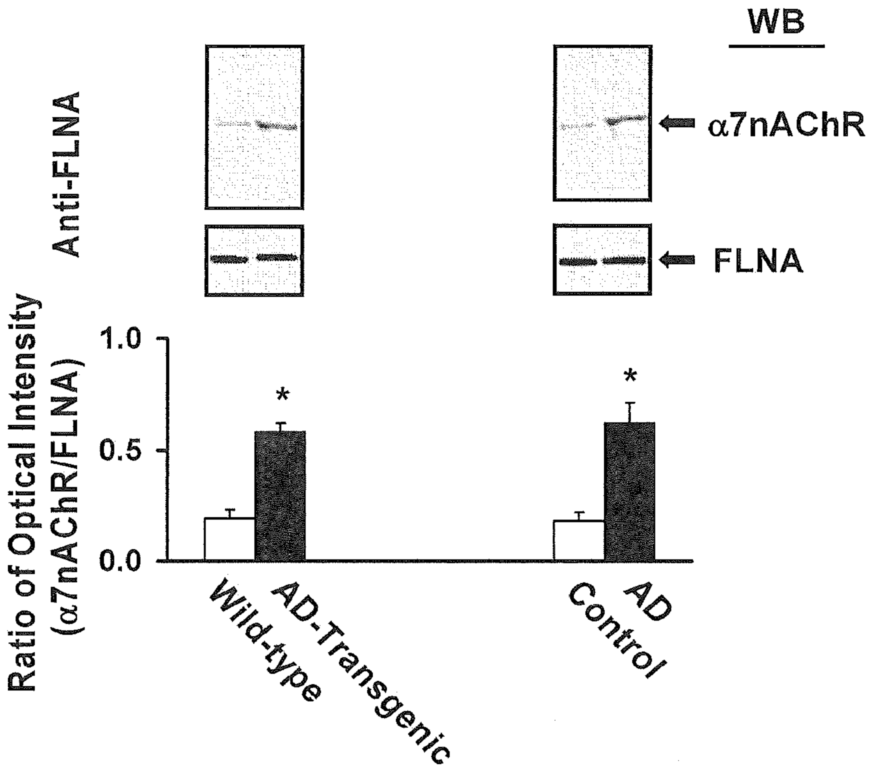
FIG. 1 shows a heightened α7nAChR-FLNA association in frontal cortex of AD transgenic mice and AD patients. Frontal cortical synaptosomes from 6-month-old AD transgenic/wild-type mice (n=4) and 4 matching AD/control human pairs were analyzed for their baseline α7nAChR-FLNA complex contents. The α7nAChR-FLNA complexes in the solubilized frontal cortical synaptosomes were immunoprecipitated with anti-FLNA and the α7nAChR levels in anti-FLNA immunoprecipitate were determined by Western blotting with anti-α7nAChR antibodies. Blots were then stripped and re-probed with anti-FLNA as a loading control. Densitometric scanning was used for quantification.

The following abbreviations and short forms are used in this specification.

"Aβ" means amyloid-beta
"$A\beta_{42}$" means a 42-residue proteolysis product of amyloid precursor protein (APP)
"α7nAchR" means alpha-7 nicotinic acetylcholine receptor
"DAMGO" means [D-Ala2, N-MePhe4, Gly-ol]-enkephalin
"ERK2" means extracellular signal-regulated kinase 2
"FCX" means frontal cortex or prefrontal cortex
"FLNA" means filamin A
"FITC" means fluorescein isothiocyanate
"Gs" means G protein stimulatory subtype, stimulates adenylyl cyclase
"HP" means hippocampus
"IHC" means immunohistochemistry
"IR" means insulin receptor
"MOR" means opioid receptor
"NLX" means naloxone
"NTX" means naltrexone
"NFTs" means neurofibrillary tangles
"NMDA" means N-methyl-D-aspartate
"NMDAR" means NMDA receptor
"pERK2" means phosphorylated ERK2
"pTau" means hyperphosphorylated tau protein
"TLR4" means toll-like receptor-4

Definitions

In the context of the present invention and the associated claims, the following terms have the following meanings:

The articles "a" and "an" are used herein to refer to one or to more than one (i.e., to at least one) of the grammatical object of the article. By way of example, "an element" means one element or more than one element.

As used herein, the term "hydrocarbyl" is a short hand term for a non-aromatic group that includes straight and branched chain aliphatic as well as alicyclic groups or radicals that contain only carbon and hydrogen. Inasmuch as alicyclic groups are cyclic aliphatic groups, such substituents are deemed hereinafter to be subsumed within the aliphatic groups. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups, substituents, moieties or radicals, as discussed hereinafter. An aralkyl substituent group such as benzyl is deemed an aromatic group as being an aromatic ring bonded to an X group, where X is $CH_2$. A substituent group containing both an aliphatic ring and an aromatic ring portion such as tetralin (tetrahydronaphthalene) that is linked directly through the aliphatic portion to the depicted ring containing the W group is deemed a non-aromatic, hydrocarbyl group. On the other hand, a similar group bonded directly via the aromatic portion, is deemed to be a substituted aromatic group. Where a specific aliphatic hydrocarbyl substituent group is intended, that group is recited; i.e., $C_1$-$C_4$ alkyl, methyl or dodecenyl. Exemplary hydrocarbyl groups contain a chain of 1 to about 12 carbon atoms, and preferably 1 to about 8 carbon atoms, and more preferably 1 to 6 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl, octyl, decyl, dodecyl and the like. Cyclic alkyl radicals such as cyclo propyl, cyclobutyl, cyclopentyl, cyclohexyl and cycloheptyl are also contemplated, as are their corresponding alkenyl and alkynyl radicals. Examples of suitable straight and branched chain alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of straight and branched chain alkynyl radicals include ethynyl, 2-propynyl, 3-propynyl, decynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. Illustrative hydrocarbyloxy groups include methoxy, ethoxy, and cyclohexenyloxy groups. On the other hand, a hydrocarbyl group containing a —C(O)— functionality is referred to as a hydrocarboyl (acyl) and that containing a —C(O)O— is a hydrocarboyloxy group inasmuch as there is no ambiguity. Exemplary hydrocarboyl and hydrocarboyloxy groups include acyl and acyloxy groups, respectively, such as acetyl and acetoxy, acryloyl and acryloyloxy.

Carboxyl-related linking groups between the central spiro ring system and an aromatic or heteroaromatic ring system, circle A, include several types of ester and amide bonds. Illustrative of such bonds are sulfonamide, sulfonate and thiosulfonate esters that can be formed between a $SO_2$-containing group [also sometimes shown as a $S(=O)_2$ group] and an amine, oxygen or sulfur atom, respectively. Amide, ester and thioester links can be formed between an aromatic or heteroaromatic ring containing a C(O) [also sometimes shown as (C=O)]group and a nitrogen, oxygen or sulfur atom, respectively. Similarly, a guanidino linker can be formed between an aromatic or heteroaromatic ring containing a NHC(NH) [NHC(=NH)]group and a nitrogen, a urethane, carbonate or thiocarbonate can be formed between an aromatic or heteroaromatic ring containing a OC(O) [or OC(=O)]group and a nitrogen, oxygen or sulfur, respectively. A compound containing a urea linker, urethane linker or isothiourea linker [NHC(O)S]{or [NHC(=O)S]}can be formed between an aromatic or heteroaromatic ring containing a NHC(O) group and a nitrogen, oxygen or sulfur, respectively. A thiourea linkage is also contemplated.

A "carboxyl" substituent is a —C(O)OH group. A $C_1$-$C_6$ hydrocarbyl carboxylate is a $C_1$-$C_6$ hydrocarbyl ester of a carboxyl group. A carboxamide is a $—C(O)NR^3R^4$ substituent, where the R groups are defined elsewhere and are numbered here as 3 and 4 for ease in further discussion, but need not be so numbered in the following chemical formulas. Similarly, a sulfonamide is a $—S(O)_2NR^3R^4$ substituent, where the R groups are defined hereinafter. Illustrative $R^3$ and $R^4$ groups that together with the depicted nitrogen of a carboxamide form a 5-7-membered ring that optionally contains 1 or 2 additional hetero atoms that independently are nitrogen, oxygen or sulfur, include morpholinyl, piperazinyl, oxathiazolyl, 1,2,3-triazolyl, 1,2,4-triazolyl, pyrazolyl, 1,2,4-oxadiazinyl and azepinyl groups.

As a skilled worker will understand, a substituent that cannot exist such as a $C_1$ alkenyl or alkynyl group is not intended to be encompassed by the word "hydrocarbyl", although such substituents with two or more carbon atoms are intended.

The term "aryl", alone or in combination, means a phenyl, naphthyl or other radical as recited hereinafter that optionally carries one or more substituents selected from hydrocarbyl, hydrocarbyloxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, and the like. The term "arylhydrocarbyl", alone or in combination, means a hydrocarbyl radical as defined above in which one hydrogen atom is replaced by an aryl radical as defined above, such as benzyl, 2-phenylethyl and the like. The term "arylhydrocarbyloxycarbonyl", alone or in combination, means a radical of the formula —C(O)—O-arylhydrocarbyl in which the term "arylhydrocarbyl" has the significance given above. An example of an arylhydrocarbyloxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

As used herein, the term "binds" refers to the specific adherence of molecules to one another, such as, but not limited to, the interaction of a ligand with its receptor, or a polypeptide of SEQ ID NO: 1 with a small molecule such as the compounds disclosed herein, or an antibody and its antigen.

As used herein, the term "FLNA-binding compound" refers to a compound that binds to the scaffolding protein filamin A, or more preferably to a polypeptide comprising residues -Val-Ala-Lys-Gly-Leu- (SEQ ID NO: 1) of the FLNA sequence that correspond to amino acid residue positions 2561-2565 of the FLNA protein sequence as noted in the sequence provided at the web address: UniProtKB/Swiss-Prot entry P21333, FLNA-HUMAN, Filamin-A protein sequence. A FLNA-binding compound can inhibit the MOR-Gs coupling caused by agonist stimulation of the opioid receptor via interactions with filamin A, preferably in the $24^{th}$ repeat region.

As used herein, the term "opioid receptor" refers to a G protein-coupled receptor located in the CNS that interacts with opioids. More specifically, the opioid receptor is activated by morphine causing analgesia, sedation, nausea, and many other side effects known to one of ordinary skill in the art.

As used herein, the term "opioid agonist" refers to a substance that upon binding to an opioid receptor can stimulate the receptor, induce G protein coupling and trigger a physiological response. More specifically, an opioid agonist is a morphine-like substance that interacts with MOR to produce analgesia.

As used herein, the term "opioid antagonist" refers to a substance that upon binding to an opioid receptor inhibits the function of an opioid agonist by interfering with the binding of the opioid agonist to the receptor.

As used herein the term "ultra-low-dose" or "ultra-low amount" refers to an amount of compound that when given in combination with an opioid agonist is sufficient to enhance the analgesic potency of the opioid agonist. More specifically, the ultra-low-dose of an opioid antagonist is admixed with an opioid agonist in an amount about 1000- to about 10,000,000-fold less, and preferably about 10,000- to about 1,000,000-fold less than the amount of opioid agonist.

As used herein an "FLNA-binding effective amount" or more simply an "effective amount" refers to an amount of a contemplated compound sufficient to bind to the FLNA pentapeptide of SEQ ID NO: 1 and perform the functions described herein, such as inhibition of tau protein phosphorylation. An effective amount of a contemplated compound is most easily determined using the in vitro assay of Example 1. Using that definition, an effective amount of a contemplated compound binds to a pentapeptide of SEQ ID NO: 1, inhibits at least about 60 percent and more preferably about 70 percent of the FITC-labeled naloxone binding when present at a 10 μM concentration and using unlabeled naloxone as the control inhibitor at the same concentration and under the same conditions as the contemplated compound, and up to about twice (200 percent) the inhibition obtained with naloxone as control.

As used herein the term "pharmacophore" is not meant to imply any pharmacological activity. A pharmacophore can be defined as the relevant groups on a molecule that interact with a receptor and are responsible for the activity of the compound. [R. B. Silverman, *The Organic Chemistry of*

*Drug Design and Drug Action,* 2nd ed., Elsevier Academic Press, Amsterdam, (2004), p. 17.] The term can also be defined and is intended herein to be the chemical features of a molecule and their distribution in three-dimensional space that constitutes the preferred requirements for molecular interaction with a receptor (See, U.S. Pat. No. 6,034,066). A pharmacophore is computer-calculated by determining the shared aromatic/hydrophobic and hydrogen bond acceptor functions and the distances there between of a group of compounds that bind similarly to a particular receptor, here, pentapeptide of SEQ ID NO: 1, using an appropriately programmed computer. Such computer programs are available commercially from companies such as Accelrys Software Inc., San Diego, CA, Schrödinger, LLC, Portland, OR, from Chemical Computing Group, Inc., Montreal, QC, Canada, or as an open access program referred to as ZINCPharmer

DETAILED DESCRIPTION OF THE INVENTION

The present invention contemplates a method of inhibiting the hyperphosphorylation (phosphorylation) of tau protein at one or more of $S^{202}$, $T^{231}$ and $T^{181}$ in vitro as well as in vivo. Such a method comprises the steps of administering to cells of the central nervous system in recognized need thereof, such as brain cells, an effective amount of a compound that binds to the FLNA pentapeptide of SEQ ID NO: 1, inhibits at least about 60 percent and more preferably about 70 percent of the FITC-labeled naloxone binding when present at a 10 μM concentration and using unlabeled naloxone as the control inhibitor at the same concentration. That compound also preferably contains at least four of the six pharmacophores of FIGS. 35-40. A more preferred compound contains five of the six pharmacophores, and a most preferred compound contains all six of those pharmacophores.

Phosphorylation of one or more of $S^{202}$, $T^{231}$ and $T^{181}$ of the tau protein is typically in addition to phosphorylation of one or more additional residues of the protein. The presence of such phosphorylation can be determined by the immunoreaction of an antibody, usually a monoclonal antibody, that immunoreacts specifically with a tau protein that is phosphorylated at one of those three amino acid residues as is illustrated herein.

The administration is preferably carried out in the absence of a MOR-binding effective amount of a separate, exogenously provided MOR agonist or antagonist molecule. Thus, an exogenously supplied MOR-binding compound such as morphine itself, codeine, oxycodone and the like MOR-binding compounds is absent when a contemplated compound is administered to the cells. The presence of an endogenously supplied MOR-binding compound such as an endorphin or an enkephalin cannot be as readily controlled and is not excluded. Some of the contemplated FLNA pentapeptide-binding compounds also bind to MOR and their use is also not excluded. However, it is preferred to use a compound that binds poorly if at all to MOR, as discussed hereinafter, and is not a MOR agonist. Such a compound exhibits less than about 80 percent the MOR stimulation provided by DAMGO at the same concentration and assay conditions.

Inhibition of the hyperphosphorylation (phosphorylation) of tau protein in vitro and in vivo can be assayed in lysates or other cell preparations of cultured CNS cells in vitro or in lysates of CNS cells such as olfactory neurons obtained via scraping the nasal cavity for neural epithelial cells or from biopsy samples for in vivo assays.

Also contemplated is a method of inhibiting TLR4-mediated immune response such as inflammation of TLR4-containing cells such as lymphocytes or cells of the CNS that comprises administering to TLR4-containing cells in recognized need thereof an effective amount of a of a compound or a pharmaceutically acceptable salt thereof that binds to a pentapeptide of filamin A (FLNA) of SEQ ID NO: 1, inhibits at least about 60 percent and more preferably about 70 percent of the FITC-labeled naloxone binding when present at a 10 μM concentration and using unlabeled naloxone as the control inhibitor at the same concentration, and contains at least four of the six pharmacophores of FIGS. 35-40. The administration is preferably carried out in the absence of a mu opioid receptor (MOR)-binding effective amount of a separate MOR agonist or antagonist molecule. An administered compound preferably binds poorly or does not bind to MOR as described hereinafter, e.g., the compound exhibits less than about 80 percent the MOR stimulation provided by DAMGO at the same concentration.

The use of a single stereoisomer or mixture of stereoisomers, or a pharmaceutically acceptable salt of a contemplated compound is also contemplated. The contemplated administration can take place in vivo or in vitro, and is typically repeated a plurality of times over a period of days or months when administered in vivo to the cells of a host animal such as a human.

An administered compound contains at least four of the six pharmacophores of FIGS. 35-40, but more preferably, such a contemplated compound contains at least five of the six pharmacophores of FIGS. 35-40. Most preferably, the administered compound contains each of the six pharmacophores of FIGS. 35-40.

TLR4-mediated immune response inflammation of CNS cells produces hyperphosphorylation of the tau protein and related tauopathies such as those that result from NFTs. As a consequence, one way to assay for the presence of TLR4-mediated inflammation is to assay for the presence of an enhanced amount of phosphorylated tau compared to the amount present in a non-inflammatory condition as was described above for hyperphosphorylated tau.

TLR4-mediated inflammation can also be recognized by the greater than background abundance of TLR4 activation protein markers such as the cytokines IL-1β, IL-6 and TNFα that are typically enhanced together, and/or the separately stimulated NF-κB and JNK proteins. As was noted earlier, enhanced expression of IL-1p, IL-6 and TNFα as compared to expression of NF-κB and JNK appear to proceed by different TLR4-mediated pathways. However, both markers of inflammation can be present at the same time due to the same immunostimulus.

Thus, the presence of an enhanced amount of one, two or three of IL-I, IL-6 and TNFα relative to the amount present in a non-inflammatory condition indicates the presence of TLR4-mediated inflammation. Similarly, the enhanced presence of the transcription factor NF-κB and the mitogen-activated protein kinase c-Jun N-terminal kinase (JNK) compared to the amount present in a non-inflammatory condition separately implies the presence of TLR4-mediated inflammation.

These proteins or polypeptides can be assayed in lysates of cultured cells such as lymphocytes such as B cells, T cells and macrophages or CNS cells such as olfactory neurons that can be obtained by scraping the nasal cavity for neural epithelial cells for in vivo assays. The proteins can also be assayed in the cell culture medium for in vitro studies using lymphocytes or CNS cells such as those illustrated hereinafter and in body fluids such as blood or its constituent plasma or serum or lymphocytes for in vivo assays.

Administration of a contemplated compound or its pharmaceutically acceptable salt is continued until tau hyperphosphorylation is no longer enhanced and/or until the amount of one or more of the TLR4 activation protein markers is at background levels. Enhancement of the level of hyperphosphorylated tau or one of the TLR4 protein markers relative to background (in the absence of a TLR4-mediated immune response) condition is determined by a difference that is statistically significant at least at the 90 percent confidence level ($p<0.1$), and preferably at the 95 percent confidence level ($p<0.05$) as are illustrated in the accompanying figures.

It is also preferred that an administered compound or a pharmaceutically acceptable salt thereof be present dissolved or dispersed in a pharmaceutically acceptable diluent as a pharmaceutical composition when administered. Most preferably, the administration is peroral.

The use of a pharmaceutically acceptable salt of a contemplated compound is also contemplated, as is the use of a single stereoisomer or mixture of stereoisomers, or of their pharmaceutically acceptable salts. The contemplated administration can take place in vivo or in vitro.

In presently preferred embodiments, the present invention contemplates a method of inhibiting 1) phosphorylation of the tau protein and/or 2) TLR4-mediated immune response (e.g., inflammation) of lymphocytes and/or cells of the CNS that comprises administering to cells of the central nervous system in recognized need thereof such as brain cells an effective amount of a compound of one or more of Series A, Series B, Series C-1, Series C-2, Series D and Series E, single enantiomer, a mixture of enantiomers or a pharmaceutically acceptable salt of any contemplated compound(s). The administration is preferably carried out in the absence of a MOR-binding effective amount of a separate MOR agonist or antagonist molecule. Illustrative of CNS cells are cells such as those of a host animal that exhibit inflammation induced by brain injury such as traumatic brain injury, chronic traumatic encephalopathy, as well as those of a host animal such as a human exhibiting Alzheimer's disease (AD) symptoms, frontotemporal dementia (FTD), progressive supranuclear palsy, dementia pugilistica and corticobasal degeneration, as well as infection by Gram positive and/or Gram negative bacteria.

The general structures of the compounds of each series are shown below. A detailed discussion of compounds of each of those series is set out in a section entitled "Contemplated Compounds" that follows.

Series A

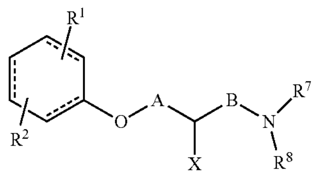

-continued

Series B

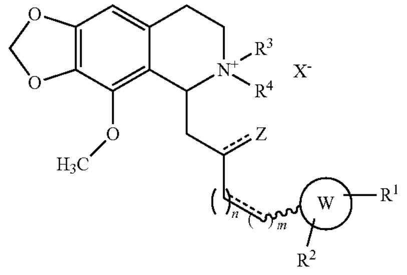

Series C-1

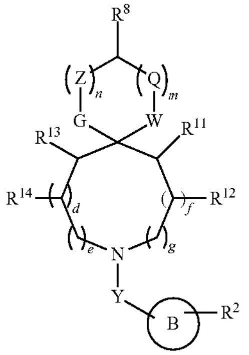

Series C-2

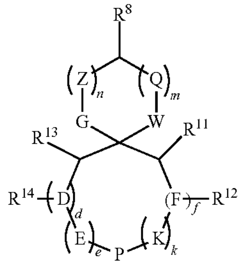

Series D

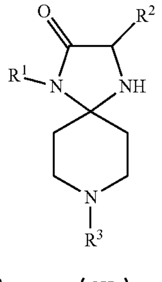

Series E

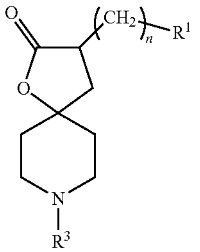

In accordance with a method described above, a composition that contains an effective amount of a contemplated compound or its pharmaceutically acceptable salt dissolved or dispersed in a pharmaceutically acceptable diluent is administered to cells of the CNS in recognized need thereof, and particularly the brain, in vivo in a living animal or in vitro in a cell preparation. When administered in vivo to an animal such as a laboratory rat or mouse or a human in recognized need, the administration inhibits the formation of phosphorylated-tau-containing NFTs in the CNS such as in the brain of a subject animal to which a contemplated compound is administered. Admixture of a composition containing a contemplated compound or its pharmaceutically acceptable salt dissolved or dispersed in a pharmaceutically acceptable diluent with CNS cells such as a brain cell preparation in vitro also inhibits the formation of NFTs as is illustrated hereinafter.

A contemplated compound binds to the scaffolding FLNA protein, and particularly to a five residue portion of the FLNA protein sequence Val-Ala-Lys-Gly-Leu (SEQ ID NO: 1) in an in vitro assay that is discussed hereinafter in Example 1, and briefly below. A contemplated compound binds only to a single site on FLNA and that site is the SEQ ID NO: 1 pentapeptide site.

Binding studies of the naltrexone inhibition of tritiated-naloxone, [$^3$H]NLX, binding to membranes from FLNA-expressing A7 cells (an astrocyte cell line produced by immortalizing optic nerve astrocytes from the embryonic Sprague-Dawley rat with SV40 large T antigen) has shown the existence of two affinity sites on FLNA; a high affinity site (H) with an $IC_{50}$—H of 3.94 picomolar and a lower affinity site (L) $IC_{50}$-L of 834 picomolar. [Wang et al., *PLoS One*. 3(2): e1554 (2008); Wang et al., *PLoS One*. 4(1): e4282 (2009).] The high affinity site was subsequently identified as the FLNA pentapeptide of SEQ ID NO: 1 (US Patent Publication 2009/0191579 and its predecessor application Ser. No. 60/985,086 that was filed on Nov. 2, 2007), whereas the lower affinity site has not yet been identified.

Compounds such as naloxone (NLX), naltrexone (NTX), methadone, fentanyl, nalorphine, nalbuphine and buprenorphine, and the like bind well to the high affinity FLNA pentapeptide of SEQ ID NO: 1 (VAKGL). However, when used at a dosage recited on the product label, those compounds also bind to the lower affinity site on FLNA, and typically also bind to the MOR. Some of the compounds are MOR antagonists such as naloxone, naltrexone, nalbuphine, whereas others such as methadone, buprenorphine and fentanyl are full or partial agonists of MOR. Binding to that lower affinity FLNA site impairs the activity of the FLNA pentapeptide of SEQ ID NO: 1 to exhibit its activities as discussed, utilized and illustrated herein. As a consequence, compounds such as naloxone, naltrexone, methadone, fentanyl, nalorphine, nalbuphine, buprenorphine and similar compounds that also bind to the lower affinity site on the FLNA protein are not contemplated for use herein.

A compound contemplated for use in the present invention inhibits the binding of fluorescein isothiocyanate-labeled naloxone (FITC-NLX) to biotin-linked SEQ ID NO: 1 (Bn-VAKGL) bound to coated streptavidin plates under conditions defined hereinafter in Example 1 to an extent that is at least about 60 percent and more preferably at least about 80 percent of the value obtained of the value obtained when present at a 10 μM concentration and using naloxone as the control inhibitor at the same concentration as the contemplated compound, and up to about twice the value obtained with naloxone as control.

Naltrexone (NTX) can also be used as a control inhibitor. Average inhibition values obtained using NTX rather than NLX tend to be 1 or 2 percent lower in absolute value than those obtained with NLX. Thus, for example, where an average inhibition value at a particular concentration of NLX is 40 percent, one can expect values obtained with NTX to be about 38 or 39 percent. The binding inhibition values for a contemplated compound are determined taking the expected NLX/NTX value difference into account.

Figures 45, 45A:
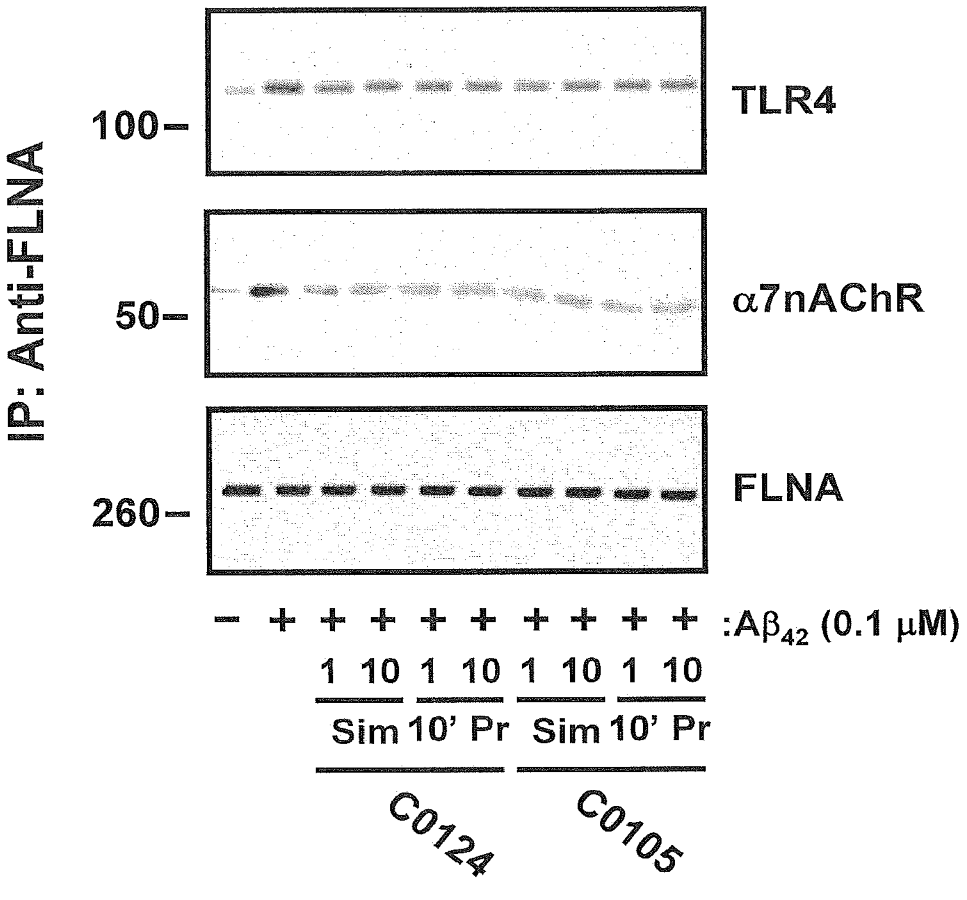
FIG. 45, in two panels.
FIG. 45A and FIG. 45B, illustrates further high-affinity FLNA-binding compounds that reduce α7nAChR-FLNA association assayed as in FIG. 2. Frontal cortical synaptosomes from 2-month-old rats were treated with 1 or 10 nM concentrations of Compound C0124, using Compound C0105 as a control, either simultaneously (Sim) or 10 minutes prior (10' pr) to $A\beta_{42}$ (0. μM) and were immunoprecipitated with immobilized anti-FLNA. The complexes in the solubilized synaptosomes, and α7nAChR, TLR4 and FLNA levels in the anti-FLNA immunoprecipitates were determined by Western blotting (FIG. 45A) in which numerals outside of and to the left of the blots are as discussed before. Amounts present in the blots were quantified by densitometry (FIG. 45B). Ratios of α7nAChR/FLNA and TLR4/FLNA were statistically different from $A\beta_{42}$ alone with **p<0.05, *p<0.01 for the compounds as shown using Dunnett's test. Structural formulas of the compounds used in this and the other figures are provided hereinafter.
Figure 45A:
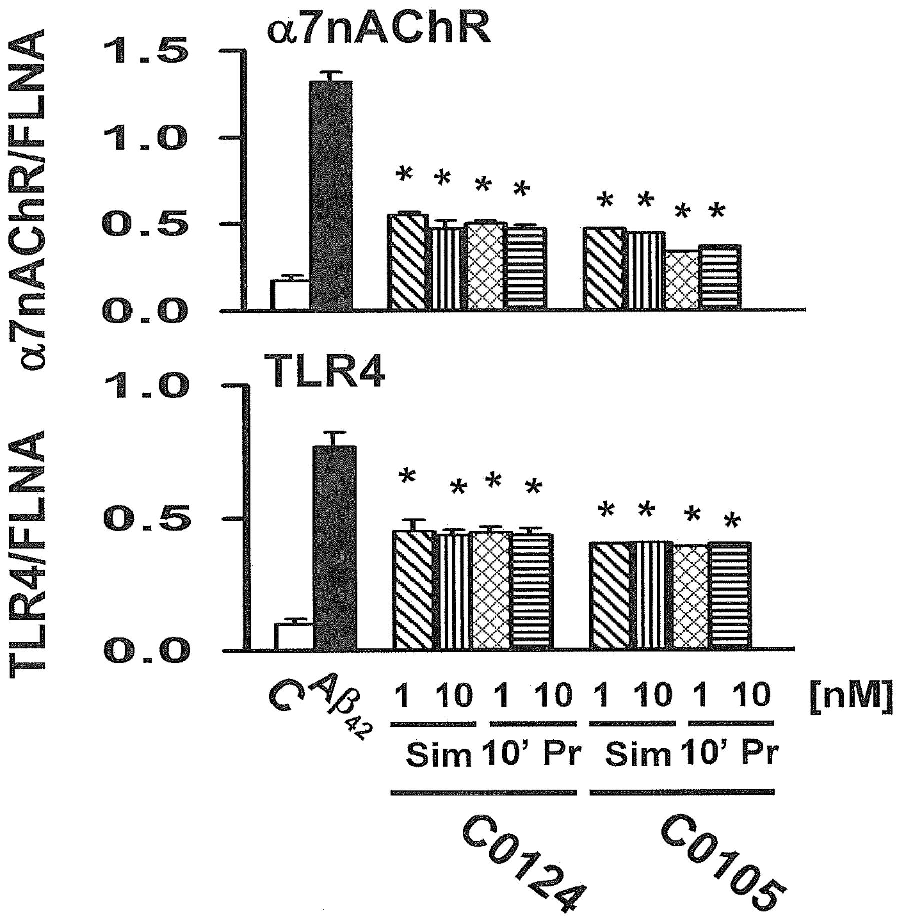
Figure 45B:
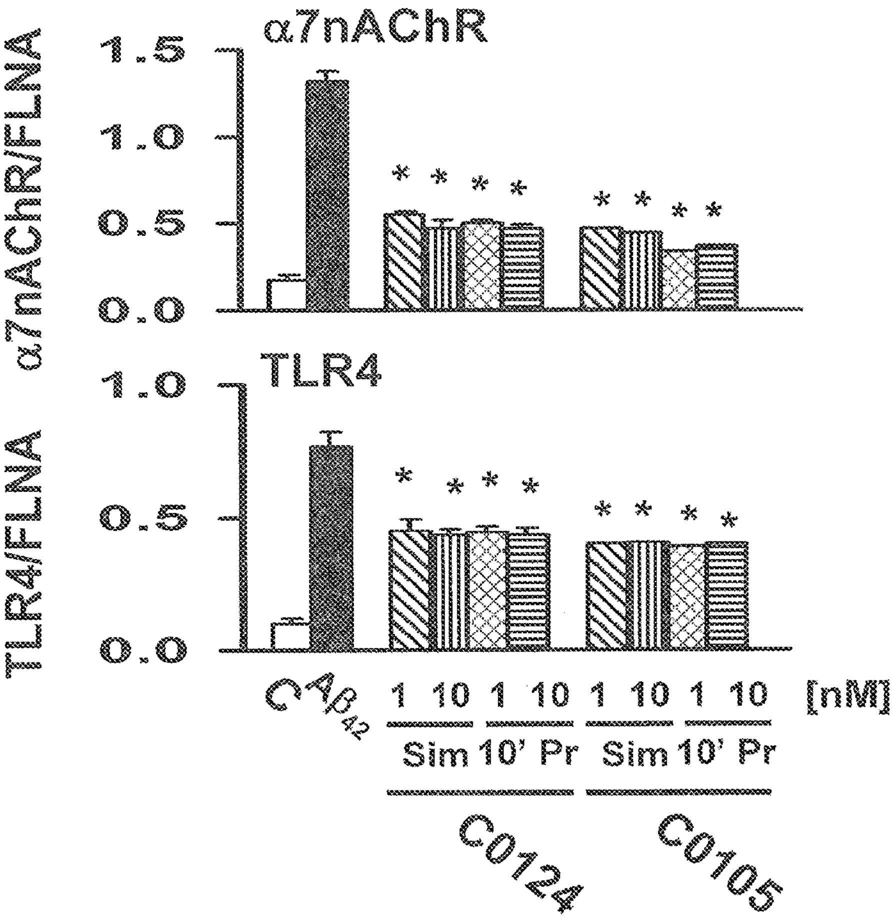
Figures 46, 46A:
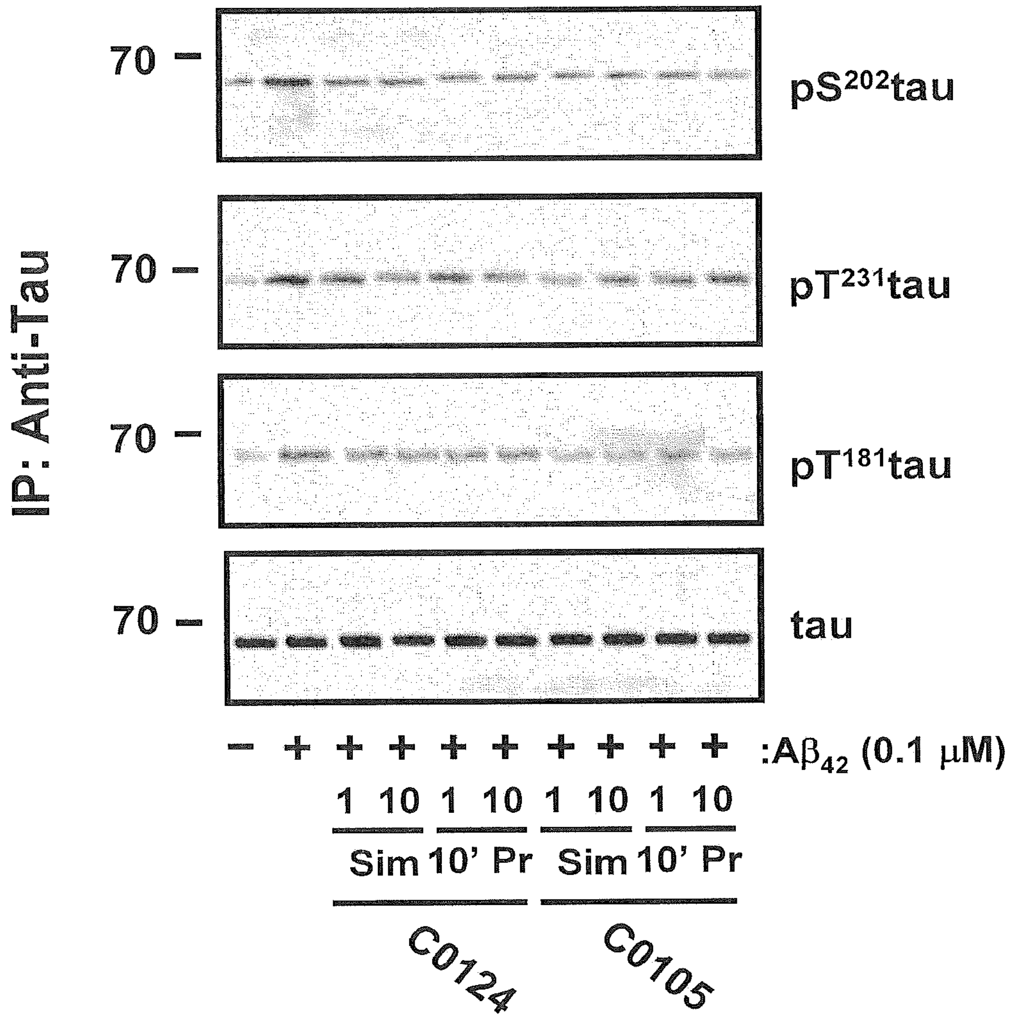
FIG. 46, also in two panels.
FIG. 46A and FIG. 46B, illustrates that FLNA-binding compounds reduce tau phosphorylation at all three phosphorylation sites using the compounds and concentrations of FIG. 45 using immunoprecipitation and Western blotting. Thus, in the same treated synaptosomes used in FIG. 45, levels of tau protein phosphorylated at $S^{202}$, $T^{231}$ and $T^{181}$ were measured in immunoprecipitates using an anti-tau antibody that does not distinguish its phosphorylation state (Tau). The three phosphoepitopes of tau were detected in immunoprecipitates using specific antibodies. $A\beta_{42}$ strongly promotes tau phosphorylation at all three sites. Densitometric analysis of the blots (FIG. 46B) showed that both of Compounds C0105 and C0124 reduced this phosphorylation at both concentrations either simultaneously administered or with 10-minute pretreatment compared to $A\beta_{42}$ alone using Dunnett's test at *p<0.01.
Figure 46B:
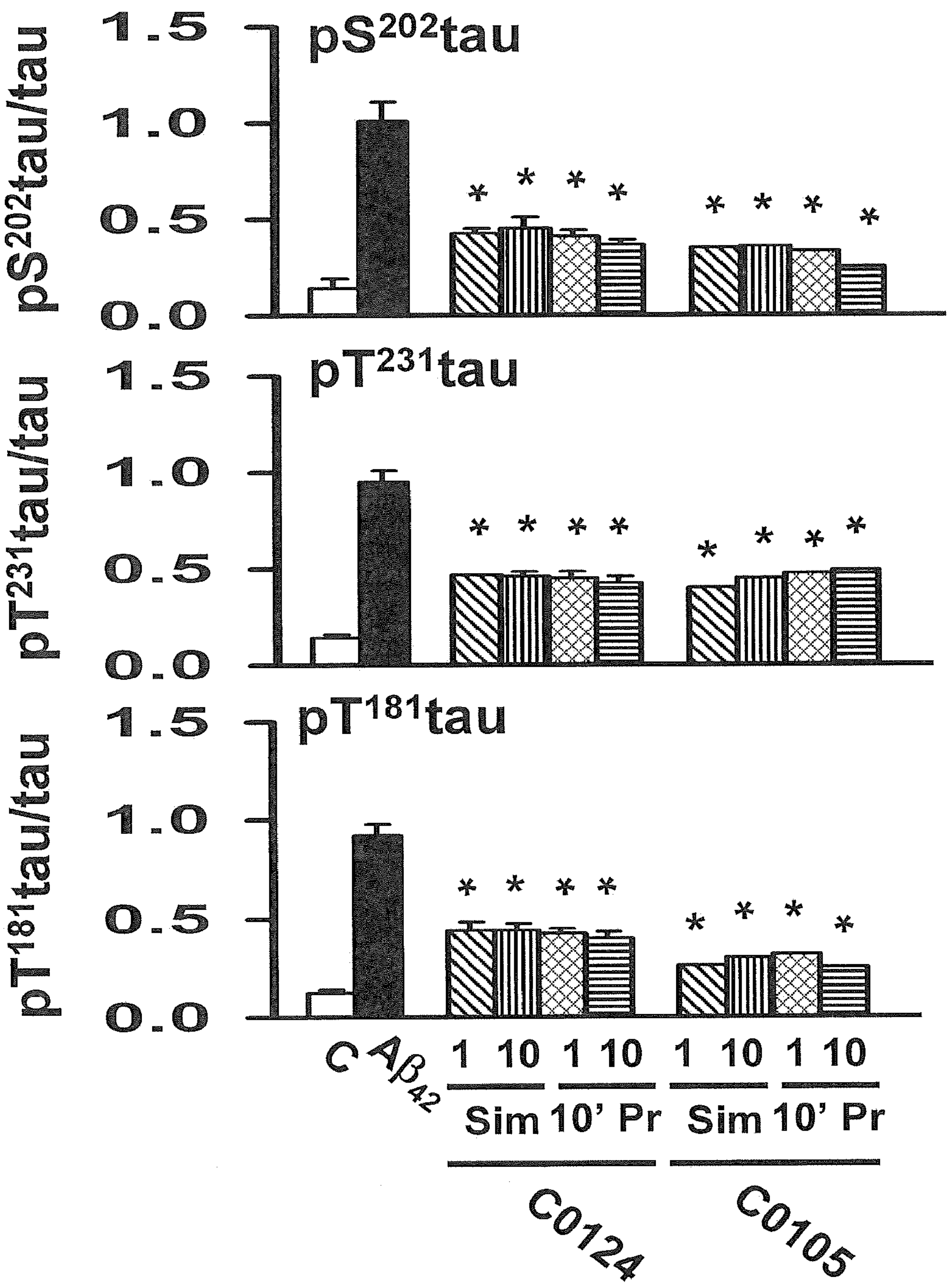

In other binding studies, U.S. Pat. Nos. 7,560,882 and 8,153,795 to Sundermann et al. teach that compounds similar to those of the C-1 and C-2 Series of compounds are useful for the inhibition of the reuptake of serotonin, noradrenalin reuptake, and have a high affinity for batrachotoxin (BTX) receptors and/or cannabinoid receptors (CB2). The results shown in FIG. 45 illustrate that compounds of Series D that are within the definition provided by Sundermann et al. U.S. Pat. No. 7,560,882 also inhibit tau hyperphosphorylation and are useful in a contemplated method.

Representative compounds from the present Series A, Series C-1 and Series C-2 groups were examined by Ricerca Biosciences LLC of Taipei, Taiwan, in competitive binding assay studies using published techniques to determine whether the compounds could competitively inhibit binding to any of more than 65 receptors, channels and transporters including adrenergic receptors to which noradrenalin binds, serotonin receptors, muscarinic receptors to which BTX binds and cannabinoid receptors. The studied compounds each exhibited no significant inhibition in each of those assays.

Pharmacophore Determinations

One aspect of the invention is the use of a compound that binds to the pentapeptide of SEQ ID NO: 1 that is present in FLNA to inhibit phosphorylation of the tau protein. In this aspect, the structures of the compounds that effectively bind to a pentapeptide of SEQ ID NO: 1 is quite varied but can be unified through the computer-assisted calculation of a group of pharmacophores shared by those compounds that so bind.

A contemplated compound useful in a method of the invention contains at least four of the six pharmacophores of FIGS. 35-40. In preferred practice, a contemplated compound contains five of the six pharmacophores of those figures, and more preferably, a contemplated compound contains all six of the pharmacophores. Aside from NLX, NTX, methadone, fentanyl, nalorphine, nalbuphine and buprenorphine that bind well to the FLNA pentapeptide of SEQ ID NO: 1 (VAKGL), compounds of four structural series discussed hereinafter are particularly preferred.

An ensemble pharmacophore model was prepared with a programmed general purpose computer using the three-dimensional conformations of compounds in the training sets. Using 0. μM data from Example 1 as a starting point, 153 compounds out of the list of compounds in the tables of Example 1 have a binding activity to the FLNA pentapeptide that is less than the mean value of 45.54 percent. A "poor binding" compound or "poor binder" is defined as a compound whose binding inhibition is equal to or less than the mean value of 45.54 percent in an assay as conducted in Example 1, whose results are shown in the tables of Example 1. The training set consists of ten compounds known to bind to the FLNA pentapeptide, the above poor binding 153 compounds and also about 1000 random compounds selected from ZINC database at zinc.docking.org.

The selection of pharmacophores involves in the following steps: 1) Three-dimensional computer-generated conformations of all compounds were first prepared. 2) A set of 4-point pharmacophores present in most of known active compounds was derived. 3) Using known inactive and random selected compounds as reference compounds, only those pharmacophores that were not present in the most of the reference compounds were identified as relevant to FLNA binding activity. 4) Six 4-point pharmacophores were finally identified from those determined above to best represent the 10 active compounds.

An untested compound that contains four out of the six pharmacophores has about a 20 percent chance to be an active binder in FLNA pentapeptide. A compound containing five of the six pharmacophores has about a 32 percent chance to be an active binder in FLNA pentapeptide, and about a 60 percent chance when containing six of the six pharmacophores.

The Molecular Operating Environment (MOE) software from Chemical Computing Group, Montreal, Quebec, Canada, was used to program a general purpose computer to generate three-dimensional conformations, to derive 4-point pharmacophores from active compounds, and to test these pharmacophores against known inactive compounds and random selected compounds. Pharmacophore modeling as used herein is carried out as discussed and explained in Penzotti et al., *J Med Chem,* 2002, 45(9):1737-1740 (2002); Siew et al., *BioorgMed Chem Lett,* 21(10):2898-2905 (15 May 2011); Leong, *Chem Res Toxicol,* 20(2):217-226 (2007); and Lin, chemcomp.com/journal/ph4.htm.

In some embodiments, it is preferred that a FLNA-binding compound also be a MOR agonist. In other embodiments, it is preferred that the FLNA-binding compound not be a MOR agonist. A compound is defined herein as not being a MOR agonist if it has less than about 80 percent the binding of [D-Ala2,N-MePhe4,Gly-ol]-enkephalin (DAMGO) at either of the two concentrations used in the Table of Example 2.

The ten known FLNA pentapeptide-binding training set compounds are shown below along with their alpha-numeric designations used herein. Of the

A0033

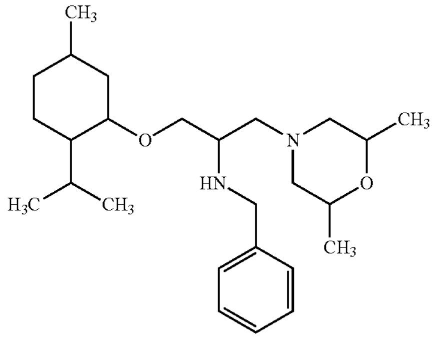

A0040

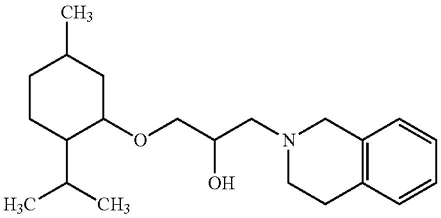

A0053

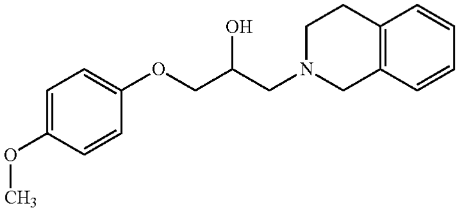

-continued

A0068

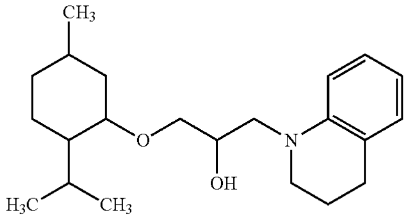

B0055

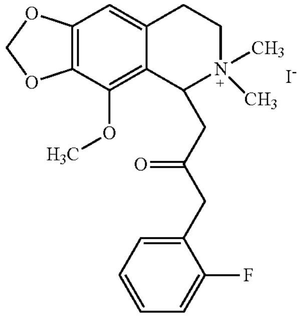

C0105 M

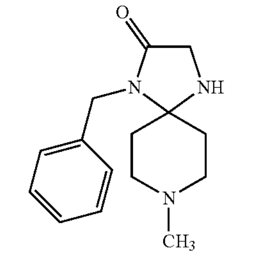

C0114M

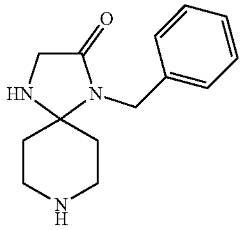

C0137 M

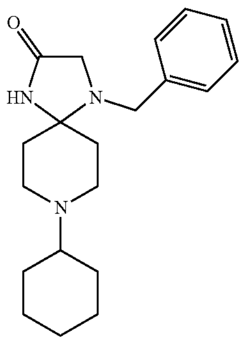

-continued

C0138 M

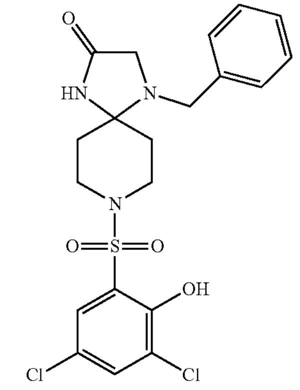

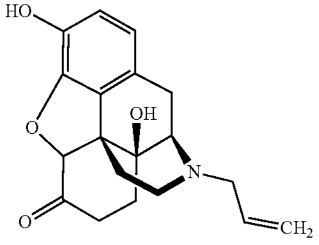

Naloxone above ten compounds used in the training set for determining the pharmacophores, nine contained all six pharmacophores. Naloxone contained five of the six. Examining several more of the structures of the four groups of compounds (Series A, Series B, Series C-1 and Series C-2) shown in the tables and assayed in Example 1 hereinafter, twenty further compounds contained to five of the six pharmacophores, and another twenty contained four of the six.

Specifically Contemplated FLNA-Binding Compounds

A compound contemplated for use in a contemplated method binds to the FLNA pentapeptide of SEQ ID NO: 1, and contains at least four of the six pharmacophores of FIGS. 35-40. Such a compound can have a varied structure as noted before. Regardless of that structural variance, a contemplated compound inhibits the binding of labeled naloxone (FITC-NLX) to the biotinylated-VAKGL pentapeptide (Bn-VAKGL; SEQ ID NO: 1) bound to coated streptavidin plates to an extent that is at least about 80 percent of the value obtained when using naloxone as an inhibitor at the same concentration and under conditions defined hereinafter in Example 1, and can be about twice the value for naloxone at the same concentration.

Compounds having four exemplary structures have been found to bind well to the pentapeptide of SEQ ID NO: 1. Those compounds are referred to herein as Series A, Series B, Series C-1, Series C-2, Series D and Series E. Inhibition of tau phosphorylation by Compounds A, B and C and Series D are illustrated herein and those compounds are representative of those structural series. Compounds of Series E overlap with those of Series C-1 and -2 and are therefore also included herein. The general structures of the compounds of each series are shown below, followed by more specific disclosures.

Series A

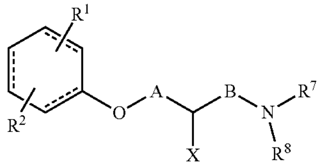

Series B

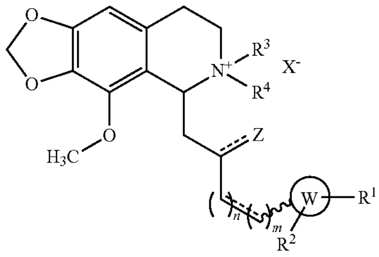

Series C-1

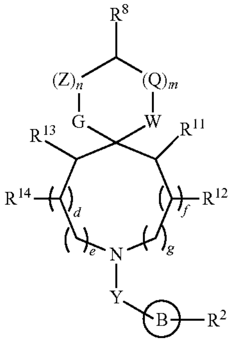

Series C-2

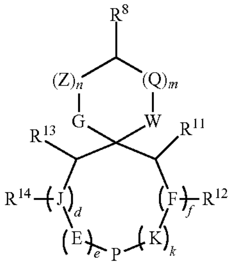

Series D

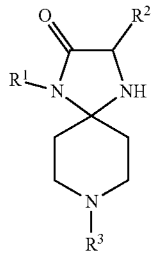

Series E

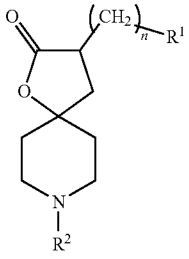

A pharmaceutically acceptable salt of a compound of each of the above Formulas is also contemplated. A compound having an asymmetrical (chiral) carbon or a salt of such a compound can exist in the form of stereoisomers, that are two enantiomers. The invention relates both to each enantiomer separately, and to their mixture; i.e., to both enantiomeric forms (d and 1, or R and S) and to their mixture. Additionally, where two or more chiral centers are present, stereoisomers called diastereomers can form, and diastereomers are also contemplated.

As will be seen from the following definitions, a contemplated compound can contain one or more deuterated carbon atoms, in which deuterium is designated by its usual chemical designation, D. Deuterated compounds can be useful in studying the mechanism of drug interactions with living organisms for the elucidation of metabolic and biosynthetic pathways. Deuteration can also extend the half-life of a contemplated compound in vivo because a carbon-deuterium (C-D) bond is stronger than a Carbon-hydrogen (C—H) bond thereby requiring more energy input for bond cleavage. See, Blake et al., 1975 *J. Pharm. Sci.* 64(3):367-391; and Nelson et al., 2003 *Drug Metab. Dispos.* 31(12): 1481-1498, and the citations therein. Contemplated deuterated compounds are prepared using well-known reactions.

More particularly, a compound of Series A corresponds in structure to Formula A, below,

A

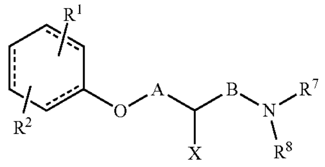

wherein $R^1$ and $R^2$ are the same or different and are independently H, halogen, $C_1$-$C_{12}$ hydrocarbyl, $C_1$-$C_6$ acyl, $C_1$-$C_6$ hydrocarbyloxy, $CF_3$ and $NR^3R^4$, wherein $R^3$ and $R^4$ are the same or different and are H, $C_1$-$C_4$ hydrocarbyl, $C_1$-$C_4$ acyl, $C_1$-$C_4$ hydrocarbylsulfonyl, or $R^3$ and $R^4$ together with the depicted nitrogen form a 5-7-membered ring that optionally contains 1 or 2 additional hetero atoms that independently are nitrogen, oxygen or sulfur;

A and B are the same or different and are $CH_2$, CDH or $CD_2$ (where D is deuterium);

X is OH or $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;

$NR^7R^8$, $R^7$ and $R^8$ are the same or different and are H, $C_1$-$C_6$ hydrocarbyl, $C_1$-$C_6$ acyl, $C_1$-$C_6$ hydrocarbylsulfonyl, or $R^7$ and $R^8$ together with the depicted nitrogen form a ring structure W;

W contains 5 to 14 atoms in the ring structure including the depicted nitrogen, and preferably up to 12 atoms. W can optionally contain:

a) 1 or 2 further hetero atoms that are independently oxygen, nitrogen or sulfur, and b) one or more substituent groups bonded to one or more ring atoms, in which the one or more substituents contain a total of up to 8 atoms, and preferably up to 6 atoms, selected from the group consisting of carbon, nitrogen, oxygen and sulfur, and mixtures thereof.

A dashed line (----) represents an optional double bond.

In regard to a contemplated compound, RI and $R^2$ are preferably other than methyl and isopropyl, respectively, when W is N-morpholinyl or dimethyl-N-morpholinyl and the optional double bonds are absent.

A preferred compound of Formula A is a compound of Formula I, below, in which A, B, X, W and RI and $R^2$ are as defined above.

I

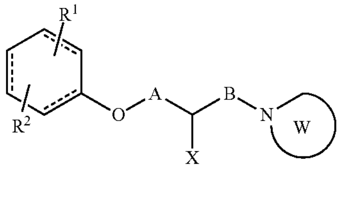

In one preferred embodiment, a contemplated compound corresponds in structure to Formula Ia Ia

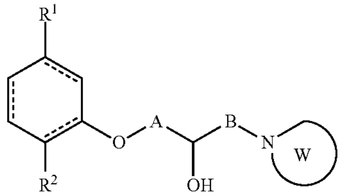

Here, $R^1$ and $R^2$ are the same or different and are independently H, or $C_1$-$C_6$ hydrocarbyl; A and B are the same or different and are $CH_2$, CDH or $CD_2$; W is a ring structure that contains 5 to 14 atoms in the ring structure including the depicted nitrogen, and can optionally contain: a) 1, 2 or 3 further hetero atoms that are independently oxygen, nitrogen or sulfur, and b) one or more substituent groups bonded to one or more ring atoms, in which the one or more substituent contain a total of up to 14 atoms, preferably up to 12 atoms and more preferably up to 8 atoms selected from the group consisting of carbon, nitrogen, oxygen and sulfur, and mixtures thereof. The dashed line (----) represents 1, 2, or 3 optional double bonds. Preferably, $R^1$ and $R^2$ are other than methyl and isopropyl, respectively, when W is N-morpholinyl or dimethyl-N-morpholinyl, and the optional double bonds are absent.

In preferred practice for some embodiments of a compound of either Formula I or Formula Ia, W further includes one or more substituent groups bonded to one or more ring atoms, in which those one or more substituents contain a total of up to 8 atoms selected from the group consisting of carbon, nitrogen, oxygen and sulfur, and mixtures thereof. Hydrogen atoms bonded to those atoms are not counted.

In one preferred embodiment, a compound of Formulas I and Ia has the structure of Formula II, whereas in another preferred embodiment, a compound of Formulas I and Ia has the structure of a compound of Formula III.

II

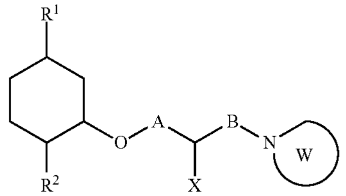

III

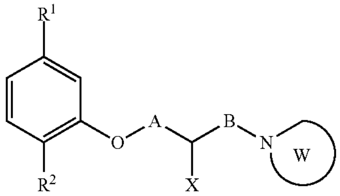

In a compound of both of Formulas II and III, A, B, W and X are as previously defined for a compound of Formulas I and Ia, above. RI and $R^2$ for a compound of Formula II are defined as RI and $R^2$ for a compound of Formula Ta, whereas RI and $R^2$ for a compound of Formula III are defined as RI and $R^2$ for a compound of Formula I.

More preferably, the RI and $R^2$ groups of a compound of Formula II contain 3 to 5 carbon atoms. For some compounds of Formula III, $R^1$ is H and $R^2$ is halogen, $C_1$-$C_6$ hydrocarbyl, $C_1$-$C_6$ acyl, $C_1$-$C_6$ hydrocarbyloxy or $NR^3R^4$, whereas for others, both R groups are other than H, but chosen as defined above.

In a compound of either Formula II or Formula III, W can optionally contain 1 or 2 further hetero atoms that are independently oxygen, nitrogen or sulfur, and more preferably still, contains at least one such hetero atom. It is also preferred that W further includes one or more substituent groups bonded to one or more ring atoms, in which the one or more substituents contain a total of up to 8 atoms selected from the group consisting of carbon, nitrogen, oxygen and sulfur, and mixtures thereof, and hydrogens bonded to those atoms are not counted.

A particularly preferred compound of Formulas II and III has a structure of Formulas IIa and IIIa, wherein the other groups A, B, W, $R^1$ and $R^2$ are as defined above.

IIa

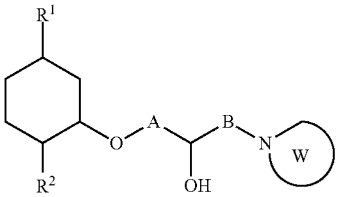

IIIa

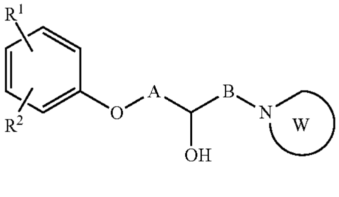

A compound of Series B corresponds generally to the Formula I, below

I

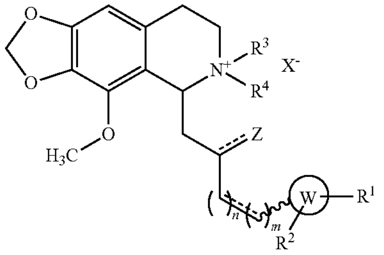

wherein n=0 or 1;

m=0 or 1;

m+n=0, 1 or 2;

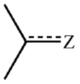 = 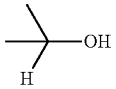 or 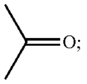;

W is an aromatic ring containing 0, 1 or 2 hetero atoms that can be nitrogen, oxygen or sulfur, or mixtures thereof in the ring;

$R^1$ is selected from the group consisting of H, $C_1$-$C_6$ hydrocarbyl, $C_1$-$C_6$ hydrocarbyloxy, halogen, cyano, $C_1$-$C_6$ hydrocarbyloxyhydrocarboxylene, trifluoromethyl, and hydroxyl;

$R^2$ is selected from the group consisting of H, $C_1$-$C_6$ hydrocarbyl, $C_1$-$C_6$ hydrocarbyloxy, $C_1$-$C_6$ hydrocarbyloxyhydrocarboxylene and halogen;

$R^3$ is absent or $C_1$-$C_6$ hydrocarbyl;

$R^4$ is $C_1$-$C_6$ hydrocarbyl;

$X^-$=an anion or is absent when $R^3$ is absent;

the dashed line indicates an optional double bond between the depicted carbon atoms; and the wavy line indicates that the depicted phenyl substituent can be in the Z or E configuration when the optional double bond is present.

Illustrative anions can be monovalent or polyvalent. A contemplated anion is pharmaceutically acceptable and includes phosphate, hydrogen phosphate, dihydrogenphosphate, sulfate, bisulfate, chloride, bromide, iodide, acetate, formate, benzenesulfonate, methanesulfonate, toluenesulfonate and the like as are well known. These and other anions are listed in Berge et al., 1977 *J. Pharm Sci.* 68(1): 1-19.

It is preferred that m+n=1 or 2, and the optional double bond is absent, and is rather a saturated, single bond.

In preferred practice, W is a six-membered ring, although five membered rings are also contemplated. Thus, a contemplated aromatic ring that can include zero, one or two hetero atoms that are nitrogen, oxygen or sulfur or mixtures thereof include phenyl, pyridyl, furanyl, imidazyl, oxazolyl and the like. In some preferred embodiments, W is free of (has zero) ring nitrogen atoms. In other embodiments, preferred compounds have W groups that are free of ring hetero atoms, having only ring carbon atoms.

W preferably further includes one or more substituent groups ($R^1$ and $R^2$) to one or more ring atoms, in which those one or more substituents contain a total of up to 12 atoms selected from the group consisting of carbon, nitrogen, oxygen and sulfur, and mixtures thereof, with hydrogen atoms not being counted. Preferred substituent groups on ring W have an oxygen atom bonded to the W ring. Such compounds are preferably $C_1$-$C_6$ hydrocarbyloxy groups such as methoxy groups.

The Z-containing group can be a keto group or can be reduced to a hydroxyl group. Both groups are preferred.

In some embodiments, both $R^3$ and $R^4$ are $C_1$-$C_6$ hydrocarbyl groups that are both methyl. In other embodiments, one is an ethyl group and the other is methyl or absent. When $R^3$ is absent, a Series B compound is a tertiary amine.

In one preferred embodiment, a Series B compound of Formula I has the structure of Formula II,

II

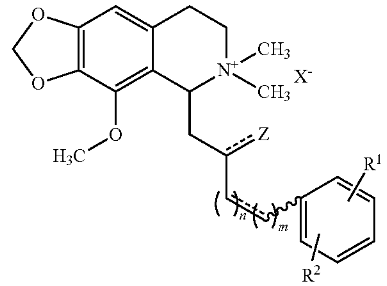

wherein n=0 or 1;

m=0 or 1;

m+n=0, 1 or 2;

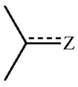 = 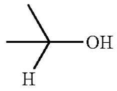 or 

$X^-$=an anion;

$R^1$ is selected from the group consisting of H, $C_1$-$C_6$ hydrocarbyl, $C_1$-$C_6$ hydrocarbyloxy, halogen, cyano, $C_1$-$C_6$ hydrocarbyloxyhydrocarboxylene, trifluoromethyl, and hydroxyl;

$R^2$ is selected from the group consisting of H, $C_1$-$C_6$ hydrocarbyl, $C_1$-$C_6$ hydrocarbyloxy, $C_1$-$C_6$ hydrocarbyloxyhydrocarboxylene and halogen;

the dashed line indicates an optional double bond between the depicted carbon atoms; and the wavy line indicates that the depicted phenyl substituent can be in the Z or E configuration when the optional double bond is present.

In some preferred embodiments, $R^2$=H. In some such embodiments, $R^1$ includes an oxygen atom bonded to the depicted phenyl ring, and that oxygen is preferably part of a $C_1$-$C_6$ hydrocarbyloxy group. For may compounds, it is preferred that

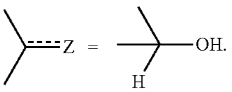

In yet other preferred embodiments, a contemplated Series B compound of has a structure that corresponds to Formula III, below

III

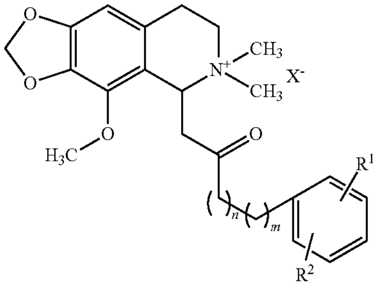

here, n=0 or 1;

m=0 or 1;

m+n=0, 1 or 2;

$X^-$=an anion;

$R^1$ is selected from the group consisting of H, $C_1$-$C_6$ hydrocarbyl, $C_1$-$C_6$ hydrocarbyloxy, halogen, cyano, $C_1$-$C_6$ hydrocarbyloxyhydrocarboxylene, trifluoromethyl, and hydroxyl; and $R^2$ is selected from the group consisting of H, $C_1$-$C_6$ hydrocarbyl, $C_1$-$C_6$ hydrocarbyloxy, $C_1$-$C_6$ hydrocarbyloxyhydrocarboxylene and halogen.

As was the case for other Series B compound embodiments, $R^2$ is sometimes H, and one or both of $R^1$ and $R^2$ are $C_1$-$C_6$ hydrocarbyloxy groups such as methoxy. A pharmaceutically acceptable salt of a compound of Formula I, II and III and all of the remaining Series B formulas disclosed herein is also contemplated.

A compound of Series C-1 corresponds generally to the Formula A, below

A

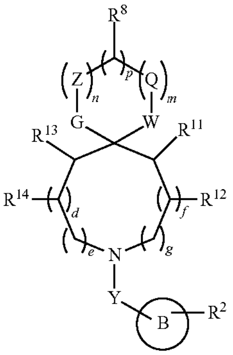

In Formula Series C-1 Formula A, G and W are selected from the group consisting of $NR^{20}$, $NR^7$, $CH_2$, S and O, where $R^7$ is H, C1-C12 hydrocarbyl, or C1-C12 hydrocarboyl (acyl) and $R^{20}$ is a group X-circle A-$R^1$ as defined hereinafter, and G and W are preferably $NR^{20}$ and $NR^7$. In one preferred embodiment, only one of G and W is $NR^7$ and one of G and W must be $NR^7$ or $NR^{20}$.

X and Y are the same or different and are $SO_2$, C(O), $CH_2$, $CD_2$ (where D is deuterium), OC(O), NHC(NH), NHC(S) or NHC(O);

Q is $CHR^9$ or C(O); Z is $CHR^{10}$ or C(O);

each of d, e, f and k is either zero or one and the sum of (d+e+f+k)=2. In some embodiments, e is zero when d is zero, and g is zero when f is zero. In other embodiments, d is zero when f is zero, or e is zero when g is zero.

Each of m, n and p is zero or one and the sum of m+n+p is 2 or 3 for all embodiments. Each of m and n is preferably 1, and p is preferably zero so that the sum of m+n+p is preferably 2.

The circles A and B are the same or different aromatic or heteroaromatic ring systems. Groups $R^1$ and $R^2$ are the same or different and each can be hydrogen or represent up to three substituents other than hydrogen that themselves can be the same or different; i.e., $R^{1a}$, $R^{1b}$, and $R^{1c}$, and $R^{2a}$, $R^{2b}$, and $R^{2c}$. Each of those six groups, $R_{1a\text{-}c}$ and $R^{2a\text{-}c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl (acyl), hydroxy-, trifluoromethyl- ($-CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen, nitro, phenyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [$S(O)_2NR^3R^4$]

wherein the amido nitrogen in either group has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is $-CH_2-$, —O— or —N═N— and Ar is a single-ringed aryl group as described previously, and $NR^5R^6$, wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;

$R^8$, $R^9$, and $R^{10}$ are each H, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms;

$R^{11}$, $R^{12}$, $R^{13}$ and $R^{14}$ are all H, or one of the pair $R^{11}$ and $R^{12}$ or the pair $R^{13}$ and $R^{14}$ together with the depicted ring form a saturated or unsaturated 6-membered ring, and the other pair are each H, or they are H and D as recited herein (in this subparagraph).

Also in the above preferred embodiment, $R^1$ and $R^2$ are not both methoxy when X and Y are both $SO_2$, W is O and p is zero.

In another preferred embodiment, i) only one of G and W is $NR^{20}$, ii) one of G and W must be $NR^{20}$, iii) one of G and W is other than $NR^7$ in which $R^7$ is H or an aliphatic $C_1$ hydrocarbyl; i.e., methyl, when (a) the sum of m+n+p is 2, and (b) the other of G and W is $NR^{20}$ bonded to a Z or Q, respectively, that is C(O), and iv) when X and Y are both $SO_2$, W is 0, Q is $CH_2$, p is zero, and d and f are both 1, $R^1$ and $R^2$ are other than (a) both H, methoxy, or $C_1$-$C_3$-hydrocarbyl, (b) H, halogen and $C_1$-$C_3$-hydrocarbyl, (c) H and $C_1$-$C_3$-hydrocarbyl, (d) halogen and $C_1$-$C_3$-hydrocarbyl, or (e) H and halogen.

$R^1$ and $R^2$ are preferably also not both methoxy when X and Y are both $SO_2$, W is O and p is zero in the above-preferred embodiment.

A pharmaceutically acceptable salt of a compound of Series C-1 Formula A and all of the remaining Series C-1 formulas disclosed herein is also contemplated.

In one preferred Series C-1 embodiment, e and g are both zero and a compound of Series C-I Formula A becomes a compound of Series C-I Formula B, below

B

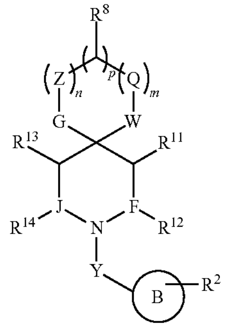

In Formula B, the letters of the formula G, J, E, F, K, W, Q, Z, d, e, f, k, n, m, p, X, Y, circle A and circle B and all R groups are as previously defined for a compound of Formula A of Series C-1. Preferably, $R^1$ and $R^2$ are not both methoxy when X and Y are both $SO_2$, W is O and p is zero.

In all of the following sub-generic formulas of a compound of Series C-1, the formula letters of G, J, E, F, K, W, Q, Z, d, e, f, k, n, m, p, X, Y, circle A and circle B and all R groups are as previously defined for a compound of Formula A of Series C-1, unless otherwise defined. Additionally, the previously stated preferences also apply unless a depicted structural formula precludes such a preference.

More preferably, a compound of Series C-I Formula B corresponds in structure to Series C-1 Formula I, below

I

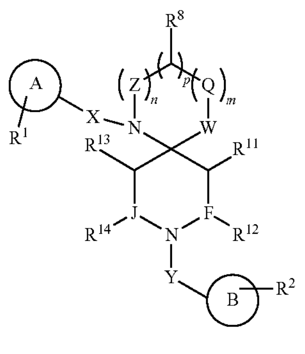

In Series C-1 Formula I, X and Y are the same or different and are $SO_2$, C(O), $CH_2$, $CD_2$, NHC(NH), OC(O), NHC(S) or NHC(O);

W is $NR^7$, $CH_2$, S or O, where $R^7$ is H, $C_1$-$C_{12}$ hydrocarbyl, or $C_1$-$C_{12}$ hydrocarboyl (acyl), and is preferably $NR^7$;

Q is $CHR^9$ or C(O);

Z is $CHR^{10}$ or C(O);

J and F are the same or different and are CH or CD (where D is deuterium);

each of m, n and p is zero or one and the sum of m+n+p is 2 or 3, preferably 2; and the circles A and B are the same or different aromatic or heteroaromatic ring systems that contain one ring or two fused rings. Groups $R^1$ and $R^2$ are the same or different and each can be hydrogen or represent up to three substituents other than hydrogen that themselves can be the same or different; i.e., $R^{1a}$, $R^{1b}$, and $R^{1c}$, and $R^{2a}$, $R^{2b}$, and $R^{2c}$. Each of those six groups, $R^{1a-c}$ and $R^{2a-c}$, is separately selected from the group consisting of H, $C_1$-$C_6$ hydrocarbyl, $C_1$-$C_6$ hydrocarbyloxy, trifluoromethyl, trifluoromethoxy, $C_1$-$C_7$ hydrocarboyl (acyl), hydroxy-, trifluoromethyl-(—$CF_3$) or halogen-substituted $C_1$-$C_7$ hydrocarboyl, $C_1$-$C_6$ hydrocarbylsulfonyl, halogen (F, Cl or Br, and preferably Cl), nitro, phenyl, cyano, carboxyl, $C_1$-$C_7$ hydrocarbyl carboxylate [C(O)O—$C_1$-$C_7$ hydrocarbyl], carboxamide [C(O)$NR^3R^4$] or sulfonamide [$SO_2NR^3R^4$]

wherein the amido nitrogen of either group (the carboxamide or sulfonamide) has the formula $NR^3R^4$ wherein $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is where M is —$CH_2$—, —O— or —N═N— and Ar is a single-ringed aryl group, and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur;

$R^8$, $R^9$, and $R^{10}$ are each H, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms; and $R^{11}$, $R^{12}$, $R^{13}$ and $R^{14}$ are all H, or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D as recited herein (in this subpargraph).

Preferably, $R^1$ and $R^2$ are not both methoxy when X and Y are both $SO_2$, W is 0 and p is zero.

In other preferred embodiments, X and Y are the same. X and Y are preferably both C(O) or both $SO_2$, and more preferably are both $SO_2$. In those and other embodiments, W is preferably 0. It is also preferred that p be zero.

A contemplated aromatic or heteroaromatic ring system of circle A or circle B can contain one ring or two fused rings, and preferably contains a single aromatic ring. An illustrative aromatic or heteroaromatic ring system is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl, isothiazolyl, naphthyl, benzofuranyl, isobenzofuranyl, benzothiophenyl, isobenzothiophenyl, benzoxazolyl, benzisoxazole, quinolyl, isoquinolyl, quinazolyl, cinnolinyl, quinoxalinyl, naphthyridinyl, benzopyrimidinyl, and mixtures thereof. The mixtures of the previous sentence occur when circle A and circle B aromatic or heteroaromatic ring systems are different.

An illustrative single-ringed aryl group of substituent MAr is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl and isothiazolyl.

Phenyl is a preferred aromatic or heteroaromatic ring system of circle A and circle B. Phenyl, pyridinyl and furanyl are preferred single-ringed aryl groups, Ar, of a MAr substituent, with phenyl being particularly preferred.

There are several independent and separate preferences regarding the substituent R groups. Thus, $R^1$ and $R^2$ are preferably the same single substituent other than hydrogen, so that circle A and circle B both contain a single substituent other than hydrogen. The single substituent of $R^1$ and $R^2$ is preferably located at the same relative position in their respective ring systems.

Thus, X and Y can form a sulfonamido, a carboxamido, a urea, a thiourea, a guanidino or methylene linkage from the circle A or circle B ring system to a depicted nitrogen atom of the central spiro ring. A compound having a central ring that is a spiro 6,6-ring system or a spiro 5,6-ring system, along with one nitrogen and one oxygen or two nitrogen atoms is contemplated. Illustrative central spiro rings are shown below where wavy lines are used to indicate the presence of covalent bonds to other entities, and where $R^7$ is defined above and $R^8$ is H.

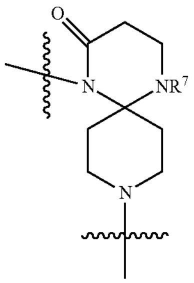
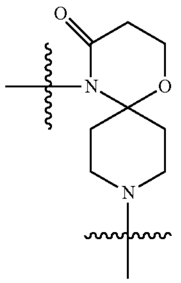
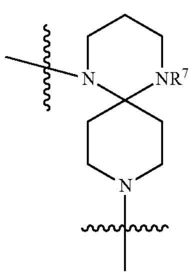
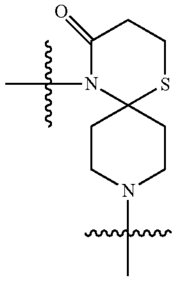
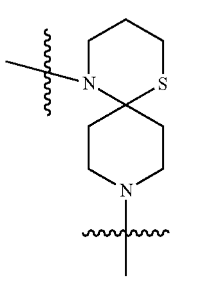
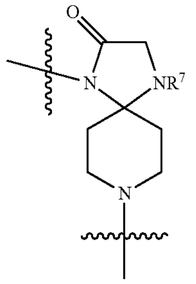
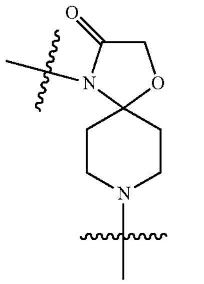
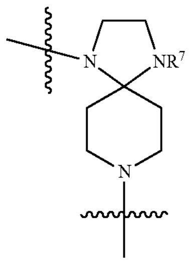

-continued

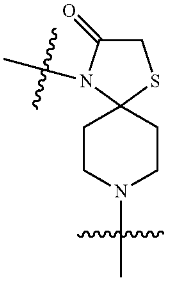
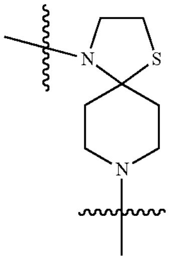
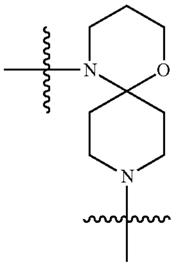
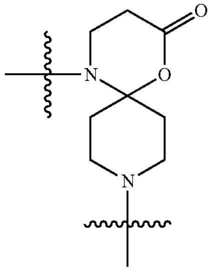
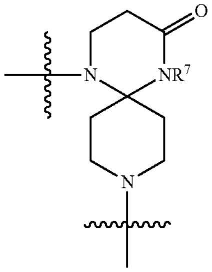
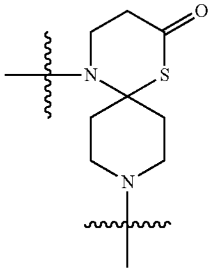
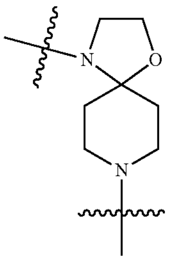
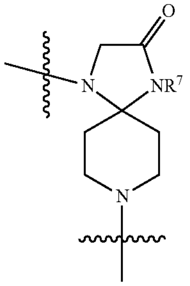
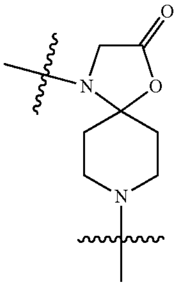
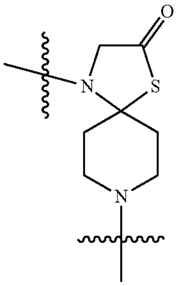

Illustrative compounds of Formula A in which d and e are each zero and $R^{11}$, $R^{12}$ and $R^{13}$ are each H have asymmetric spiro ring structures a few of which are shown below with wavy lines indicating the presence of covalent bonds to other entities, and $R^7$ is defined above and $R^8$ is H.

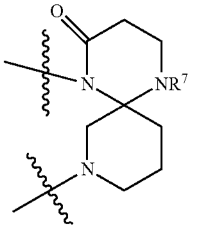
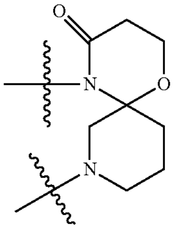
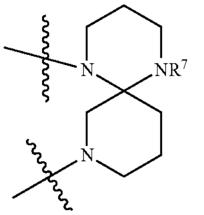
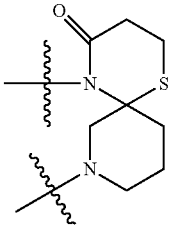
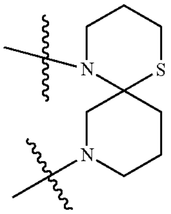
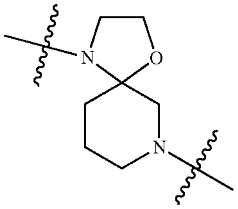
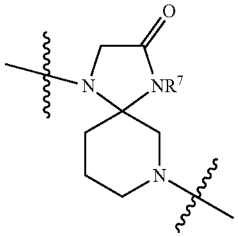
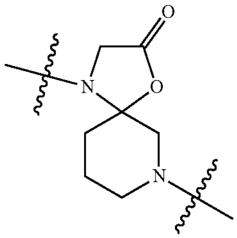
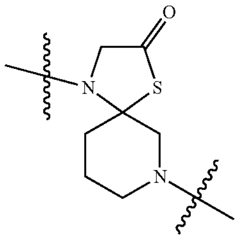
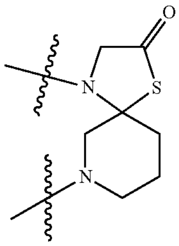
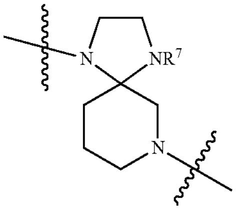
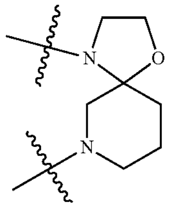
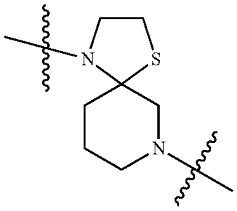
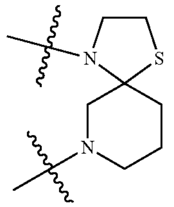

In preferred practice, p is zero, e and g are both zero and $R^{11}$, $R^{12}$ and $R^{13}$ are all H, so the central ring is a spiro 5,6-ring system whose 6-membered ring is unsubstituted and in which the spiro bonds are in the 4-position relative to the nitrogen of the 6-membered ring. It is separately preferred that W be O. A compound in which X and Y are the same is preferred. It is also separately preferred that X and Y both be $SO_2$ (sulfonyl).

A particularly preferred compound of Series C-1 Formula A that embodies the above separate preferences is a compound of Series C-I Formula II

II

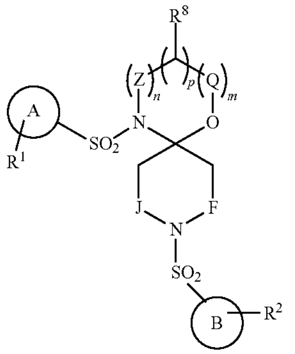

wherein circle A and circle B, Z, Q, m, n, p, $R^1$, $R^2$ and $R^8$ are as described above for a compound of Series C-1, unless the formula as shown precludes a definition provided for a compound of Formula A; and J and F are the same or different and are $CH_2$, CHD or $CD_2$ (where D is deuterium).

It is more preferred that circle A and circle B are each phenyl, furanyl or pyridyl and $R^1$ and $R^2$ is each a single substituent. There are several independent and separate preferences regarding the substituent R groups. Thus, $R^1$ and $R^2$ are preferably the same. $R^1$ and $R^2$ are also preferably located at the same relative position in their respective rings. Thus, if $R^1$ is 4-cyano, $R^2$ is also 4-cyano. It is also preferred that the sum of m+n+p=2 so that the upper depicted ring contains 5-ring atoms.

Preferred $R^1$ and $R^2$ substituent groups do not themselves provide a positive or negative charge to a compound at a pH value of about 7.2~7.4.

In other embodiments, a particularly preferred compound of Series C-I Formula A is a compound of Series C-I Formula III

III

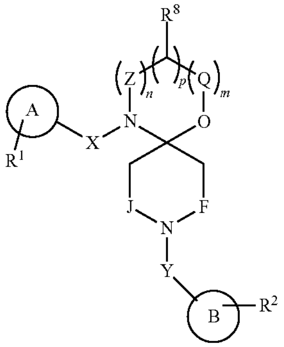

wherein circle A and circle B, Z, Q, m, n, p, $R^1$, $R^2$ and $R^8$ are as described previously for a compound of Series C-I unless the formula as shown precludes a prior definition; J and F are the same or different and are $CH_2$, CHD or $CD_2$ (where D is deuterium); and X and Y are both CO, or X and Y are different and are $SO_2$, C(O), $CH_2$, $CD_2$ (where D is deuterium), OC(O), NHC(NH), NHC(S) or NHC(O). Previous preferences are also applicable unless precluded by the above structural formula.

More preferably, circle A and circle B are each phenyl, furanyl or pyridyl. $R^1$ and $R^2$ are the same and are selected from the group consisting of trifluoromethyl, $C_1$-$C_6$ acyl, $C_1$-$C_4$ alkylsulfonyl, halogen, nitro, cyano, carboxyl, $C_1$-$C_4$ alkyl carboxylate, carboxamide wherein the amido nitrogen has the formula $NR^3R^4$ wherein $R^3$ and $R^4$ are the same or different and are H, $C_1$-$C_4$ alkyl, and $NR^5R^6$ wherein $R^5$ and $R^6$ are the same or different and are H, $C_1$-$C_4$ alkyl, $C_1$-$C_4$ acyl, $C_1$-$C_4$ alkylsulfonyl.

It is still more preferred that $R^1$ and $R^2$ each be a single substituent. There are several independent and separate preferences regarding the substituent R groups. $R^1$ and $R^2$ are preferably the same. $R^1$ and $R^2$ are also preferably located at the same relative position in their respective rings. Thus, if $R^1$ is 4-cyano, $R^2$ is also 4-cyano. It is also preferred that p=0, and that the sum of m+n+p=2, so that the upper depicted ring contains 5-ring atoms.

In still further embodiments, a particularly preferred compound of Series C-1 Formula A is a compound of Series C-1 Formula IV

IV

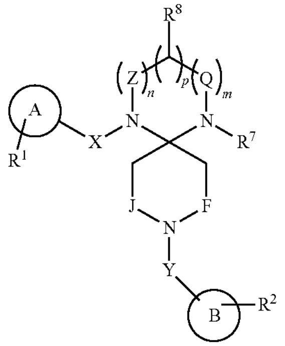

wherein circle A and circle B, Z, Q, m, n, p, $R^1$, $R^2$, $R^7$ and $R^8$ are as described previously for a compound of Series C-1 unless the formula as shown precludes such a prior definition; J and F are the same or different and are $CH_2$, CHD or $CD_2$ (where D is deuterium); and X and Y are the same or different and are $SO_2$, C(O), $CH_2$, $CD_2$ (where D is deuterium), OC(O), NHC(NH), NHC (S) or NHC(O). Previous preferences are also applicable unless precluded by the above structural formula.

More preferably, circle A and circle B are each phenyl, furanyl or pyridyl. $R^1$ and $R^2$ are the same and are selected from the group consisting of trifluoromethyl, $C_1$-$C_6$ acyl, $C_1$-$C_4$ alkylsulfonyl, halogen, nitro, cyano, carboxyl, $C_1$-$C_4$ alkyl carboxylate, carboxamide wherein the amido nitrogen has the formula $NR^3R^4$ wherein $R^3$ and $R^4$ are the same or different and are H, $C_1$-$C_4$ alkyl, and $NR^5R^6$ wherein $R^5$ and $R^6$ are the same or different and are H, $C_1$-$C_4$ alkyl, $C_1$-$C_4$ acyl, $C_1$-$C_4$ alkylsulfonyl.

It is still more preferred that $R^1$ and $R^2$ each be a single substituent. There are several independent and separate preferences regarding the substituent R groups. $R^1$ and $R^2$ are preferably the same. $R^1$ and $R^2$ are also preferably located at the same relative position in their respective rings. Thus, if $R^1$ is 4-cyano, $R^2$ is also 4-cyano. It is also preferred that the sum of m+n=1, so that the upper depicted ring contains 5-ring atoms.

It is noted that the previously mentioned preferences regarding E, J, F, G, K, Q, W, X, Y, Z, d, e, f, k, n, m, p, circle A and circle B, and all of the R groups as are appropriate for a particular formula apply to a compound of Series C-1 Formulas A, B, and I-IV.

A compound of Series C-2 corresponds generally to the Formula A, below

A

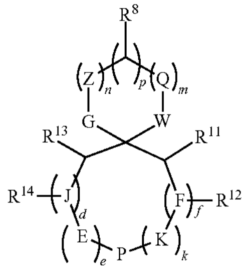

In Series C-2 Formula A,

Q is $CHR^9$ or C(O), Z is $CHR^{10}$ or C(O), and only one of Q and Z is C(O);

each of m and n and p is zero or one and the sum of m+n+p is 2 or 3, preferably 2;

each of G, P and W is selected from the group consisting of $NR^{20}$, $NR^2$, $NR^7$, S and O, where $R^7$ and $R^2$ are the same or different and are H, $C(H)_v(D)_h$ where each of v and h is 0, 1, 2 or 3 and v+h=3, $C(H)_q(D)_r$-aliphatic $C_1$-$C_{11}$ hydrocarbyl where each of q and r is 0, 1, or 2 and q+r=0, 1 or 2, (including aliphatic $C_1$-$C_{12}$ hydrocarbyl when q+r=0), aliphatic $C_1$-$C_{12}$ hydrocarbyl sulfonyl or aliphatic $C_1$-$C_{12}$ hydrocarboyl (acyl), and $R^{20}$ is X-circle A-$R^1$ as defined hereinafter.

Preferably, in one embodiment, i) only one of G, P and W is $NR^{20}$, ii) one of G, P and W must be $NR^{20}$, iii) P is $NR^2$ when other than $NR^{20}$, iv) one of G and W is other than $NR^2$ or $NR^7$ in which $R^2$ and $R^7$ is H or an aliphatic $C_1$ hydrocarbyl when (a) the sum of m+n+p is 2 and (b) the other of G and W is $NR^{20}$, $NR^2$, or $NR^7$ bonded to a Z or Q, respectively, that is C(O), and v) P is $NR^2$ in which $R^2$ is other than —$S(O)_2C_1$-$C_3$-hydrocarbyl when (a) the sum of m+n+p is 2 and the Q or Z present is $CH_2$, (b) the G or W that is not $NR^{20}$ is 0, and (c) $R^{20}$ is —$S(O)_2$phenyl-$R^1$, where $R^1$ is H, $C_1$-$C_3$-hydrocarbyl or halogen.

Each of d, e, f and k is either zero or one and the sum of (d+e+f+k)=2. In some embodiments, e is zero when d is zero, and k is zero when f is zero. In other embodiments, e is zero when k is zero, and f is zero when d is zero.

J and F are the same or different and are CH or CD (where D is deuterium).

E and K are the same or different and are $CH_2$, CHD or $CD_2$ (where D is deuterium).

X is $SO_2$, C(O), $CH_2$, $CD_2$, OC(O), NHC(NH), NHC(S) or NHC(O), preferably $SO_2$, C(O) or $CH_2$. In some embodiments, X is more preferably $CH_2$ or $SO_2$. In other embodiments, X is preferably $SO_2$, NHC(NH), NHC(S) or NHC (O).

Circle A is an aromatic or heteroaromatic ring system that preferably contains a single ring, but can also contain two fused rings. $R^1$ is H or represents up to three substituents, $R^{1a}$, $R^{1b}$, and $R^{1c}$, that themselves can be the same or different, wherein each of those three groups, $R^{1a-c}$, is separately selected from the group consisting of H, $C_1$-$C_6$ hydrocarbyl, $C_1$-$C_6$ hydrocarbyloxy, $C_1$-$C_6$ hydrocarbyloxycarbonyl, trifluoromethyl, trifluoromethoxy, $C_1$-$C_7$ hydrocarboyl, hydroxy-, trifluoromethyl- (—$CF_3$) or halogen-substituted $C_1$-$C_7$ hydrocarboyl, $C_1$-$C_6$ hydrocarbylsulfonyl, $C_1$-$C_6$ hydrocarbyloxysulfonyl, halogen (F, Cl, or Br, and preferably Cl) nitro, phenyl, cyano, carboxyl, $C_1$-$C_7$ hydrocarbyl carboxylate [C(O)O—$C_1$-$C_7$ hydrocarbyl], carboxamide [$C(O)NR^3R^4$] or sulfonamide [$S(O)_2NR^3R^4$], wherein the amido nitrogen in either amide group has the formula $NR^3R^4$ in which $R^3$ and $R^4$ are the same or different and are H, $C_1$-$C_4$ hydrocarbyl, or $R^3$ and $R^4$ together with the depicted nitrogen form a 5-7-membered ring that optionally contains 1 or 2 additional hetero atoms that independently are nitrogen, oxygen or sulfur, MAr, where M is —$CH_2$—, —O— or —N═N— and Ar is a single-ringed aryl or heteroaryl group and $NR^5R^6$ wherein $R^5$ and $R^6$ are the same or different and are H, $C_1$-$C_4$ hydrocarbyl, $C_1$-$C_4$ acyl, $C_1$-$C_4$ hydrocarbylsulfonyl, or $R^5$ and $R^6$ together with the depicted nitrogen form a 5-7-membered ring that optionally contains 1 or 2 additional hetero atoms that independently are nitrogen, oxygen or sulfur.

$R^8$, $R^9$, and $R^{10}$ are each H, which is preferred, or two of $R^8$, $R^9$, and $R^{10}$ are H and one is a $C_1$-$C_8$ hydrocarbyl group that is unsubstituted or is substituted with up to three atoms that are the same or different and are oxygen or nitrogen atoms (including hydrogens as appropriate).

$R^{11}$, $R^{12}$, $R^{13}$ and $R^{14}$ are all H, or $R^{11}$ and $R^{13}$ are H and $R^{12}$ and $R^{14}$ are H or D, or one of the pair $R^{11}$ and $R^{12}$ or the pair $R^{13}$ and $R^{14}$ together with the depicted ring form a saturated or unsaturated 6-membered ring, and the other pair are each H or they are H and D as recited herein (in this subparagraph).

In another preferred embodiment of a compound of Formula A, above, i) only one of G, P and W is $NR^{20}$, ii) one of G, P and W must be $NR^{20}$, and iii) P is $NR^2$ when other than $NR^{20}$ Additionally, Q is $CHR^9$ or C(O); and Z is $CHR^{10}$ or C(O), with the other of J, E, F, K, X, Z, d, e, f, k, n, m, p, circle A, and all of the R groups being defined as discussed above unless precluded by the structural formula.

A pharmaceutically acceptable salt of a compound of Series C-2 Formula A and all of the remaining formulas disclosed herein is also contemplated.

In preferred embodiments, a compound of Series C-2 Formula A corresponds in structure to either Formula B or Formula C, can be present as a pharmaceutically acceptable salt, and can optionally be present including both individual enantiomeric forms, a racemate, diastereomers and mixtures thereof.

B

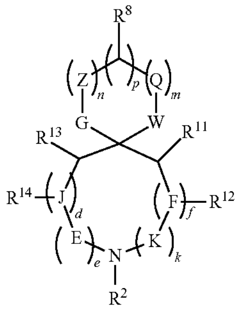

C

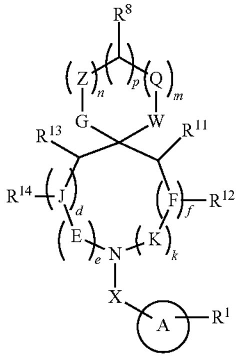

In a compound of Series C-2 that corresponds in structure to Series C-2 Formula B, G and W are selected from the group consisting of $NR^{20}$, $NR^7$, S and O, where $R^2$ and $R^7$ are the same or different and are $C(H)_v(D)_h$ (where D is deuterium) and where each of v and h is 0, 1, 2 or 3 and v+h=3, $C(H)_q(D)_r$-aliphatic $C_1$-$C_{11}$ hydrocarbyl (where D is deuterium) where each of q and r is 0, 1, or 2 and q+r=0, 1 or 2, aliphatic $C_1$-$C_{12}$ hydrocarbyl sulfonyl or aliphatic $C_1$-$C_{12}$ hydrocarboyl, or $R^2$ and $R^{20}$ are the same or different, and $R^{20}$ is X-circle A-$R^1$.

Preferably in one embodiment, i) only one of G and W is $NR^{20}$, ii) one of G and W must be $NR^{20}$, iii) the G or W that is not $NR^{20}$ is other than $NR^2$ or $NR^7$ in which $R^2$ or $R^7$ is H or an aliphatic $C_1$ hydrocarbyl when (a) the sum of m+n+p is 2 and (b) the G or W that is $NR^{20}$ is bonded to a Z or Q, respectively, that is C(O), and iv) $R^2$ of the depicted $NR^2$ is other than —$S(O)_2C_1$-$C_3$-hydrocarbyl when (a) the sum of m+n+p is 2 and the Q or Z that is present is $CH_2$, (b) the G or W that is not $NR^{20}$ is 0, and (c) $R^{20}$ is —$S(O)_2$phenyl-$R^1$, where $R^1$ is H, $C_1$-$C_3$-hydrocarbyl or halogen.

In another preferred embodiment:

i) only one of G and W is $NR^{20}$, ii) one of G and W must be $NR^{20}$, iii) the G or W that is not $NR^{20}$ is $NR^2$ or $NR^7$ in which $R^2$ or $R^7$ is H or an aliphatic $C_1$ hydrocarbyl, (iv) the sum of m+n+p is 2, and (v) the G or W that is $NR^{20}$ is bonded to a Z or Q, respectively, that is C(O).

In yet another preferred embodiment:

i) only one of G and W is $NR^{20}$, ii) one of G and W must be $NR^{20}$, iii) the G or W that is not $NR^{20}$ is $NR^7$ that is H or an aliphatic $C_1$ hydrocarbyl, (iv) the sum of m+n+p is 2, (v) the G or W that is $NR^{20}$ is bonded to a Z or Q, respectively, that is C(O), (vi) $R^2$ of the depicted $NR^2$ is the same or different $R^{20}$, and (vii) $R^{20}$ is X-circle A-$R^1$.

For a compound of Formula C, G and W are selected from the group consisting of $NR^2$, $NR^7$, S and O, where $R^2$ and $R^7$ are the same or different and are H, $C(H)_v(D)_h$ (where D is deuterium) and where each of v and h is 0, 1, 2 or 3 and v+h=3, $C(H)_q(D)_r$-aliphatic $C_1$-$C_{11}$ hydrocarbyl where each of q and r is 0, 1, or 2 and q+r=0, 1 or 2, aliphatic $C_1$-$C_{12}$ hydrocarbyl sulfonyl or aliphatic $C_1$-$C_{12}$ hydrocarboyl.

Preferably, in another embodiment:

i) one of G and W must be $NR^2$ or $NR^7$, and ii) one of G and W is other than $NR^2$ or $NR^7$ in which $R^2$ or $R^7$ is H or an aliphatic $C_1$ hydrocarbyl when (a) the sum of m+n+p is 2 and (b) the other of G and W is $NR^2$ or $NR^7$ bonded to a Z or Q, respectively, that is C(O).

In both of Series C-2 Formulas B and C, the symbols X, Z, Q, d, e, f, g, n, m, circle A, and all of the R groups not otherwise defined in the paragraphs following their structural formulas are as defined previously for a compound of Series C-2 Formula A unless the formula as shown precludes a prior definition. The previously noted preferences are also as discussed before unless the formula as shown precludes a prior preference.

In one embodiment, a preferred compound of Series C-2 Formulas A and B has the structure of Formula I

I

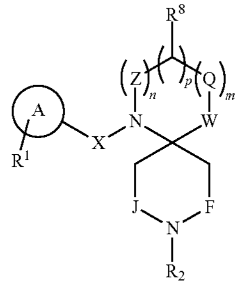

wherein J and F are the same or different and are $CH_2$, CHD or $CD_2$ (where D is deuterium); and W, X, Z, Q, n, m, p, circle A, $R^1$, $R^2$, $R^8$ and the R groups therein defined are as described previously for a compound of Series C-2 Formula A, unless the formula as shown precludes a prior definition. Preferably, i) $R^2$ of the depicted $NR^2$ is other than —$S(O)_2C_1$-$C_3$-hydrocarbyl when (a) the sum of m+n+p is 2 and the Q or Z present is $CH_2$, (b) the G or W that is not $NR^{20}$ is O, and (c) $R^{20}$ is —$S(O)_2$phenyl-$R^1$, where $R^1$ is H, $C_1$-$C_3$-hydrocarbyl or halogen, and ii) W is other than $NR^2$ or $NR^7$ in which $R^2$ or $R^7$ is H or an aliphatic $C_1$ hydrocarbyl when (a) the sum of m+n+p is 2 and (b) Z is C(O).

In another preferred embodiment where $R^8$ is H, one of n and m is zero and the remaining Z or Q is $CH_2$, a compound of Series C-2 Formulas A, B and I has the structure of Series C-2 Formula II

II

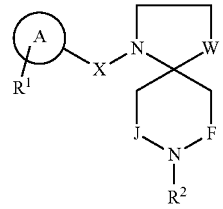

wherein J and F are the same or different and are $CH_2$, CHD or $CD_2$ (where D is deuterium); and X, W, circle A, $R^1$, $R^2$ and the R groups therein defined are as described previously for a compound of Series C-2 Formula A, unless the formula as shown precludes a prior definition. Preferably, $R^2$ of the depicted $NR^2$ is other than —$S(O)_2C_1$-$C_3$-hydrocarbyl when W is 0, and X-circle A-$R^1$ is —$S(O)_2$phenyl-$R^1$, where $R^1$ is H, $C_1$-$C_3$-hydrocarbyl or halogen.

In a further preferred embodiment, where $R^8$ is H, a compound of Series C-2 Formulas A, B and I has the structure of Series C-2 Formula III

III

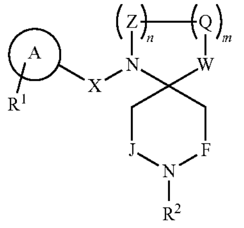

wherein J and F are the same or different and are $CH_2$, CHD or $CD_2$ (where D is deuterium);

each of m and n is one; and

W, X, Z, Q, circle A, $R^1$, $R^2$ and the R groups therein defined are as described previously for a compound of Series C-2 Formula A, unless the formula as shown precludes a prior definition.

In one preferred embodiment, i) Z is C(O), ii) Q is $CH_2$, iii) W is NH, and $R^2$ is H or $C_1$-$C_{12}$ aliphatic straight, branched or cyclic hydrocarbyl, iv) X is preferably $CH_2$, $SO_2$, NHC(NH), NHC(S) or NHC(O), and more preferably $CH_2$. In another preferred embodiment, i) one of Z and Q is C(O), and ii) W is other than $NR^2$ or $NR^7$ in which $R^2$ and $R^7$ is H or an aliphatic $C_1$ hydrocarbyl when Z is C(O), and iii) X is preferably $CH_2$, $SO_2$, NHC(NH), NHC(S) or NHC(O).

In a still further preferred embodiment, i) Z is C(O), ii) Q is $CH_2$, iii) W is NH, (vi) $R^2$ is the same or different $R^{20}$, and (vii) $R^{20}$ is X-circle A-$R^1$. In this embodiment, X is preferably $CH_2$, $SO_2$, NHC(NH), NHC(S) or NHC(O), more preferably $CH_2$.

A presently most preferred compound for carrying out a contemplated method corresponds in structure to Formula III, above, in which i) Z is C(O), ii) Q is $CH_2$, iii) W is NH, and $R^2$ is H or a $C_1$-$C_{12}$, preferably $C_1$-$C_8$, and more preferably a $C_1$-$C_6$, aliphatic straight, branched or cyclic hydrocarbyl group, iv) X is $CH_2$, and circle A-$R^1$ is unsubstituted phenyl so that the substituent X-circle A-$R^1$ is a benzyl group. Illustrative presently most preferred N-(benzylamido)-unsubstituted-amine compounds include Compounds C0105M, C0115M and C0124M, whose structural formulas are shown below.

C0105M

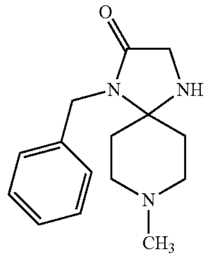

C0114M

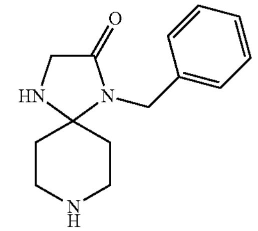

C0124M

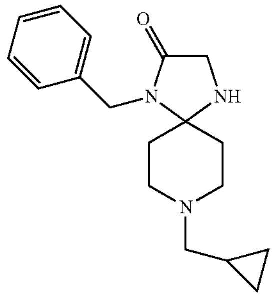

In a still further preferred embodiment, a compound of Series C-2 Formulas A and C has the structure of Series C-2 Formula IV

IV

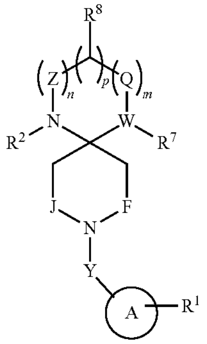

wherein J and F are the same or different and are $CH_2$, CHD or $CD_2$ (where D is deuterium); and W, X, Z, Q, circle A, $R^1$, $R^2$, $R^8$ and the R groups therein defined are as described previously for a compound of Series C-2 Formula A, unless the formula as shown precludes a prior definition.

In one preferred embodiment, i) W is other than $NR^2$ or $NR^7$ in which $R^2$ or $R^7$ is H or an aliphatic $C_1$ hydrocarbyl, when p is zero and the sum of m+n+p is 2 and Z is C(O), and ii) $R^2$ of the depicted $NR^2$ group is other than H or an aliphatic $C_1$ hydrocarbyl, when p is zero and the sum of m+n+p is 2, W is $NR^2$ or $NR^7$, and Q is C(O).

In yet another preferred embodiment where $R^8$ is H, one of n and m is zero and the remaining Z or Q is $CH_2$, a compound of Formulas A, C and IV has the structure of Series C-2 Formula V

V

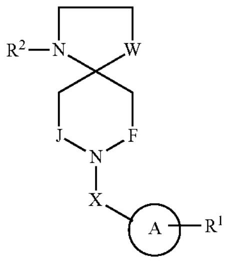

wherein J and F are the same or different and are $CH_2$, CHD or $CD_2$ (where D is deuterium); and X, W, circle A, $R^1$, $R^2$ and the R groups therein defined are as described previously for a compound of Series C-2, unless the formula as shown precludes a prior definition.

In still another preferred embodiment, where $R^8$ is H, a compound of Series C-2 Formulas A, C and I has the structure of Series C-2 Formula VI

VI

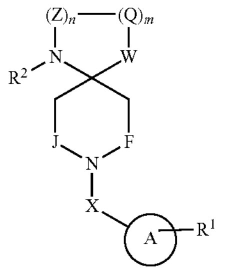

wherein J and F are the same or different and are $CH_2$, CHD or $CD_2$ (where D is deuterium); and each of m and n is one; W, X, Z, Q, circle A, $R^1$, $R^2$ and the R groups therein defined are as described previously for a compound of Series C-2, unless the formula as shown precludes a prior definition.

Preferably, i) one of Z and Q is C(O), ii) W is other than $NR^2$ or $NR^7$ in which $R^2$ or $R^7$ is H or an aliphatic $C_1$ hydrocarbyl when Z is C(O), and iii) $R^2$ of the depicted $NR^2$ group is other than H or an aliphatic $C_1$ hydrocarbyl when W is $NR^2$ or $NR^7$, and Q is C(O). In a compound of the above formula, X is preferably $SO_2$, NHC(NH), NHC(S) or NHC(O).

It is also noted that the previously mentioned preferences regarding apply to X, W, Z, Q, d, e, f, k, n, m, circle A, and all of the R groups apply to a compound of Series C-2 Formulas A, B, C, and I-VI, unless the formula as shown precludes a prior definition.

A contemplated aromatic ring (aryl) system of circle A of one of the contemplated compounds preferably contains a single aromatic ring, but can also contain two fused aromatic rings. An illustrative circle A aromatic ring system is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl, isothiazolyl, naphthyl, benzofuranyl, isobenzofuranyl, benzothiophenyl, isobenzothiophenyl, benzoxazolyl, benzisoxazole, quinolyl, isoquinolyl, quinazolyl, cinnolinyl, quinoxalinyl, naphthyridinyl, and benzopyrimidinyl.

An illustrative single-ringed aryl or heteroaryl group of a circle A group or of a substituent of circle A, MAr, is selected from the group consisting of phenyl, pyridyl, pyrazinyl, pyrimidinyl, pyridazinyl, triazinyl (1,3,5-triazinyl, 1,2,4-triazinyl and 1,2,3-triazinyl), furanyl, thienyl, oxazolyl, isoxazolyl, thiazolyl and isothiazolyl groups.

Phenyl, pyridinyl and furanyl are a preferred aromatic or heteroaromatic ring system of circle A, with phenyl being more preferred. Phenyl, pyridinyl and furanyl are also preferred single-ringed aryl or heteroaryl groups, Ar, of a MAr substituent, with phenyl being particularly preferred.

From a depicted nitrogen atom of the central spiro rings to the circle A ring system, X and Y can form a sulfonamido (N—$SO_2$-circle A), a carboxamido [N—C(═O)-circle A), a urea [carbonyldiimino; N—C(═O)—NH-circle A], a thiourea [thiocarbonyldiimino; N—C(═S)—NH-circle A], a guanidino [N—C(═NH)—NH-circle A] or aminomethylene (N—$CH_2$-circle A) linkage.

Examining a compound of the above Series C-2 formulas more closely, it is seen that that formula defines a double ringed, substituted spiro compound that can have two six-membered rings or one six- and one five-membered ring, as when one of "m" and "n" is one and the other zero. One of those rings (the lower ring in the formulas) contains one nitrogen atom in the 6-membered ring and the remaining ring atoms are carbons. The ring that can contain 5- or 6-ring atoms (upper ring in the formulas) can contain one ring nitrogen and four or five carbons, or two nitrogens, a nitrogen and a sulfur or a nitrogen and an oxygen atom along with three or four ring carbons. Illustrative central spiro rings are shown below where wavy lines are used to indicate the presence of covalent bonds to other entities, and where $R^7$ is defined above and $R^8$ is H for clarity.

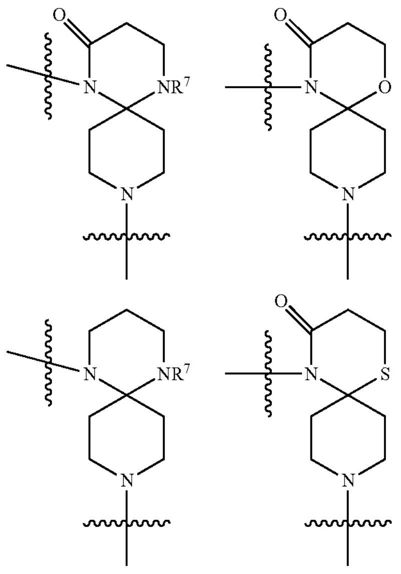

-continued
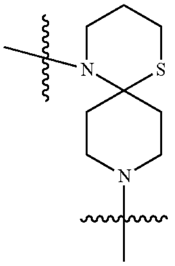
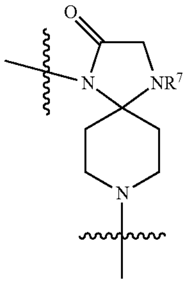
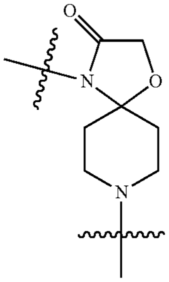
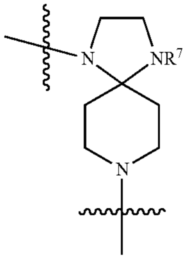
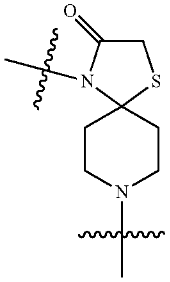
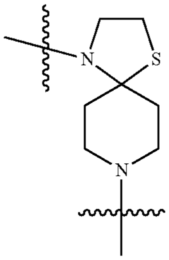
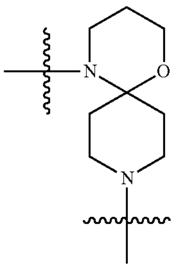
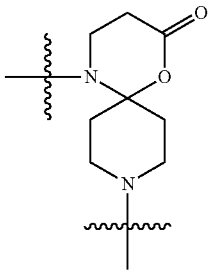
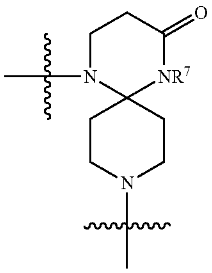
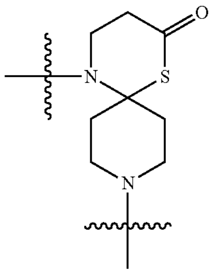
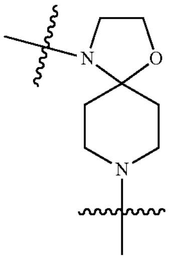
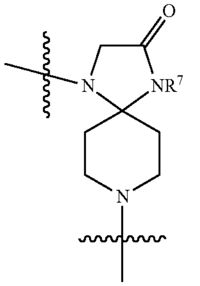
-continued
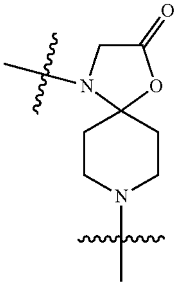
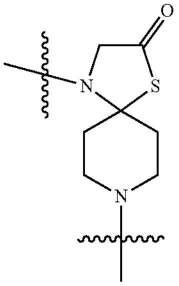
Illustrative compounds of Series C-2 Formula A in which d and e are each zero and $R^{11}$, $R^{12}$ and $R^{13}$ are each H have asymmetric spiro ring structures a few of which are shown below with wavy lines indicating the presence of covalent bonds to other entities, and $R^7$ is defined above and $R^8$ is again H for clarity.
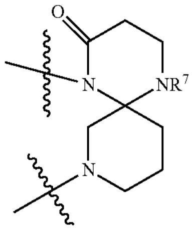
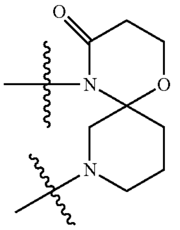
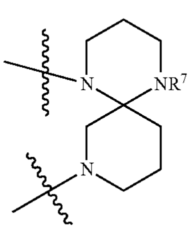
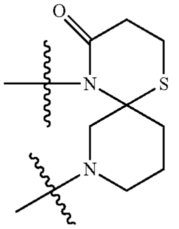
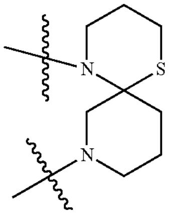
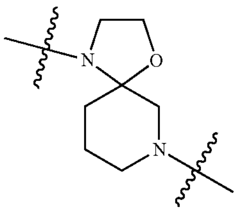
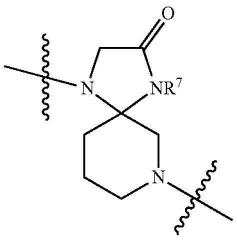
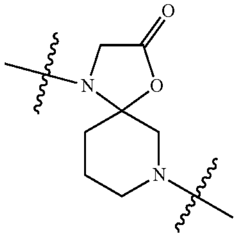
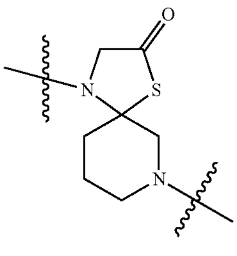
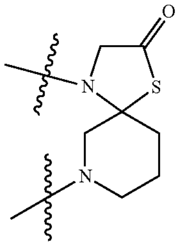

-continued

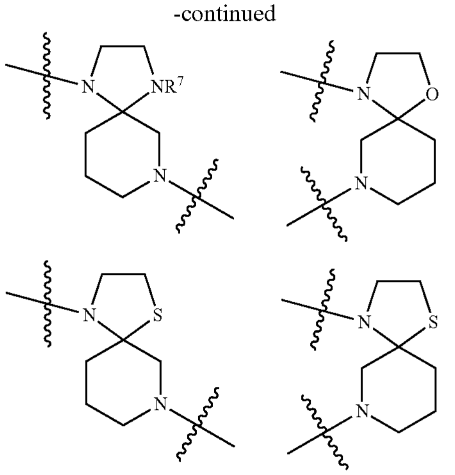

In preferred practice for the compounds of Series C-2 Formulas A, B and C, p is zero, e and g are both zero and $R^{11}$, $R^{12}$ and $R^{13}$ are all H, so the central ring is a spiro 5,6-ring system whose 6-membered ring is unsubstituted and in which the spiro bonds are in the 4-position relative to the nitrogen of the 6-membered ring. It is separately preferred that W be O, S or $NR^7$. It is also preferred that X be $SO_2$ (sulfonyl).

The aromatic substituent, the circle A, is linked to one nitrogen atom of the spiro rings by a X group that is $SO_2$, C(O), $CH_2$, $CD_2$, OC(═O), NHC(═NH), NHC(═S) or NHC(═O), preferably $SO_2$, C(O), $CH_2$, or $CD_2$, and most preferably $CH_2$ and $SO_2$. The resulting aromatic substituent is thereby linked to the spiro ring portion by a sulfonamide, an amide, a methylene, a urea, a thiourea or a guanidino linkage. Aryl sulfonamide bridges, aryl amide bridges and phenylmethylene bridges (benzyl compounds) are preferred, with aryl sulfonamide and phenylmethylene being particularly preferred.

Many of the compounds of Series A, Series B, Series C-1, Series C-2, Series D and Series E, as well as compounds such as naloxone and naltrexone not only bind to the peptide of SEQ ID NO: 1, but also bind to MOR and activate or stimulate that receptor. Naloxone and naltrexone bind to MOR about 200 times more poorly than they bind to the pentapeptide of SEQ ID NO: 1. The tables of Example 2 illustrate relative binding abilities of exemplary compounds of Series A, Series B, Series C-1, and Series C-2 based on MOR stimulatory activity.

In some embodiments it is preferred that a compound useful in a contemplated method binds well to and activates MOR. In those cases, it is preferred that the compound bind to MOR to an extent of at least about ±20 percent as well as DAMGO at a concentration shown in the tables, indicating the compound is a complete agonist for the receptor. In other embodiments, it is preferred that a compound useful herein not bind well to MOR. In those embodiments, it is preferred that the compound exhibit less than about 80 percent the MOR stimulation provided by DAMGO at the same concentration and conditions, down to zero binding/stimulation. Illustrative binding percentages in the presence of stated concentrations of DAMGO are illustrated for exemplary compounds of Series A, Series B, Series C-1, and Series C-2 in the tables of Example 2, hereinafter.

A 1,4,8-triazaspiro[4,5]-decan-2-one compound of Series D corresponds in structure to the formula

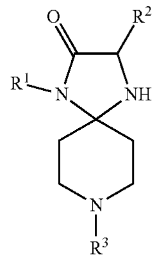

wherein $R^1$ represents hydrogen; a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which aryl and heteroaryl groups may be bonded via a linear or branched alkylene group that can comprise at least one heteroatom as a link; or a —C(═O)$OR^7$ group that can be bonded via a linear or branched alkylene group;

$R^2$ represents hydrogen; a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which aryl and heteroaryl group may be bonded via a linear or branched alkylene group that can comprise at least one heteroatom as a link;

$R^3$ represents a —S(═O)$_2$-$R^4$ group; a —C(═S)NH—$R^5$ group; or a —C(═O)NH—$R^6$ group;

$R^4$ represents a —$NR^{10}R^{11}$ group; a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which groups may be bonded via a linear or branched unsubstituted or at least monosubstituted alkylene group that can comprise at least one heteroatom as a link and may be condensed with an unsubstituted or at least monosubstituted monocyclic ring system; an unsubstituted or at least monosubstituted cycloaliphatic group, that can comprise at least one heteroatom as a ring member and that can be bonded via a linear or branched unsubstituted or at least monosubstituted alkylene group that can comprise at least one heteroatom as a link and that can be bridged by a linear or branched unsubstituted or at least monosubstituted alkylene group;

$R^5$ represents a linear or branched unsubstituted or at least monosubstituted alkyl group that can comprise at least one heteroatom as a link; a linear or branched unsubstituted or at least monosubstituted alkenyl group that can comprise at least one heteroatom as a link; a linear or branched unsubstituted or at least monosubstituted alkynyl group that can comprise at least one heteroatom as a link; an unsubstituted or at least monosubstituted aryl group or an unsubstituted or at least monosubstituted heteroaryl group, which group may be bonded via a linear or branched unsubstituted or at least monosubstituted alkylene group that can comprise at least one heteroatom as a link; an unsubstituted or at least monosubstituted cycloaliphatic group, that can comprise at least one heteroatom as a ring member or that can be bonded via a linear or branched unsubstituted or at least monosubstituted alkylene group that can comprise at least one heteroatom as a link; a —C(═O)OR$^8$ group or a —C(═O)OR$^9$ group, that can, in either case, be bonded via a linear or branched alkylene group;

$R^6$ represents an unsubstituted or at least monosubstituted aryl group or an unsubstituted or at least monosubstituted heteroaryl group, which aryl and heteroaryl groups may be bonded via a linear or branched unsubstituted or at least monosubstituted alkylene group that can comprise at least one heteroatom as a link; or for an unsubstituted or at least monosubstituted cycloaliphatic group, that can comprise at least one heteroatom as a ring member or that can be bonded via a linear or branched unsubstituted or at least monosubstituted alkylene group that can comprise at least one heteroatom as a link;

$R^7$, $R^8$, $R^9$, $R^{10}$, and $R^{11}$, each independently represent a linear or branched alkyl group, a linear or branched alkenyl group, or a linear or branched alkynyl group, or a physiologically acceptable salt thereof.

Preferably for a 1,4,8-triazaspiro[4,5]-decan-2-one compound corresponding to the formula above, $R^1$ represents hydrogen; a linear or branched unsubstituted or at least monosubstituted $C_{1-10}$ alkyl group that can comprise at least one heteroatom as a link; a linear or branched unsubstituted or at least monosubstituted $C_{2-10}$ alkenyl group that can comprise at least one heteroatom as a link; a linear or branched unsubstituted or at least monosubstituted $C_{2-10}$ alkynyl group that can comprise at least one heteroatom as a link; an unsubstituted or at least monosubstituted five-membered to fourteen-membered aryl group or heteroaryl group, that can be bonded via a linear or branched $C_{1-5}$ alkylene group that can comprise at least one heteroatom as a link; a —C═O)OR$^7$ group that can be bonded via a linear or branched $C_{1-5}$ alkylene group;

$R^2$ represents hydrogen; a linear or branched unsubstituted or at least monosubstituted $C_{1-10}$ alkyl group that can comprise at least one heteroatom as a link; a linear or branched unsubstituted or at least monosubstituted $C_{2-10}$ alkenyl group that can comprise at least one heteroatom as a link; a linear or branched unsubstituted or at least monosubstituted $C_{2-10}$ alkynyl group that can comprise at least one heteroatom as a link; an unsubstituted or at least monosubstituted five-membered to fourteen-membered aryl or heteroaryl group, that can be bonded via a linear or branched $C_{1-5}$ alkylene group that can comprise at least one heteroatom as a link;

$R^4$ represents an NR$^{10}$R$^{11}$ group; a linear or branched unsubstituted or at least monosubstituted $C_{1-10}$ alkyl group that can comprise at least one heteroatom as a link; a linear or branched unsubstituted or at least monosubstituted $C_{2-10}$ alkenyl group that can comprise at least one heteroatom as a link; a linear or branched unsubstituted or at least monosubstituted $C_{2-10}$ alkynyl group that can comprise at least one heteroatom as a link; an unsubstituted or at least monosubstituted five-membered to fourteen-membered aryl group or heteroaryl group, that can be bonded via a linear or branched unsubstituted or at least monosubstituted $C_{1-5}$ alkylene group that can comprise at least one heteroatom as a link and may be condensed with a five-membered or six-membered monocyclic ring system; an unsubstituted or at least monosubstituted $C_{3-8}$-cycloaliphatic group that can comprise at least one heteroatom as a ring member or that can be bonded via a linear or branched unsubstituted or at least monosubstituted $C_{1-5}$ alkylene group that can comprise at least one heteroatom as a link and that can be bridged by a linear or branched unsubstituted or at least monosubstituted C.sub.1-5 alkylene group;

$R^5$ represents a linear or branched unsubstituted or at least monosubstituted $C_{1-10}$ alkyl group that can comprise at least one heteroatom as a link; a linear or branched unsubstituted or at least monosubstituted $C_{2-10}$ alkenyl group that can comprise at least one heteroatom as a link; a linear or branched unsubstituted or at least monosubstituted $C_{2-10}$ alkynyl group that can comprise at least one heteroatom as a link; an unsubstituted or at least monosubstituted five-membered to fourteen-membered aryl or heteroaryl group, that can be bonded via a linear or branched unsubstituted or at least monosubstituted $C_{1-5}$ alkylene group that can comprise at least one heteroatom as a link; an unsubstituted or at least monosubstituted $C_{3-8}$-cycloaliphatic group that can comprise at least one heteroatom as a ring member and that can be bonded via a linear or branched unsubstituted or at least monosubstituted $C_{1-5}$ alkylene group that can comprise at least one heteroatom as a link; a —C(═O)OR$^8$ group or a —C(═O)OR$^9$ group either of that can be bonded via a linear or branched $C_{1-10}$ alkylene group;

$R^6$ represents an unsubstituted or at least monosubstituted five-membered to fourteen-membered aryl or heteroaryl group, which aryl or heteroaryl group may be bonded via a linear or branched unsubstituted or at least monosubstituted $C_{1-5}$ alkylene group that can comprise at least one heteroatom as a link; an unsubstituted or at least monosubstituted $C_{3-8}$-cycloaliphatic group that can comprise at least one heteroatom as a ring member, or that can be bonded via a linear or branched unsubstituted or at least monosubstituted $C_{1-5}$ alkylene group that can comprise at least one heteroatom as a link; and $R^7$, $R^8$, $R^9$, $R^{10}$, and $R^{11}$, independently represent a linear or branched $C_{1-5}$ alkyl group, a linear or branched $C_{2-5}$ alkenyl group, or a linear or branched $C_{2-5}$ alkynyl group.

Compounds A, B and C whose structural formulas are shown below are illustrative preferred compounds of Series D.

Compound A

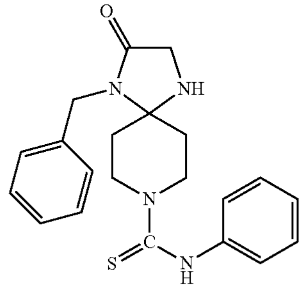

Compound B

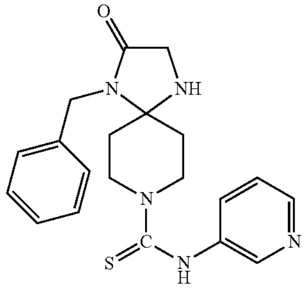

Compound C

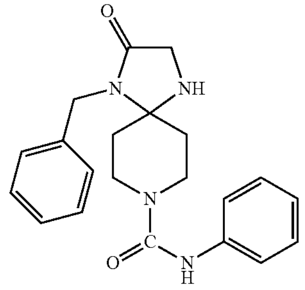

A substituted 1-oxa-3,8-diazaspiro[4.5]-decan-2-one compound of Series E corresponds in structure to the formula

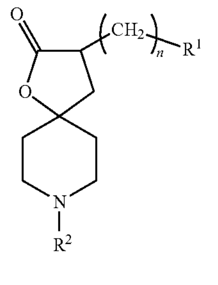

wherein n is 1, 2, 3, 4 or 5;

$R^1$ denotes:

an optionally substituted 6- or 10-membered aryl group or an optionally substituted 5- to 14-membered heteroaryl group, wherein the aryl or heteroaryl group optionally can be fused with a saturated or unsaturated, optionally substituted mono- or bicyclic ring system;

$R^2$ denotes:

—C(=S)—NH—$R^3$; —C(=O)—NH—$R^4$; —S(=O)$_2$—$R^5$; —(CH$_2$)—C(=O)—NH—$R^6$; —(CH$_2$)-$D_{aa}$-(CH$_2$)$_{bb}$-$E_{cc}$-(CH$_2$)$_{dd}$—$R^7$, wherein aa=0 or 1;

bb=0, 1 or 2;

cc=0 or 1; dd=0 or 1; and the sum of aa and cc does not equal 0; and

D and E each independently denote O, S, NH, N($CH_3$), N($C_2H_5$) or N[CH($CH_3$)$_2$];

—C(=O)—$R^8$, or —S(=O)$_2$-N$R^9R^{10}$;

$R^3$ denotes:

—(CH$R^{11}$)—(CH$_2$)$_w$—C(=O)—O—$R^{12}$, wherein w=0 or 1;

—(CH$R^{13}$)—(CH$_2$)$_a$—$K_b$—(CH$_2$)$_c$-$L_d$-$R^{14}$, wherein a=0, 1 or 2; b=0 or 1; c=0, 1 or 2; d=0 or 1, and K and L each independently denote O, S, NH, N($CH_3$), N($C_2H_5$) or N[CH($CH_3$)$_2$];

a linear or branched, saturated or unsaturated, optionally substituted $C_{1-10}$ aliphatic group;

an unsaturated or saturated, optionally substituted 3-, 4-, 5-, 6-, 7-, 8- or 9-membered cycloaliphatic group which optionally can be bridged with 1 or 2 linear or branched, optionally substituted $C_{1-5}$ alkylene groups or fused with a saturated, unsaturated or aromatic, optionally substituted mono- or bicyclic ring system, or both; or an optionally substituted 6- or 10-membered aryl group; or an optionally substituted 5- to 14-membered heteroaryl group, wherein the aryl or heteroaryl group optionally can be fused with a saturated or unsaturated, optionally substituted mono- or bicyclic ring system;

$R^4$ denotes:

—(CH$R^{15}$)—(CH$_2$)$_e$-$M_f$-(CH$_2$)$_g$—$P_h$—$R^{16}$, wherein e=0, 1 or 2; f=0 or 1; g=0, 1 or 2; h=0 or 1; and M and P each independently denote O, S, NH, N($CH_3$), N($C_2H_5$) or N[CH($CH_3$)$_2$];

a linear or branched, saturated or unsaturated, optionally substituted $C_{1-10}$ aliphatic group;

an unsaturated or saturated, optionally substituted 3-, 4-, 5-, 6-, 7-, 8- or 9-membered cycloaliphatic group which optionally can be bridged with 1 or 2 linear or branched, optionally substituted $C_{1-5}$ alkylene groups or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein said aryl or heteroaryl group optionally can be fused with a saturated or unsaturated, optionally substituted mono- or bicyclic ring system;

$R^5$ denotes:

—(CH$R^{17}$)—(CH$_2$)$_k$-$Q_l$-(CH$_2$)$_m$-$T_o$-$R^{18}$, wherein k=0, 1 or 2; l=0 or 1; m=0, 1 or 2; o=0 or 1; and Q and T each independently denote O, S, NH, N($CH_3$), N($C_2H_5$) or N[CH($CH_3$)$_2$];

a linear or branched, saturated or unsaturated, optionally substituted $C_{1-10}$ aliphatic group;

an unsaturated or saturated, optionally substituted 3-, 4-, 5-, 6-, 7-, 8- or 9-membered cycloaliphatic group which optionally can be bridged with 1 or 2 linear or branched, optionally substituted $C_{1-5}$ alkylene groups or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system;

$R^6$ denotes:

a linear or branched, saturated or unsaturated, optionally substituted $C_{1-10}$ aliphatic group;

an unsaturated or saturated, optionally substituted 3-, 4-, 5-, 6-, 7-, 8- or 9-membered cycloaliphatic group which optionally can be bridged with 1 or 2 linear or branched, optionally substituted $C_{1-5}$ alkylene groups or fused with a saturated, unsaturated or aromatic, optionally substituted mono- or bicyclic ring system, or both; an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system;

$R^7$ denotes:

a group selected from the group consisting of cyclopropyl, cyclobutyl, cyclopentyl, cyclohexyl, cycloheptyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl, wherein said group optionally can be substituted with 1, 2, 3, 4 or 5 substituents independently selected from the group consisting of oxo (═O), thioxo (═S), —OH, —O—$CH_3$, —O—$C_2H_5$, —O—CH$(CH_3)_2$, —O—$CH_2$—$CH_2$—$CH_3$, —O—C$(CH_3)_3$, —O—$CH_2$—$CH_2$—$CH_2$—$CH_3$, —O—$CF_3$, —S—$CF_3$, —S—$CF_2$H, —S—$CFH_2$, methyl, ethyl, n-propyl, isopropyl, n-butyl, sec-butyl, isobutyl, tert-butyl, n-pentyl, n-hexyl, n-heptyl, —C(═O)—$CH_3$, —C(═O)—$C_2H_5$, —C(═O)—C$(CH_3)_3$, —C(═O)—$CF_3$, —C(═O)—$C_2F_5$, —C(═O)—$NH_2$, —C(═O)—NH—$CH_3$, —C(═O)—NH—$C_2H_5$, —C(═O)—NH—C$(CH_3)_3$, —C(═O)—N$(CH_3)_2$, —C(═O)—N$(C_2H_5)_2$, —S(═O)$_3$—$CH_3$, —S(═O)$_2$—$C_2H_5$, —NH—S(═O)$_2$—$CH_3$, —S(═O)$_2$—NH—$CH_3$ and —S(═O)$_2$—$NH_2$;

or a group selected from the group consisting of phenyl, naphthyl, and [1,2,3,4]-tetrahydronaphthyl, wherein said group optionally can be substituted with 1, 2, 3, 4 or 5 substituents independently selected from the group consisting of F, Cl, Br, I, —CN, —$CF_3$, —$SF_5$, —OH, —O—$CH_3$, —O—$C_2H_5$, —O—CH$(CH_3)_3$, —O—$CH_2$—$CH_2$—$CH_3$, —O—C$(CH_3)_3$, —O—$CH_2$—$CH_2$—$CH_2$—$CH_3$, —$NO_2$, —O—$CF_3$, —S—$CF_3$, —S—$CF_2$H, —S—$CFH_2$, SH, —S—$CH_3$, —S—$C_2H_5$, —S—CH$(CH_3)_2$, —S—$CH_2$—$CH_2$—$CH_3$, —S—C$(CH_3)_3$, methyl, ethyl, n-propyl, isopropyl, n-butyl, sec-butyl, isobutyl, tert-butyl, n-pentyl, —C$(CH_3)_2$—$C_2H_5$, n-hexyl, n-heptyl, —NH—C(═O)—O—$CH_3$, —NH—C(═O)—O—$C_2H_5$, —NH—C(═O)—O—C$(CH_3)_3$, —O—$CH_2$—$CH_3$—$CH_2$—$CH_3$, —NH—C(═O)—$CH_3$, —NH—C(═O)—$C_2H_5$, —NH—C(═O)—C$(CH_3)_3$, —C(═O)—OH, —($CH_2$)—C(═O)—OH, —C(═O)—O—$CH_3$, —C(═O)—O—$CH_2$—$CH_3$, —C(═O)—O—CH$(CH_3)_2$, —C(═O)—O—C$(CH_3)_3$, —NH—$CH_3$, —NH—$C_2H_5$, —NH—CH$(CH_3)_2$, —NH—C$(CH_3)_3$, —N$(CH_3)_2$, —N$(C_2H_5)_2$, —N($CH_3$)($C_2H_5$), —C(═O)—H, —C(═O)—$CH_3$, —C(═O)—$C_2H_5$, —C(═O)—C$(CH_3)_3$, —C(═O)—$CF_3$, —C(═O)—$C_2F_5$, —C(═O)—$NH_3$, —C(═O)—NH—$CH_3$, —C(═O)—NH—$C_2H_5$, —C(═O)—NH—C$(CH_3)_3$, —C(═O)—N$(CH_3)_2$, —C(═O)—N$(C_2H_5)_2$, —S(═O)$_2$—$CH_3$, —S(═O)$_2$—$C_2H_5$, —NH—S(═O)$_2$—$CH_3$, —S(═O)$_3$—NH—$CH_3$, —S(═O)$_2$—$NH_2$, —S(═O)$_2$—NH-phenyl, phenyl and benzyl, wherein the cyclic moiety of the groups —S(═O)$_2$—NH-phenyl, phenyl and benzyl optionally can be substituted with 1, 2, 3, 4 or 5 substituents independently selected from the group consisting of F, Cl, Br, —OH, —$CF_3$, —$SF_5$, —$NO_2$, methyl, ethyl, n-propyl, isopropyl, n-butyl, sec-butyl, isobutyl, tert-butyl, n-pentyl, n-hexyl, n-heptyl, —O—$CH_3$, —O—$C_2H_5$, —O—CH$(CH_3)_3$, —O—$CH_2$—$CH_3$—$CH_3$, —O—C$(CH_3)_3$, —O—$CH_2$—$CH_2$—$CH_2$—$CH_3$, —O—$CF_3$, —S—$CF_3$, phenyl and —O-benzyl;

$R^8$ denotes

—($CHR^{19}$)—$V_p$—$(CH_2)_q$—$(CH_2)_r$—$W_s$—$R^{20}$, wherein p=0 or 1;

q=0, 1 or 2;

r=0, 1 or 2;

s=0 or 1; and

V and W each independently denote O, S, NH, —NH—$CH_3$, —NH—$C_2H_5$, —NH—CH$(CH_3)_2$;

—(CH═CH)—$R^{21}$;

—($CR^{22}R^{23}$)—$Y_t$—$(CR^{24}R^{25})_u$—$(CH_2)_v$—C(═O)—$OR^{26}$, wherein t=0 or 1, u=0 or 1;

v=0 or 1, and Y denotes O, S, NH, —NH—$CH_3$, —NH—$C_2H_5$, —NH—CH$(CH_3)_2$;

—($CHR^{27}$)—O—C(═O)—$R^{28}$;

—CH[$(CH_2)R^{29}$][NH—S(═O)$_2$—$R^{30}$];

—CH[$(CH_2)R^{31}$][NH—C(═O)—O—$R^{32}$];

a linear or branched, saturated or unsaturated, optionally substituted $C_{1-10}$ aliphatic group selected from the group consisting of methyl, ethyl, n-propyl, isopropyl, n-butyl, sec-butyl, isobutyl, tert-butyl, n-pentyl, sec-pentyl, 3-pentyl, —($CH_2$)—($CH_2$)—(C$(CH_3)_3$), n-hexyl, 2-hexyl, 3-hexyl, n-heptyl, 2-heptyl, 3-heptyl, 4-heptyl, n-octyl, —($CH_2$)—(CH)($C_2H_5$)—($CH_2$)—($CH_2$)—($CH_2$)—($CH_3$), vinyl, 1-propenyl, 2-propenyl, 1-butenyl, 2-butenyl and 3-butenyl;

an unsaturated or saturated, optionally substituted 3-, 4-, 5-, 6-, 7-, 8- or 9-membered cycloaliphatic group that optionally can be bridged with 1 or 2 linear or branched, optionally substituted $C_{1-5}$ alkylene groups, or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system;

$R^9$ and $R^{10}$ each independently denote a linear or branched, saturated or unsaturated, optionally substituted $C_{1-10}$ aliphatic group; R 1, $R^{13}$, $R^{15}$, $R^{17}$, $R^{19}$, $R^{22}$, $R^{23}$, $R^{24}$, $R^{25}$ and $R^{26}$ each independently denote a hydrogen or a linear or branched, saturated or unsaturated, optionally substituted $C_{1-10}$ aliphatic group;

$R^{12}$, $R^{28}$ and $R^{32}$ each independently denote a linear or branched, saturated or unsaturated, optionally substituted $C_{1-10}$ aliphatic group;

$R^{14}$, $R^{16}$, $R^{18}$ and $R^{20}$ each independently denote a linear or branched, saturated or unsaturated, optionally substituted $C_{1-10}$ aliphatic group;

an unsaturated or saturated, optionally substituted 3-, 4-, 5-, 6-, 7-, 8- or 9-membered cycloaliphatic group that optionally can be bridged with 1 or 2 linear or branched, optionally substituted $C_{1-5}$ alkylene groups, or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system; and $R^{21}$, $R^{27}$, $R^{29}$, $R^{30}$ and $R^{31}$ each independently denote an unsaturated or saturated, optionally substituted 3-, 4-, 5-, 6-, 7-, 8- or 9-membered cycloaliphatic group which optionally can be bridged with 1 or 2 linear or branched, optionally substituted $C_{1-5}$ alkylene groups, or fused with a saturated, unsaturated or aromatic, optionally substituted mono- or bicyclic ring system, or both; or an optionally substituted 6- or 10-membered aryl group or optionally substituted 5- to 14-membered heteroaryl group, wherein the aryl or heteroaryl group optionally can be fused with a saturated or unsaturated, optionally substituted mono- or bicyclic ring system; wherein the above-stated $C_{1-10}$ aliphatic groups each independently may optionally be substituted with 1, 2, 3, 4 or 5 substituents independently selected from the group consisting of F, Cl, Br, I, —CN, —$NO_2$, —OH, —SH and —$NH_2$;

the above-stated cycloaliphatic groups each independently can optionally be substituted with 1, 2, 3, 4 or 5 substituents independently selected from the group consisting of oxo (═O), thioxo (═S), F, Cl, Br, I, —CN, —$CF_3$, —$SF_5$, —OH, —O—$C_{1-5}$alkyl, —$NH_2$, —$NO_2$, —O—$CF_3$, —S—$CF_3$, —S—$CF_2$H, —S—$CFH_2$, —SH, —S—$C_{1-5}$-alkyl, —$C_{1-5}$alkyl, —C(═O)—OH, —($CH_2$)—C(═O)—OH, —C(═O)—O—$C_{1-5}$alkyl, —($CH_2$)—C(═O)—O—$C_{1-5}$alkyl, —O—C(═O)—$C_{1-5}$alkyl, —NH—$C_{1-5}$alkyl, —N($C_{1-5}$alkyl)$_2$, —NH-phenyl, —NH-pyridinyl, —N($C_{1-5}$alkyl)-phenyl, —N($C_1$-5alkyl)-pyridinyl, —NH—C(═O)—O—$C_{1-5}$alkyl, —C(═O)—H, —C(═O)—$C_{1-5}$alkyl, —C(═O)—$C_{1-5}$-perfluoroalkyl, —C(═O)—$NH_2$, —C(═O)—NH—$C_{1-5}$alkyl, C(═O)—N—($C_{1-5}$alkyl)$_2$, —S(═O)$_2$—$C_{1-5}$alkyl, —S(═O)$_2$-phenyl, —NH—S(═O)$_2$—$C_{1-5}$alkyl, —S(═O)$_2$—NH—$C_{1-5}$alkyl, —S(═O)$_2$—$NH_2$, —S(═O)$_2$—NH-phenyl, cyclohexyl, cyclopentyl, pyridinyl, [1,2,5]-thiadiazolyl, pyridazinyl, —($CH_2$)-benzo[b]furanyl, —O-phenyl, —O-benzyl, phenyl and benzyl, wherein the cyclic moiety of the groups —S(═O)$_2$—NH-phenyl, —NH-phenyl, —NH-pyridinyl, —N($C_{1-5}$alkyl)phenyl, —N($C_{1-5}$alkyl)pyridinyl, pyridinyl, cyclopentyl, [1,2,5]-thiadiazolyl, cyclohexyl, pyridazinyl, —S(═O)$_2$-phenyl, —O-phenyl, —O-benzyl, phenyl, —($CH_2$)-benzo[b]furanyl and benzyl optionally can be substituted with 1, 2, 3, 4 or 5 substituents independently selected from the group consisting of F, Cl, Br, —OH, —$CF_3$, —$SF_5$, —CN, —$NO_2$, —$C_{1-5}$alkyl, —O—$C_{1-5}$alkyl, —O—$CF_3$, —S—$CF_3$, phenyl and —O-benzyl, and comprise 1, 2, 3, 4 or 5 heteroatom(s) mutually independently selected from the group consisting of oxygen, nitrogen and sulfur;

the above-stated $C_{1-5}$-alkylene groups each independently may optionally be substituted with 1, 2, 3, 4 or 5 substituents independently selected from the group consisting of F, Cl, Br, I, —CN, —$NO_2$, —OH, —SH and —$NH_2$;

the rings of the above-stated mono- or polycyclic ring systems each independently may optionally be substituted with 1, 2, 3, 4 or 5 substituents independently selected from the group consisting of oxo (═O), thioxo (═S), F, Cl, Br, I, —CN, —$CF_3$, —$SF_5$, —OH, —O—$C_{1-5}$alkyl —$NH_2$, —$NO_2$, —O—$CF_3$, —S—$CF_3$, —S—$CF_2$H, —S—$CFH_2$, —SH, —S—$C_{1-5}$-alkyl, —$C_{1-5}$alkyl, —C(═O)—OH, —($CH_2$)—C(═O)—OH, —C(═O)—O—$C_{1-5}$alkyl, —($CH_2$)—C(═O)—O—$C_{1-5}$alkyl, —O—C(═O)—$C_{1-5}$alkyl, —NH—$C_{1-5}$alkyl, —N($C_{1-5}$alkyl)$_2$, —NH-phenyl, —NH— pyridinyl, —N($C_{1-5}$alkyl)-phenyl, —N($C_{1-5}$alkyl)-pyridinyl, —NH—C(═O)—O—$C_{1-5}$alkyl, —C(═O)—H, —C(═O)—$C_{1-5}$alkyl, —C(═O)—$C_{1-5}$-perfluoroalkyl, —C(═O)—$NH_2$, —C(═O)—NH—$C_{1-5}$alkyl, C(═O)—N—($C_{1-5}$ alkyl)$_2$, —S(═O)$_2$—$C_{1-5}$alkyl, —S(═O)$_2$-phenyl, —NH—S(═O)$_2$—$C_{1-5}$alkyl, —S(═O)$_2$—NH—$C_{1-5}$alkyl, —S(═O)$_2$—$NH_2$, —S(═O)$_2$—NH-phenyl, cyclohexyl, cyclopentyl, pyridinyl, [1,2,5]-thiadiazolyl, pyridazinyl, —($CH_2$)-benzo[b]furanyl, —O-phenyl, —O-benzyl, phenyl and benzyl, wherein the cyclic moiety of the groups —S(═O)$_2$—NH-phenyl, —NH— phenyl, —NH-pyridinyl, —N($C_{1-5}$alkyl)phenyl, —N($C_{1-5}$alkyl)pyridinyl, pyridinyl, cyclopentyl, [1,2,5]-thiadiazolyl, cyclohexyl, pyridazinyl, —S(═O)$_2$-phenyl, —O-phenyl, —O-benzyl, phenyl, —($CH_2$)-benzo[b]furanyl and benzyl optionally can be substituted with 1, 2, 3, 4 or 5 substituents independently selected from the group consisting of F, Cl, Br, —OH, —$CF_3$, —$SF_5$, —CN, —$NO_2$, $C_{1-5}$alkyl, —O—$C_{1-5}$alkyl, —$NH_2$, —O—$CF_3$, —S—$CF_3$, phenyl and —O-benzyl;

the rings of the above-stated mono- or bicyclic ring systems are each independently 5-, 6- or 7-membered and each independently may optionally comprise as ring member(s), 1, 2, 3, 4 or 5 heteroatom(s) independently selected from the group consisting of oxygen, nitrogen and sulfur; the above-stated aryl or heteroaryl groups each independently may optionally be substituted with 1, 2, 3, 4 or 5 substituents independently selected from the group consisting of F, Cl, Br, I, —CN, —$CF_3$, —$SF_5$, —OH, —O—$C_{1-5}$alkyl —$NH_2$, —$NO_2$, —O—$CF_3$, —S—$CF_3$, —S—$CF_2$H, —S—$CFH_2$, —SH, —S—$C_{1-5}$-alkyl, —$C_{1-5}$alkyl, —C(═O)—OH, —($CH_2$)—C(═O)—OH, —C(═O)—O—$C_{1-5}$alkyl, —($CH_2$)—C(═O)—O—$C_{1-5}$alkyl, —O—C(═O)—$C_{1-5}$alkyl, —NH—$C_{1-5}$alkyl, —N($C_{1-5}$alkyl)$_2$, —NH—C(═O)—O—$C_{1-5}$alkyl, —NH—C(═O)—$C_{1-5}$alkyl, —C(═O)—H, —C(═O)—$C_{1-5}$-alkyl, —C(═O)—$C_{1-5}$-perfluoroalkyl, —C(═O)—$NH_2$, —C(═O)—NH—$C_{1-5}$alkyl, C(═O)—N—($C_{1-5}$alkyl)$_2$, —S(═O)$_2$—$C_{1-5}$alkyl, —S(═O)$_2$-phenyl, —NH—S(═O)$_2$—$C_{1-5}$alkyl, —S(═O)$_2$—NH—$C_{1-5}$alkyl, —S(═O)$_2$—$NH_2$, —S(═O)$_2$—NH-phenyl, cyclohexyl, cyclopentyl, pyridinyl, —($CH_2$)-benzo[b]furanyl, —O-phenyl, —O-benzyl, phenyl and benzyl, wherein the cyclic moiety of the groups pyridinyl, cyclopentyl, cyclohexyl, pyridazinyl, —S(═O)$_2$-phenyl, —S(═O)$_2$—NH-phenyl, —O-phenyl, —O-benzyl, phenyl, —($CH_2$)-benzo[b]furanyl, optionally can be substituted with 1, 2, 3, 4 or 5 substituents independently selected from the group consisting of F, Cl, Br, —OH, —$CF_3$, —$SF_5$, —$NO_2$, $C_{1-5}$alkyl, —O—$C_{1-5}$alkyl, —O—$CF_3$, —S—$CF_3$, phenyl and -o-benzyl;

and the above-stated heteroaryl groups each independently may optionally comprise as ring member(s), 1, 2, 3, 4 or 5 heteroatom(s) independently selected from the group consisting of oxygen, nitrogen and sulfur; or a pharmaceutically acceptable salt or solvate thereof.

Preferably, in a contemplated compound, $R^1$ denotes a group selected from the group consisting of phenyl, naphthyl, (1,3)-benzodioxolyl, (1,4)-benzodioxanyl, 2H-chromenyl, thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, [1,2,3]-thiadiazolyl, [1,2,4]-oxadiazolyl, benzo[2,1,3]thiadiazolyl, [1,2,3]-benzothiadiazolyl, [2,1,3]-benzoxadiazolyl, [1,2,3]-benzoxadiazolyl, [1,2,3,4]-tetrahydronaphthyl, [1,2,3,4]-tetrahydroquinolinyl, [1,2,3,4]-tetrahydroisoquinolinyl, [1,2,3,4]-tetrahydroquinazolinyl, [3,4]-dihydro-2H-1,4-benzoxazinyl, oxazolyl, isoxazolyl, pyridazinyl, pyrazinyl, pyrimidinyl, indazolyl, quinazolinyl, quinolinyl and isoquinolinyl. That $R^1$ group can optionally be substituted with 1, 2, 3, 4 or 5 substituents independently selected from the group consisting of F, Cl, Br, I, —CN, $-CF_3$, $-SF_5$, —OH, $-O-CH_3$, $-O-C_2H_5$, $-O-CH(CH_3)_2$, $-O-CH_2-CH_2-CH_3$, $-O-C(CH_3)_3$, $-O-CH_2-CH_2-CH_2-CH_3$, $-NO_2$, $-O-CF_3$, $-S-CF_3$, $-S-CF_2H$, $-S-CFH_2$, —SH, $-S-CH_3$, $-S-C_2H_5$, $-S-CH(CH_3)_2$, $-S-CH_2-CH_2-CH_3$, $-S-C(CH_3)_3$, methyl, ethyl, n-propyl, isopropyl, n-butyl, sec-butyl, isobutyl, tert-butyl, n-pentyl, n-hexyl, n-heptyl, $-NH-C(=O)-O-CH_3$, $-NH-C(=O)-O-C_2H_5$, $-NH-C(=O)-O-C(CH_3)_3$, $-NH-C(=O)-CH_3$, $-NH-C(=O)-C_2H_5$, $-NH-C(=O)-C(CH_3)_3$, $-C(=O)-H$, $-C(=O)-CH_3$, $-C(=O)-C_2H_5$, $-C(=O)-C(CH_3)_3$, $-C(=O)-CF_3$, $-C(=O)-C_2F_5$, $-C(=O)-NH_2$, $-C(=O)-NH-CH_3$, $-C(=O)-NH-C_2H_5$, $-C(=O)-NH-C(CH_3)_3$, $-C(=O)-N(CH_3)_2$, $-C(=O)-N(C_2H_5)_2$, $-S(=O)_3-CH_3$, $-S(=O)_3-C_2H_5$, $-NH-S(=O)_2-CH_3$, $-S(=O)_3-NH-CH_3$, $-S(=O)_2-NH_2$, $-S(=O)_2-$NH-phenyl and -benzyl, wherein the cyclic moiety of each phenyl or benzyl group independently can optionally be substituted with 1,2,3,4, or 5 substituents independently selected from the group consisting of F, Cl, Br, $-CF_3$, $-SF_5$, $-NO_2$, methyl, ethyl, n-propyl, isopropyl, n-butyl, sec-butyl, isobutyl, tert-butyl, n-pentyl, n-hexyl, n-heptyl, $-O-CH_3$, $-O-C_2H_5$, $-O-CH(CH_3)_3$, $-O-CH_2-CH_2-CH_3$, $-O-C(CH_3)_3$, $-O-CH_2-CH_2-CH_2-CH_3$, $-O-CF_3$, $-S-CF_3$, phenyl and —O-benzyl.

It is also preferred that the $R^2$ group of a contemplated compound denote $C(=S)-NH-R^3$; $-C(=O)-NH-R^4$; $-S(=O)_2R^5$; $-(CH_2)-C(=O)-NH-R^6$; $-(CH_2)-O-R^7$, $-(CH_2)-S-R^7$, $-(CH_2)-NH-R^7$, $-(CH_2)-N(CH_3)-R^7$, $-(CH_2)-(CH_2)-O-R^7$, $-(CH_2)-(CH_2)-S-R^7$, $-(CH_2)-NH-R^7$, $-(CH_2)-N(CH_3)-R^7$, $-(CH_2)-(CH_2)-(CH_2)-O-R^7$, $-(CH_2)-(CH_2)-(CH_2)-S-R^7$, $-(CH_2)-(CH_2)-(CH_2)-NH-R^7$, $-(CH_2)-(CH_2)-(CH_2)-N(CH_3)-R^7$, $-(CH_2)-O-(CH_2)-R^7$, $-(CH_2)-S-(CH_2)-R^7$, $-(CH_2)-NH-(CH_2)-R^7$, $-C(=O)-R^8$, or $-S(=O)_2-NR^9R^{10}$.

Pharmaceutical Compositions

A contemplated compound useful in the invention can be provided for use by itself, or as a pharmaceutically acceptable salt. Regardless of whether in the form of a salt or not, a contemplated composition is typically dissolved or dispersed in a pharmaceutically acceptable diluent that forms a pharmaceutical composition and that pharmaceutical composition is administered the CNS and/or other cells.

A contemplated compound can be used in the manufacture of a medicament (pharmaceutical composition) that is useful at least for inhibiting tau protein phosphorylation in mammalian cells and mammalian cell preparations. A contemplated compound can be used in the manufacture of a medicament that is useful at least for inhibiting the interaction of FLNA with α7nAChR and TLR4, as well as of $A\beta_{42}$ with α7nAChR in mammalian cells and mammalian cell preparations.

A contemplated pharmaceutical composition contains an effective amount of a contemplated compound or a pharmaceutically acceptable salt thereof dissolved or dispersed in a physiologically tolerable carrier. Such a composition can be administered to mammalian cells in vitro as in a cell culture, or in vivo as in a living, host mammal in need.

A contemplated composition is typically administered a plurality of times over a period of days. More usually, a contemplated composition is administered once or twice daily. It is contemplated that once administration of a contemplated compound has begun the compound will be administered chronically for the duration of the study being carried out or for a recipient's lifetime.

A contemplated compound can bind to FLNA at a 100 femtomolar concentration and effectively inhibit cytokine release from LPS-stimulated astrocytes in vitro. A contemplated compound is more usually utilized at picomolar to micromolar amounts. Thus, an effective amount of a contemplated compound present in a contemplated pharmaceutical composition is that which provides a concentration of about 100 femtomolar to about micromolar to a host animal's blood stream or to an in vitro cell medium in practicing a contemplated method of the invention. A more usual amount is about picomolar to about micromolar. A still more usual amount is about picomolar to about nanomolar. A skilled worker can readily determine an appropriate dosage level of a contemplated compound to inhibit a desired amount of tau protein phosphorylation.

A contemplated pharmaceutical composition can be administered orally (perorally), parenterally, by inhalation spray in a formulation containing conventional nontoxic pharmaceutically acceptable carriers, adjuvants, and vehicles as desired. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences*, Mack Publishing Co., Easton, Pennsylvania; 1975 and Liberman, H. A. and Lachman, L., Eds., Pharmaceutical Dosage Forms, Marcel Decker, New York, N.Y., 1980.

For injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution, phosphate-buffered saline. Liquid pharmaceutical compositions include, for example, solutions suitable for parenteral administration. Sterile water solutions of an active component or sterile solution of the active component in solvents comprising water, ethanol, or propylene glycol are examples of liquid compositions suitable for parenteral administration.

In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Sterile solutions can be prepared by dissolving the active component in the desired solvent system, and then passing the resulting solution through a membrane filter to sterilize it or, alternatively, by dissolving the sterile compound in a previously sterilized solvent under sterile conditions.

Solid dosage forms for oral administration can include capsules, tablets, pills, powders, and granules. In such solid dosage forms, a contemplated compound is ordinarily combined with one or more excipients appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets, capsules and pills can additionally be prepared with enteric coatings.

A mammal in need of treatment and to which a pharmaceutical composition containing a contemplated compound is administered can be a primate such as a human, an ape such as a chimpanzee or gorilla, a monkey such as a cynomolgus monkey or a macaque, a laboratory animal such as a rat, mouse or rabbit, a companion animal such as a dog, cat, horse, or a food animal such as a cow or steer, sheep, lamb, pig, goat, llama or the like. Where in vitro mammalian cell contact is contemplated, a CNS tissue culture of cells from an illustrative mammal is often utilized, as is illustrated hereinafter.

Preferably, the pharmaceutical composition is in unit dosage form. In such form, the composition is divided into unit doses containing appropriate quantities of the active agent. The unit dosage form can be a packaged preparation, the package containing discrete quantities of the preparation, for example, in vials or ampules.

Several useful contemplated compounds are amines and can typically be used in the form of a pharmaceutically acceptable acid addition salt derived from an inorganic or organic acid. Exemplary salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Other compounds useful in this invention that contain acid functionalities can also form salts with a base. Illustrative bases include amine bases such as mono-, di- and tri-$C_1$-$C_4$-alkyl or hydroxyalkyl amines like triethyl amine, dimethylamine, 2-hydroxyethylamine, and dimethyl-2-hydroxyethylamine, and bases such as alkali metal, alkaline earth metal quaternary $C_1$-$C_6$-alkyl ammonium hydroxides, such as sodium, potassium, calcium, magnesium and tetramethylammonium hydroxides. Basic salts such as alkali metal or alkaline earth metal and ammonium carbonates and phosphates are also contemplated.

The reader is directed to Berge, *J. Pharm. Sci.* 68(1):1-19 (1977) for lists of commonly used pharmaceutically acceptable acids and bases that form pharmaceutically acceptable salts with pharmaceutical compounds.

In some cases, the salts can also be used as an aid in the isolation, purification or resolution of the compounds of this invention. In such uses, the acid used and the salt prepared need not be pharmaceutically acceptable.

Discussion

The discussion that follows illustrates compounds and compositions that contain one or more of those compounds that bind the scaffolding protein FLNA, and particularly the VAKGL (SEQ ID NO: 1) pentapeptide binding site present in the FLNA protein, and inhibit the phosphorylation of the tau protein. Some compounds of such compositions also disrupt the toxic signaling of amyloid-P42 ($A\beta_{42}$), as well as reduce the inflammation caused by both $A\beta_{42}$ and ongoing neurodegeneration. These compounds diminish many aspects of AD-like pathology, including impairments in normal receptor functioning.

Initial studies were carried out with compounds of each of the four structural series using Compounds A0033, A0040, A0053, A0068, B0055, C0105, C0114, C0137 and C0138 as illustrative or exemplary. Additional studies were also carried out using Compounds C0134, Compound A, Compound B, and Compound C. The results shown in the Figures and discussed hereinafter are indicative of the generality of results obtained using these structurally very different compounds. Initial results indicated that the compounds appear to be orally available and well tolerated because notable plasma and CNS levels were produced but negligible side effects were noted at 2 g/kg administered orally in rats. Those results also indicated similar activities among the nine compounds, with Compounds C0105 and C0114 being used for further studies because of their high activity, ease of synthesis, solubility and absence of enantiomers.

The fact that $A\beta_{42}$ binding blocks $Ca^{+2}$ influx by α7nAChRs [Wang et al., *J Neurosci* 35:10961-10973 (2009); Wang et al., *Biol Psychiatry* 67:522-530 (2010)] suggests that one conformational change in α7nAChRs may occur in the interface between extracellular and transmembrane domains, the area governing channel opening/desensitization [Bouzat et al., *J Neurosci* 28:7808-7819 (2008)]. This conformational change likely exposes a positive charge-rich transmembrane region close to the $A\beta_{42}$ binding site. FLNA binds this positive charge to stabilize the bound $A\beta_{42}$ and additional binding of $A\beta_{42}$ peptides, leading to eventual internalization of $A\beta_{42}$-α7nAChR complexes [(Nagele et al., *Neuroscience* 110:199-211(2002)]. Compound C0105 disruption of the FLNA-α7nAChR interaction stops the pathological signaling and stops $A\beta_{42}$ high-affinity anchoring to the receptor.

Using organotypic frontocortical slice cultures of adult rats, AR signaling through the α7 nicotinic acetylcholine receptor (α7nAChR) is shown to require the recruitment of FLNA. By binding a critical pentapeptide segment of FLNA, these compounds block the FLNA-α7nAChR association and the signaling cascade of $A\beta_{42}$. In the illustrative $A\beta_{42}$-treated organotypic frontocortical slice cultures, exemplary Compounds C0105 and C0114 each separately dramatically reduce phosphorylation of tau at all three phosphorylation sites of tau found in neurofibrillary tangles (FIGS. 4D, 6B and 6C), and fully restore normal functioning of α7nAChR and downstream N-methyl-D-aspartate receptors (NMDARs), critical for learning and memory.

Figures 5, 5A:
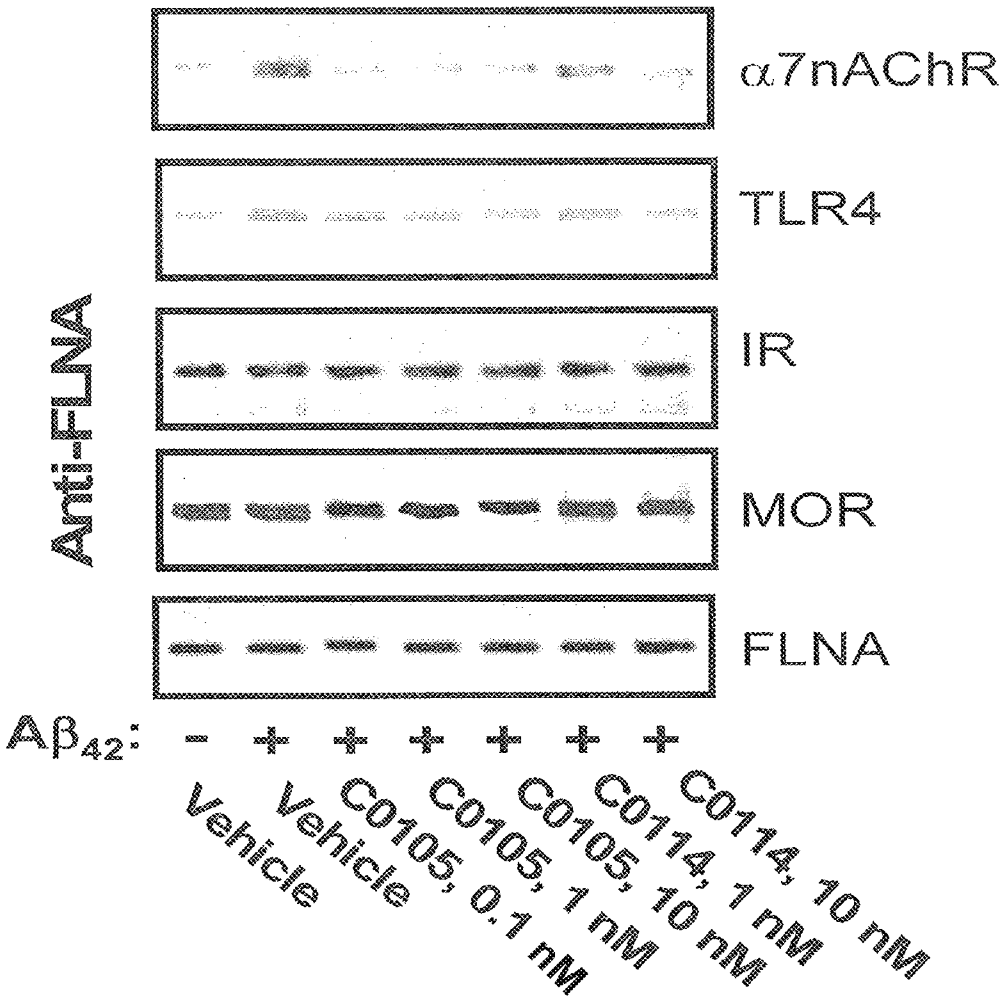
FIG. 5 in three panels illustrates that compounds C0105 and C0114 reduce $A\beta_{42}$-induced increases in association of FLNA with α7nAChR and TLR4. Synaptosomes were prepared from organotypic FCX slice cultures treated with 0.1 or 1 nM concentrations of compounds simultaneously with $A\beta_{42}$ and analyzed for their α7nAChR-FLNA complex contents. The extent of FLNA association with α7nAChR, TLR4, IR and MOR was assessed in the solubilized synaptosomes by immunoprecipitating with immobilized anti-FLNA and Western blot detection (FIG. 5A) using antibodies specific to each receptor. Blots were analyzed by densitometric quantitation (FIG. 5B). Although $A\beta_{42}$ greatly increased association of α7nAChR and TLR4 with FLNA, levels of IR and MOR association with FLNA were unchanged. C0105 and C0114 decreased these $A\beta_{42}$-induced increases. Percent inhibition is depicted in FIG. 5C. n=3. Data are means±SEM. **p<0.05, *p<0.01 vs. $A\beta_{42}$ alone; #p<0.01 vs. vehicle.
Figure 5B:
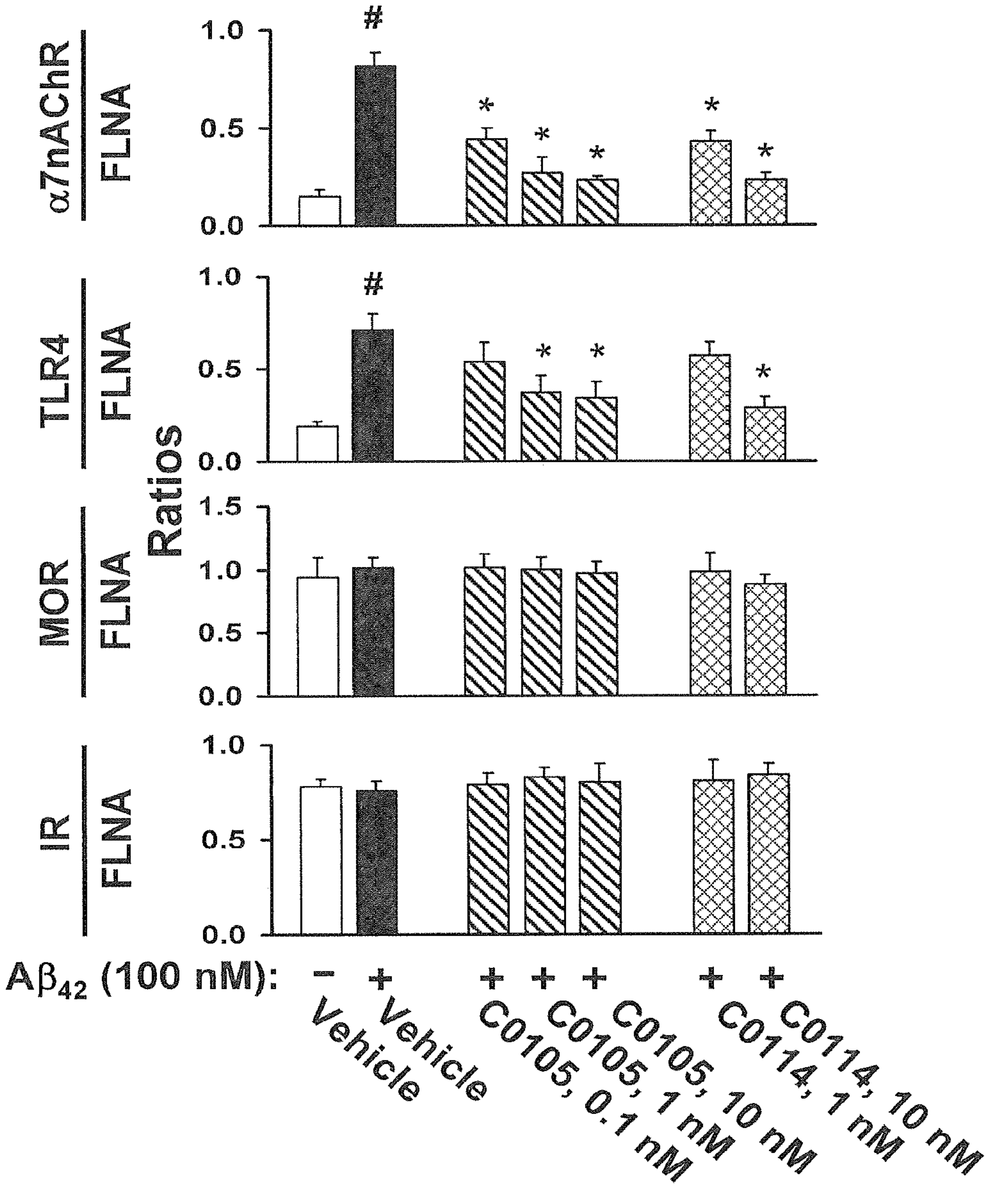
Figure 5C:
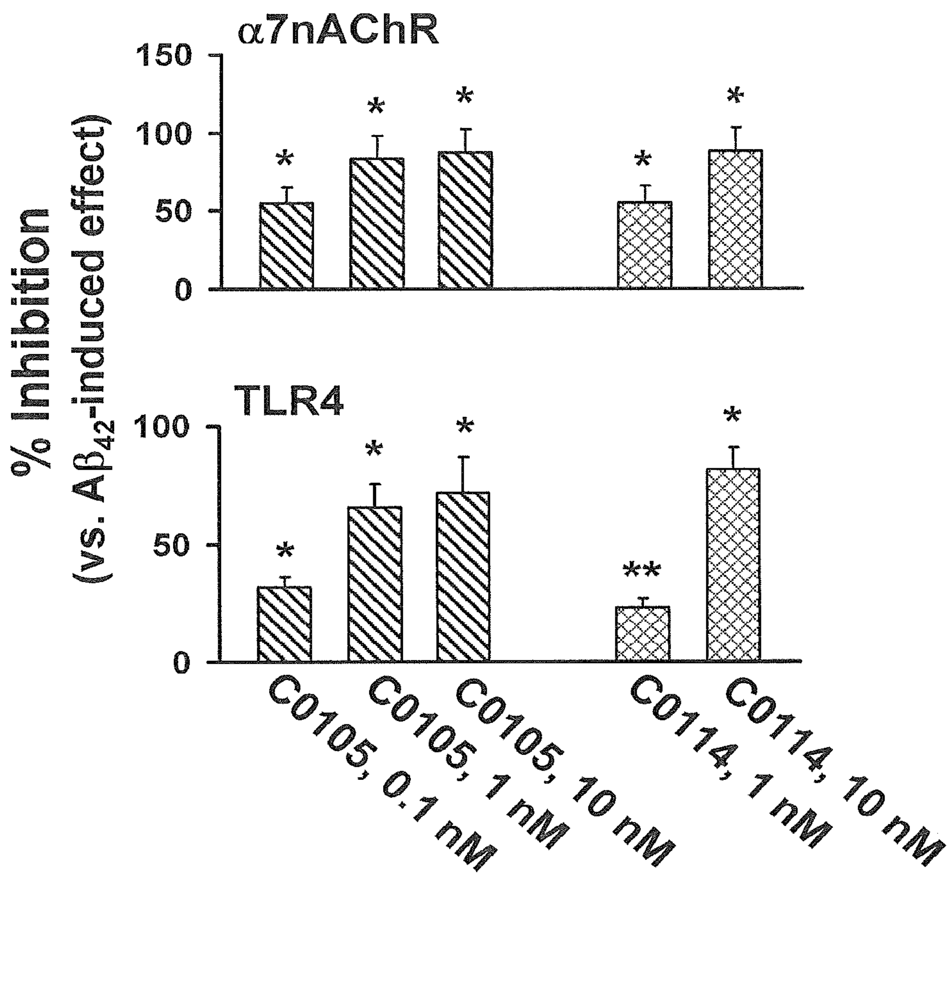

Further, indicative of the insulin resistance common to AD patients [Neumann et al., *Curr Alzheimer Res* 5:438-447 (2008)], the function of $A\beta_{42}$-impaired IRs in the illustrative slice cultures was also restored by each of exemplary Compounds C0105 and C0114 (FIG. 5B). These compounds, with a novel mechanism of disrupting the toxic signaling of $A\beta_{42}$, confer a restoration of multiple $A\beta_{42}$-induced dysfunctions. Moreover, disabling the Aβ-induced α7nAChR signaling without directly affecting α7nAChRs avoids altering the sensitivity or cell surface level of the receptors, an insidious problem with using chronic receptor agonists or antagonists.

In an ICV $A\beta_{42}$ infusion mouse model of Alzheimer's disease, Compound C0105 greatly reduced tau phosphorylation, multiple $A\beta_{42}$-induced signaling impairments, inflammatory cytokine release as well as neurofibrillary tangles and $A\beta_{42}$ aggregates. Illustrative Compound C0105 accomplished all these effects via its high-affinity binding to FLNA. $A\beta_{42}$ dramatically increases FLNA association with α7nAChR to enable its binding and toxic signaling through this receptor, and illustrative Compound C0105 prevented this cascade.

The anti-inflammatory effect of Compound C0105 occurs by a similar disruption of $A\beta_{42}$-induced FLNA association with TLR4. $A\beta_{42}$ increases FLNA association with TLR4, and this association appears to be critical to inflammatory cytokine production due to $A\beta_{42}$ exposure, because illustrative Compound C0105 nearly abolishes this cytokine production. Although $A\beta_{42}$ does not itself interact with TLR4, $A\beta_{42}$ binds to CD14, which in turn binds TLR4 to produce the inflammation noted in AD [Reed-Geaghan et al., *J. Neurosci.* 29(38):11982-11992 (Sep. 23, 2009)].

The normalization of function of (7nAChR, NMDAR and IRs further illustrates the broad spectrum of benefits of a contemplated compound such as Compound C0105 as a potential therapeutic for AD. Although NMDARs are downstream of α7nAChR and are likely compromised as a direct result of the $A\beta_{42}$ toxic signaling via α7nAChR, IRs are not directly downstream of α7nAChR in neural networks. Additionally, although FLNA interacts with IR, this interaction is unchanged by $A\beta_{42}$ or Compound C0105. Nevertheless, $A\beta_{42}$ impairs IR signaling, and a contemplated compound such as Compound C0105 restores that signaling, suggesting a therapeutic effect on this component of AD as well.

Current thinking points to the need for several different simultaneous approaches to treat AD. With its multitude of therapeutic effects and novel target, a contemplated compound such as Compound C0105 has great potential as a disease-modifying therapeutic for AD.

The toxicities of A42 in AD as well as in the mild cognitive impairment of senile dementia are believed by many in the field to be due to its capacity to signal through α7nAChR. This toxic signaling activates ERK2 and phosphorylates tau, a critical component of NFTs. The novel FLNA-binding compounds presented here potently suppress $A\beta_{42}$ signaling through the α7nAChR at nanomolar (nM) or sub-nM concentrations. These compounds accomplish this blockade of signaling by preventing the increased association of FLNA with α7nAChR caused by $A\beta_{42}$. Specifically, their binding may alter the conformation of FLNA so that it is not recruited to the receptor.

Further, the disabling of this interaction appears also to decrease the affinity of $A\beta_{42}$ binding to α7nAChR, as shown by decreased binding of FITC-$A\beta_{42}$ in the presence of a contemplated compound such as compounds C0105 or C0114. The resulting blockade of signaling was evidenced by decreased ERK2 activation and decreased tau phosphorylation at all three phosphorylation sites of tau found in NFTs in AD brains.

In addition to disrupting the FLNA-α7nAChR association that is increased by $A\beta_{42}$, illustrative Compounds C0105 and C0114 prevent an $A\beta_{42}$-induced association of FLNA with TLR4 (FIG. 5), the immune receptor responsible for cytokine release. This association, along with the ongoing neurodegeneration, may drive the massive inflammation in AD brains, [Lee et al., *Arch Pharm Res* 33:1539-1556 (2010)] and its disruption is the probable mechanism of action for anti-inflammatory effects of our FLNA-binding compounds [Burns et al., *Recent Patents on CNS Drug Discovery* 5:210-220 (2010)].

The anti-inflammatory activity of illustrative Compound C0105 was demonstrated in an ICV $A\beta_{42}$ infusion mouse model of AD. Levels of IL-6, TNF-α and IL-1β were decreased by 80-100% in mice receiving C0105. In addition, previous results showed that other compounds that bind the same pentapeptide region of FLNA dramatically decreased inflammatory cytokine release from LPS-stimulated primary human astrocytes [Burns et al., *Recent Patents on CNS Drug Discovery* 5:210-220 (2010)]. An anti-inflammatory property should be a great benefit in an AD therapeutic.

The fact that a contemplated compound such as Compounds C0105 and C0114 also restore normal functioning of the downstream NMDAR (FIG. 8) and the IR suggests that the benefits of preventing AR signaling via the α7nAChR are not isolated to the health of α7nAChRs, but instead can be the critical point of pathogenesis in AD. Because NMDAR signaling is essential for long-term potentiation (LTP) and hence learning and memory, maintaining normal functioning of this neurotransmitter system is crucial for preserving memory in AD.

The reason that these compounds preserve IR function remains speculative because the FLNA-IR linkage is not affected by $A\beta_{42}$, nor by these compounds and because IRs are not directly downstream of α7nAChRs. Nevertheless, preserving sensitivity of IRs to insulin (FIG. 10) represents a divergent benefit of preventing the toxic signaling of Aβ through α7nAChRs in AD pathology. Moreover, the FLNA-binding compounds presented here represent a novel and perhaps safer approach to preventing this toxic signaling without directly antagonizing or desensitizing the receptor.

Furthermore, their efficacy at low nM concentrations indicates a large window for therapeutic efficacy. Additionally, the ability to remove bound AR from α7nAChRs by decreasing the normally high affinity to the receptor [Wang et al., *J Biol Chem* 275:5626-5632 (2000)]suggests that a contemplated compound can be effective not just in preventing AD but can also provide some cognitive recovery and help stop further degeneration in later stages of AD.

Twice daily intraperitoneal administration to E129 mice with 10 mg/kg of illustrative Compound C0105 greatly reduced $A\beta_{42}$-induced increases in FLNA associations with both α7nAChR and TLR4, suppressed tau phosphorylation at all three phosphorylation sites of tau found in neurofibrillary tangles, reduced the level of $A\beta_{42}$-α7nAChR complexes, prevented the $A\beta_{42}$-induced functional impairments in α7nAChR, NMDAR and IR signaling, and suppressed inflammatory cytokine levels (FIGS. 14-24). Illustrative Compound C0105 accomplished all these effects via its high-affinity binding to FLNA. $A\beta_{42}$ dramatically increases FLNA association with α7nAChR to enable its binding and toxic signaling through this receptor.

Specific Results

Increased α7nAChR-FLNA Coupling in Frontal Cortex of AD Transgenic Mice and AD Patients Incubation of synaptosomes with $A\beta_{42}$ in vitro increases α7nAChR coupling to a scaffolding protein with 300 KDa molecular mass, which was suspected to be FLNA. Although FLNA is known to couple with many receptor proteins, this data is the first to reveal the α7nAChR-FLNA connection and suggests that AD, with elevated $A\beta_{42}$ burdens, may have increased α7nAChR-FLNA coupling. This hypothesis was directly tested in synaptosomes prepared from frontal cortices of 6-month-old AD transgenic and wild-type mice, as well as AD-control human pairs matched closely for the age and postmortem delays.

The data presented in FIG. 1 show a 3-fold increase in the abundance of α7nAChR-FLNA complexes in frontal cortex of both AD transgenic mice and AD patients. Because FLNA is known to regulate signaling of its associated receptors, increases in the α7nAChR-FLNA association induced by $A\beta_{42}$ can be related to $A\beta_{42}$-evoked α7nAChR signaling and tau phosphorylation. Thus, compounds that reduce $A\beta_{42}$-elicited α7nAChR-FLNA association may reduce neurofibrillary pathology in AD.

Ex Vivo in Synaptosomes

High-Affinity FLNA-Binding Compounds Reduce $A\beta_{42}$-Induced α7nAChR-FLNA Association, ERK2 Activation and Tau Phosphorylation Ex Vivo in Synaptosomes Nine high-affinity FLNA-binding compounds [A0033, A0040, A0053, A0068, B0055, C0105, C0114, C0137 and C0138]were assayed to determine whether they could disrupt the association of FLNA and α7nAChR in synaptosomes prepared from frontal cortices of adult rats. Synaptosomes were exposed to 100 nM $A\beta_{42}$ for 30 minutes, and with 0.1 or 1 μM compounds added either simultaneously or 10 minutes earlier. Controls were a vehicle (no $A\beta_{42}$) and an $A\beta_{42}$ alone condition.

Figures 2, 2A:
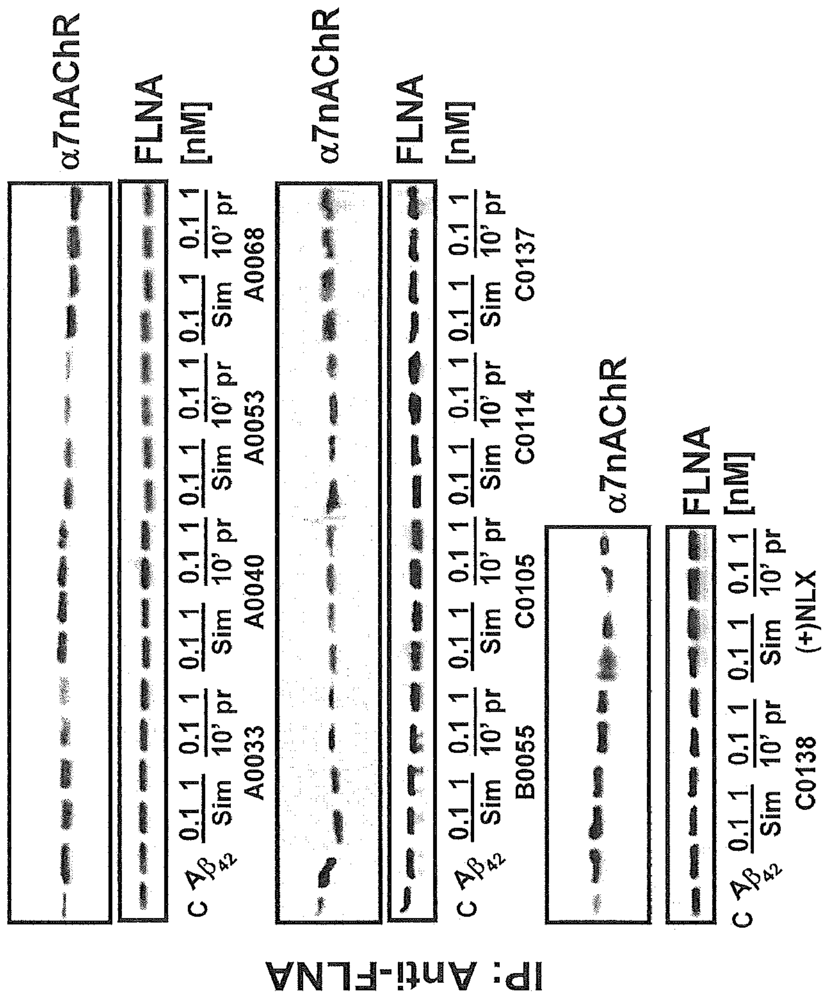
FIG. 2 in two panels as FIG. 2A and FIG. 2B, illustrates high-affinity FLNA-binding compounds reduce α7nAChR-FLNA association. Frontal cortical synaptosomes from 2-month-old rats (n=4) were treated with 0.1 or 1 nM concentrations of compounds [A0033, A0040, A0053, A0068, B0055, C0105M, C0114M, C0137M and C0138M] either simultaneously (Sim) with or 10 minutes prior (10' pr) to $A\beta_{42}$ and were analyzed for their α7nAChR-FLNA complex contents. The α7nAChR-FLNA complexes in the solubilized synaptosomes were immunoprecipitated with immobilized anti-FLNA and the α7nAChR and FLNA levels in the anti-FLNA immunoprecipitates determined by Western blotting (FIG. 2A) and quantified by densitometry (FIG. 2B). n=3. Data are means±SEM. **p<0.05, *p<0.01 vs. $A\beta_{42}$ alone. The letter designation "M" that accompanies many of the "C-series" compounds is omitted from FIG. 2, the remaining figures and most discussions of the figures and compounds hereinafter for ease in expression. Structural formulas of the compounds used in this and the other figures are provided hereinafter.
Figure 2B:
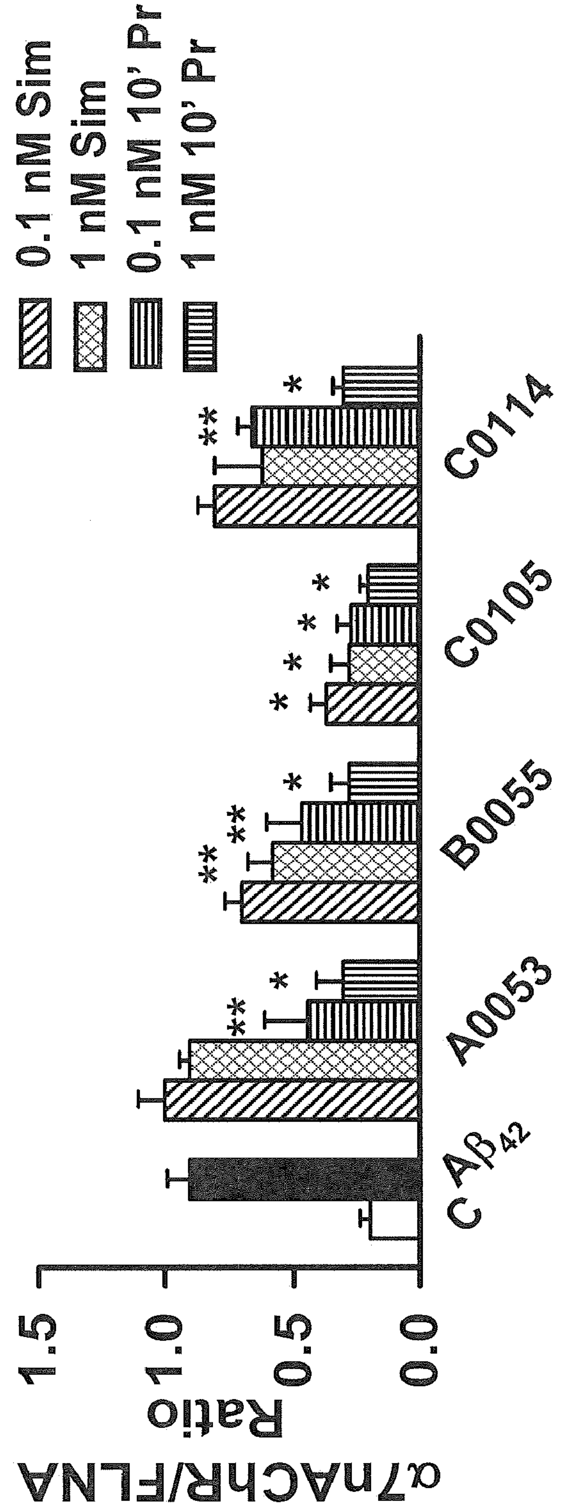

FIG. 2 shows the Western blots from all nine compounds assayed, plus (+)naloxone (NLX), as well as the quantitation of the blots for the four most active compounds. All four of those compounds reduced the α7nAChR-FLNA association with 10-minute pre-incubation, and Compound C0105 also markedly reduced this coupling with simultaneous administration.

Figures 3, 3A:
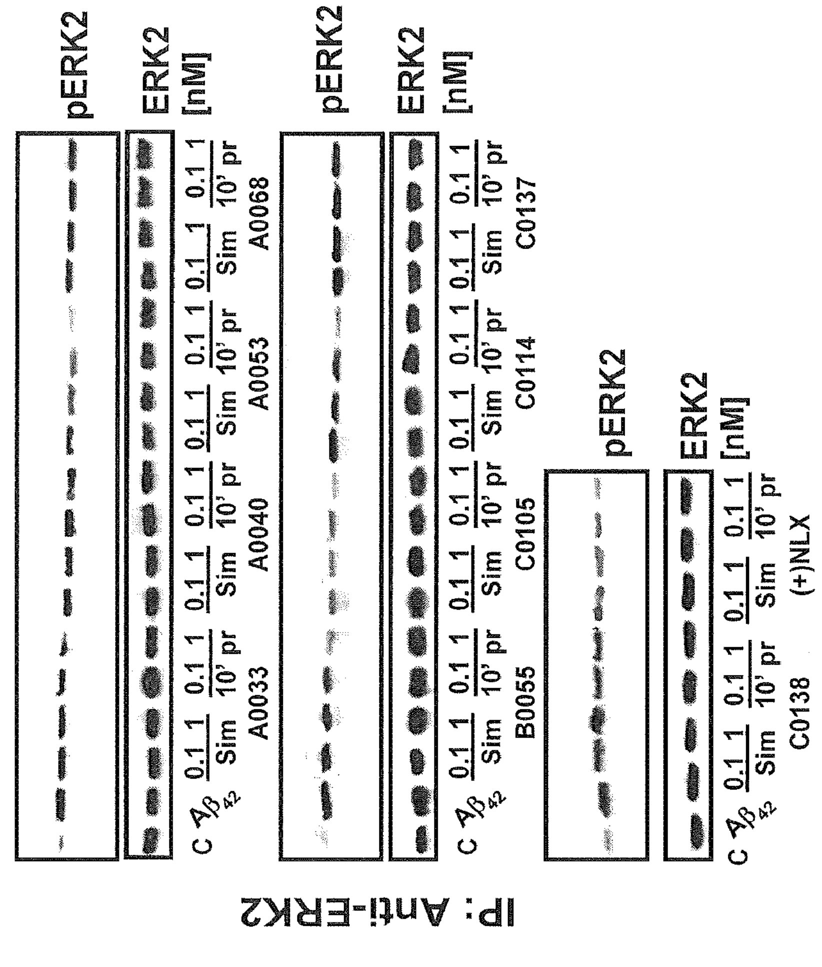
FIG. 3 in two panels as FIG. 3A and FIG. 3B, illustrates that FLNA-binding compounds reduce Aβ-induced α7nAChR-mediated ERK2 signaling. In the same treated synaptosomes used in FIG. 2, levels of phosphorylated (activated) ERK2 were measured in immunoprecipitates of ERK2. $A\beta_{42}$ strongly activated extracellular signal-regulated kinase 2 [ERK2; also known as mitogen-activated protein kinase 1 (MAPK1)], and all compounds studied reduced this activation with 10-minutes of pretreatment. Compound C0105 also reduced pERK2 with simultaneous administration. Immunoprecipitates were determined by Western blotting (FIG. 3A) and quantified for four compounds by densitometry (FIG. 3B). n=3. Data are means±SEM. **p<0.05, *p<0.01 vs. $A\beta_{42}$ alone.
Figure 3B:
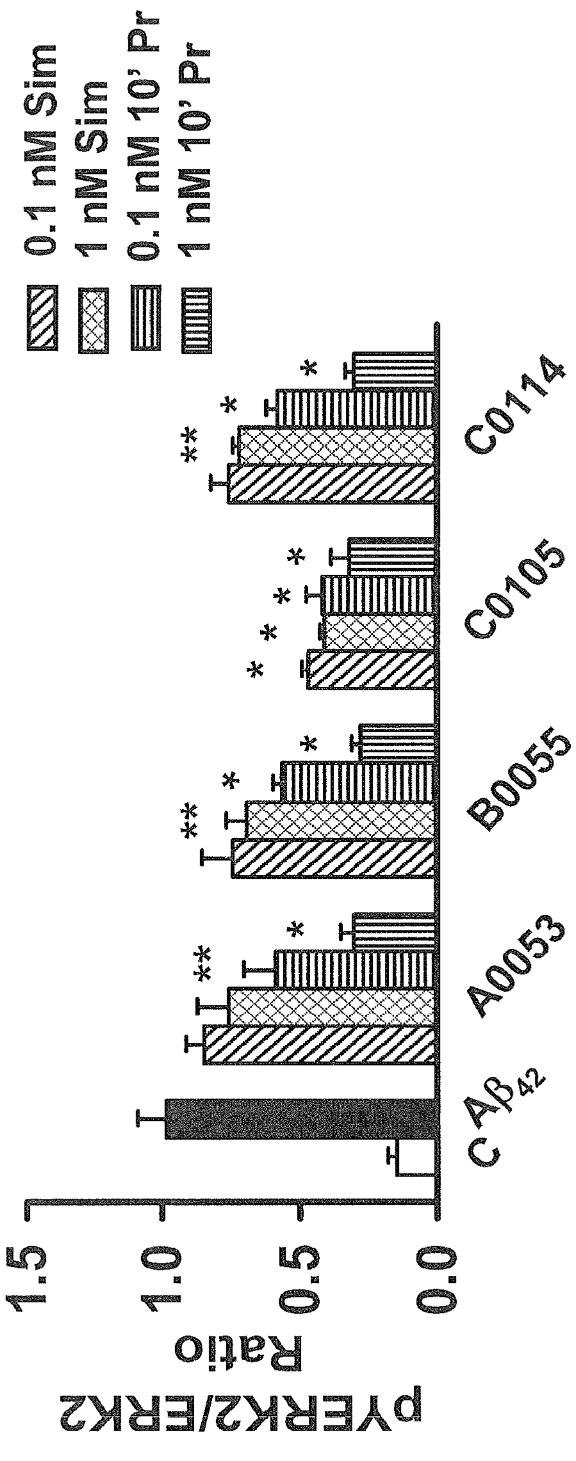

To assess $A\beta_{42}$ signaling via α7nAChR after compound administration, levels of phosphorylated ERK2 were measured in the same synaptosome preparations treated with $A\beta_{42}$ and compounds. Phosphorylation of ERK2 indicates its activation, which leads to tau phosphorylation. Compared to the control condition, $A\beta_{42}$ strongly activates ERK2, and this activation is greatly suppressed by all four compounds at 0.1 and 1 nM with 10 minute pretreatment, and also by Compound C0105 with simultaneous treatment (FIG. 3).

Figures 4, 4A:
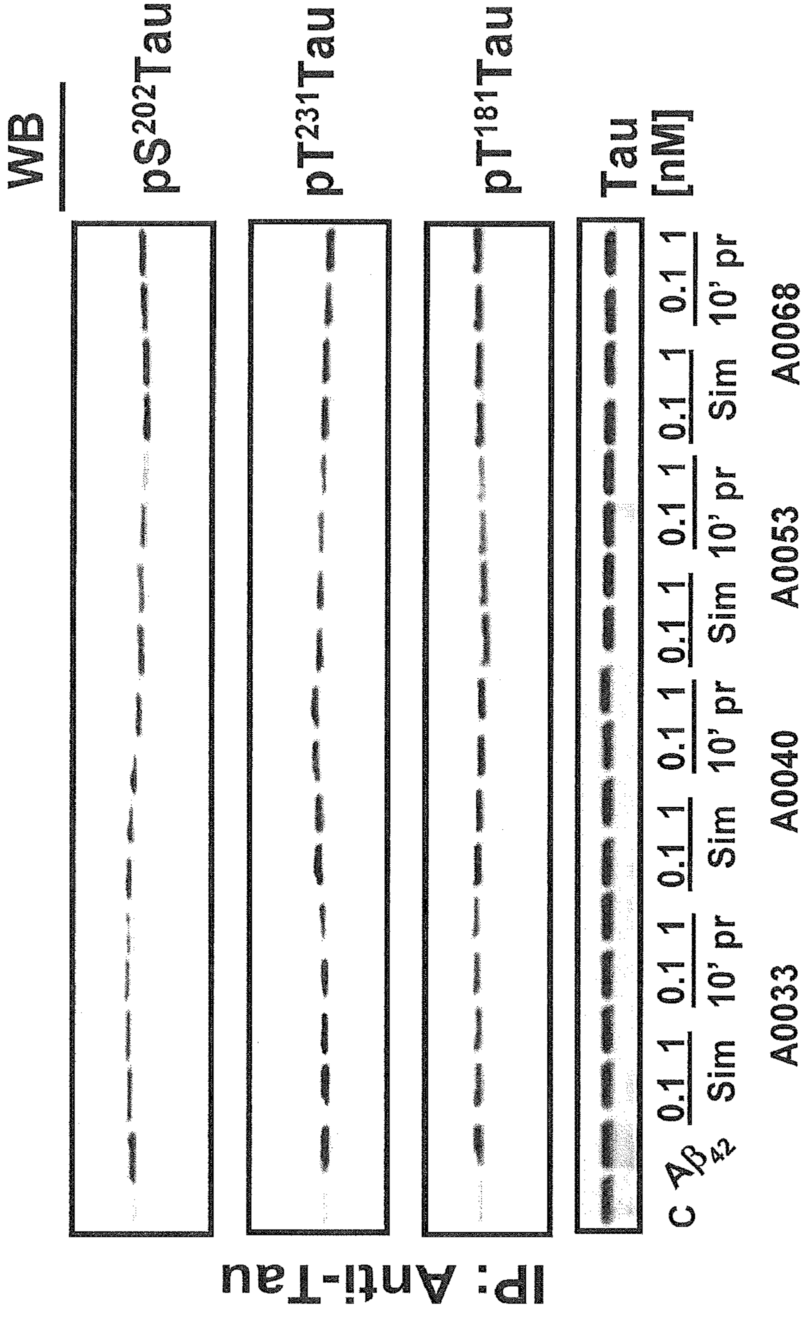
FIG. 4 in four panels as FIGS. 4A-4D, illustrates that FLNA-binding compounds reduce tau phosphorylation at all three phosphorylation sites. In the same treated synaptosomes used in FIGS. 2 and 3, levels of tau protein phosphorylated at $S^{202}$, $T^{231}$ and $T^{181}$ were measured in immunoprecipitates using an anti-tau antibody that does not distinguish its phosphorylation state. The three phosphoepitopes of tau were detected in immunoprecipitates using specific antibodies. $A\beta_{42}$ strongly promotes tau phosphorylation at all three sites, and all compounds reduced this phosphorylation with 10-minute pretreatment. Compound C0105 also reduced tau phosphorylation with simultaneous administration. Immunoprecipitates were determined by Western blotting (FIGS. 4A-4C) and quantified by densitometry (FIG. 4D). Data are means±SEM. **p<0.05, *p<0.01 vs. $A\beta_{42}$ alone.
Figure 4B:
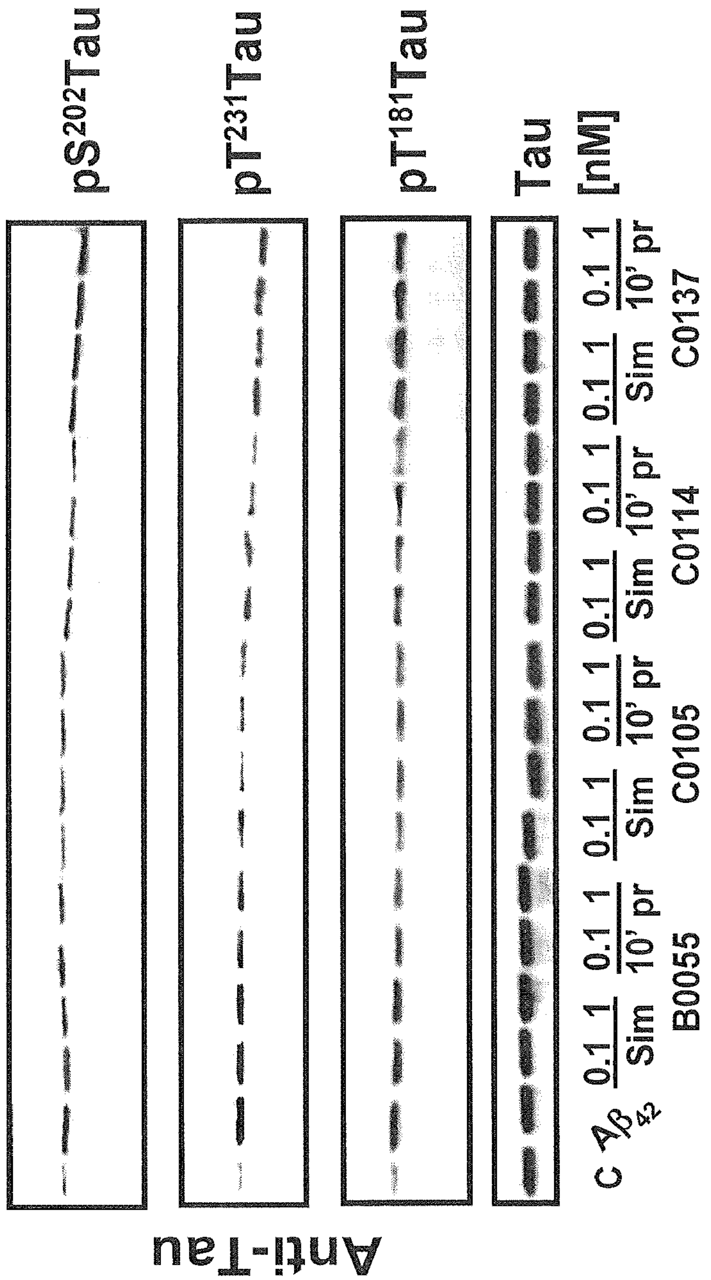
Figure 4C:
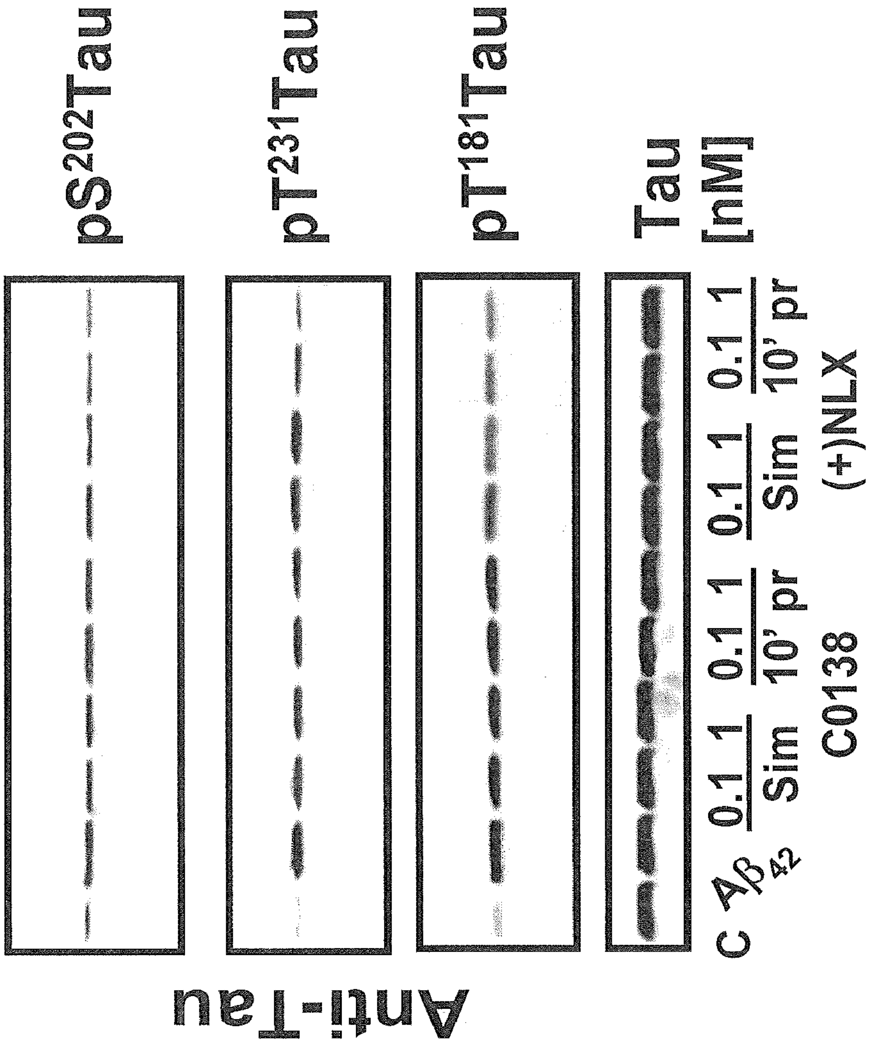
Figure 4D:
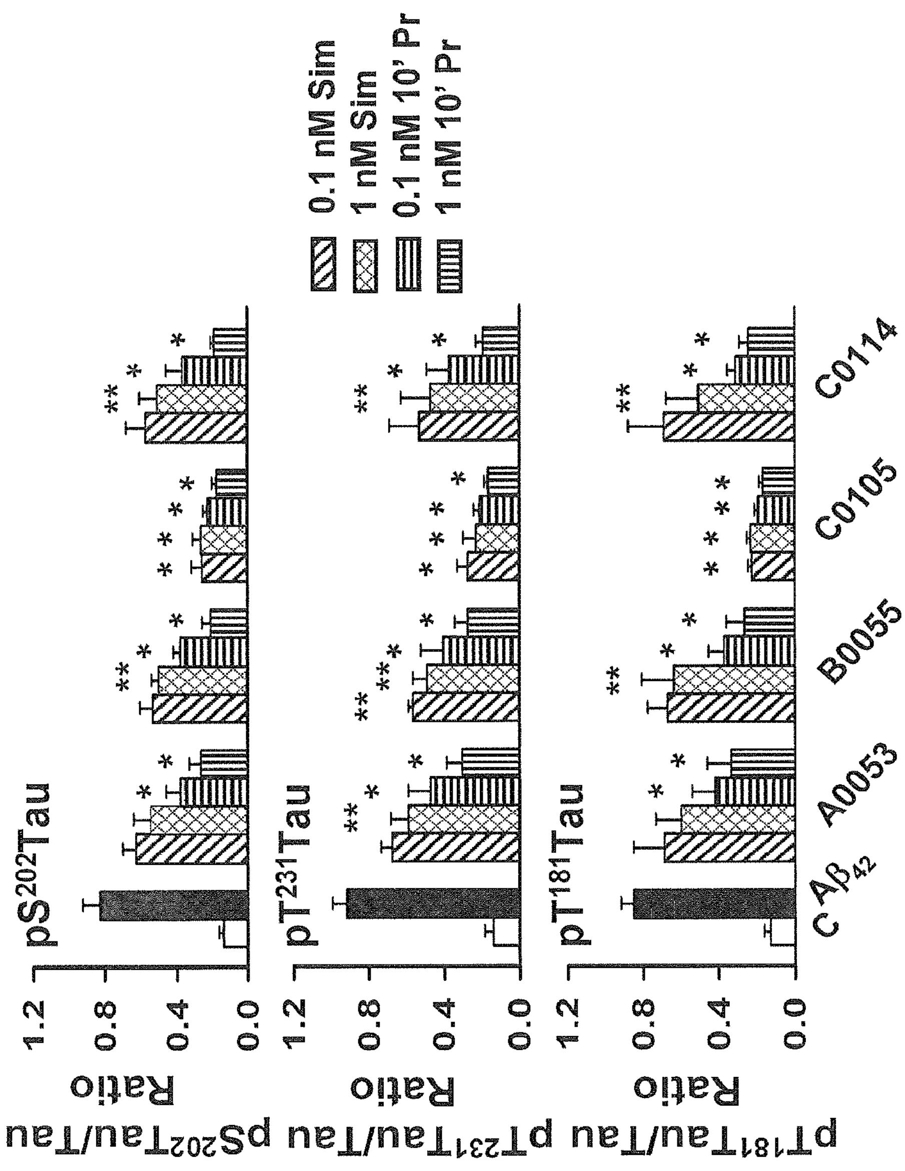

Next assessed was whether the FLNA-binding compounds also decrease phosphorylation of tau, a downstream effect of $A\beta_{42}$ binding to α7nAChR and ERK2 activation. The three primary phosphorylation sites on tau protein were examined for their phosphorylation levels compared to total tau protein content. Tau, phosphorylated at these three sites, is a constituent of NFTs. Consistent with effects on FLNA-α7nAChR association, and ERK2 activation, all of the FLNA-binding compounds assayed, with 10 minute pre-incubation, decreased $A\beta_{42}$-induced phosphorylation of tau at all three sites (FIG. 4).

Compounds C0105 and C0114 Decrease Binding of FITC-$A\beta_{42}$ to Membrane Fractions Containing α7nAChR and FLNA Using biotinylated α7nAChR-containing SK-N-MC cell fragments, compounds and FITC-$A\beta_{42}$ were added simultaneously and incubated at 30° C. for 30 minutes. Compound C0105 at 0.1, 1 and 10 nM concentration inhibited FITC-$A\beta_{42}$ binding by 52.3±3.7%, 55.1±3.0%, and 56.5±4.2%, respectively. Compound C0114 was less effective, decreasing FITC-$A\beta_{42}$ binding by 27.8±3.3%, 40.0±2.1%, and 53.4±3.6% at these three concentrations. These data suggest that by binding to FLNA and likely changing its conformation, Illustrative Compound C0105, and to a lesser extent Compound C0114, are able to affect the affinity of $A\beta_{42}$ binding to α7nAChR.

FLNA-α7nAChR/TLR4 and $A\beta_{42}$-α7nAChR Associations are Increased in AD Lymphocytes Because lymphocytes contain α7nAChR and TLR4, whether the associations of these receptors with FLNA are increased in the lymphocytes of AD patients and whether Compound C0105 treatment ex vivo could disrupt these associations were assessed. Also assayed was the effect of Compound C0105 on $A\beta_{42}$-α7nAChR complexes in AD lymphocytes and $A\beta_{42}$-treated lymphocytes from age-matched control subjects.

FLNA associations with α7nAChR and with TLR4 were dramatically increased in AD and $A\beta_{42}$-treated control lymphocytes compared with vehicle-treated control lymphocytes. Additionally, the level of $A\beta_{42}$-α7nAChR complexes was elevated in AD or $A\beta_{42}$-treated control lymphocytes. Incubation with 1 nM Compound C0105 for 30 minutes significantly reduced the increased associations with FLNA and the level of $A\beta_{42}$-α7nAChR complexes.

Studies in Organotypic Frontocortical Brain Slice Cultures from Adult Rats

Compounds C0105 and C0114 Reduce $A\beta_{42}$-Induced FLNA Association with Both α7nAChR and TLR4

Organotypic frontocortical brain slices of adult rats were incubated for 16 hours with 100 nM $A\beta_{42}$ and either illustrative Compound C0105 or C0114, added simultaneously. Tissue was harvested and solubilized, and a specific antibody against FLNA was used to immunoprecipitate FLNA and associated proteins. The FLNA immunoprecipitate was size-fractionated using SDS-PAGE, transferred and probed with specific antibodies directed against each of the following receptors: α7nAChR, TLR4, IR and MOR. $A\beta_{42}$ (100 nM) caused an increase in FLNA association with both α7nAChR and TLR4, but not with IR or MOR (FIG. 5). Compound C0105 reduced the $A\beta_{42}$-induced increase in FLNA-α7nAChR association at 0.1, 1 and 10 nM, and it reduced the increase in FLNA-TLR4 at 1 and 10 nM. Compound C0114, tested only at 1 and 10 nM, reduced the FLNA-α7AchR association at both concentrations and the FLNA-TLR4 association at 10 nM.

Compounds C0105 and C0114 Reduce $A\beta_{42}$-Induced Tau Phosphorylation

Figures 6, 6A:
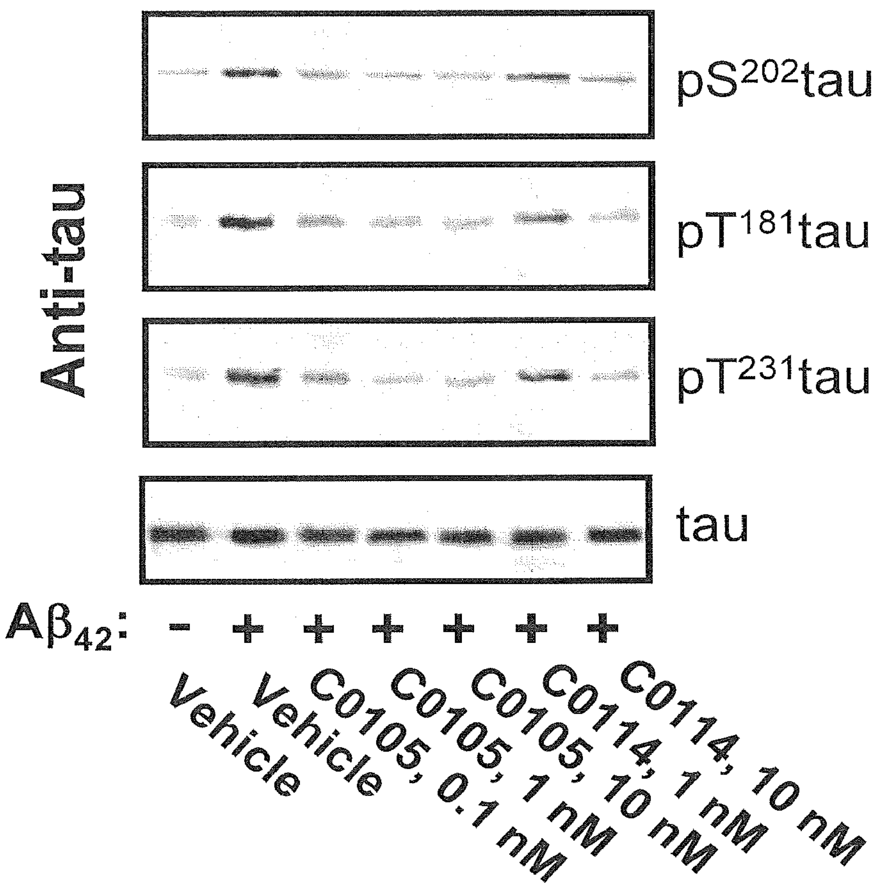
FIG. 6 in three panels illustrates that contacting the synaptosomes with compounds C0105 (0.1, 1 and 10 nM) and C0114 (1 and 10 nM) reduced tau phosphorylation at all three phosphorylation sites. In the same treated synaptosomes used in FIG. 5, levels of tau protein phosphorylated at $S^{202}$, $T^{231}$ and $T^{181}$ were measured in immunoprecipitates using an anti-tau antibody that does not distinguish its phosphorylation state. The three phosphoepitopes of tau were detected in immunoprecipitates using specific antibodies. $A\beta_{42}$ strongly promotes tau phosphorylation at all three sites, and both compounds significantly reduced this phosphorylation. Western blots (FIG. 6A) were analyzed by densitometric quantitation (FIG. 6B). Percent inhibition is depicted in FIG. 6C. n=3. Data are means±SEM. **p<0.05, *p<0.01 vs. $A\beta_{42}$ alone; #p<0.001, ##p<0.007, ###p<0.003 vs. $A\beta_{42}$-free vehicle group.
Figure 6B:
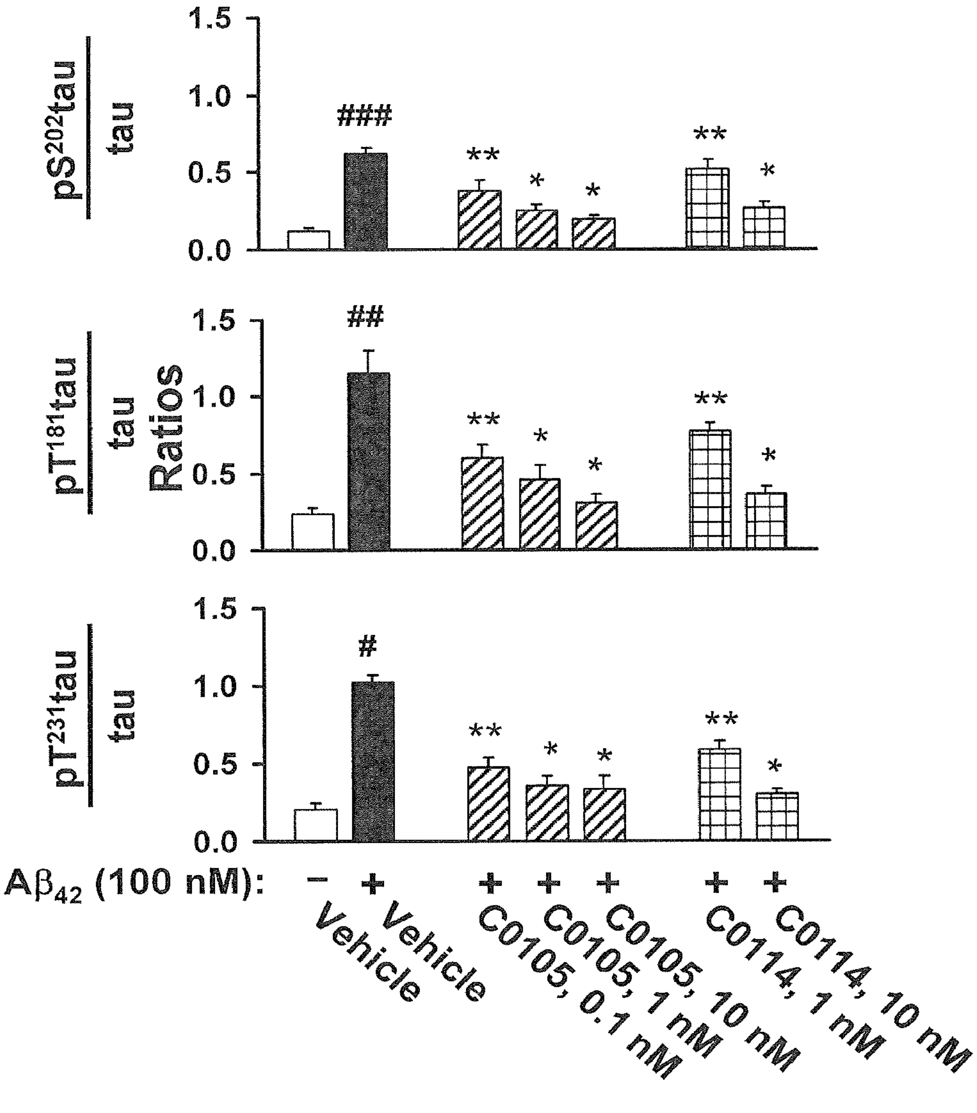
Figure 6C:
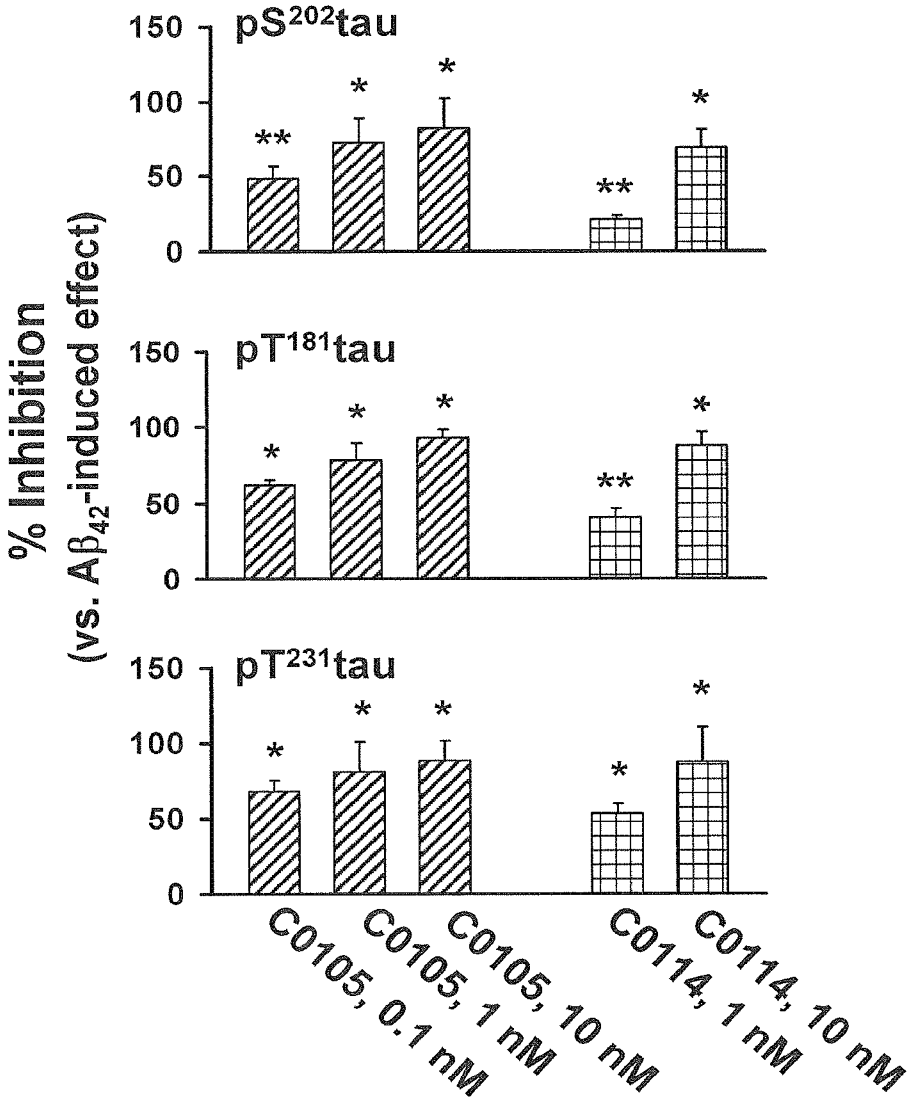

In organotypic frontocortical brain slice cultures treated simultaneously with $A\beta_{42}$ and either of Compounds C0105 or C0114, all three concentrations of Compound C0105 and both concentrations of Compound C0114 reduced tau phosphorylation at all three phosphorylation sites of tau found in neurofibrillary tangles (FIG. 6).

Figure 7:
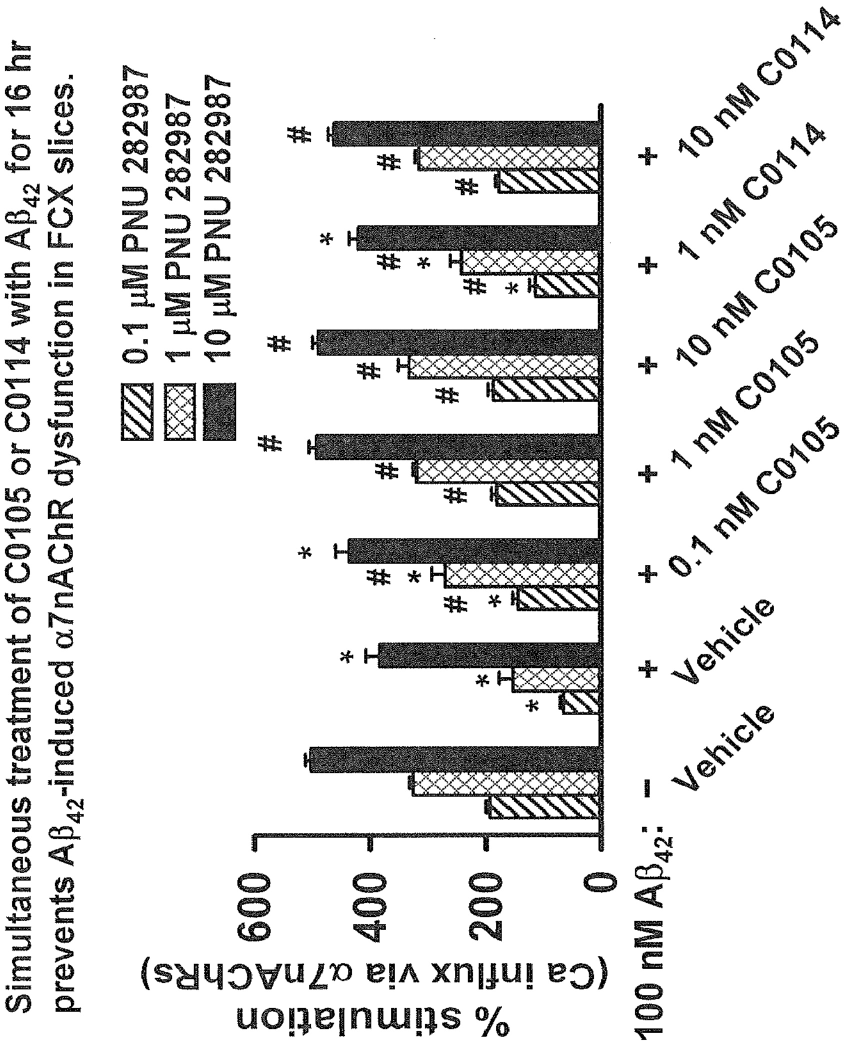
FIG. 7 illustrates that each of Compounds C0105 and C0114 restores $A\beta_{42}$-induced impairment in α7nAChR function. In the same synaptosomes from treated FCX cultures, $A\beta_{42}$ significantly impairs calcium influx after stimulating with PNU282987, a full agonist of α7nAChR, and Compounds C0105 and C0114 each prevent this impairment. n=3. Data are means±SEM. *p<0.01 vs. vehicle; #p<0.01 vs. $A\beta_{42}$ alone.

Compounds C0105 and C0114 Restore Impairment in α7nAChR Function Induced by $A\beta_{42}$ Normal functioning of the α7nAChR is compromised by $A\beta_{42}$, as indicated by reduced calcium influx after stimulating the receptor with a full agonist (PNU282987; N-[(3R)-1-azabicyclo[2.2.2]oct-3-yl]-4-chlorobenzamide). Both of Compounds C0105 and C0114 restored functioning of this receptor, with 1 and 10 nM of Compound C0105 fully restoring function (FIG. 7).

Figure 8:
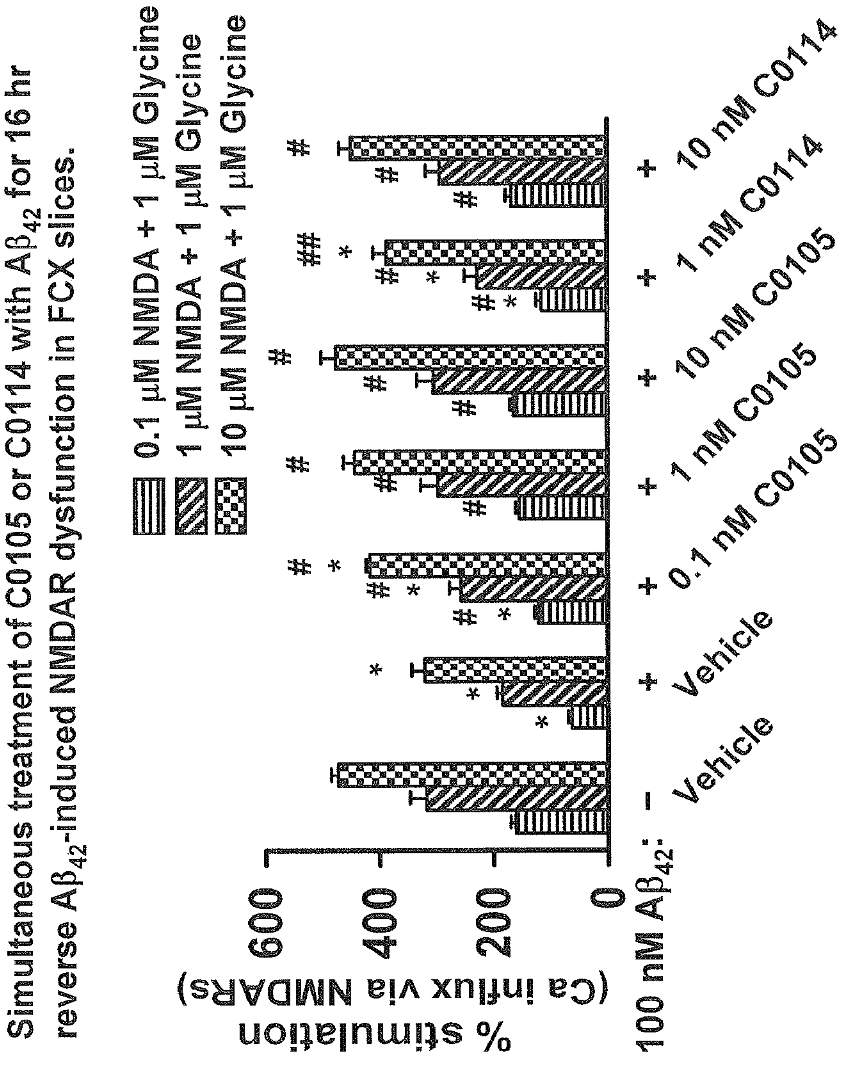
FIG. 8 illustrates that each of Compounds C0105 and C0114 restores $A\beta_{42}$-induced impairment in NMDAR function. $A\beta_{42}$ significantly impairs calcium influx after stimulating with NMDA and glycine, co-agonists of NMDAR, and Compounds C0105 and C0114 prevent this impairment. n=3. Data are means±SEM. *p<0.01 vs. vehicle; ##p<0.05, #p<0.01 vs. $A\beta_{42}$ alone.

Compounds C0105 and C0114 Restore Impairment in NMDAR Function Induced by $A\beta_{42}$ Similar to the assessment of α7nAChR function after $A\beta_{42}$ exposure, NMDAR function was assessed by measuring calcium influx after stimulation with the co-agonist, glycine and NMDA. The $A\beta_{42}$-induced impairment was completely prevented by 1 and 10 nM Compound C0105, with 0.1 nM compounds C0105 and C0114 also significantly restoring NMDAR function (FIG. 8).

Figures 9, 9A:
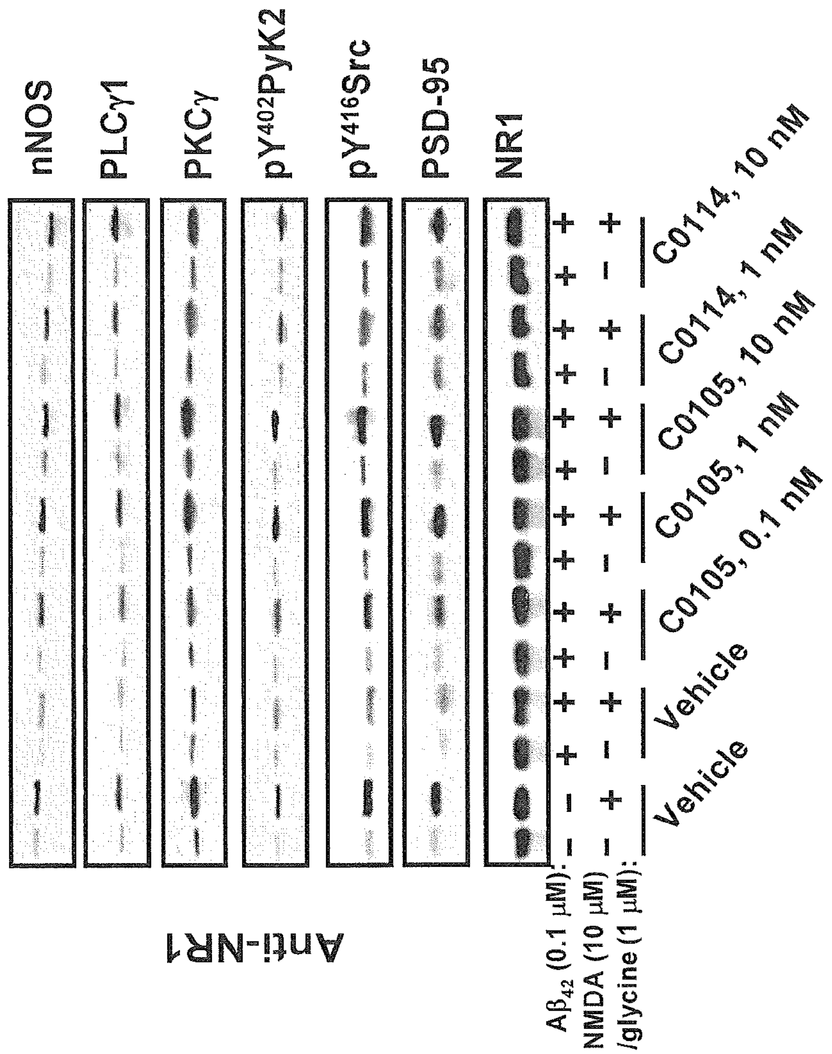
FIG. 9 in two panels illustrates that each of compounds C0105 and C0114 restores levels of NMDAR-associated signaling molecules. Signaling function of NMDAR was also assessed by measuring levels of six different signaling molecules co-immunoprecipitating with NR-1, the obligatory subunit of NMDAR, after co-stimulation with glycine and NMDA (FIG. 9A). $A\beta_{42}$ suppressed levels of association of all six signaling components with NR-1 confirming the NMDAR dysfunction illustrated in FIG. 8 (FIG. 9B). n=3. Data are means±SEM. **p<0.05, *p<0.01 vs. $A\beta_{42}$ alone; #p<0.01 vs. vehicle.
Figure 9B:
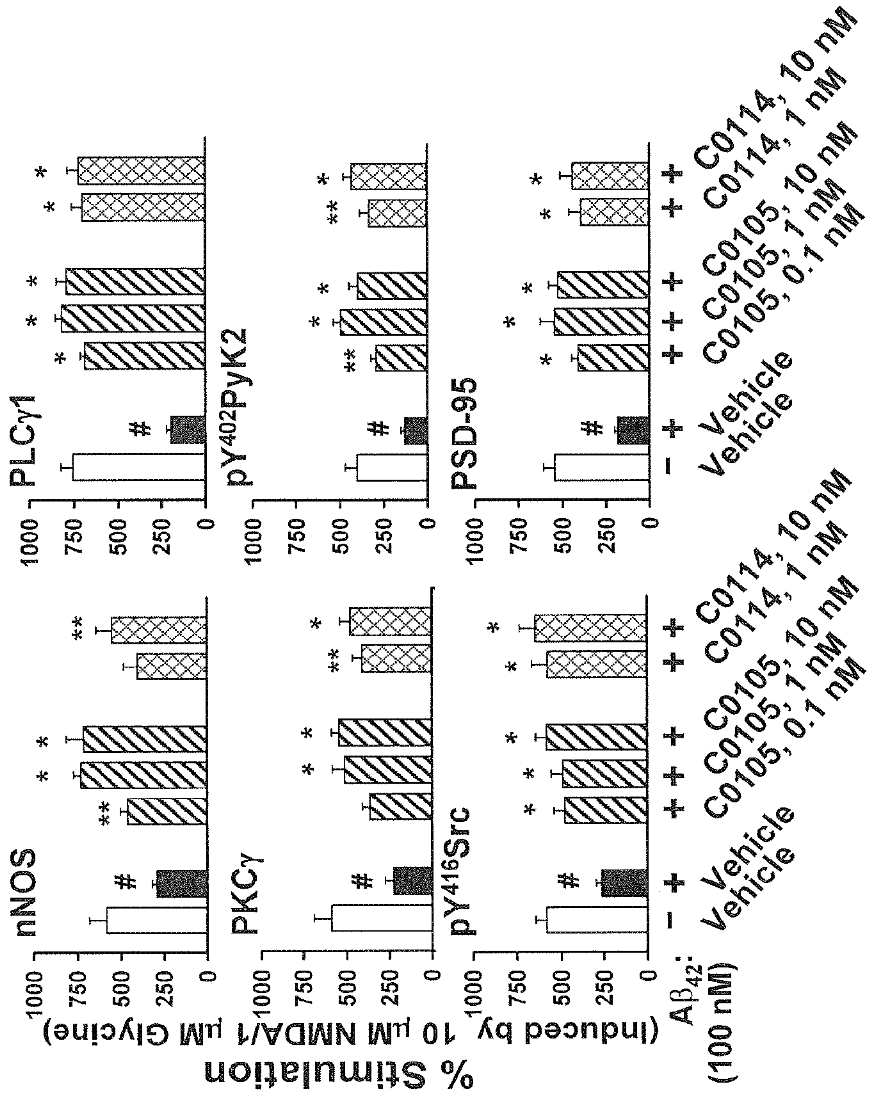

The NMDAR dysfunction was also assessed by measuring levels of six different signaling molecules (nNOS, PLCγ1, PKCγ, $pY^{402}$PyK2, $pY^{416}$Src, and PSD-95) in association with the obligatory NMDAR subunit, $NR^1$, after stimulation with NMDA and glycine. NMDA with glycine intensified the association of NMDARs with PSD-95, increased the recruitment of nNOS, PLCγ1 and PKCγ to NMDAR complexes and elevated levels of active PyK2 ($pY^{402}$PyK2) and Src ($pY^{416}$Src) in the vehicle control condition; all these elevations were severely compromised by $A\beta_{42}$ (FIG. 9). Both of Compounds C0105 and C0114 fully restored function as evidenced by full restorations in the levels of these molecules with the receptor.

Figure 10:
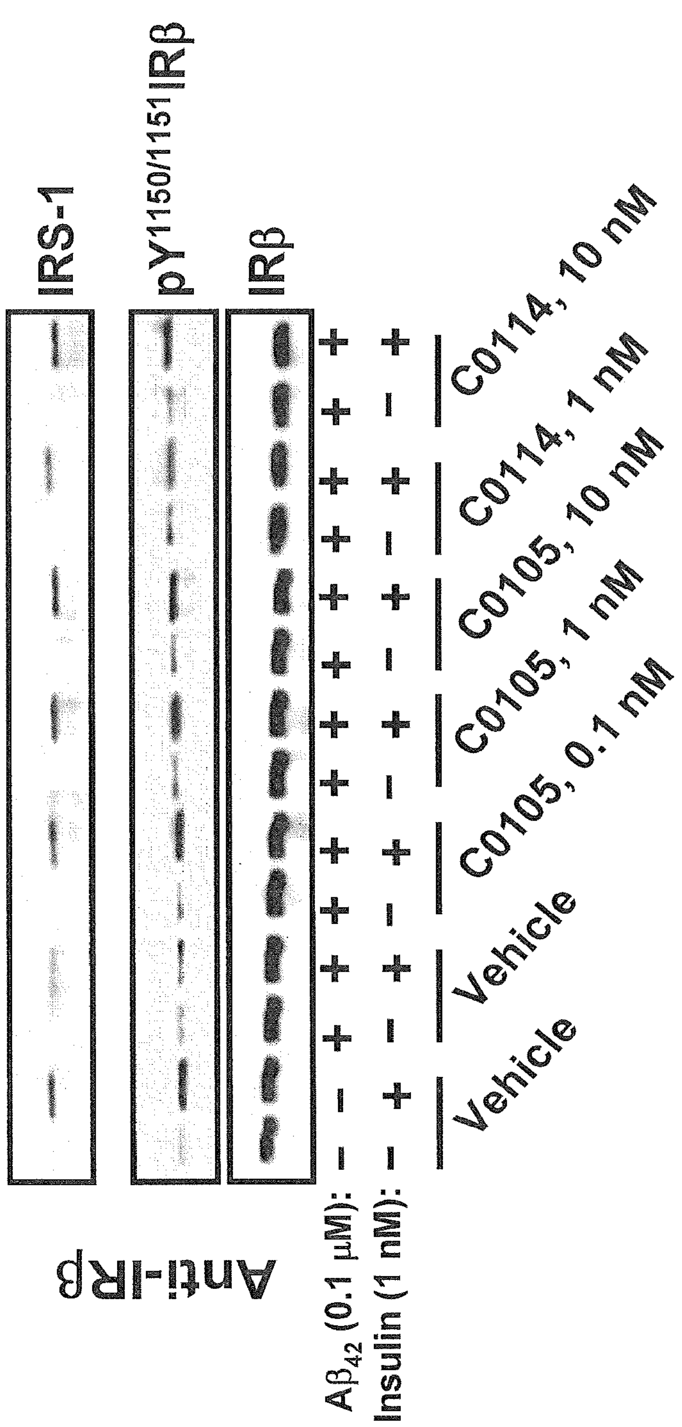
FIG. 10 in two panels C0105 and C0114 illustrates that each of Compounds C0105 and C0114 restores impairment in IR function induced by $A\beta_{42}$. $A\beta_{42}$ impaired signaling of IR as measured by phosphorylation of IRP and its association with the signaling molecule IRS-1 as shown by western blots (FIG. 10A) and densitometric measurements (FIG. 10B). *p<0.01 vs. $A\beta_{42}$ alone; #p<0.01 vs. vehicle.
Figure 10:
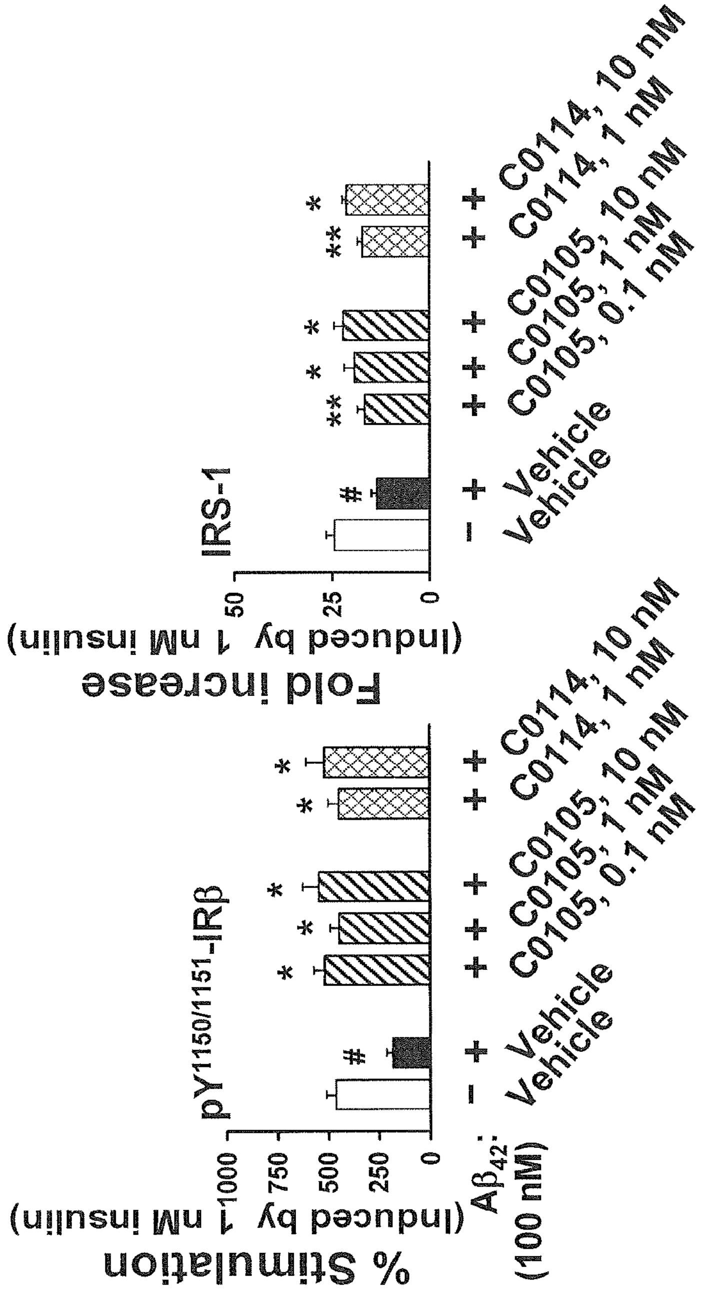

Compounds C0105 and C0114 Restore Impairment in IR Function Induced by $A\beta_{42}$ A third receptor examined, the IR, also showed $A\beta_{42}$-induced dysfunction (FIG. 10). In the vehicle condition, after agonist (insulin) stimulation of the receptor, the association of the adaptor protein for downstream signaling molecule IRS-1 with IR (detected by immunoprecipitation with an antibody to IRβ) is increased, and the level of activated IR as indicated by the phosphorylated IRβ, $pY^{1150/1151}$IRβ. With $A\beta_{42}$ exposure, levels of both the IRS-1 association and the $pY^{1150/1151}$IRβ are dramatically reduced, indicating a desensitization of the receptor or a resistance to insulin. Despite observation that the IR-FLNA association is not affected by $A\beta_{42}$nor by the compounds studied here, each of Compounds C0105 and C0114 normalized the signaling impairments induced by $A\beta_{42}$ exposure.

Figure 11:
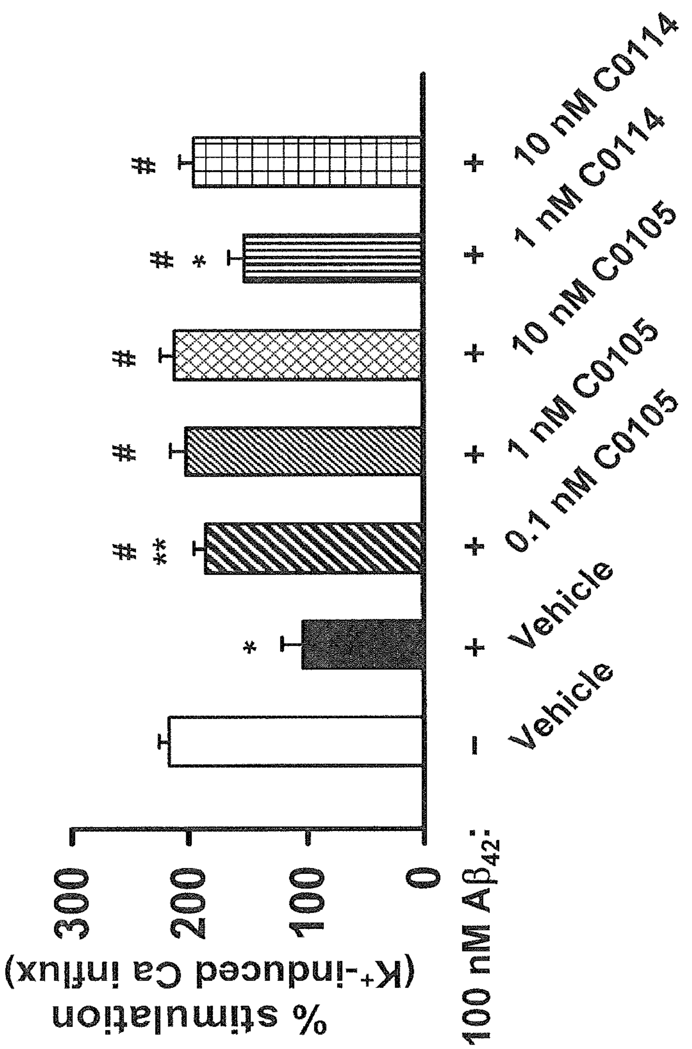
FIG. 11 illustrates that each of compounds C0105 and C0114 can reduce cell death as indicated by reduced $K^+$-evoked calcium influx. $A\beta_{42}$ reduced $K^+$-evoked $Ca^{+2}$ influx, indicating dying or non-functional cells. Contacting the cells with either of compounds C0105 and C0114 prevent that $A\beta_{42}$-induced impairment. n=3. Data are means±SEM. **p<0.05, *p<0.01 vs. vehicle; #p<0.01 vs. $A\beta_{42}$ alone.

Compounds C0105 and C0114 Prevent $A\beta_{42}$-Induced Cell Death as Indicated by $K^+$-Evoked Calcium Influx One indication of non-functional or dying cells is their inability to depolarize and let in calcium. Hence, to measure cell death or non-functionality in the slice cultures, calcium influx was measured in response to $K^+$-evoked depolarization. Calcium influx was greatly reduced by $A\beta_{42}$, and this reduction was completely reversed by 1 and 10 nM compound C0105 and by 10 nM compound C0114 (FIG. 11). The lower concentrations of compound C0105 (0.1 nM) and of Compound C0114 (1 nM) were also very effective in preventing cell death.

Figure 12:
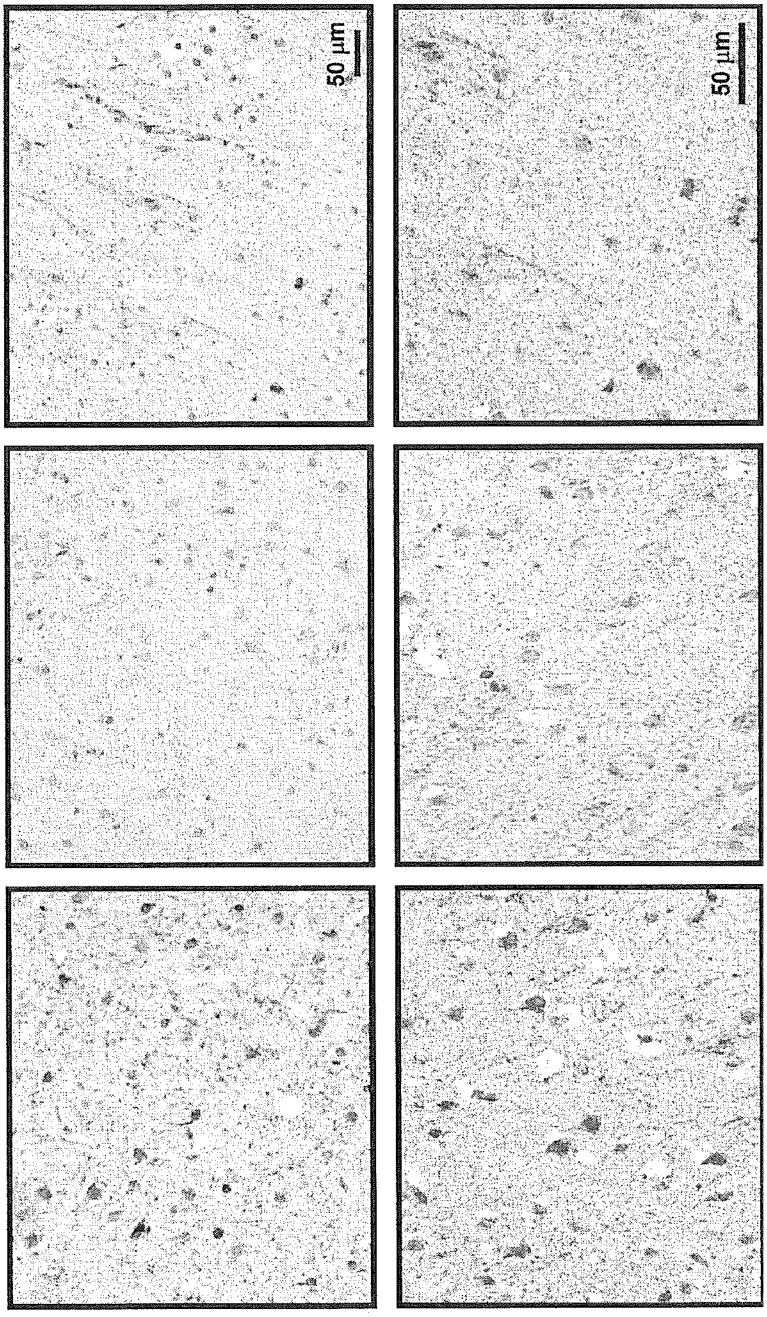
FIG. 12 in two sets of three panels illustrates that administration of compound C0105 to frontocortical brain slice cultures prevents $A\beta_{42}$-induced NFTs. Incubation with $A\beta_{42}$ produced NFTs as visualized by phosphorylated tau (pTau) immunoreactivity (FIG. 12A). Co-incubation of $A\beta_{42}$ with compound C0105 prevented this neuropathology (FIG. 12B). Vehicle-treated slices are depicted in FIG. 12C. Lower panels are higher magnification.
Figure 13:
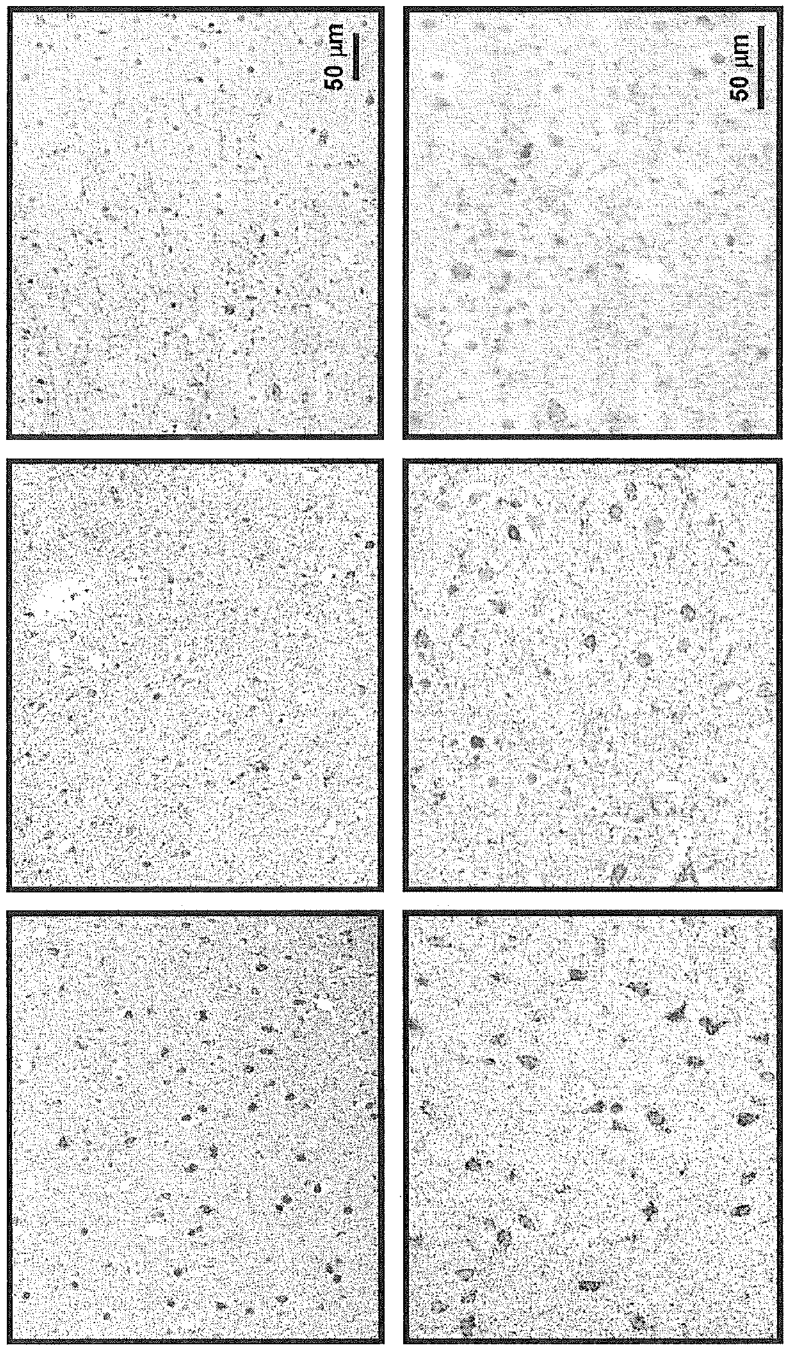
FIG. 13 in two sets of three panels illustrates that administration of compound C0105 to frontocortical brain slice cultures dramatically reduces immunostaining of $A\beta_{42}$ aggregates. Incubation with $A\beta_{42}$ produced amyloid deposits as visualized by $A\beta_{42}$ immunoreactivity (FIG. 13A), and co-incubation with $A\beta_{42}$ and Compound C0105 prevented this neuropathology (FIG. 13B). Vehicle treated slices are depicted in FIG. 13C. Lower panels are higher magnification.
Figure 14:
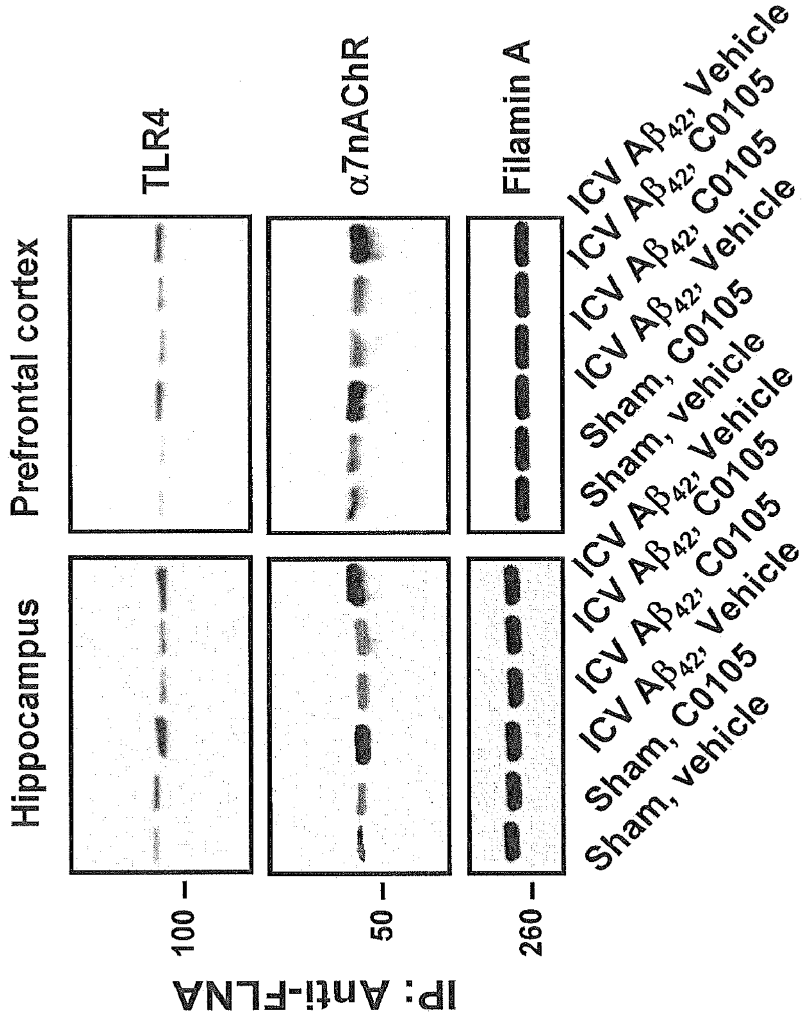
FIG. 14 in three parts illustrates that the systemic administration of Compound C0105 to mice decreased $A\beta_{42}$-induced FLNA association with both α7nAChR and toll-like receptor 4 (TLR4). Thus, synaptosomes prepared from prefrontal cortex and hippocampus of mice receiving continuous intracerebroventricular (ICV) infusion of A42 or vehicle and twice daily injections of Compound C0105 or vehicle were analyzed for their FLNA-0α7nAChR/TLR4 interactions. The extent of FLNA association with α7nAChR or TLR4 was assessed in the solubilized synaptosomes by immunoprecipitation with immobilized anti-FLNA and Western blot detection (FIG. 14A) using antibodies specific to each receptor. Numerals outside of and to the left of the blots are molecular weight positions within the blots. Blots were analyzed by densitometric quantitation (FIG. 14B). $A\beta_{42}$ greatly increased association of α7nAChR and TLR4 with FLNA, and Compound C0105 decreased these $A\beta_{42}$-induced increases. Percent inhibition is depicted in FIG. 14C. n=3. Data are means SEM. *p<0.01 vs. sham, vehicle; #p<0.01 vs. $A\beta_{42}$, vehicle.
Figure 14B:
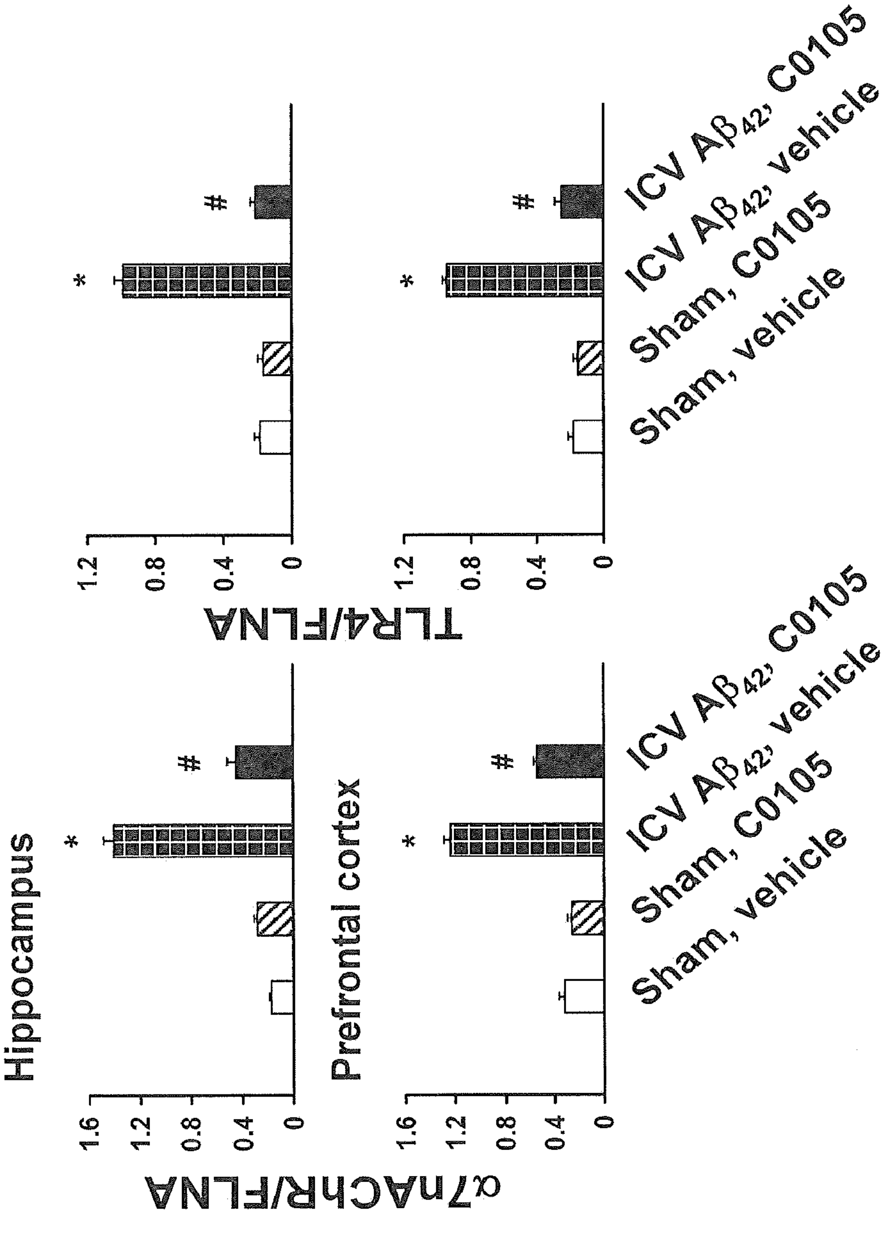
Figure 14C:
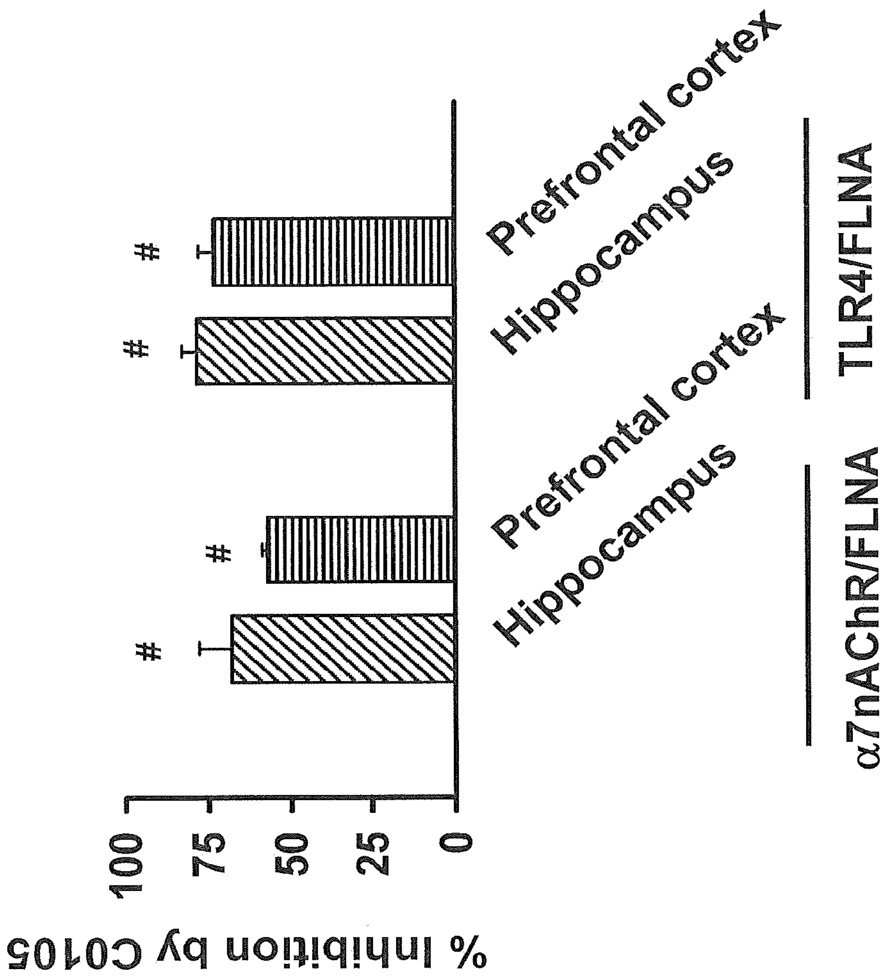
Figures 15, 15A:
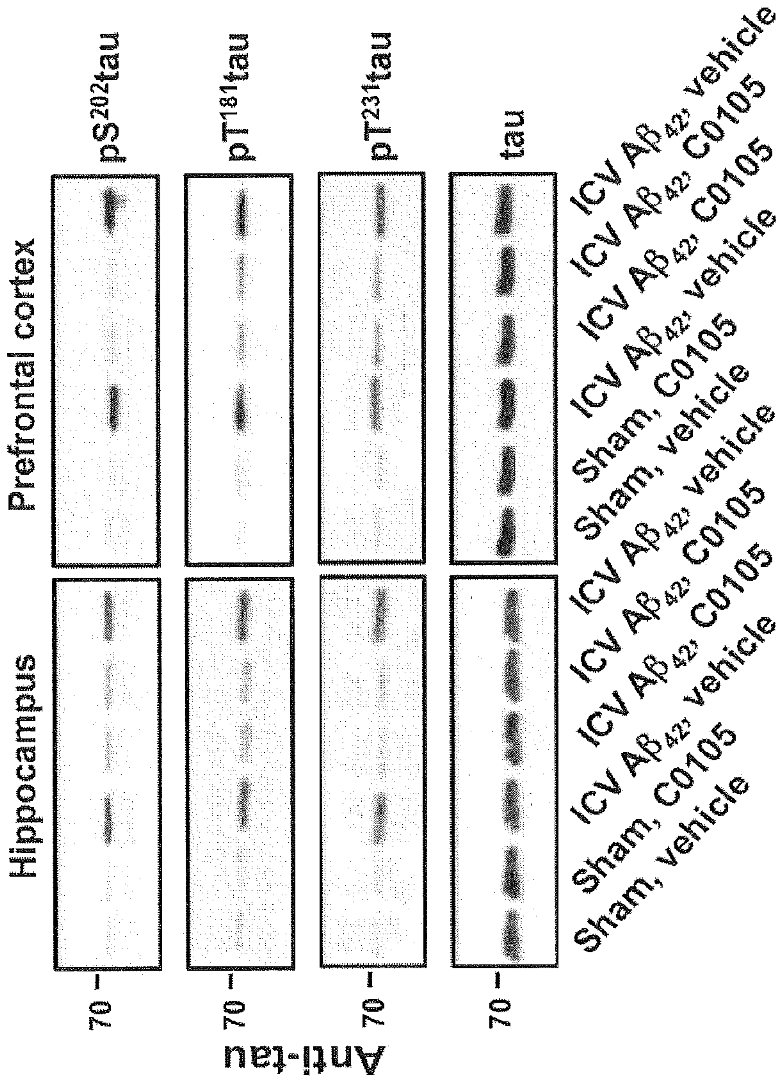
FIG. 15 in three parts illustrates that administration of Compound C0105 to mice reduces tau phosphorylation at all three phosphorylation sites. In the same treated synaptosomes used in FIG. 14, levels of tau protein phosphorylated at $S^{202}$, $T^{231}$ and $T^{181}$ were measured in immunoprecipitates using an anti-tau antibody that does not distinguish its phosphorylation state. The three phosphoepitopes of tau were detected in immunoprecipitates using specific antibodies. $A\beta_{42}$ strongly promotes tau phosphorylation at all three sites, and both compounds significantly reduced this phosphorylation. Western blots (FIG. 15A) were analyzed by densitometric quantitation (FIG. 15B). Numerals outside of and to the left of the blots of FIG. 15A are molecular weight positions within the blots. Percent inhibition is depicted in FIG. 15C. Data are means±SEM. *p<0.01 vs. sham, vehicle; #p<0.01 vs. $A\beta_{42}$, vehicle.
Figure 15B:
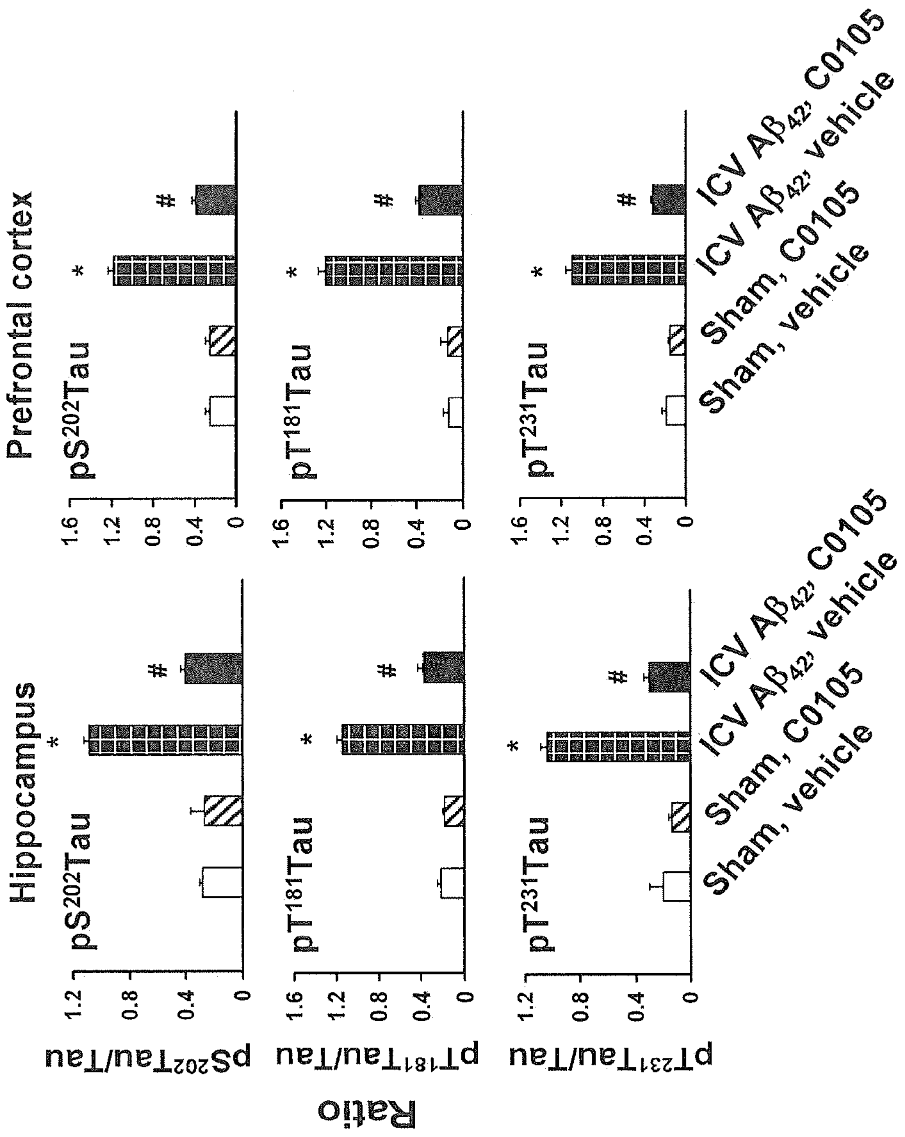
Figure 15C:
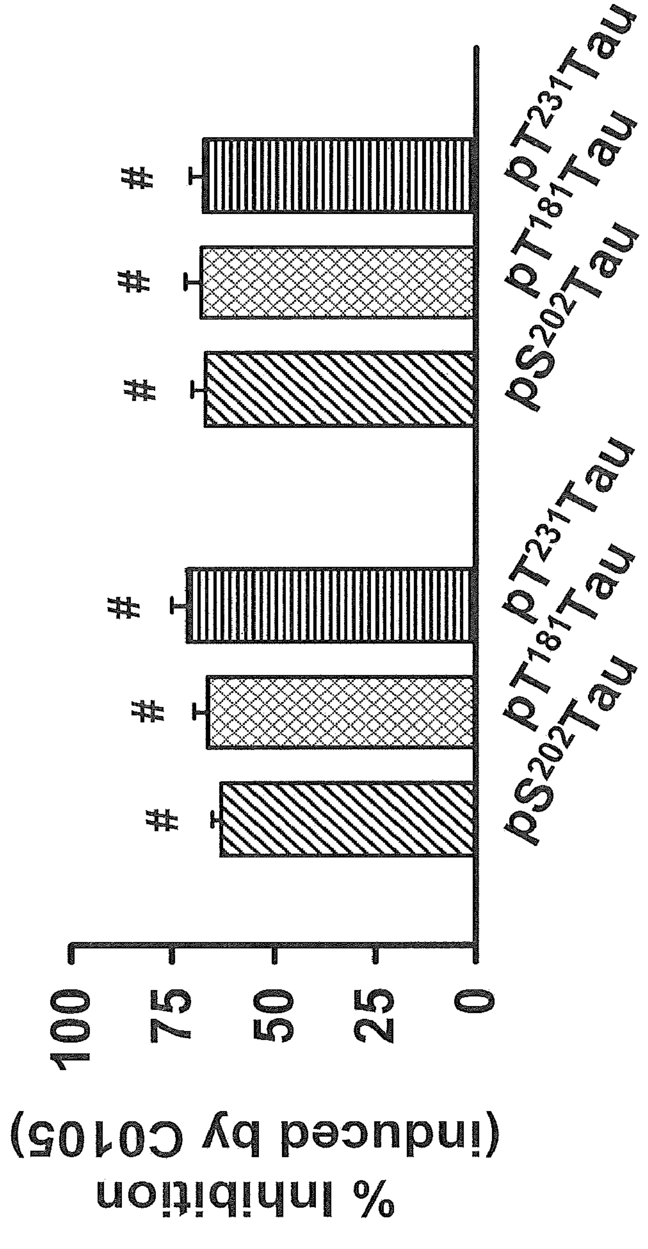

Compound C0105 Dramatically Reduces Immunostaining for NFT and $A\beta_{42}$ Deposits Immunohistochemistry using antibodies to pTau and $A\beta_{42}$, respectively, shows that administration of compound C0105 dramatically reduces both NFT (FIG. 12) and $A\beta_{42}$ aggregates (FIG. 13) in organotypic frontocortical brain slice cultures incubated with $A\beta_{42}$.

ICV $A\beta_{42}$ Infusion Mouse Model

In an intracerebroventricular (ICV) $A\beta_{42}$ infusion mouse model of Alzheimer's disease, $A\beta_{42}$ dramatically increased FLNA association with both α7nAChR and TLR4, caused tau phosphorylation at all three phosphorylation sites of tau found in neurofibrillary tangles, and impaired signaling of α7nAChR, NMDAR and IR. Twice daily systemic treatment with 10 mg/kg of Compound C0105 markedly reduced these effects of the $A\beta_{42}$ infusion. Compound C0105 reduced $A\beta_{42}$-induced increases in FLNA associations with both α7nAChR and TLR4 (FIG. 14), suggesting a reduction in $A\beta_{42}$-mediated signaling of both these receptors.

Figures 16, 16A:
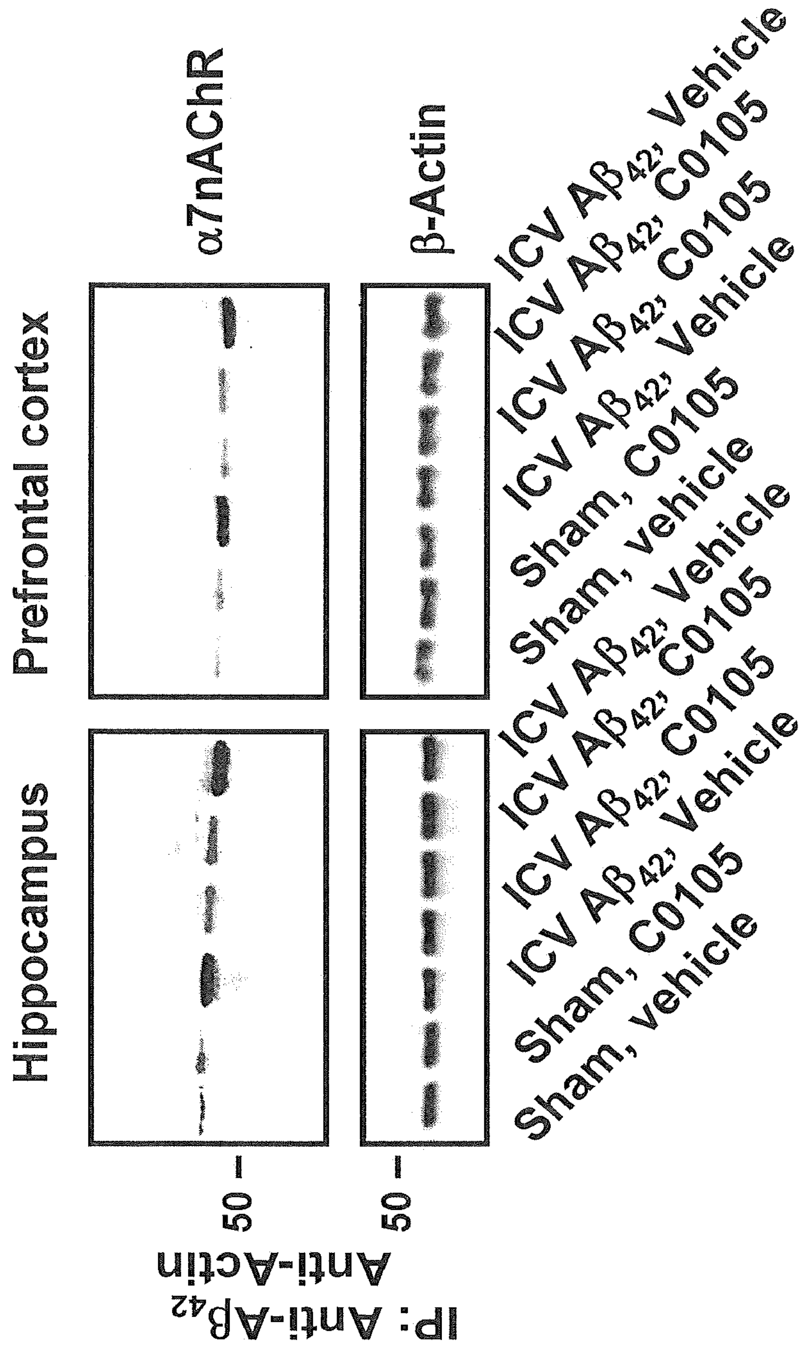
FIG. 16 in three parts illustrates that administration of Compound C0105 to mice reduces $A\beta_{42}$-α7nAChR complexes. Twice daily treatment of mice with Compound C0105 greatly reduced the level of $A\beta_{42}$-α7nAChR complexes in both prefrontal cortex and hippocampus, n=7 or n=8. Western blots (FIG. 16A) were analyzed by densitometric quantitation (FIG. 16B). Numerals outside of and to the left of the blots of FIG. 16A are molecular weight positions within the blots. Percent inhibition is depicted in FIG. 16C. Data are means±SEM. *p<0.01 vs. sham, vehicle; #p<0.01 vs. $A\beta_{42}$, vehicle.

Compound C0105 treatment suppressed tau phosphorylation at all three phosphorylation sites (FIG. 15), again indicating that $A\beta_{42}$ signaling via α7nAChR is disrupted. The high-affinity binding of compound C0105 to FLNA appears to reduce $A\beta_{42}$ signaling via α7nAChR by reducing $A\beta_{42}$ binding to α7nAChR: the level of these $A\beta_{42}$-α7nAChR complexes is reduced in C0105-treated animals (FIG. 16).

Figure 17:
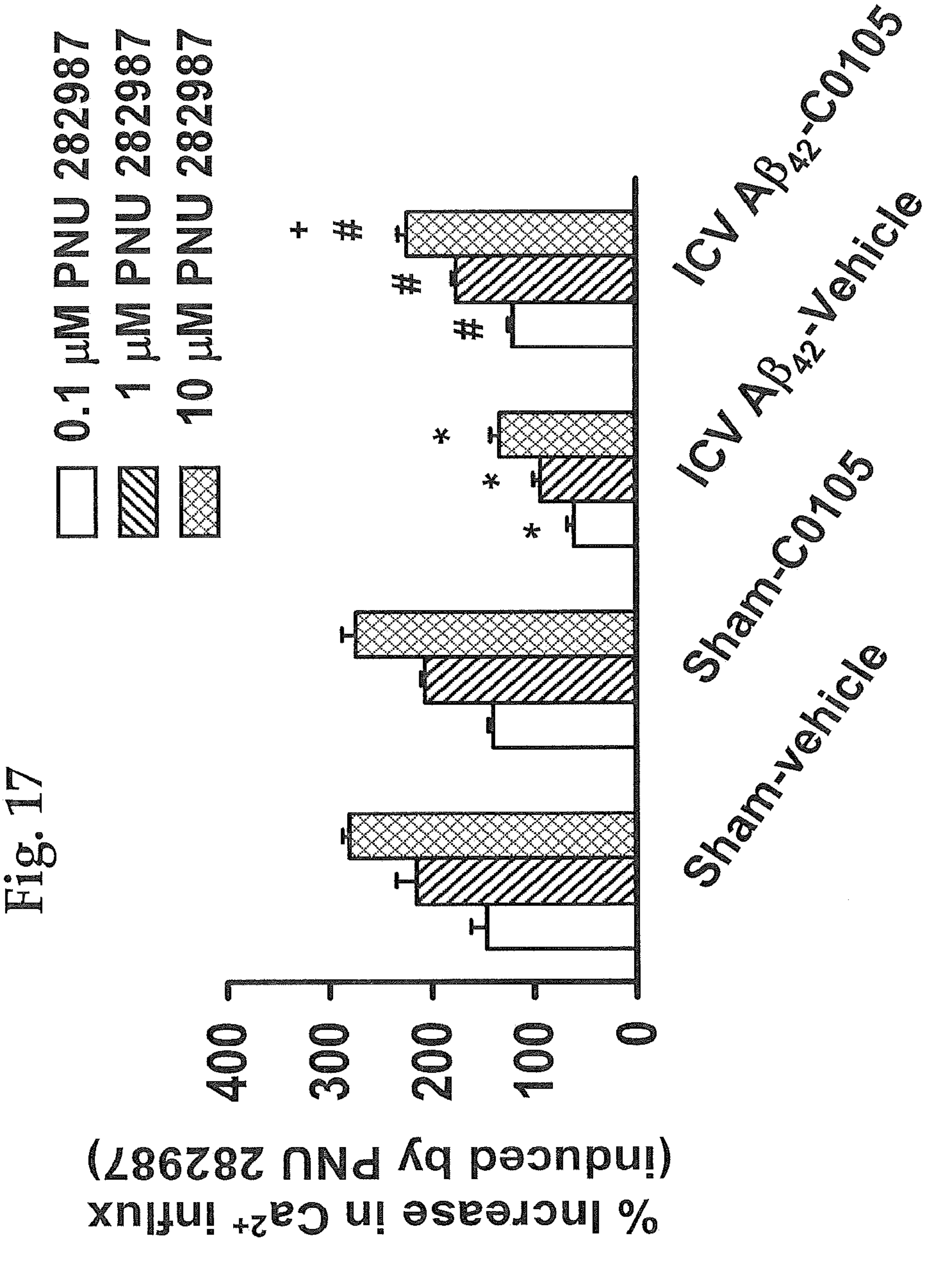
FIG. 17 illustrates that Compound C0105 treatment reduces $A\beta_{42}$-induced α7nAChR dysfunction. Twice daily treatment of mice with Compound C0105 normalized the $A\beta_{42}$-induced impairment in calcium influx following stimulation with the full α7nAChR agonist PNU282987. n=7 or n=8. Data are means±SEM. *p<0.01 vs. sham, vehicle; #p<0.01 vs. $A\beta_{42}$, vehicle; +p<0.01 vs. vehicle- and Compound C0105-treated sham groups.
Figure 18:
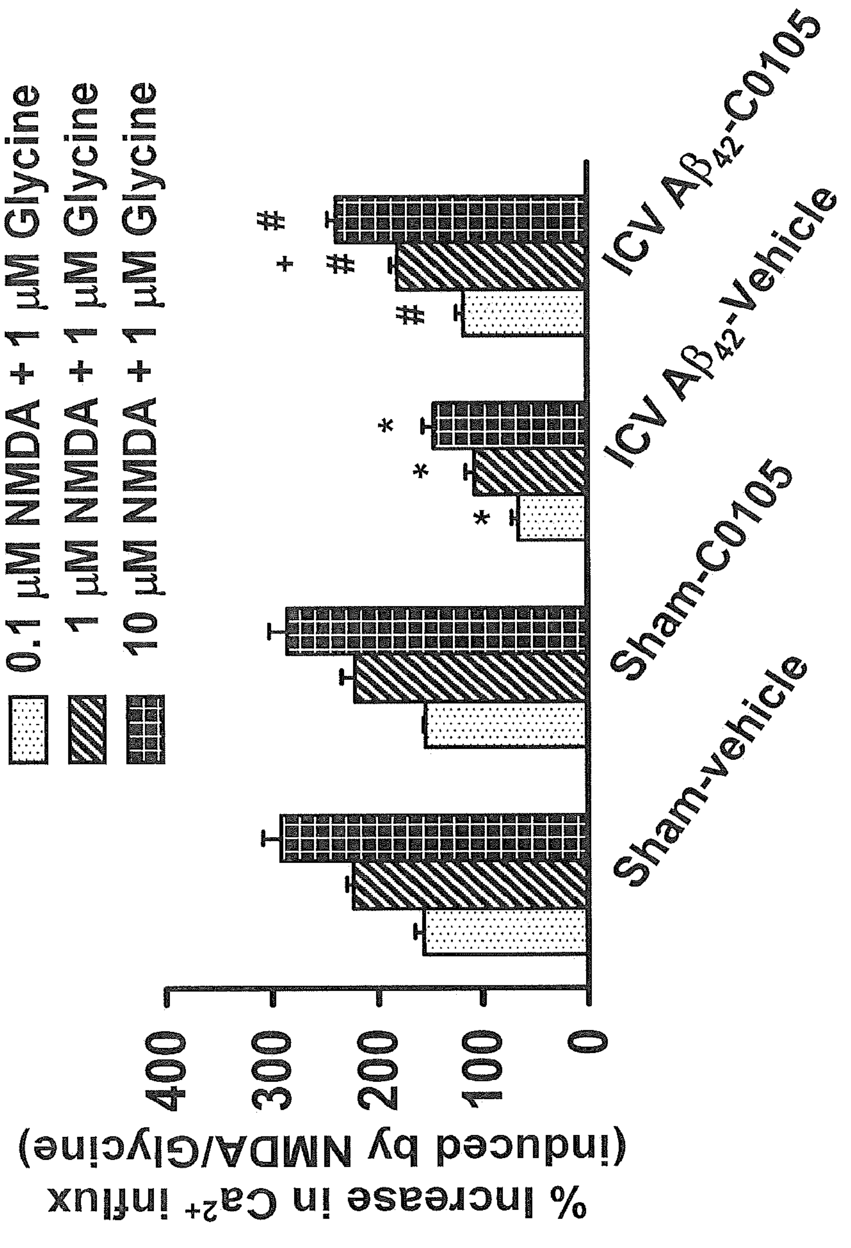
FIG. 18 illustrates that Compound C0105 treatment of mice reduces $A\beta_{42}$-induced NMDAR dysfunction. $A\beta_{42}$ significantly impairs calcium influx after stimulating with NMDA and glycine, co-agonists of NMDAR, and Compound C0105 prevents this impairment. n=7 or n=8. Data are means±SEM. *p<0.01 vs. sham, vehicle; #p<0.01 vs. $A\beta_{42}$, vehicle; +p<0.01 vs. vehicle- and Compound C0105-treated sham groups.
Figure 19:
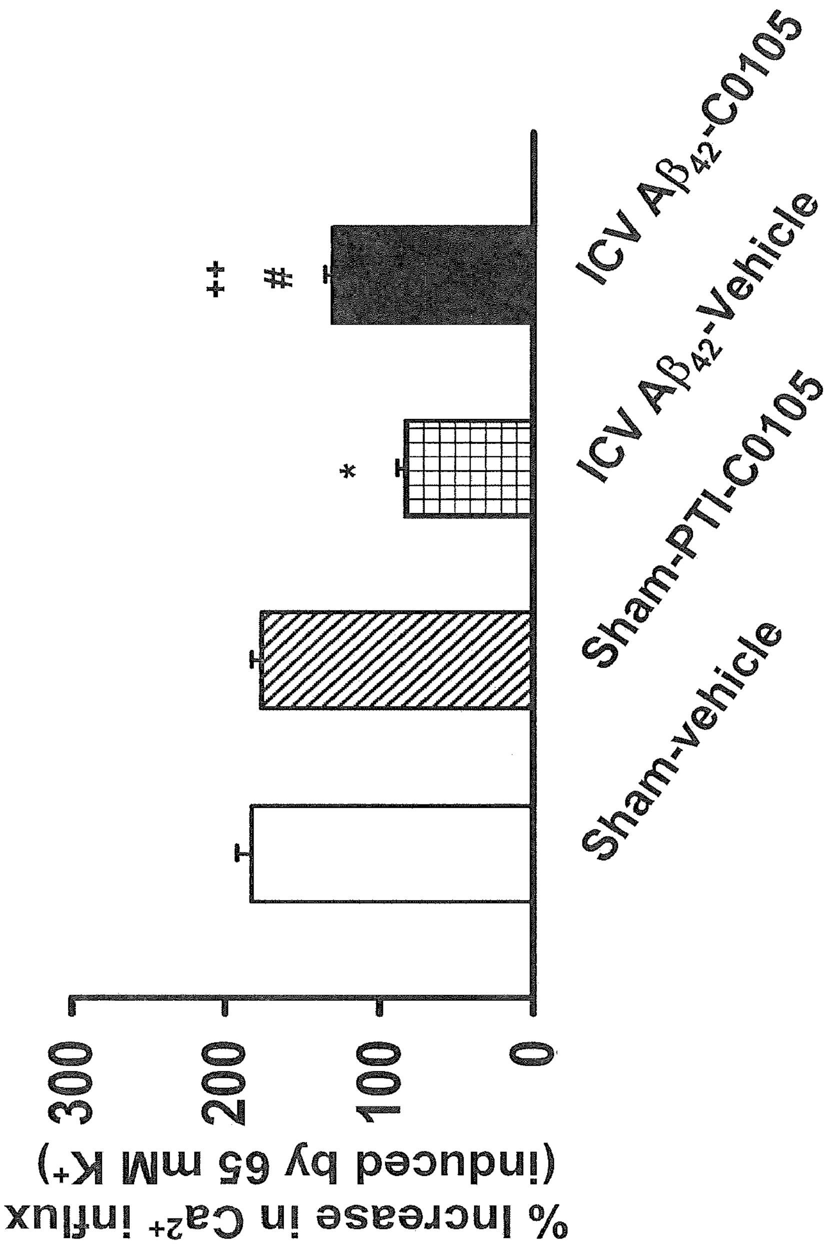
FIG. 19 illustrates that Compound C0105 treatment of mice reduces cell death as measured by $K^+$-evoked $Ca^{+2}$ influx. $A\beta_{42}$ reduced $K^+$-evoked $Ca^{+2}$ influx, indicating dying or non-functional cells. Compound C0105 reduces this $A\beta_{42}$-induced impairment. n=7 or n=8. Data are means±SEM. *p<0.01 vs. sham, vehicle; #p<0.01 vs. $A\beta_{42}$, vehicle; ++p<0.05 vs. vehicle- and Compound C0105-treated sham groups.

$A\beta_{42}$-induced dysfunction of α7nAChR was illustrated by calcium influx after stimulation of α7nAChR with its full agonist PNU282987. The $A\beta_{42}$-induced reduction in this calcium influx was normalized in the Compound C0105-treated animals (FIG. 17). Likewise, downstream NMDAR function was also impaired by ICV $A\beta_{42}$ infusion, illustrated by calcium influx after co-stimulation with NMDA and glycine (FIG. 18). Again, Compound C0105 treatment restored the $A\beta_{42}$-induced NMDAR dysfunction. Calcium influx after depolarization by $K^+$ was used to assess overall cellular dysfunction or dying cells. ICV $A\beta_{42}$ infusion greatly reduced this $K^+$-evoked calcium influx, and C0105 treatment restored it (FIG. 19).

Figures 20, 20A:
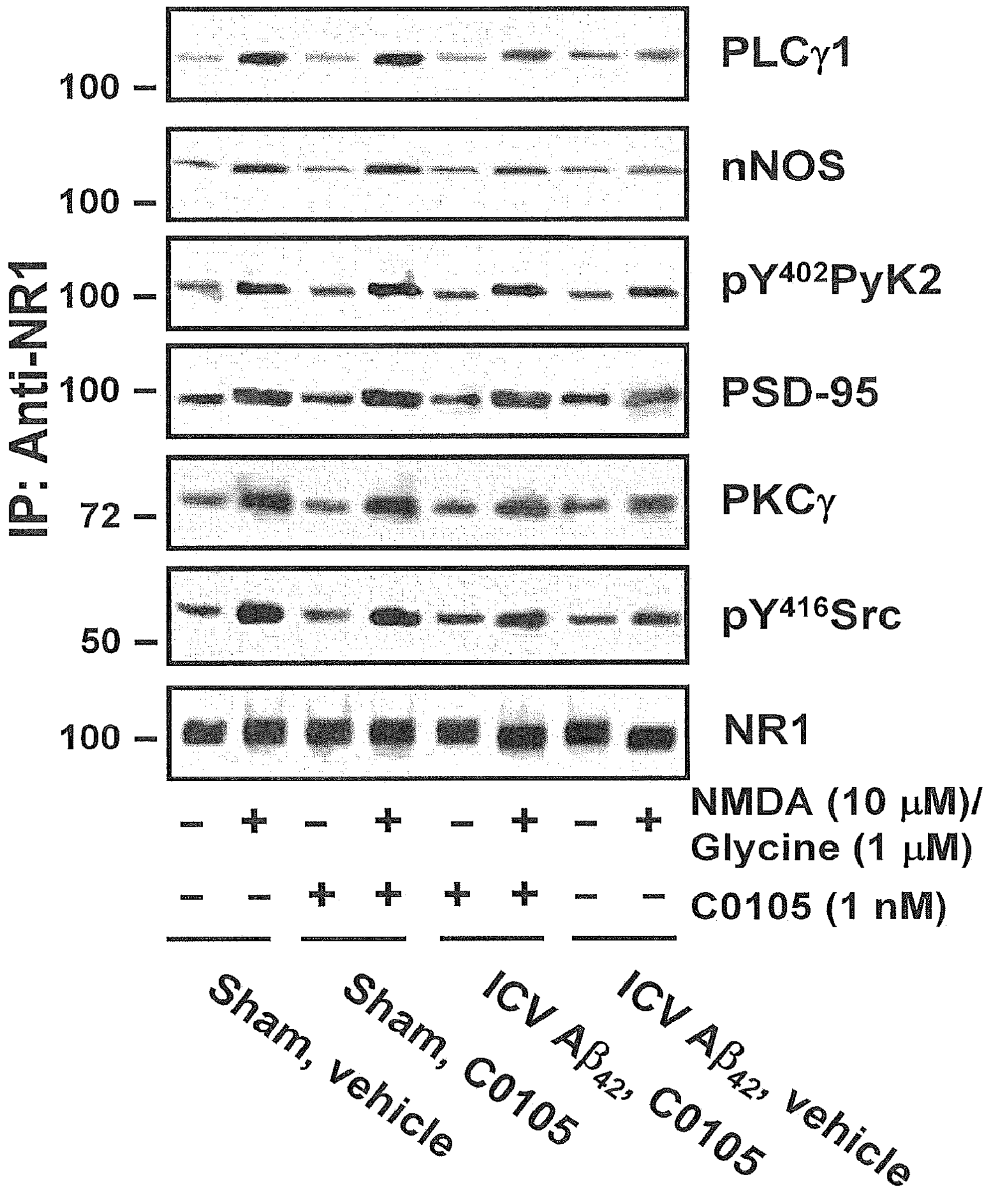
FIG. 20 in two panels illustrates that Compound C0105 treatment of mice normalizes $A\beta_{42}$-induced NMDAR signaling impairments. Signaling function of NMDAR was also assessed by measuring levels of six different signaling molecules (PLCγ, nNOS, $pY^{402}$PyK2, PSD-95, PKCγ, $pY^{416}$Src, and NR1) co-immunoprecipitating with NR-1, the obligatory subunit of NMDAR, after co-stimulation with glycine and NMDA (FIG. 20A). Numerals outside of and to the left of the blots are as discussed before. $A\beta_{42}$ suppressed levels of association of all six signaling components with NR-1 confirming the NMDAR dysfunction illustrated in FIG. 18 (FIG. 20B). n=7 or n=8. Data are means±SEM. +p<0.01 vs. basal level in control vehicle group; *p<0.01 vs. NMDA/glycine-stimulated level in sham, vehicle group; #p<0.01 vs. NMDA/glycine-stimulated level in ICV $A\beta_{42}$, vehicle.
Figure 20B:
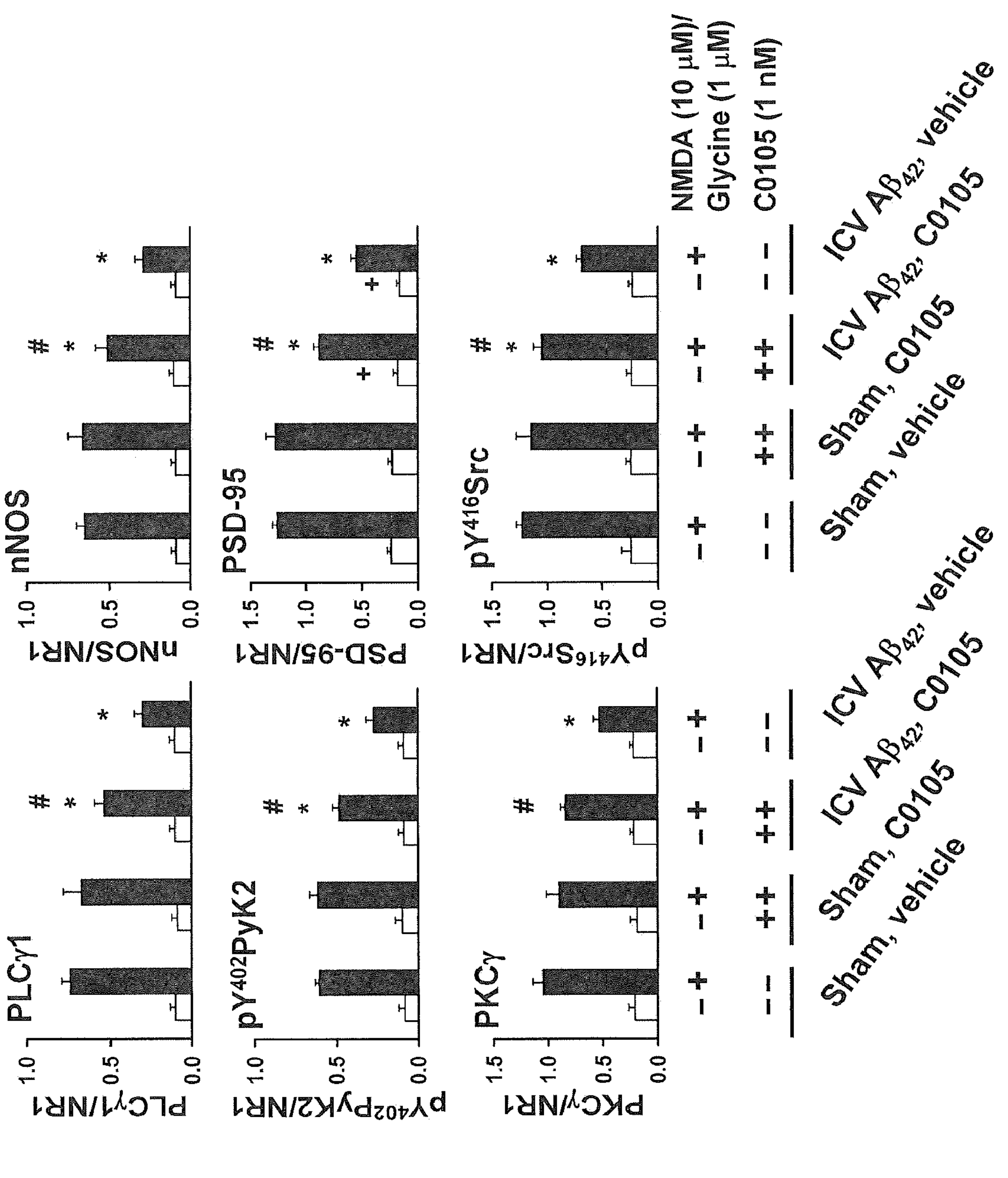
Figure 21A:
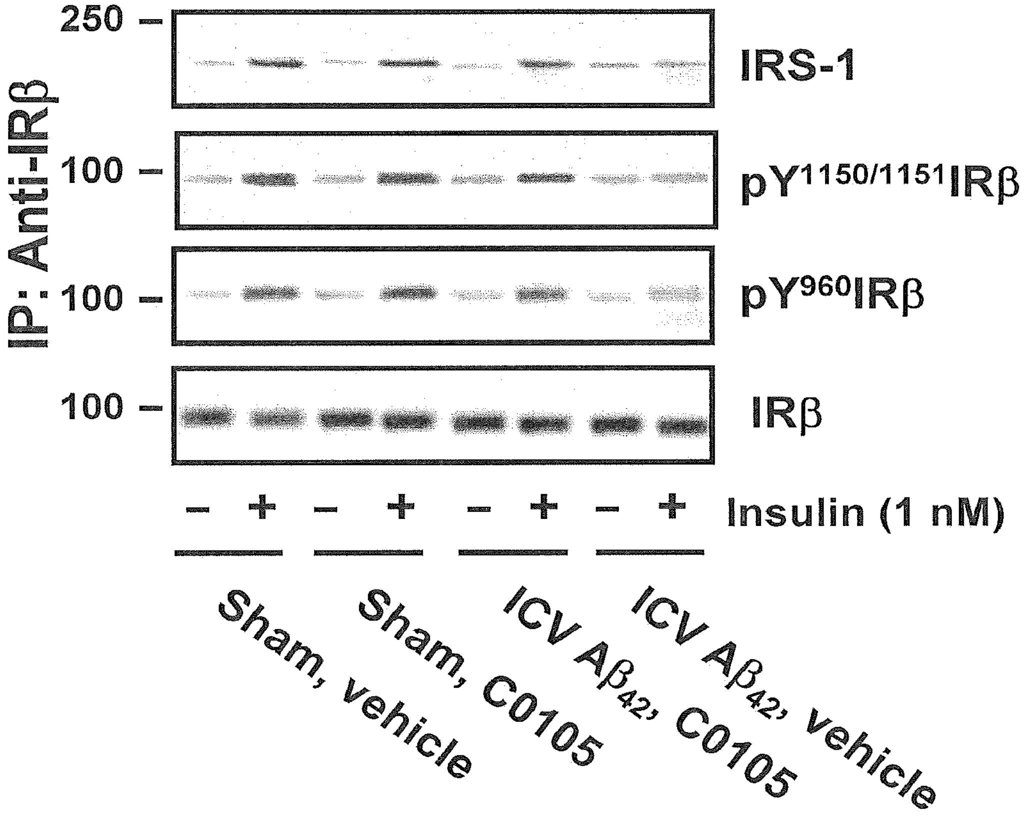
FIG. 21 in two panels illustrates that Compound C0105 treatment of mice normalizes $A\beta_{42}$-induced insulin receptor signaling impairments. $A\beta_{42}$ impaired signaling of IR as measured by phosphorylation of IRP and its association with the signaling molecule IRS-1. Immunoprecipitates prepared using immobilized anti-IRP are shown in FIG. 21A, wherein numerals outside of and to the left of the blots are as discussed before.
FIG. 21B shows results obtained after removal of the antibodies, transfer to nitrocellulose membranes and Western blotting with antibodies to the species noted on the ordinates, followed by quantitation using densitometry. Compound C0105 normalized these impairments. n=7 or n=8. Data are means±SEM. *p<0.01 vs. insulin-stimulated level in sham, vehicle group; #p<0.01 vs. insulin-stimulated level in ICV $A\beta_{42}$, vehicle group.
Figure 21B:
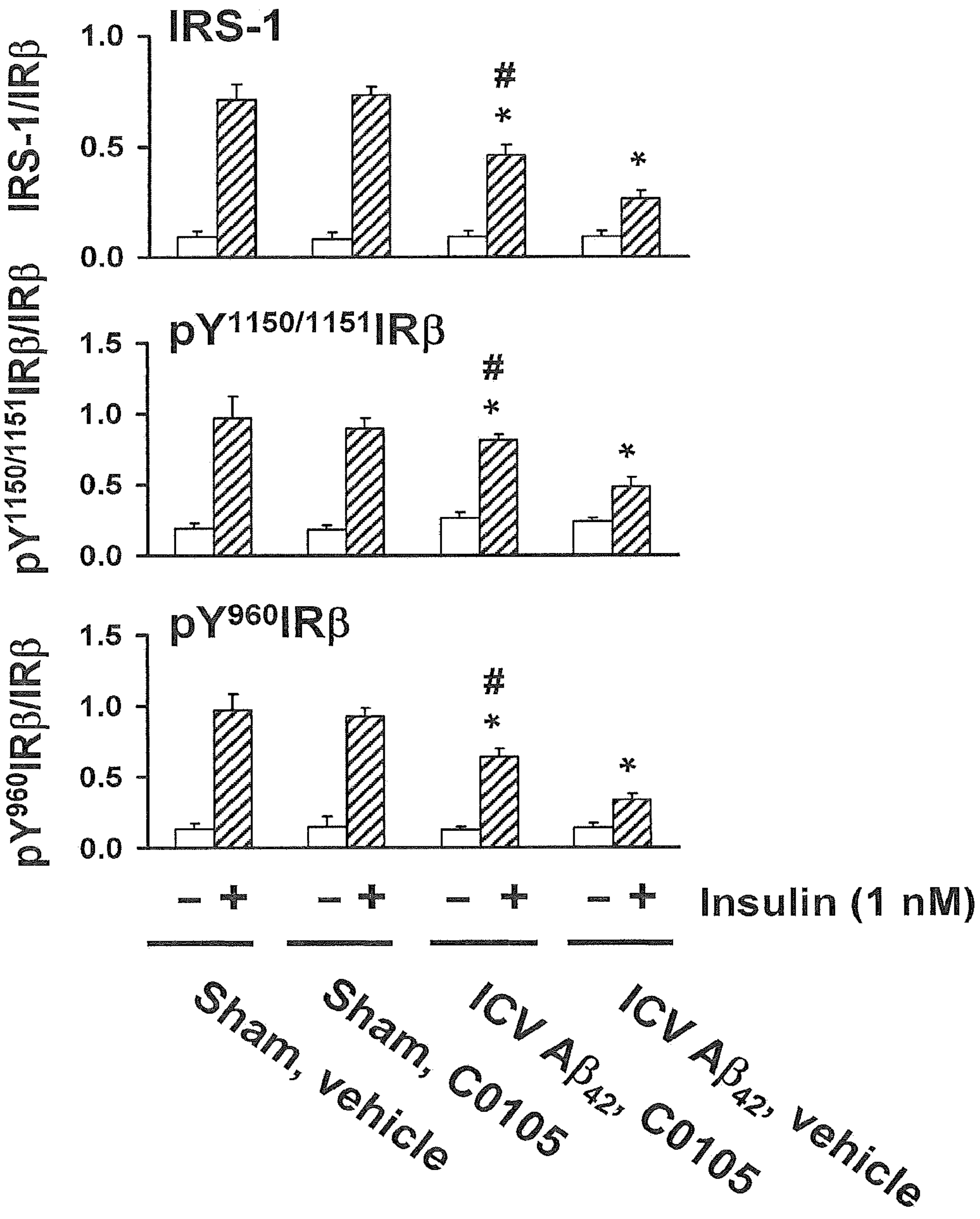

That Compound C0105 treatment can reverse NMDAR dysfunction is also evidenced by measuring NMDAR signaling. $A\beta_{42}$-infused mice showed reductions in NMDA/glycine-induced activation (phosphorylation) and in recruitment to NMDAR of six signaling components. Compound C0105 treatment of ICV $A\beta_{42}$-infused mice produced virtually identical results. NMDAR signaling impairment was also assessed by levels of six signaling components (PLCγ, nNOS, $pY^{402}$PyK2, PSD-95, PKCγ, $pY^{416}$Src, and $NR^1$) co-immunoprecipitating with NR-1, the obligatory subunit of NMDAR, after co-stimulating with NMDA and glycine. $A\beta_{42}$ reduced levels of all six signaling molecules, and these were normalized by C0105 treatment (FIG. 20). Similarly, IR signaling was assessed by phosphorylation of IPP and its association with the signaling molecule IRS-1 after stimulating with insulin. Like NMDAR signaling, these measures were reduced by $A\beta_{42}$ and restored by C0105 treatment (FIG. 21).

Figure 22:
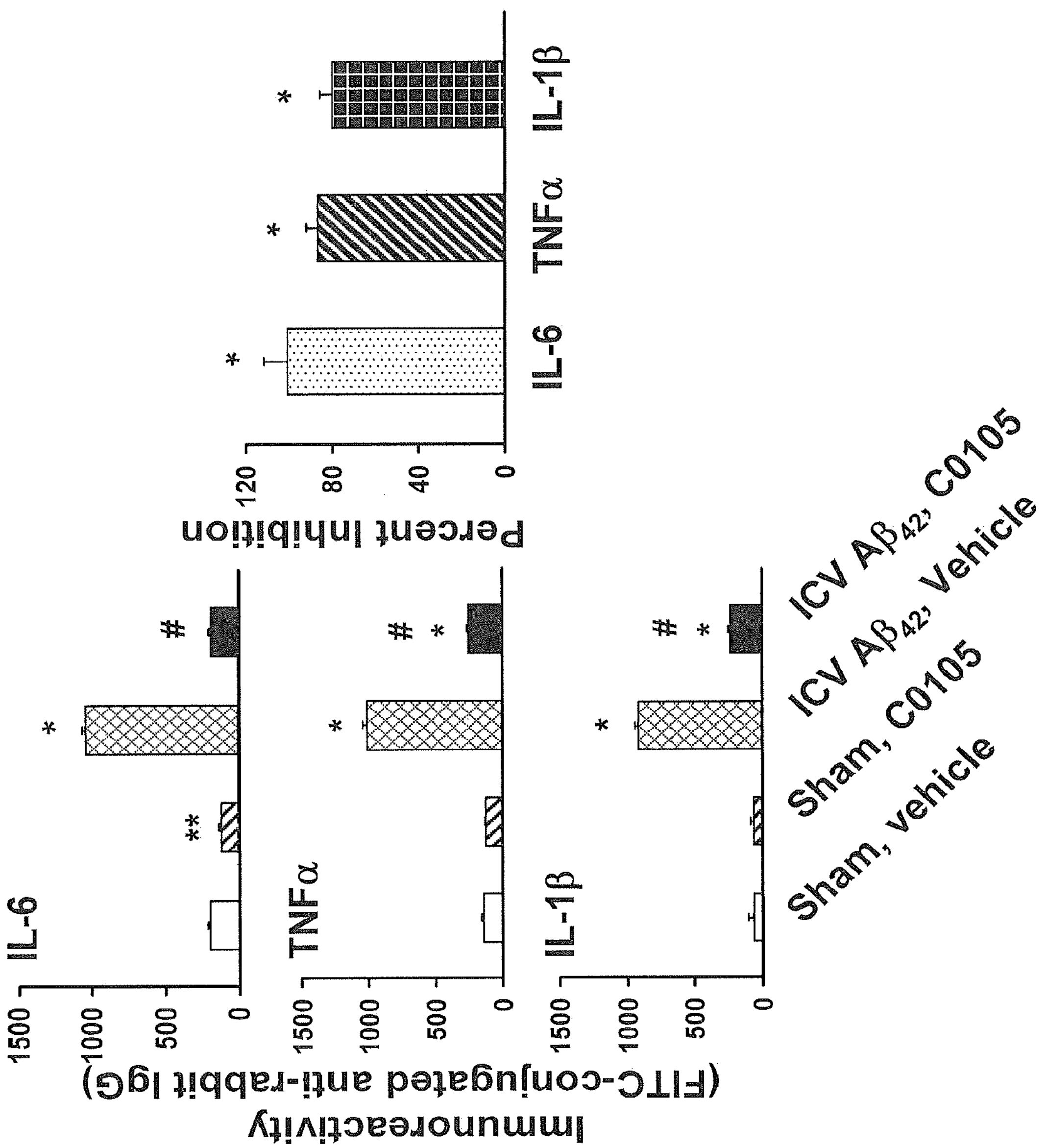
FIG. 22 illustrates that Compound C0105 treatment of mice nearly abolishes $A\beta_{42}$-induced cytokine production. $A\beta_{42}$ increased levels of cytokines IL-6, TNFα and IL-1β measured by a fluorescence ELISA assay using FITC. Compound C0105 almost abolished the production of these 3 cytokines. n=7 or n=8. Data are means±SEM. *p<0.01 vs. respective cytokine level in sham, vehicle group; #p<0.01 vs. respective cytokine level in ICV $A\beta_{42}$, vehicle group.
Figures 23, 23A:
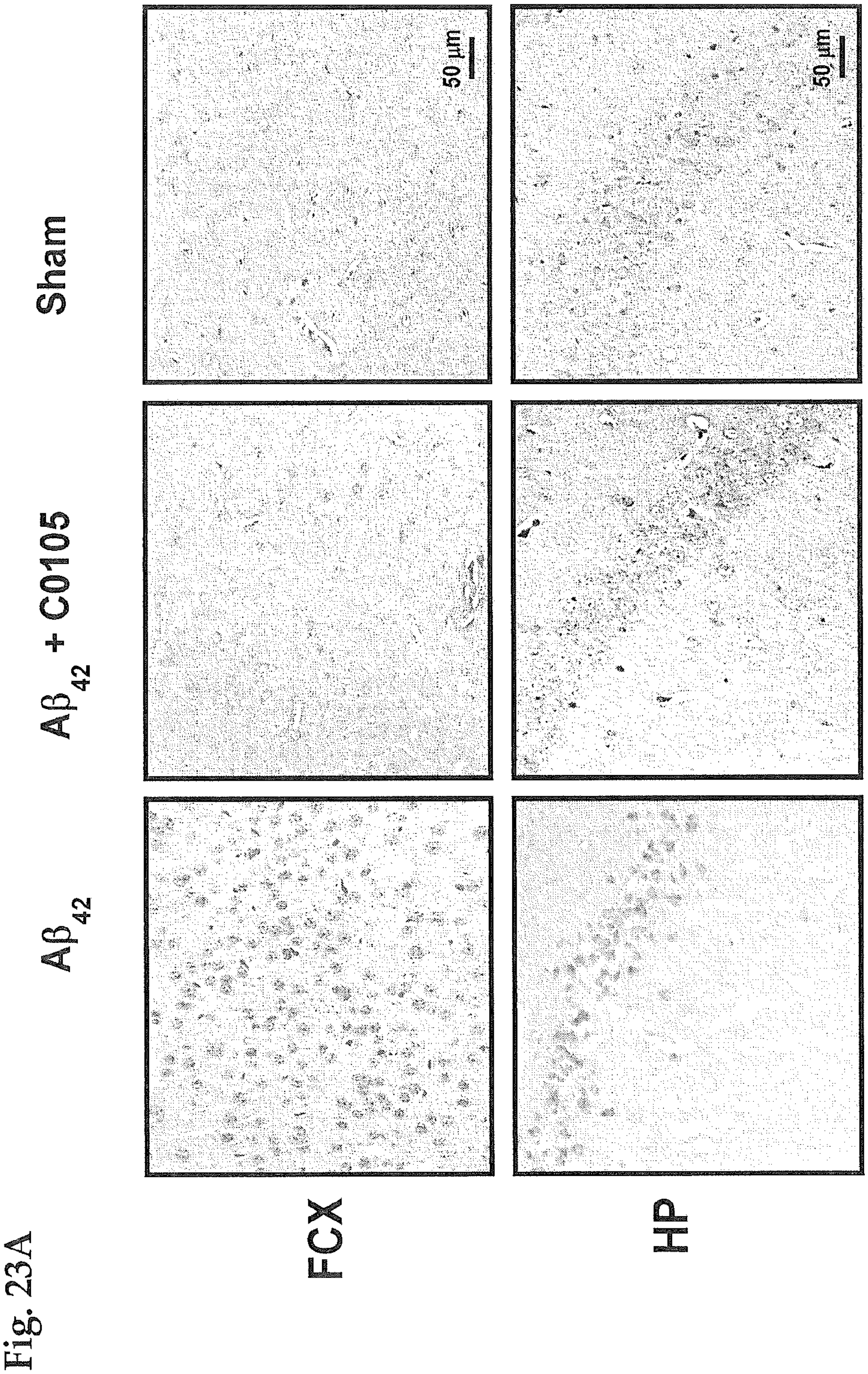
FIG. 23 in two panels contains photomicrographs that illustrate that Compound C0105 treatment of mice dramatically reduces NFT immunostaining. Representative sections immunostained with an anti-phospho-tau antibody (FIG. 23A) clearly show that Compound C0105 treatment greatly reduced NFT immunoreactivity in both prefrontal cortex (FCX) and hippocampus (HP) of mice receiving ICV $A\beta_{42}$ infusions. Quantitation of optical density in all animals (FIG. 23B) shows that Compound C0105 significantly reduced $A\beta_{42}$-induced NFT immunoreactivity in both regions. #p<0.01 $A\beta_{42}$ vs. $A\beta_{42}$+C0105, *p<0.01 vs. sham.
Figure 23B:
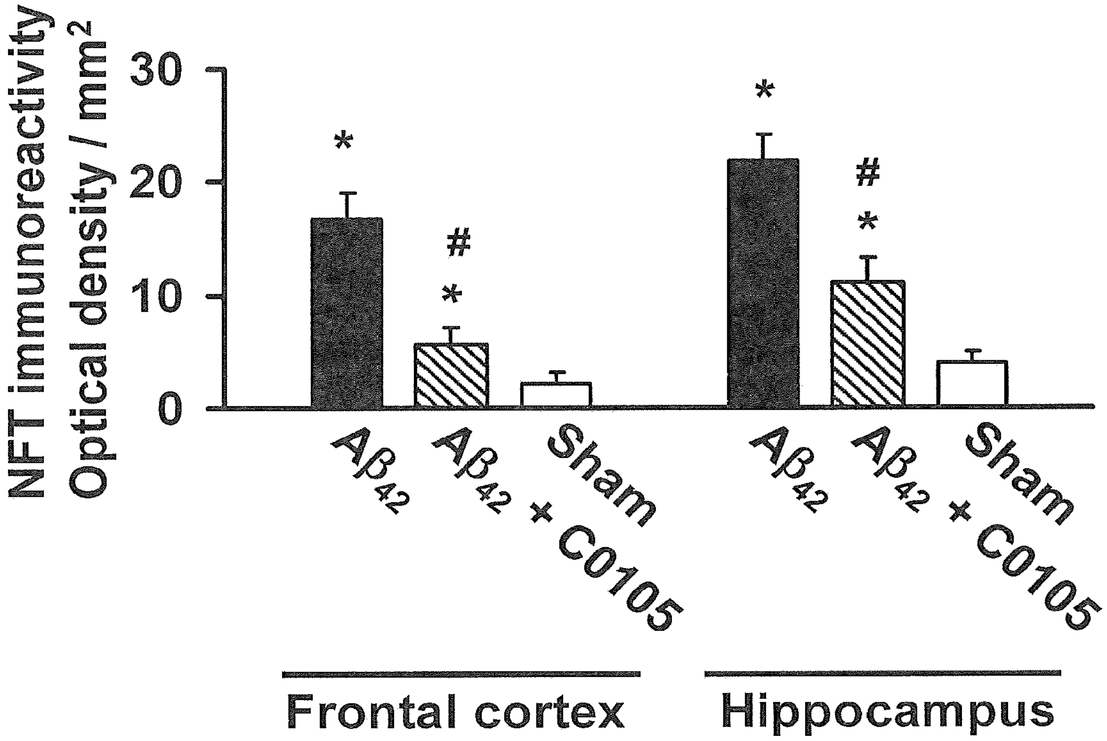
Figures 24, 24A:
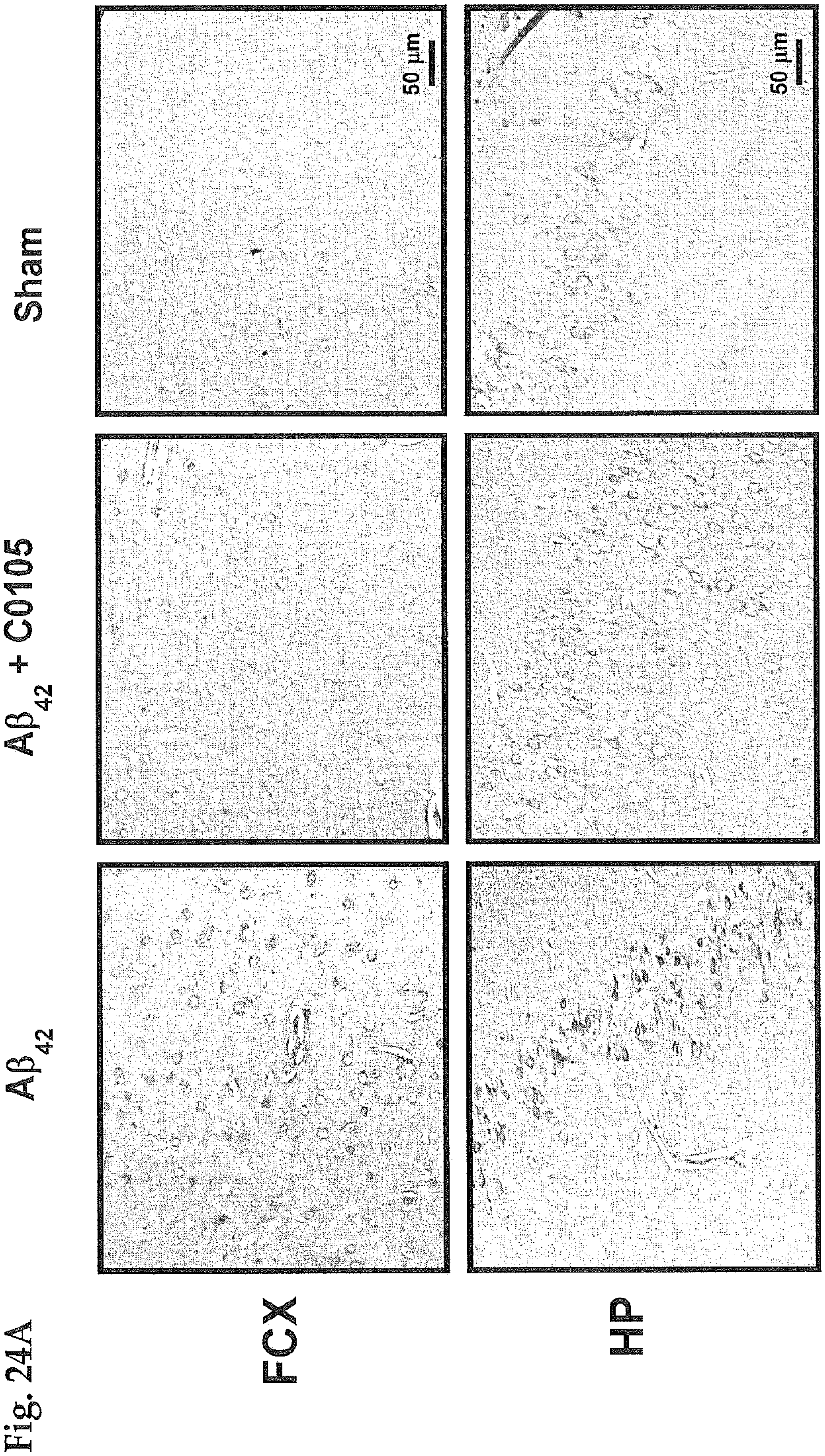
FIG. 24 in two panels contains photomicrographs that illustrate that Compound C0105 treatment of mice dramatically reduces immunostaining of $A\beta_{42}$ aggregates. Representative sections immunostained for $A\beta_{42}$ aggregates (FIG. 24A) clearly show that Compound C0105 treatment greatly reduced immunostaining of $A\beta_{42}$ aggregates in both prefrontal cortex (FCX) and hippocampus (HP) of mice receiving ICV $A\beta_{42}$ infusions. Quantitation of optical density in all animals (FIG. 24B) shows that Compound C0105 significantly reduced $A\beta_{42}$-induced NFT immunoreactivity in both regions. #p<0.01 $A\beta_{42}$ vs. $A\beta_{42}$+C0105, *p<0.01 vs. sham.
Figure 24B:
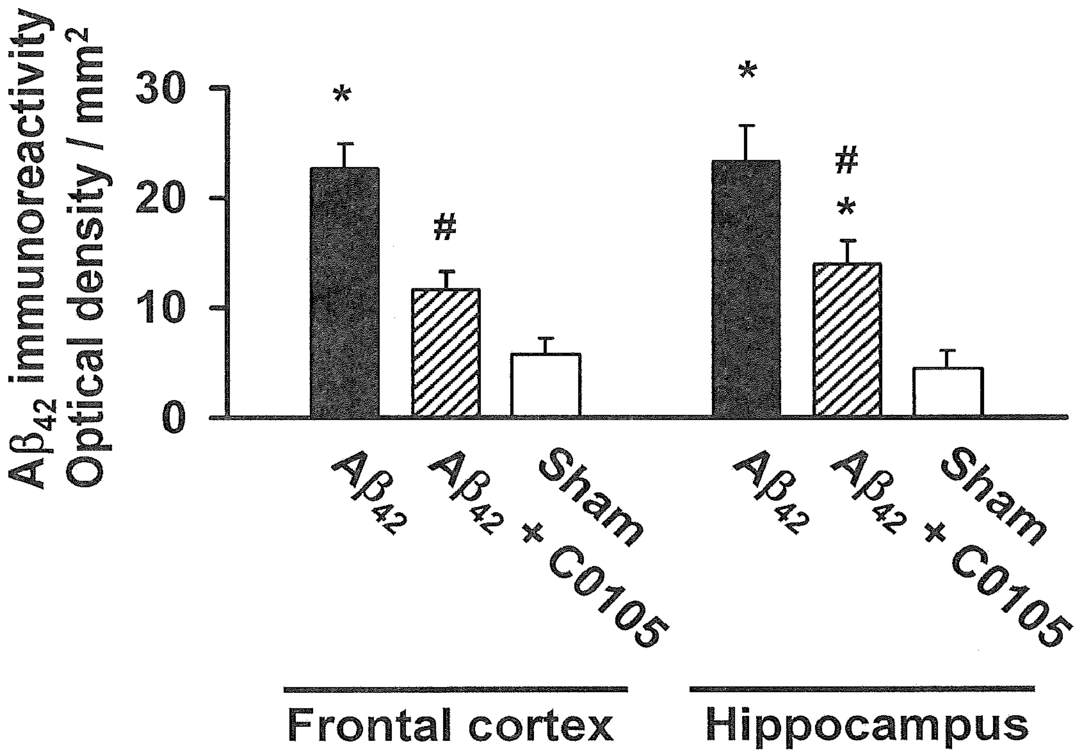

Importantly, because FLNA association with TLR4 is increased by $A\beta_{42}$ and normalized by Compound C0105, whether the inflammatory cytokine release after ICV $A\beta_{42}$ infusion would be suppressed by Compound C0105 treatment was assessed. ICV $A\beta_{42}$ infusion did increase IL-6, TNF-α and IL-13 production. Compound C0105 treatment completely abolished the $A\beta_{42}$-induced IL-6 production and suppressed TNF-α and IL-13 levels by 86 and 80%, respectively (FIG. 22). Finally, immunohistochemistry (IHC) of prefrontal cortex (FCX) and hippocampus (HP) shows that Compound C0105 treatment prevents not only NFT formation (FIG. 23) but also amyloid deposits (FIG. 24).

Postmortem Human Brain Tissue Study

Figure 25C:
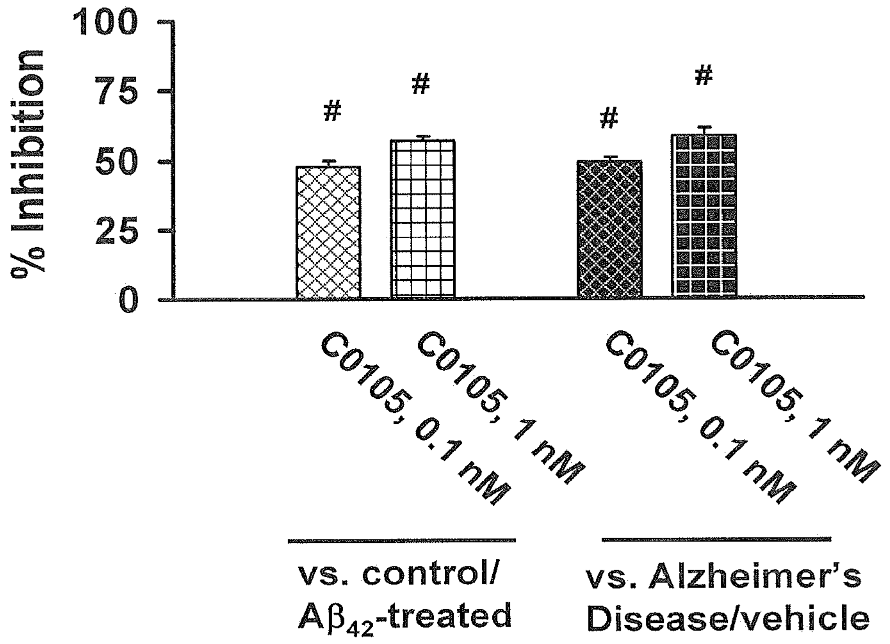
FIG. 25 in five panels illustrates that Compound C0105 decreased $A\beta_{42}$-induced FLNA association with both α7nAChR and TLR4 in human postmortem AD and control brain tissue. AD and age-matched control brain slices were treated with 0.1 or 1 nM concentrations of Compound C0105, and control brain slices were simultaneously treated with $A\beta_{42}$. The extent of FLNA association with α7nAChR or TLR4 was assessed in the solubilized synaptosomes by immunoprecipitating with immobilized anti-FLNA and Western blot detection (FIG. 25A) using antibodies specific to each receptor, and wherein numerals outside of and to the left of the blots are as discussed before. Blots were analyzed by densitometric quantitation (FIG. 25B and FIG. 25D). AD tissue and $A\beta_{42}$-treated control tissue showed a markedly increased association of α7nAChR and TLR4 with FLNA, and Compound C0105 reduced these associations. Percent inhibition is depicted in FIG. 25C and FIG. 25E. n=11. Data are means±SEM. *p<0.01 vs. vehicle-treated control, #p<0.01 vs. $A\beta_{42}$-treated control or vehicle-treated AD.
Figure 25D:
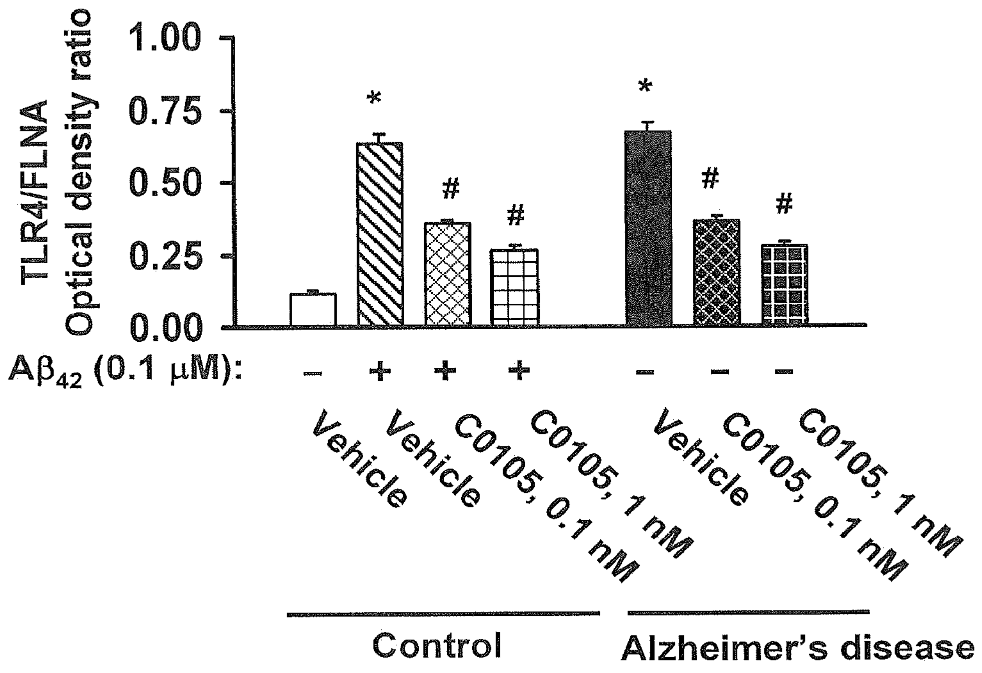
Figure 25E:
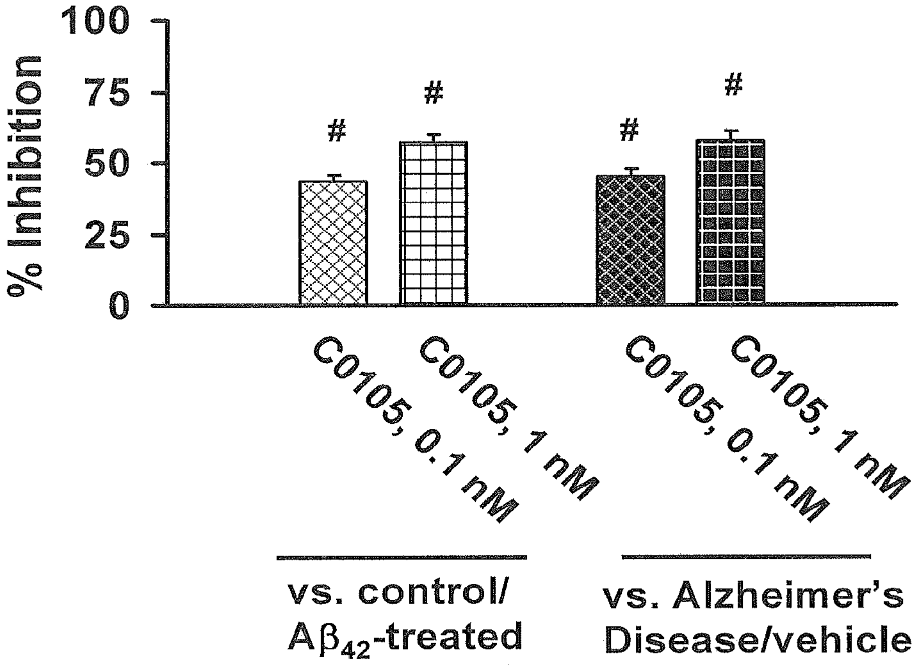
Figure 28:
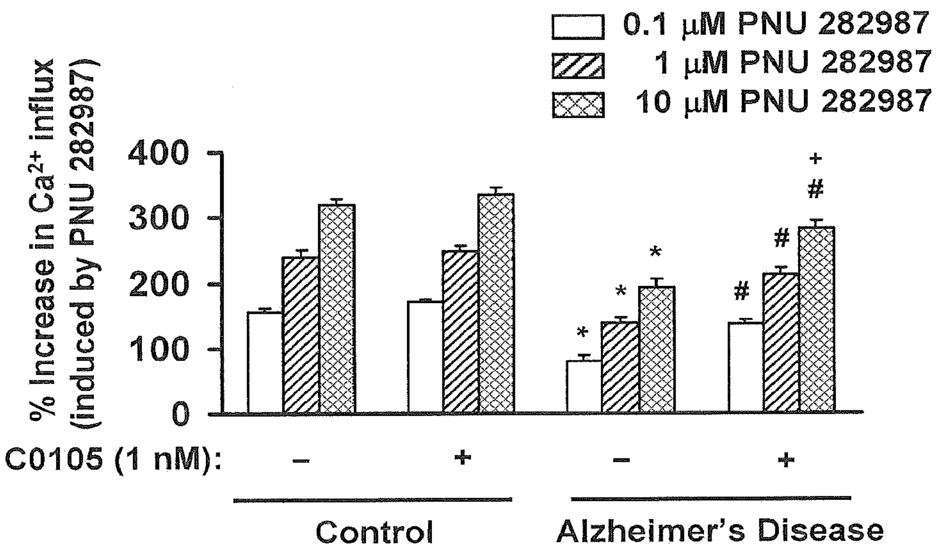
FIG. 28 is a bar graph that illustrates that Compound C0105 reduces α7nAChR dysfunction. AD brain slices and $A\beta_{42}$-treated control brain slices had significantly impaired calcium influx after stimulating with the α7nAChR full agonist PNU282987. Compound C0105 treatment normalized this impairment. Data are means±SEM. n=11. *p<0.01 vs. vehicle-treated control, #p<0.01 vs. vehicle-treated AD group, +p<0.01 vs. vehicle- and Compound C0105-treated control groups.
Figure 29:
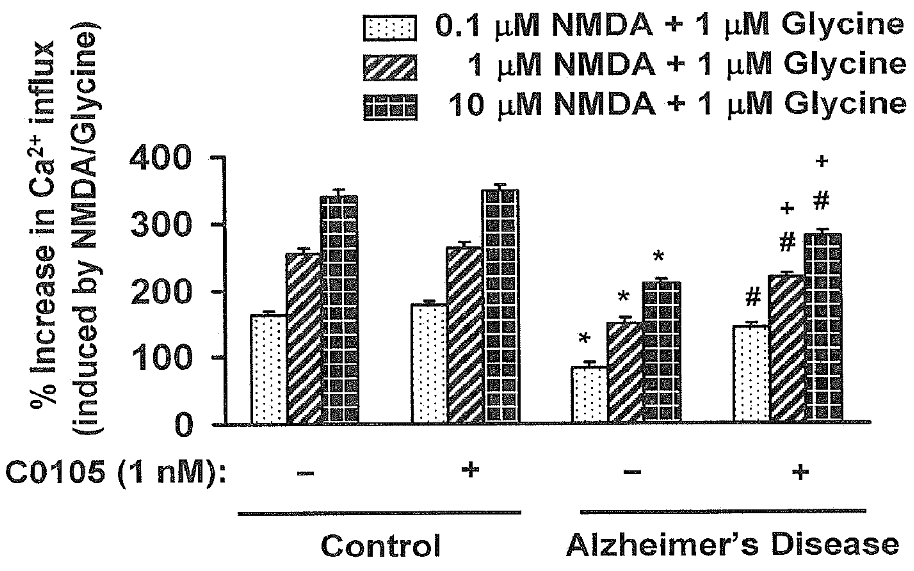
FIG. 29 is a bar graph that illustrates that Compound C0105 reduces NMDAR dysfunction. AD brain slices and $A\beta_{42}$-treated control brain slices had significantly impaired $Ca^{+2}$ influx after stimulating with NMDA and glycine, co-agonists of NMDAR. Compound C0105 treatment normalized this impairment. Data are means±SEM. n=11. *p<0.01 vs. basal level in control, #p<0.01 vs. vehicle-treated AD group, +p<0.01 compared to vehicle- and Compound C0105-treated control groups.
Figure 30:
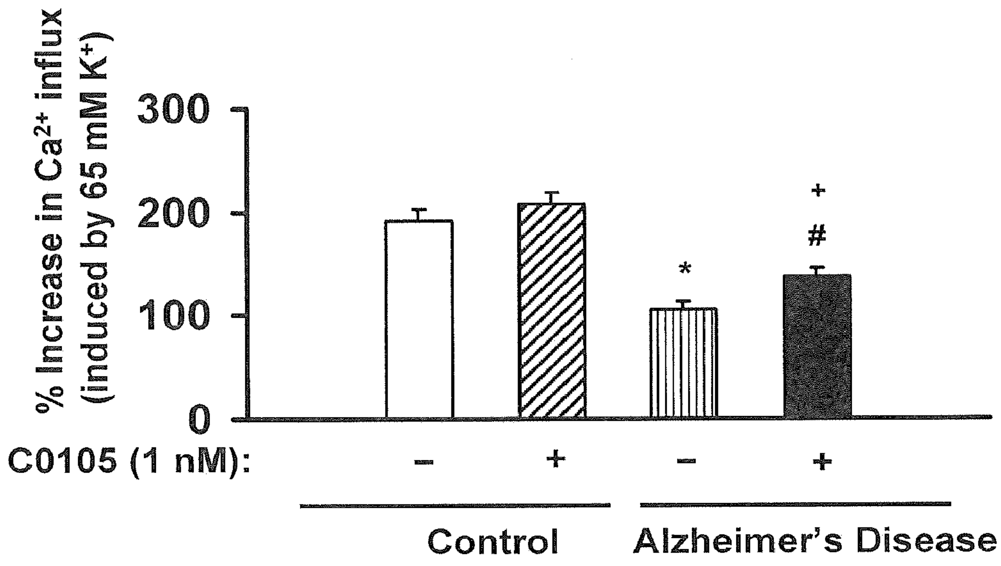
FIG. 30 is a bar graph that illustrates that 1 nM Compound C0105 partially normalizes $K^+$-evoked $Ca^{+2}$ influx. $K^+$-evoked $Ca^{+2}$ influx is dramatically decreased in AD brain slices and in $A\beta_{42}$-treated control brain slices, indicating nonfunctioning cells or cell death. Compound C0105 incubation significantly elevates this depolarization-induced $Ca^{+2}$ influx, rescuing some of the nonfunctioning cells. Data are means±SEM. n=11. *p<0.01 vs. vehicle-treated control group; #p<0.01 vs. vehicle-treated AD group; +p<0.01 vs. vehicle- and Compound C0105-treated control groups.
Figure 31:
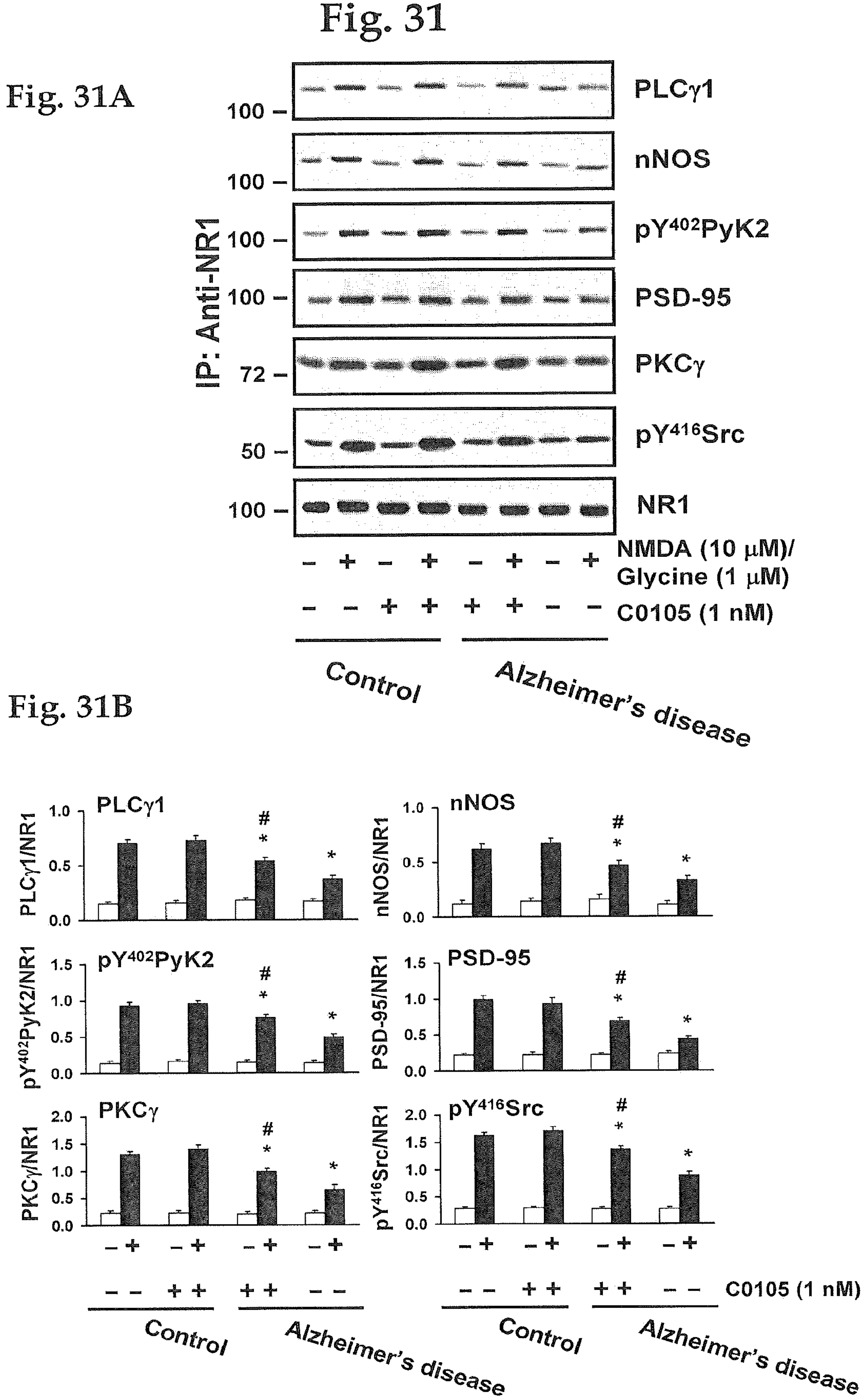
FIG. 31 in two panels illustrates that Compound C0105 normalizes NMDAR signaling impairments. NMDAR dysfunction in AD or $A\beta_{42}$-treated control brain slices is also evidenced by reductions in linkages of several signaling molecules to NR-1, the obligatory NMDAR subunit. Compound C0105 (1 nM) mitigates these reductions. Western blots (FIG. 31A), in which numerals outside of and to the left of the blots are as discussed before, were analyzed by densitometric quantitation (FIG. 31B). Data are means±SEM. n=11. *p<0.01 vs. NMDA/glycine-stimulated level in vehicle-treated control group; #p<0.01 vs. NMDA/glycine-stimulated level in vehicle-treated AD group.
Figure 35:
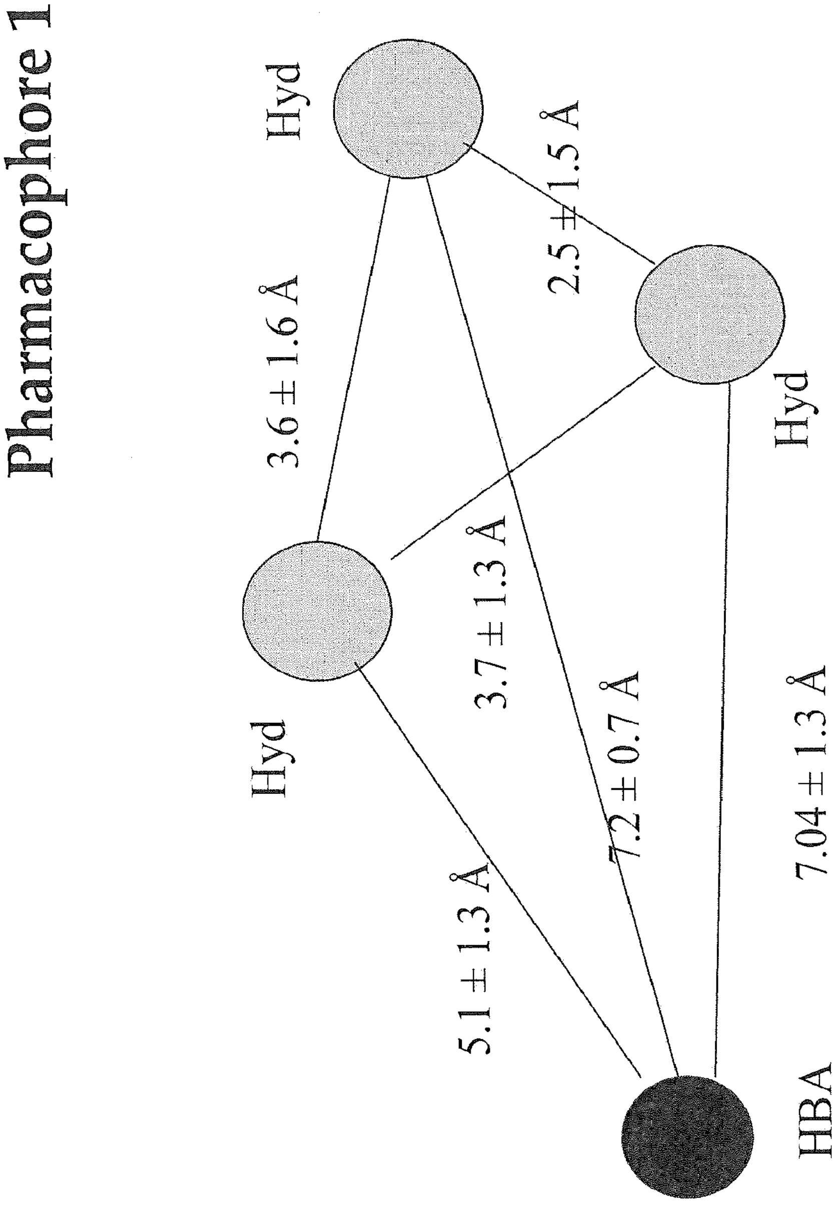
FIG. 35 through FIG. 40 represent schematic pharmacophores (Pharmacophores 1-6, respectively) showing relative locations of chemical features such as a hydrogen bond acceptor (HBA), an aromatic/hydrophobe (ARO/HYD) center, and the intramolecular distances there between in Ångstroms for a compound that binds to the pentameric peptide of FLNA of SEQ ID NO: 1.
Figure 36:
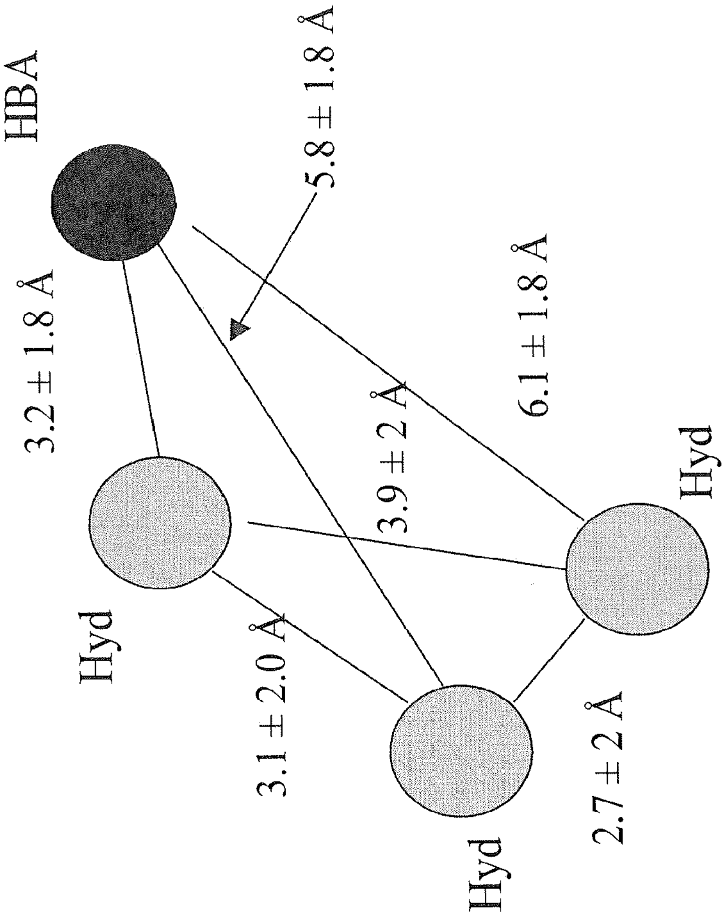
Figure 37:
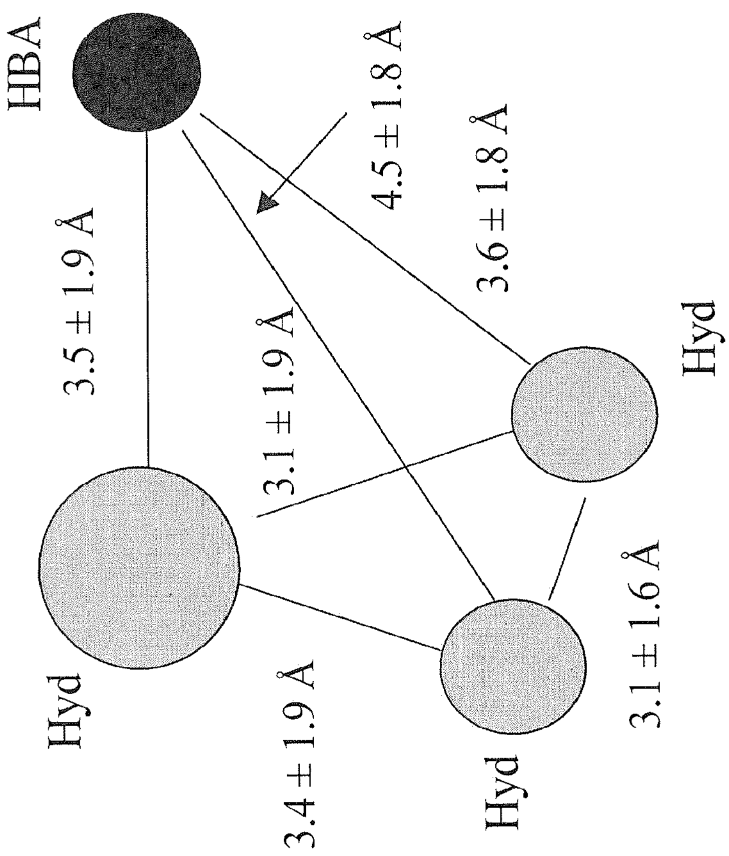
Figure 38:
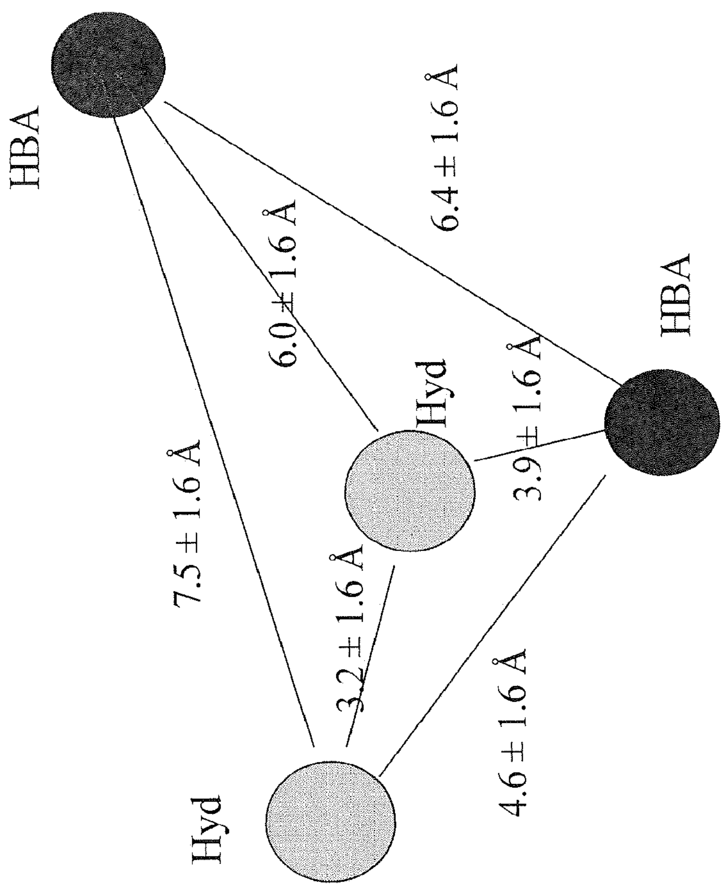
Figure 39:
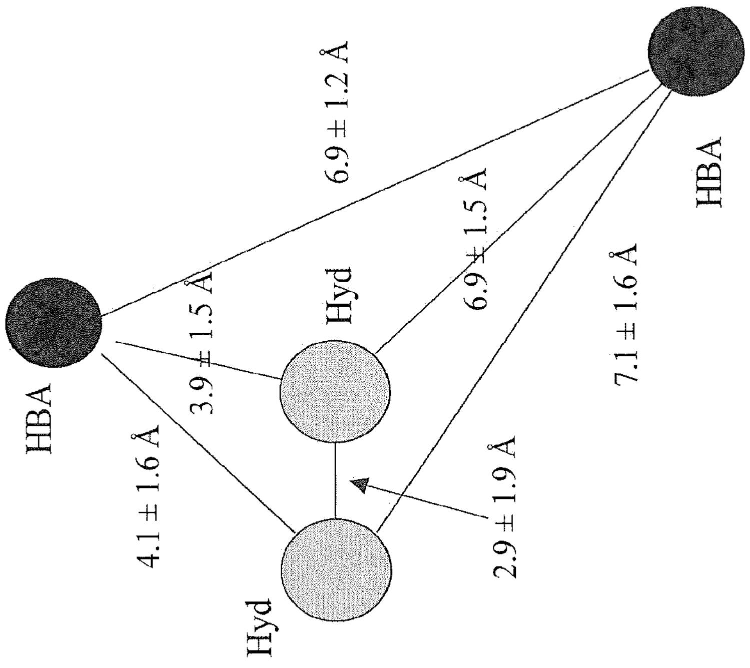
Figure 40:
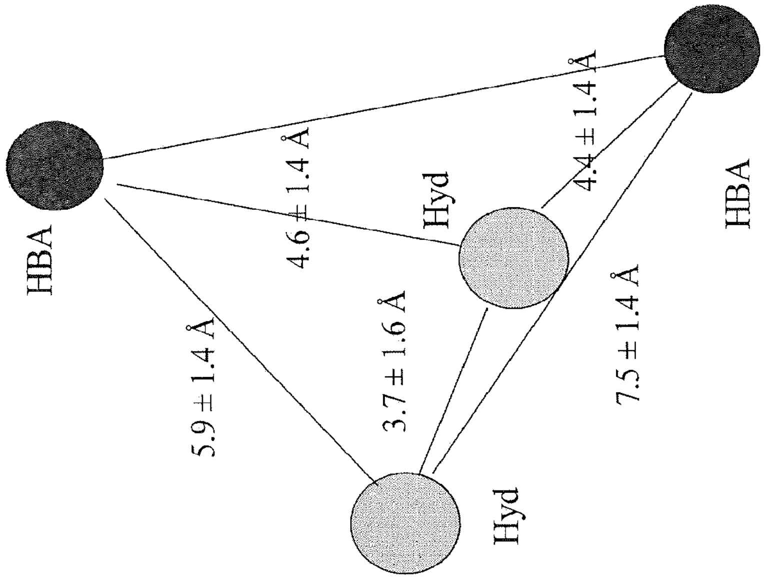
Figures 41, 41A:
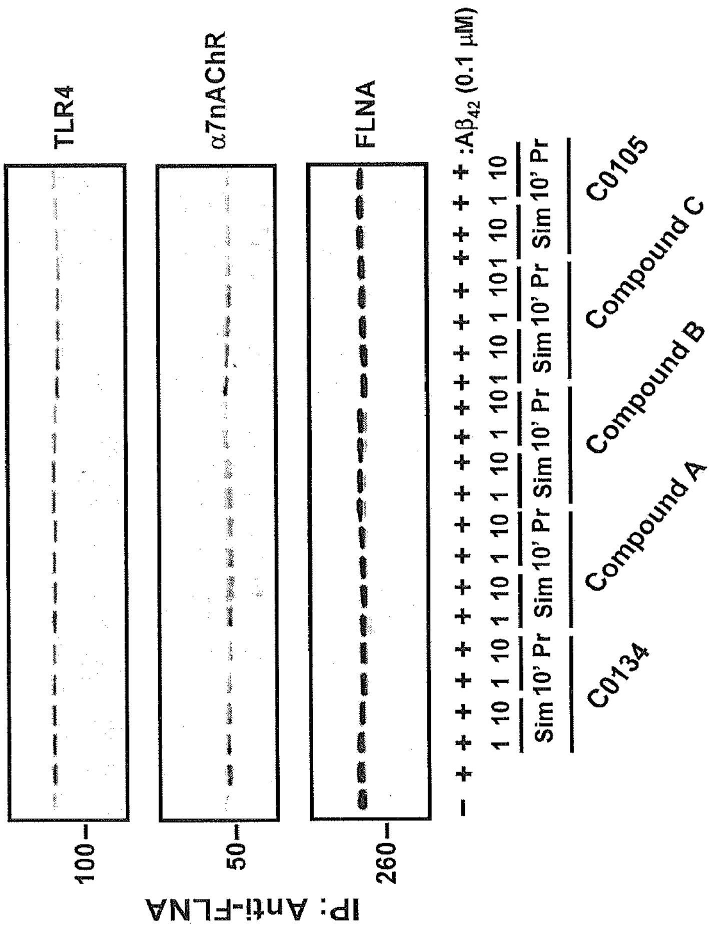
FIG. 41, in two panels.
Figure 41B:
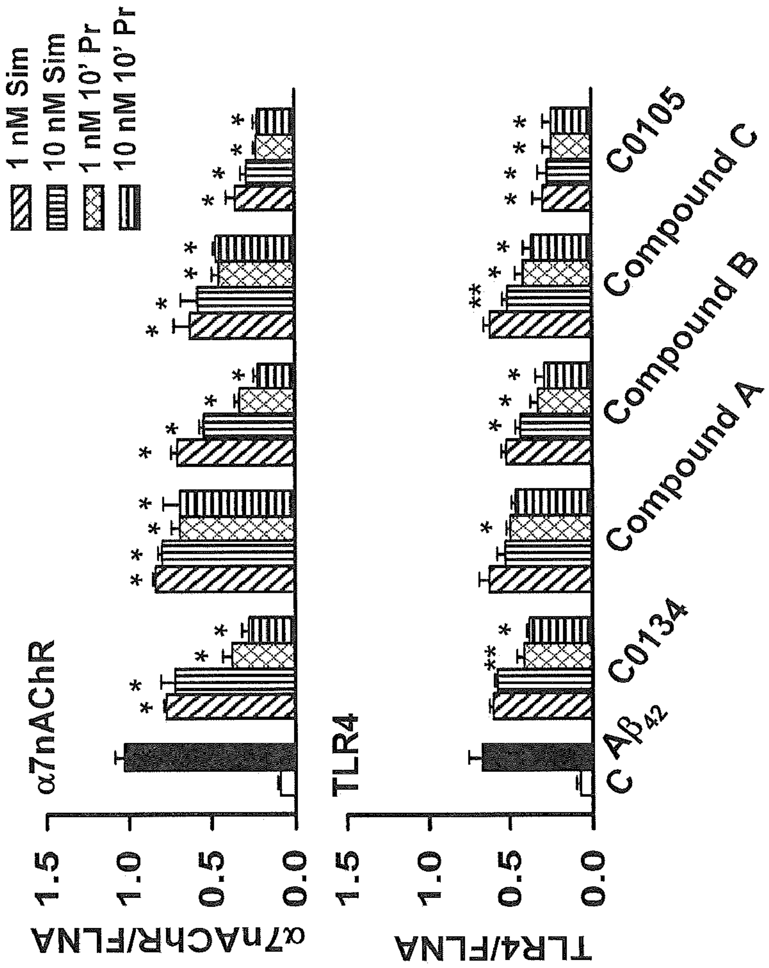
Figures 42, 42A:
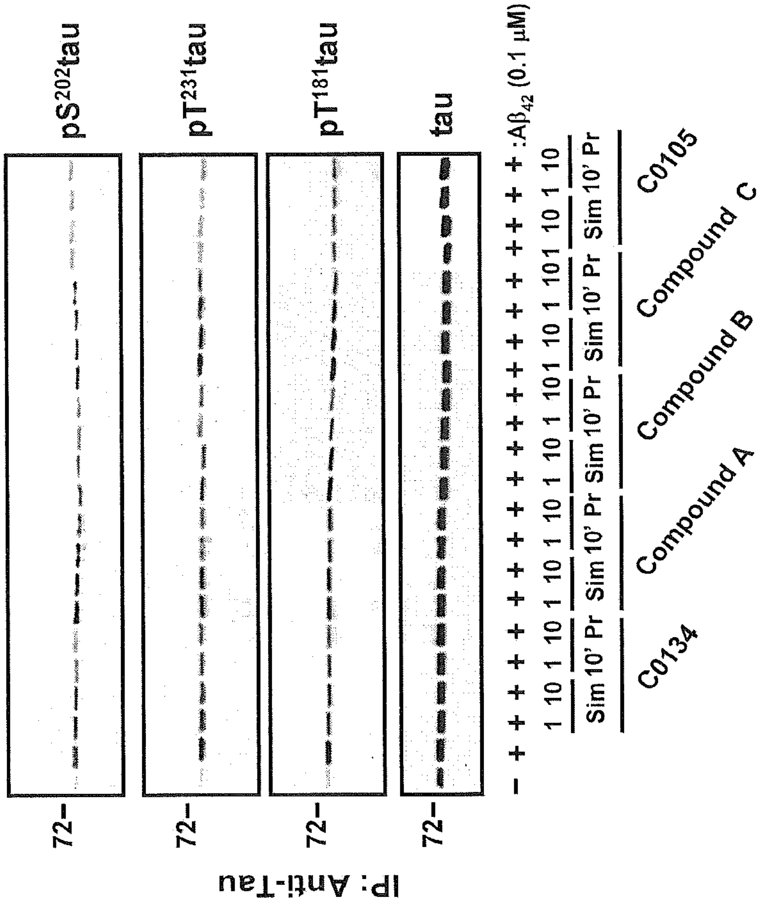
FIG. 42, also in two panels.
FIGS. 42A and 42B, illustrates that FLNA-binding compounds reduce tau phosphorylation at all three phosphorylation sites using the compounds and concentrations of FIG. 41 using immunoprecipitation and Western blotting. Thus, in the same treated synaptosomes used in FIG. 41, levels of tau protein phosphorylated at $S^{202}$, $T^{231}$ and $T^{181}$ were measured in immunoprecipitates using an anti-tau antibody that does not distinguish its phosphorylation state (Tau). The three phosphoepitopes of tau were detected in immunoprecipitates using specific antibodies. $A\beta_{42}$ strongly promotes tau phosphorylation at all three sites (FIG. 42A). Densitometric analysis of the blots (FIG. 42B) showed that all five compounds reduced this phosphorylation at 10 nM concentration either when simultaneously administered, or with 10-minute pretreatment at both concentrations compared to $A\beta_{42}$ alone using Dunnett's test at *p<0.01. Compound A also reduced tau phosphorylation with simultaneous administration at 1 nM with **p<0.05 or *p<0.01, whereas Compound C did not provide a statistically significant result at two phosphorylation positions when simultaneously administered.
Figure 42B:
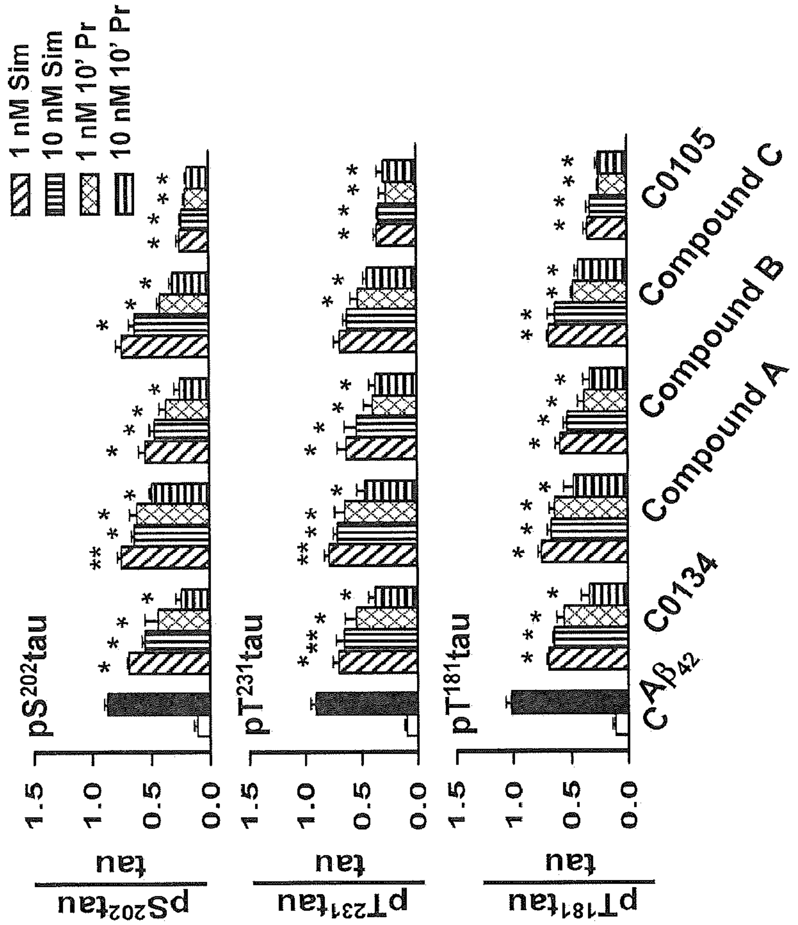
Figures 43, 43A:
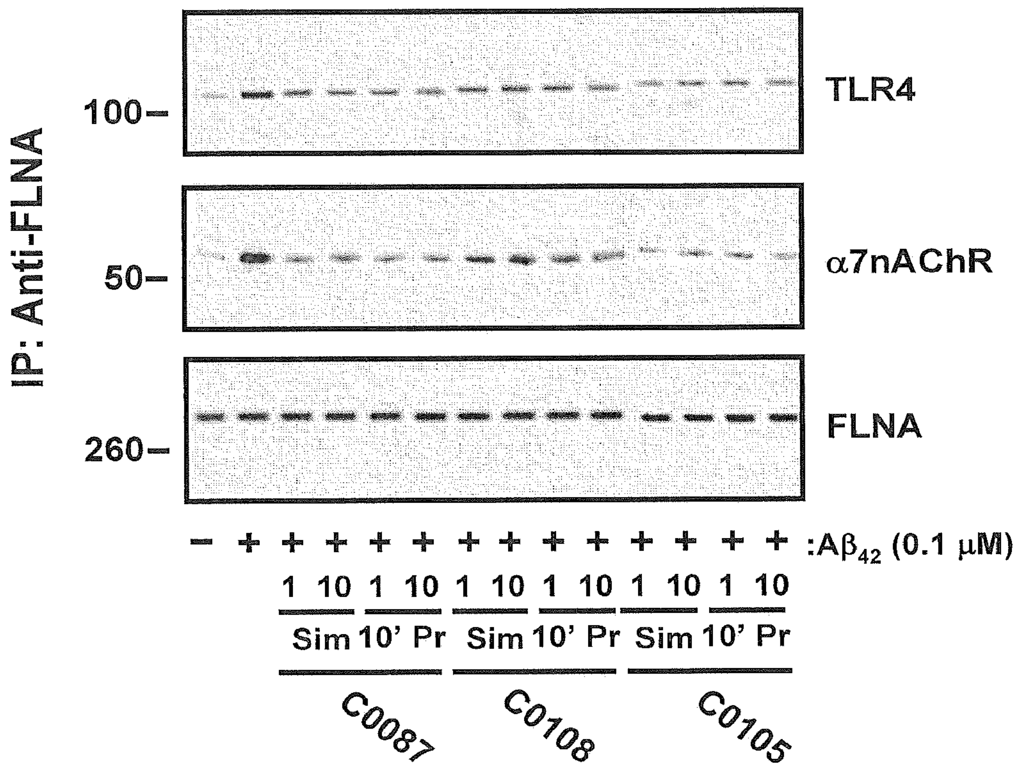
FIG. 43, in two panels.
FIG. 43A and FIG. 43B, illustrates further high-affinity FLNA-binding compounds that reduce α7nAChR-FLNA association assayed as in FIG. 2. Frontal cortical synaptosomes from 2-month-old rats were treated with 1 or 10 nM concentrations of Compound C0087 and Compound C0108, using Compound C0105 as a control, either simultaneously (Sim) or 10 minutes prior (10' pr) to $A\beta_{42}$ (0. μM) and were immunoprecipitated with immobilized anti-FLNA. The complexes in the solubilized synaptosomes, and α7nAChR, TLR4 and FLNA levels in the anti-FLNA immunoprecipitates were determined by Western blotting (FIG. 43A) in which numerals outside of and to the left of the blots are as discussed before. Amounts present in the blots were quantified by densitometry (FIG. 43B). Ratios of α7nAChR/FLNA and TLR4/FLNA were statistically different from $A\beta_{42}$ alone with **p<0.05, *p<0.01 for the compounds as shown using Dunnett's test. Structural formulas of the compounds used in this and the other figures are provided hereinafter.
Figure 43B:
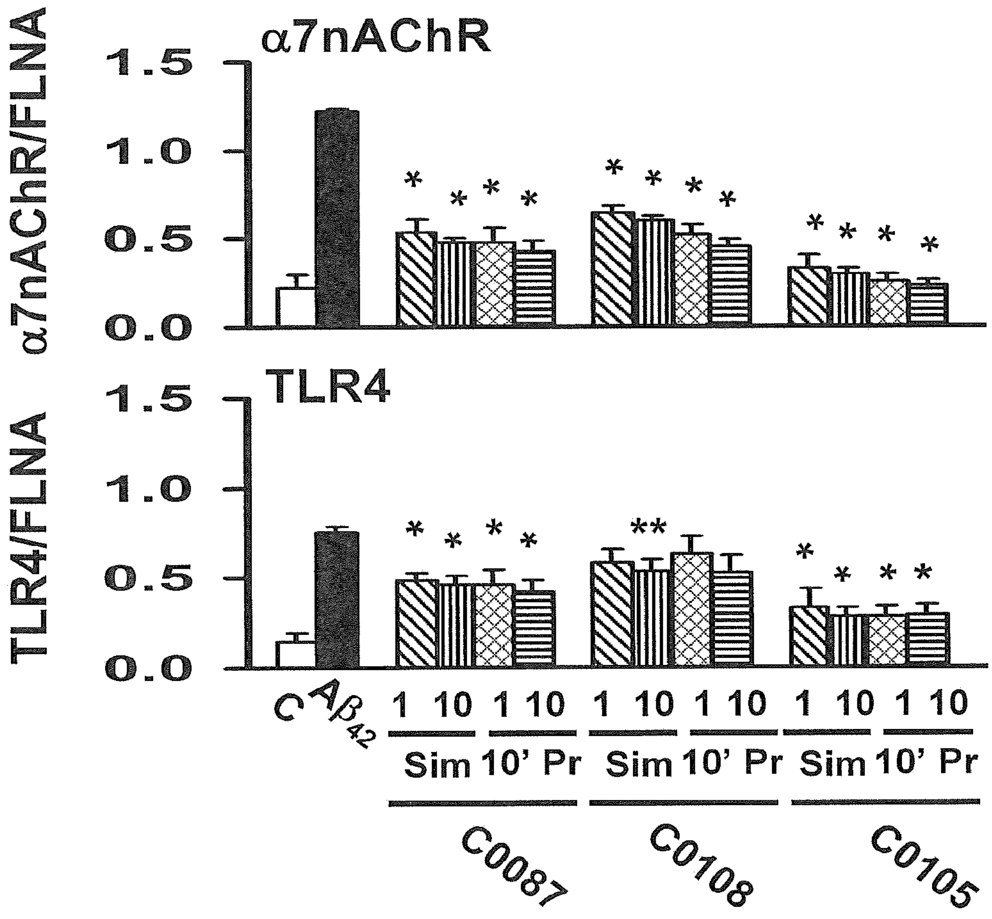
Figures 44, 44A:
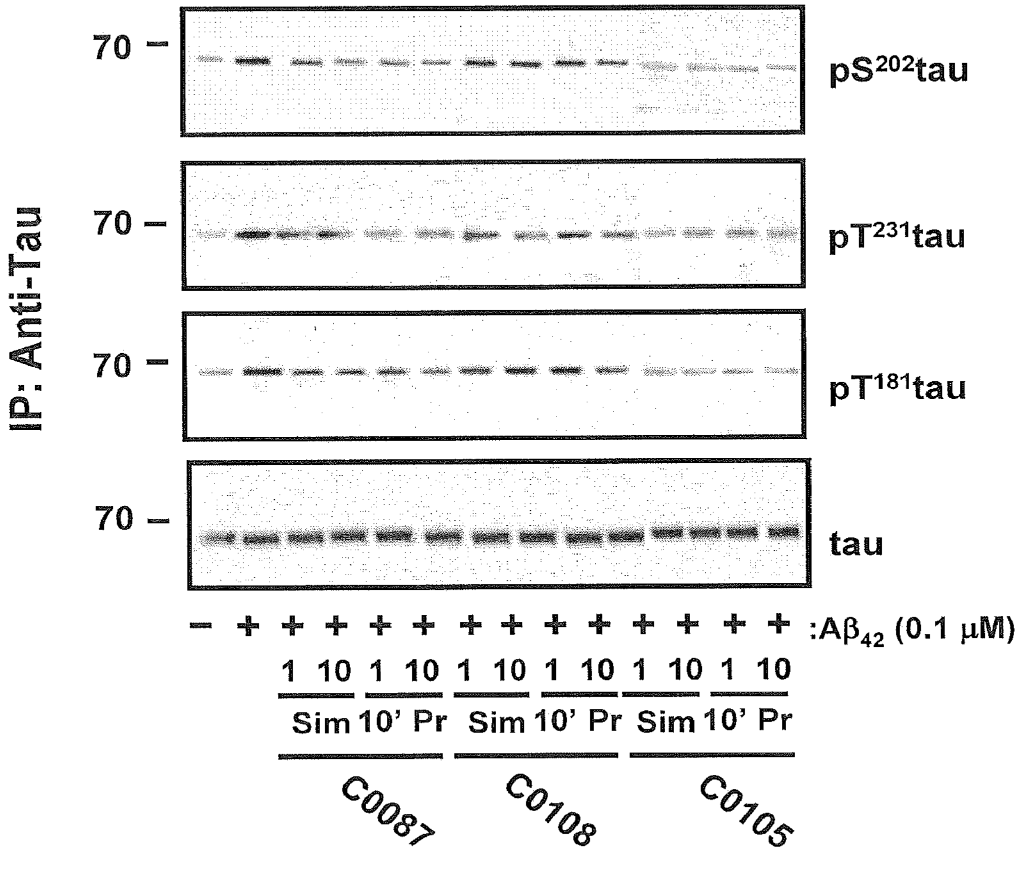
FIG. 44, also in two panels.
FIG. 44A and FIG. 44B, illustrates that FLNA-binding compounds reduce tau phosphorylation at all three phosphorylation sites using the compounds and concentrations of FIG. 43 using immunoprecipitation and Western blotting. Thus, in the same treated synaptosomes used in FIG. 43, levels of tau protein phosphorylated at $S^{202}$, $T^{231}$ and $T^{181}$ were measured in immunoprecipitates using an anti-tau antibody that does not distinguish its phosphorylation state (Tau). The three phosphoepitopes of tau were detected in immunoprecipitates using specific antibodies. $A\beta_{42}$ strongly promotes tau phosphorylation at all three sites. Densitometric analysis of the blots (FIG. 44B) showed that both compounds reduced this phosphorylation at both concentrations either simultaneously administered or with 10-minute pretreatment compared to $A\beta_{42}$ alone using Dunnett's test at **p<0.05, *p<0.01.
Figure 44B:
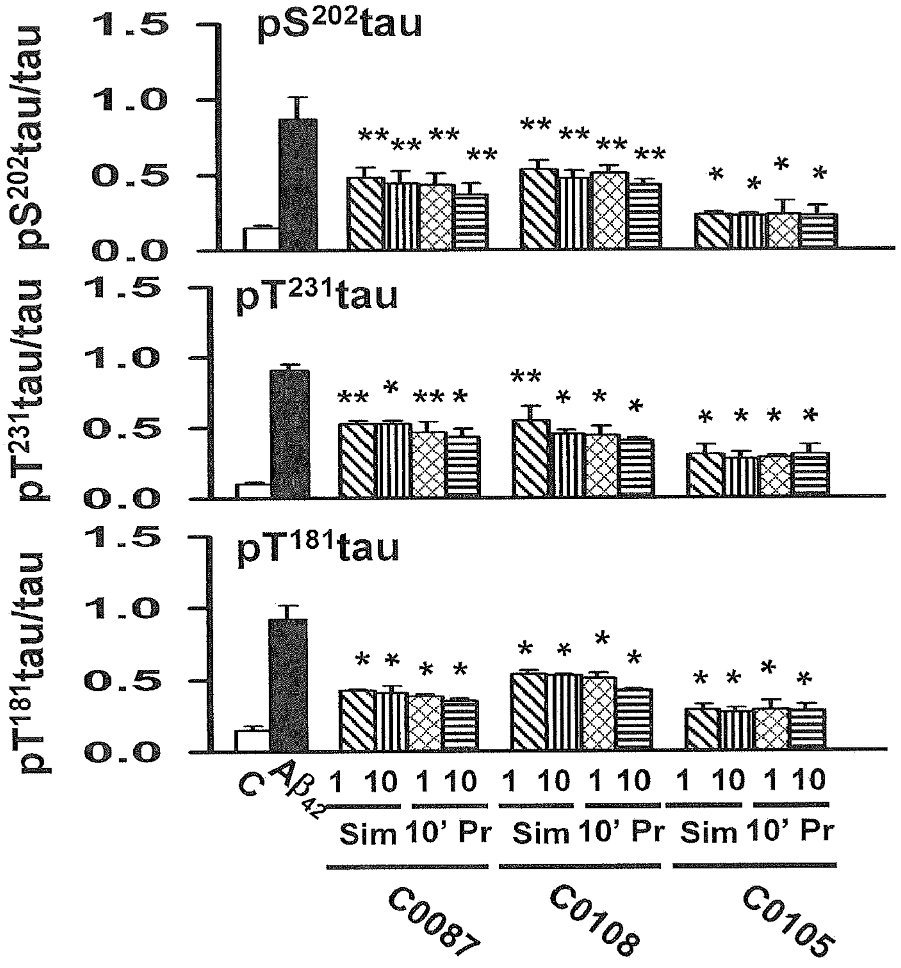

In AD and $A\beta_{42}$-treated control tissue, Compound C0105 reduces $A\beta_{42}$-induced FLNA association with α7nAChR and TLR4 (FIG. 25). Contact with compound C0105 reduces $A\beta_{42}$-α7nAChR complexes (FIG. 26) by reducing the affinity for this interaction about 1,000-10,000-fold (FIG. 27). Contact with Compound C0105 preserves functioning of α7nAChR (FIG. 28) and NMDAR (FIG. 29) as demonstrated by calcium influx after receptor stimulation. Normalization of receptor function was also demonstrated by levels of signaling assemblies of NMDAR (FIG. 31) and IR (FIG. 32). Remarkably, one hour incubation of AD brain slices with 1 nM Compound C0105 normalized all six measures of this NMDAR signaling impairment without affecting the NMDAR subunit assemblies. Similar to findings in the mouse model, Compound C0105 incubation also attenuated the deficit in depolarization-induced calcium influx in postmortem AD tissue that indicates nonfunctioning or dying cells (FIG. 30).

In postmortem control frontocortical tissue, the FLNA pentapeptide binding site of Compound C0105 (VAKGL of SEQ ID NO: 1) was used as a decoy to block the attenuation of FLNA association with α7nAChR and TLR4 by Compound C0105 (FIG. 33). A similar blockade of the prevention of tau phosphorylation was demonstrated with this decoy pentapeptide (FIG. 34). Together these results confirm that Compound C0105 inhibits tau phosphorylation and preserves multiple receptor functions via its binding to FLNA.

Figures 47, 47A:
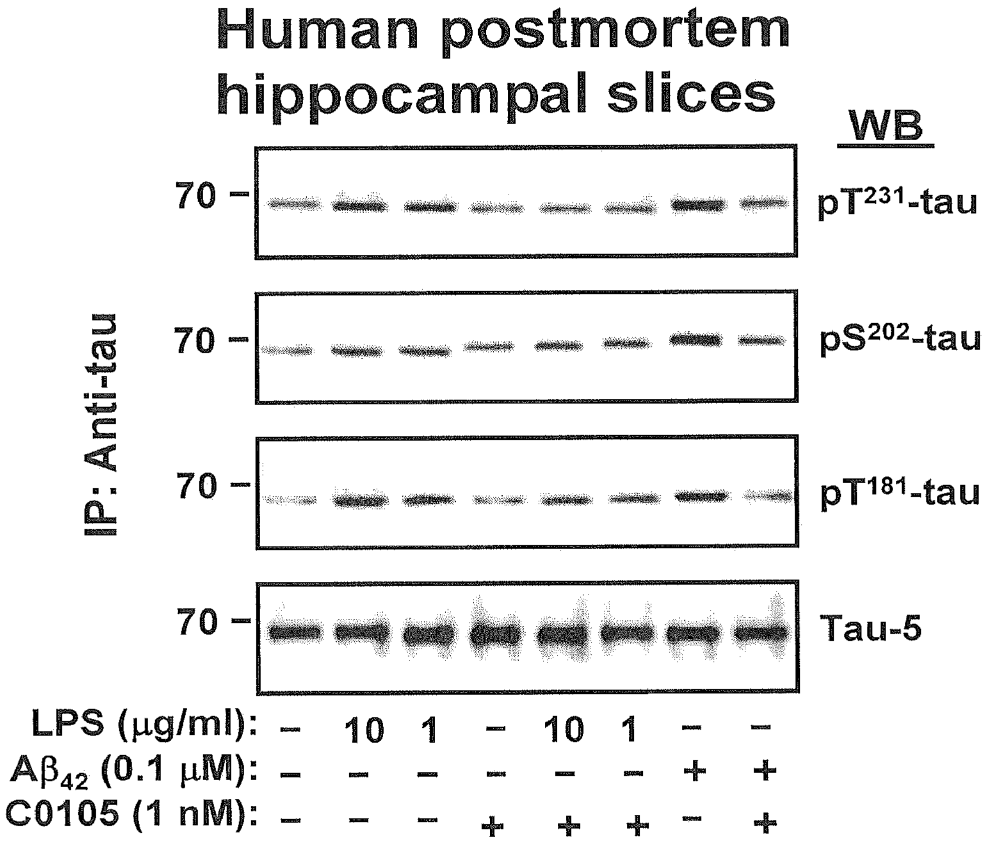
FIG. 47, in three panels as FIGS. 47A-47C, illustrates that LPS at each of two concentrations (10 g/ml and 10 g/ml) induces tau phosphorylation at all three phosphorylation sites in human postmortem hippocampal cell slices, and that that phosphorylation is inhibited by compound C0105 at a concentration of 1 nM using immunoprecipitation and Western blotting. The levels of tau protein phosphorylated at $S^{202}$, $T^{231}$ and $T^{181}$ were measured in immunoprecipitates using an anti-tau antibody that does not distinguish its phosphorylation state (Tau). The three phosphoepitopes of tau were detected in immunoprecipitates using specific antibodies using Western blots (WB). $A\beta_{42}$ was used as a control that also promotes tau phosphorylation at all three sites. Densitometric analysis of the blots (FIGS. 47B and 47C) provides a quantitative illustration that Compound C0105 reduced this phosphorylation using Newman-Keuls multiple comparisons: *p<0.01, p<0.05 compared to vehicle-incubated group, and #p<0.01 compared to respective LPS or $A\beta_{42}$ treated group. The graphs in FIG. 47C are in the same order as those shown in FIG. 47**B.

Postmortem control frontocortical tissue was also used to demonstrate that Compound C0105 also reduces LPS-induced tau phosphorylation (FIG. 47).

In postmortem control frontocortical tissue, $A\beta_{42}$-induced FLNA recruitment to α7nAChRs was mimicked by 10-fold higher concentrations of $A\beta_{40}$ or of the α7nAChR agonists nicotine and PNU282987 with significantly lesser magnitudes. The α7nAChR antagonists α-bungarotoxin and methyllycaconitine and the cholinesterase inhibitor/positive allosteric nicotinic receptor modulator galantamine showed no effect (Table, below). Interestingly, memantine, an antagonist of both NMDAR and α7nAChR, elicited the recruitment of FLNA to α7nAChRs with a magnitude not far from that of $A\beta_{40}$.

sure or under elevated pressure, preferably MPLC and HPLC methods, and also methods involving fractional crystallization. This can particularly involve the separation of individual enantiomers, e.g., diastereoisomeric salts separated by means of HPLC in the chiral phase or by means of crystallization with chiral acids, for example (+)-tartaric acid, (−)-tartaric acid, or (+)-10-camphorsulfonic acid. An enantiomer separated by chiral salt formation can readily be converted into an achiral or racemic pharmaceutically acceptable salt for use.

A compound of Series A, B, C-1, C-2, D or E or a pharmaceutically acceptable salt thereof is contemplated to be optionally used in a process of the invention in enantiomerically pure form; i.e., in (S) or (R) configuration or d and l forms, or in the form of a racemic mixture showing an (S,R) or (d,l) configuration, or as one or more diastereomers, and mixtures thereof.

Thus, a contemplated compound or its pharmaceutically acceptable salt can optionally be present in one or more forms. Illustratively, the compound or its salt can be in the form of an individual enantiomer or diastereoisomer. A contemplated compound or its salt can also be present in the form of a mixture of stereoisomers. A contemplated compound or salt can also be present in the form of a racemic mixture.

TABLE

Effects of α7nAChR agents on FLNA recruitment to α7nAChR

| Agent | FLNA/α7nAChR ratio (stimulation vs vehicle, %) | Statistics vs vehicle, p | Aβ42 effect, % | Statistics vs Aβ42, p |
|---|---|---|---|---|
| Vehicle | 0.07 ± 0.01 | — | — | — |
| 0.1 μM Aβ42 | 0.73 ± 0.05 (1012.3 ± 104.9) | <0.0001 | 100 | — |
| 1 μM Aβ40 0. | 28 ± 0.03 (341.9 ± 65.1) | 0.001 | 34.8 ± 6.6 | <0.001 |
| 1 μM Nicotine | 0.13 ± 0.02 (107.7 ± 31.4) | <0.001 | 11.0 ± 3.2 | 0.001 |
| 1 μM PNU282987 | 0.12 ± 0.02 (87.1 ± 37.9) | 0.01 | 8.9 ± 3.9 | 0.001 |
| 1 μM α-Bungarotoxin | 0.07 ± 0.01 (7.5 ± 6.6) | 0.65 | 0.8 ± 0.7 | <0.001 |
| 1 μM Methyllycaconitine | 0.08 ± 0.02 (19.8 ± 12.2) | 0.21 | 2.0 ± 1.2 | <0.001 |
| 1 μM Galantamine | 0.08 ± 0.02 (17.1 ± 14.6) | 0.37 | 1.7 ± 1.5 | <0.001 |
| 1 μM Memantine | 0.21 ± 0.03 (225.9 ± 38.5) | <0.00001 | 23.0 ± 3.9 | 0.001 |

Compounds

Compounds were synthesized and provided by Medicilon, Shanghai. Aside from the three syntheses described herein, more detailed syntheses are set out in one or more of US Patent Publications or patents No. 2009/0191579 A1 (U.S. Pat. No. 8,722,851 B2), No. 2010/0279996 A1, No. 2010/0279997 A1, No. 2010/0280061 A1, No. 2011/0105481 A1, 2011/0105484 A1 (U.S. Pat. No. 8,580,808 B2), No. 2011/0105487 A1 (U.S. Pat. No. 8,653,068 B2), and No. 2011/0105547 A1 (U.S. Pat. No. 8,580,809 B2), whose disclosures are incorporated by reference.

A compound having an asymmetrical (chiral) carbon or a salt thereof can exist in the form of two enantiomers. The invention relates both to each enantiomer and to their mixture; i.e., to both enantiomeric forms and to their mixture. Additionally, where two or more chiral centers are present, diastereomers can form.

Where a contemplated compound or a pharmaceutically acceptable salt of a compound of Series A, B, C-1, C-2, D or E, or any of the other formulas herein is obtained in the form of a mixture of the stereoisomers, preferably in the form of the racemates or other mixtures of the various enantiomers and/or diastereoisomers, they can be separated and optionally isolated by conventional methods known to the person skilled in the art. Illustratively, for example, chromatographic separation processes are useful, particularly liquid chromatography processes under standard pres- A compound useful as an active ingredient in a contemplated method can be readily synthesized. An illustrative synthetic scheme (Scheme 1) is shown below for the compounds of Series A. Similar schemes are set out thereafter for the preferred compound types.

Scheme 1

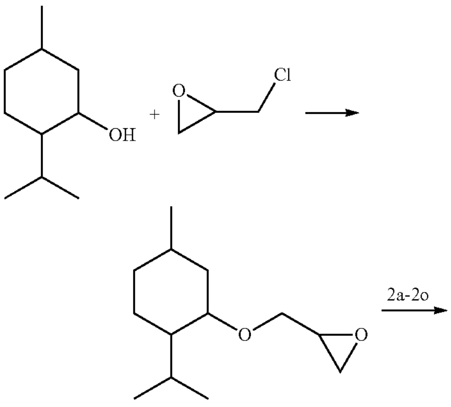

1

R = 2a-2o

-continued

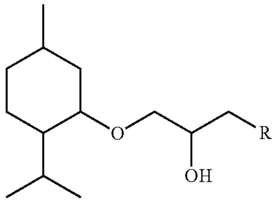

A1-A12

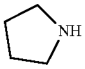

2a

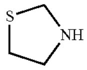

2b

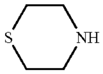

2c

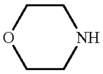

2d

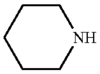

2e

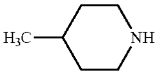

2f

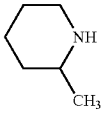

2g

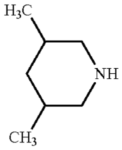

2h

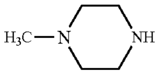

2i

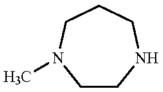

2j

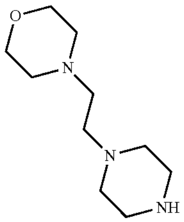

2k

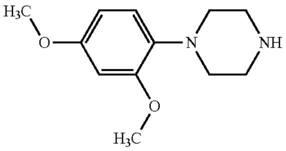

2l

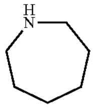

2m

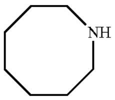

2n

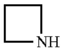

2o

Similar syntheses can be carried out for phenolic compounds, starting with phenol or a substituted phenol in place of D-menthol that is shown in Scheme 1. Another cyclohexanol or cyclohexenol can also be used in place of D-menthol. The alcohol formed by reaction of Compound 1 with an amine can be readily oxidized by known methods.

| Table of Series-A Compounds | |
|---|---|
| 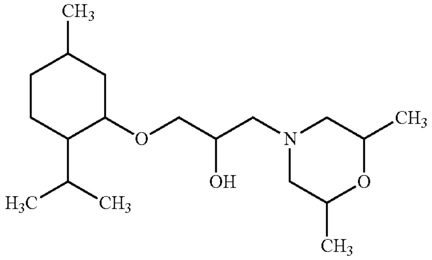 [SMILES: CC1CCC(C(C)C)C(OCC(O)CN2CC(C)OC(C)C2)C1] | A3333 |

-continued

| Table of Series-A Compounds | |
|---|---|
| 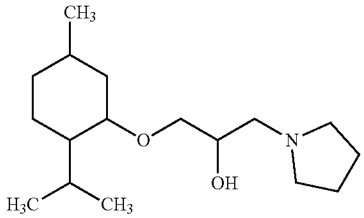 | A0001 |
| 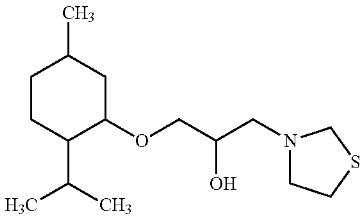 [SMILES: CC1CCC(C(C)C)C(OCC(O)CN2CCSC2)C1] | A0002 |
| 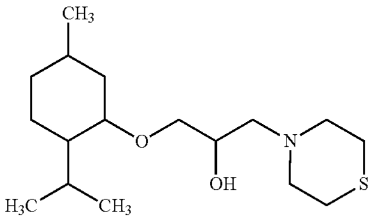 [SMILES: CC1CCC(C(C)C)C(OCC(O)CN2CCOCC2)C1] | A0003 |
| 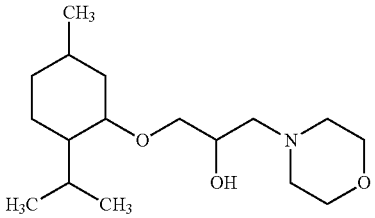 | AOOO4 |
| 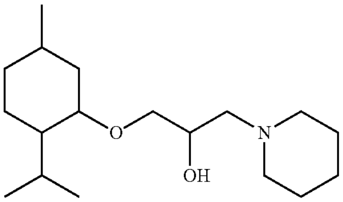 [SMILES: CC1CCC(C(C)C)C(OCC(O)CN2CCCCC2)C1] | A0005 |
| 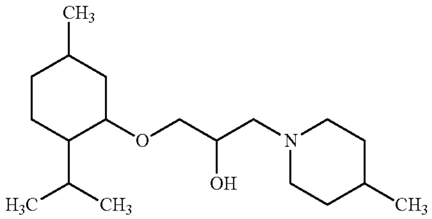 [SMILES: CC1CCN(CC(O)COC2CC(C)CCC2C(C)C)CC1] | A0006 |
| 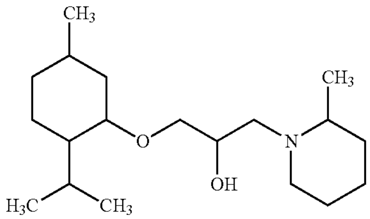 | A0007 |

-continued
Table of Series-A Compounds
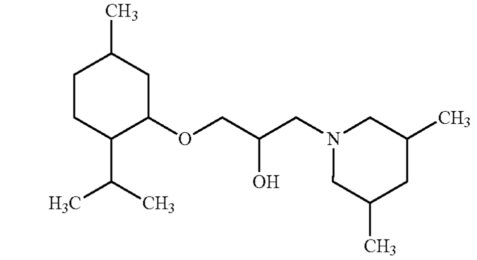
A0008
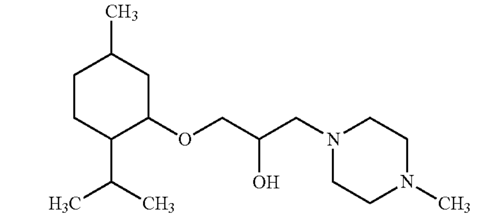
AOOO9
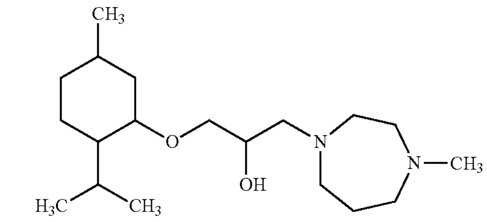 [SMILES: CC1CCC(C(C)C)C(OCC(O)CN2CCCN(C)CC2)C1]
A0010
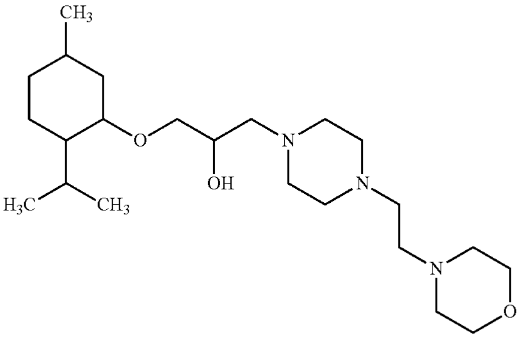 [SMILES: CC1CCC(C(C)C)C(OCC(O)CN2CCN(CCN3CCOCC3)CC2)C1]
A0011
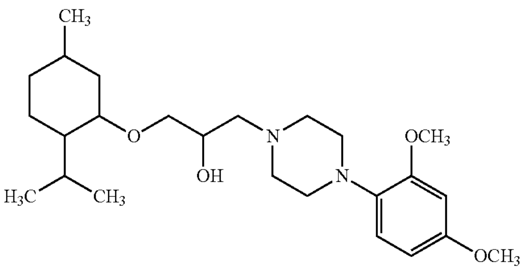 [SMILES: COc1ccc(N2CCN(CC(O)COC3CC(C)CCC3C(C)C)CC2)c(OC)c1]
A0012
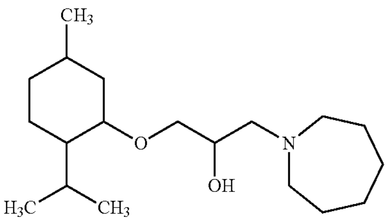 [SMILES: CC1CCC(C(C)C)C(OCC(O)CN2CCCCCC2)C1]
A0013
-continued
Table of Series-A Compounds
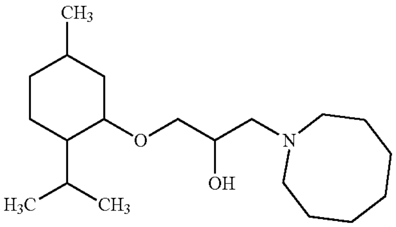 [SMILES: CC1CCC(C(C)C)C(OCC(O)CN2CCCCCCC2)C1]
A0014
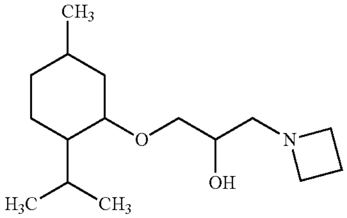 [SMILES: CC1CCC(C(C)C)C(OCC(O)CN2CCC2)C1]
A0015
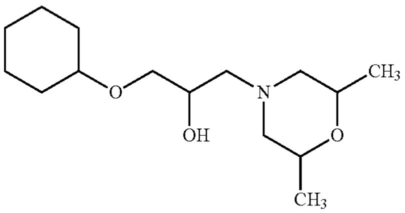 [SMILES: CC1CN(CC(O)COC2CCCCC2)CC(C)O1]
A0017
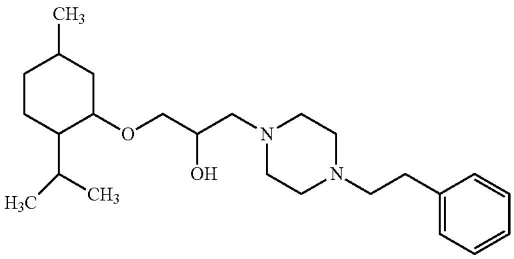 [SMILES: CC1CCC(C(C)C)C(OCC(O)CN2CCN(CCc3ccccc3)CC2)C1]
A0020
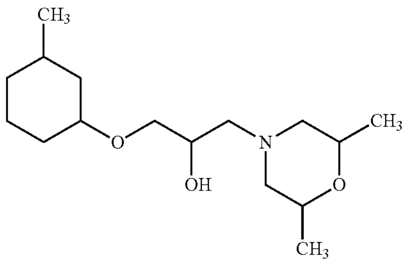 [SMILES: CC1CCCC(OCC(O)CN2CC(C)OC(C)C2)C1]
A0021
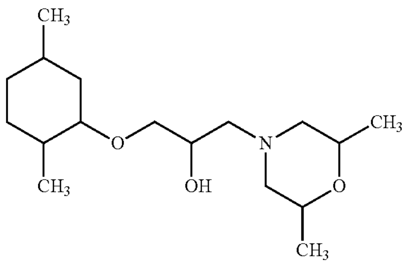 [SMILES: CC1CCC(C)C(OCC(O)CN2CC(C)OC(C)C2)C1]
A0022

-continued
Table of Series-A Compounds
A0025
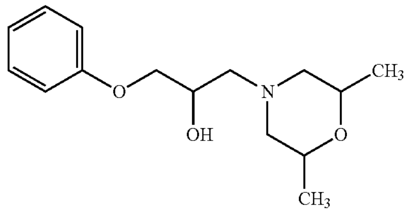 [SMILES: CC1CN(CC(O)COc2ccccc2)CC(C)O1]
A0026
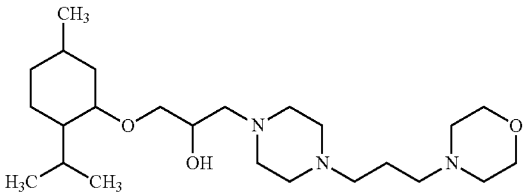 [SMILES: CC1CCC(C(C)C)C(OCC(O)CN2CCN(CCCN3CCOCC3)CC2)C1]
A0028
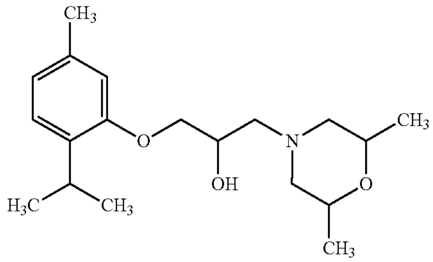 [SMILES: Cc1ccc(C(C)C)c(OCC(O)CN2CC(C)OC(C)C2)c1]
A0029
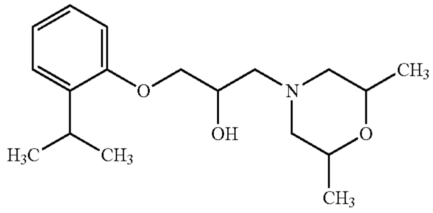 [SMILES: CC1CN(CC(O)COc2ccccc2C(C)C)CC(C)O1]
A0030
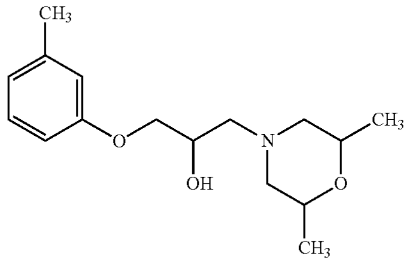 [SMILES: Cc1cccc(OCC(O)CN2CC(C)OC(C)C2)c1]
A0031
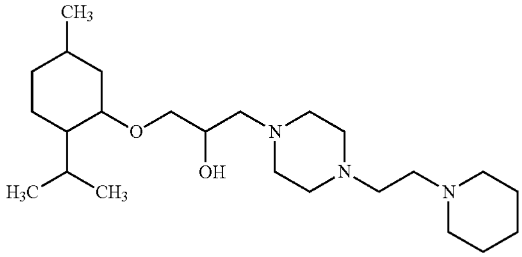 [SMILES: CC1CCC(C(C)C)C(OCC(O)CN2CCN(CCN3CCCCC3)CC2)C1]
-continued
Table of Series-A Compounds
A0032-1
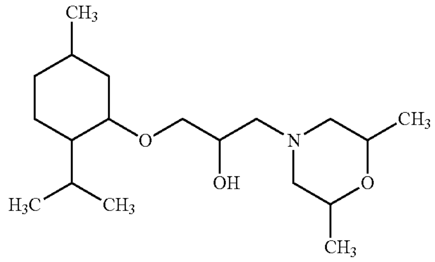 [SMILES: CC1CCC(C(C)C)C(OCC(O)CN2CC(C)OC(C)C2)C1]
A0032
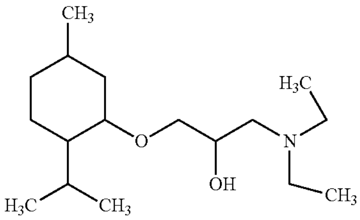 [SMILES: CCN(CC)CC(O)COC1CC(C)CCC1C(C)C]
A0033
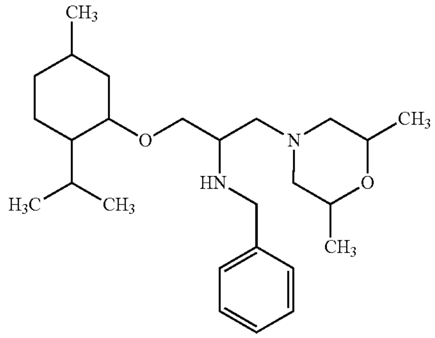 [SMILES: CC1CCC(C(C)C)C(OCC(CN2CC(C)OC(C)C2)NCc2ccccc2)C1]
A0035
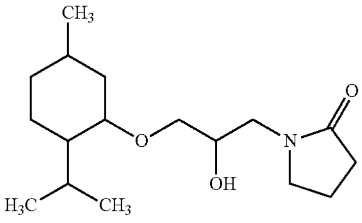 [SMILES: CC1CCC(C(C)C)C(OCC(O)CN2CCCC2=O)C1]
A0036
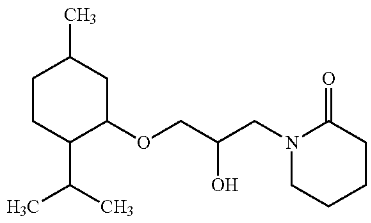 [SMILES: CC1CCC(C(C)C)C(OCC(O)CN2CCCCC2=O)C1]
A0037
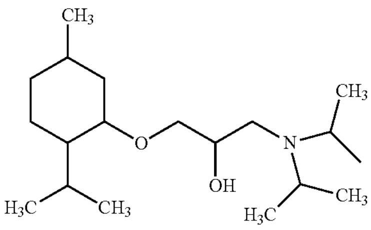 [SMILES: CC1CCC(C(C)C)C(OCC(O)CN(C(C)C)C(C)C)C1]

-continued
Table of Series-A Compounds
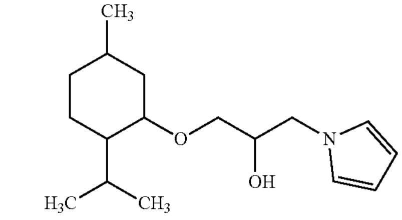 [SMILES: CC1CCC(C(C)C)C(OCC(O)Cn2cccc2)C1]
A0038
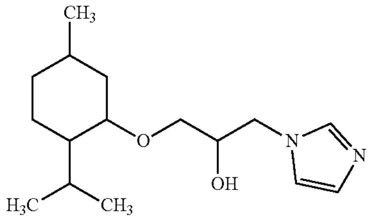 [SMILES: CC1CCC(C(C)C)C(OCC(O)Cn2ccnc2)C1]
A0039
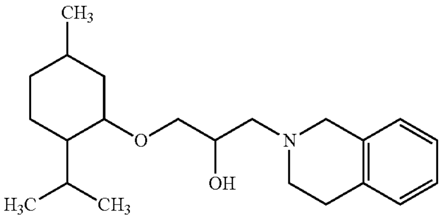 [SMILES: CC1CCC(C(C)C)C(OCC(O)CN2CCc3ccccc3C2)C1]
A0040
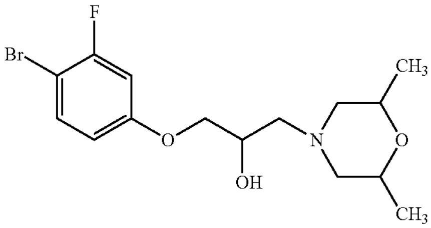
A0041
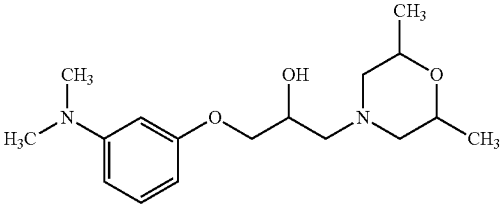
A0042
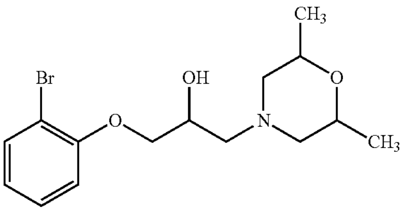 [SMILES: CC1CN(CC(O)COc2ccccc2Br)CC(C)O1]
A0043
-continued
Table of Series-A Compounds
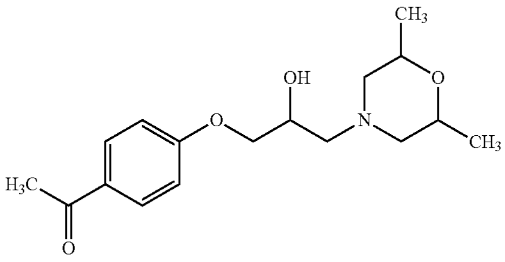 [SMILES: CC(=O)c1ccc(OCC(O)CN2CC(C)OC(C)C2)cc1]
A0044
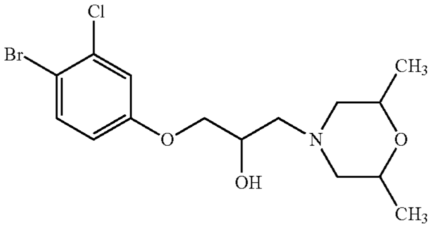 [SMILES: CC1CN(CC(O)COc2ccc(Br)c(Cl)c2)CC(C)O1]
A0045
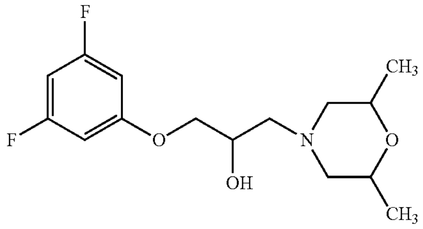 [SMILES: CC1CN(CC(O)COc2cc(F)cc(F)c2)CC(C)O1]
A0046
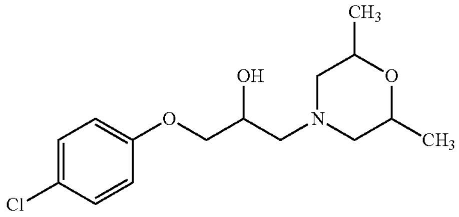 [SMILES: CC1CN(CC(O)COc2ccc(Cl)cc2)CC(C)O1]
A0047
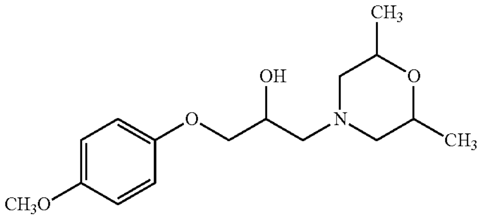
A0048
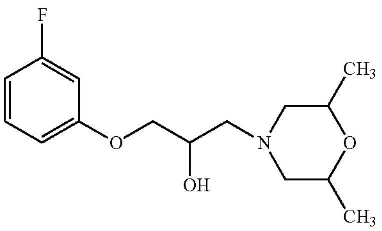 [SMILES: CC1CN(CC(O)COc2cccc(F)c2)CC(C)O1]
A0049
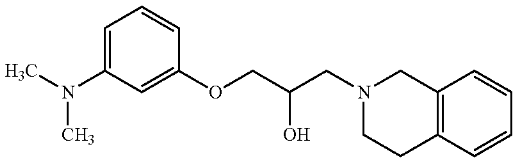 [SMILES: CN(C)c1cccc(OCC(O)CN2CCc3ccccc3C2)c1]
A0050

-continued
Table of Series-A Compounds
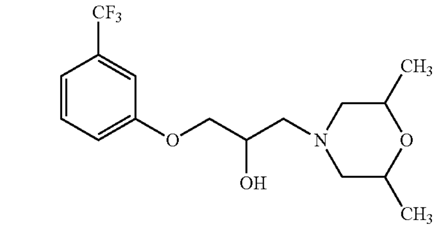 [SMILES: CC1CN(CC(O)COc2cccc(C(F)(F)F)c2)CC(C)O1]
A0051
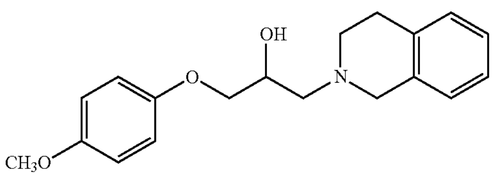
A0053
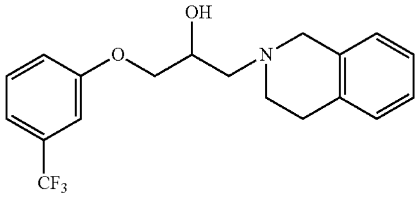 [SMILES: OC(COc1cccc(C(F)(F)F)c1)CN1CCc2ccccc2C1]
A0054
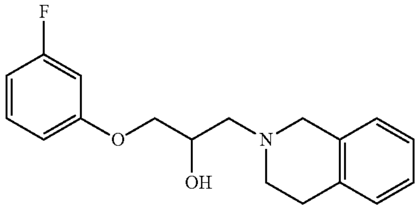 [SMILES: OC(COc1cccc(F)c1)CN1CCc2ccccc2C1]
A0055
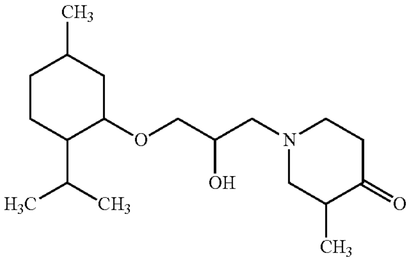 [SMILES: CC1CCC(C(C)C)C(OCC(O)CN2CCC(=O)C(C)C2)C1]
A0056
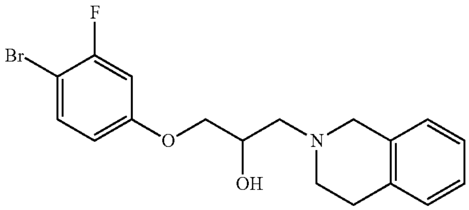 [SMILES: OC(COc1ccc(Br)c(F)c1)CN1CCc2ccccc2C1]
A0057
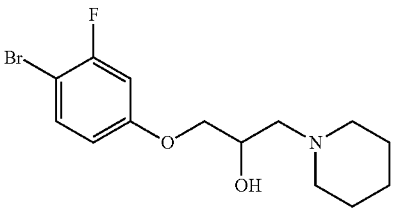 [SMILES: OC(COc1ccc(Br)c(F)c1)CN1CCCCC1]
A0058
-continued
Table of Series-A Compounds
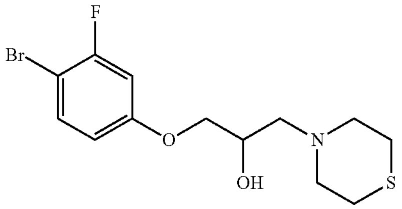 [SMILES: OC(COc1ccc(Br)c(F)c1)CN1CCSCC1]
A0059
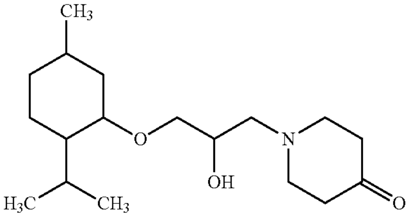
A0060
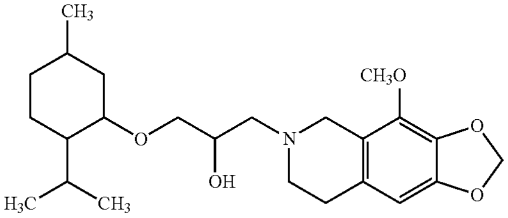
A0061
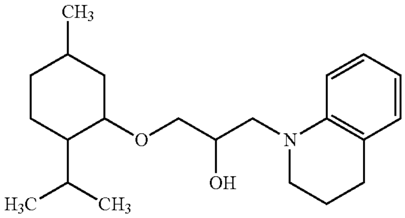 [SMILES: CC1CCC(C(C)C)C(OCC(O)CN2CCCc3ccccc32)C1]
A0068
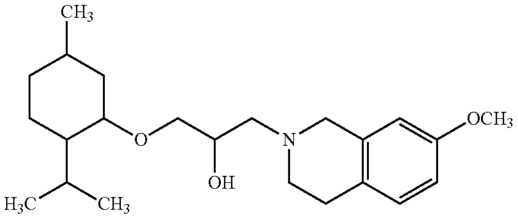 [SMILES: COc1ccc2c(c1)CN(CC(O)COC1CC(C)CCC1C(C)C)CC2]
A0075
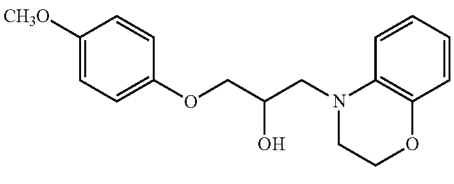
A0076
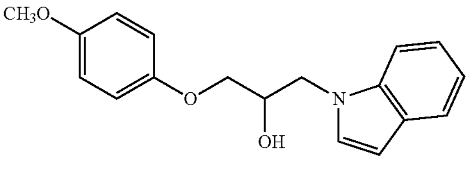
A0077

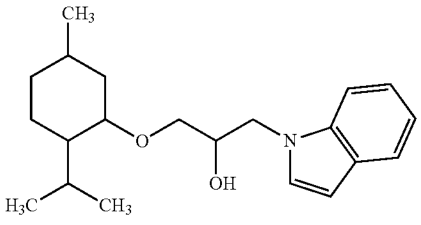 [SMILES: CC1CCC(C(C)C)C(OCC(O)Cn2ccc3ccccc32)C1]

A0078

A compound of Series B can be prepared by following the synthetic route illustrated in Scheme 2, below. An illustrative synthetic scheme is shown below for the preparation of a first portion of a contemplated compound, with the second portion being added by a reaction with an appropriately substituted methylketone compound in the presence of a strong base such as sodium ethoxide. The resulting ketone can be converted into the corresponding alcohol by mild reduction as with sodium borohydride. A ketone or alcohol can be converted to the quaternary nitrogen atom-containing compound using an alkylating agent such as methyl iodide.

Scheme 2

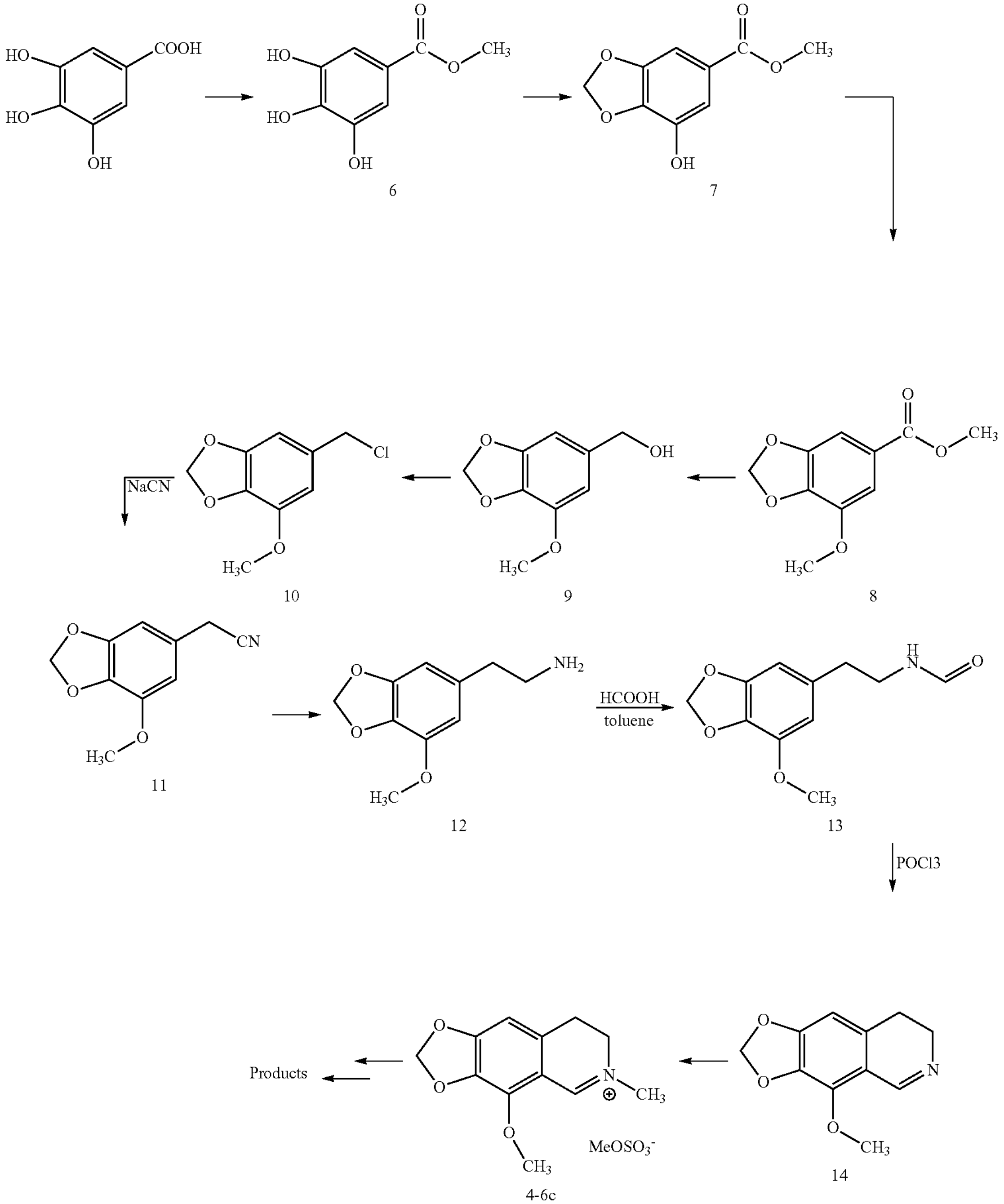

6, 7, 8, 9, 10, 11, 12, 13, 14, 4-6c

| Table of Series-B Compounds | |
|---|---|
| 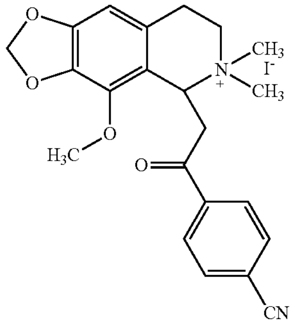 | B0001 |
| 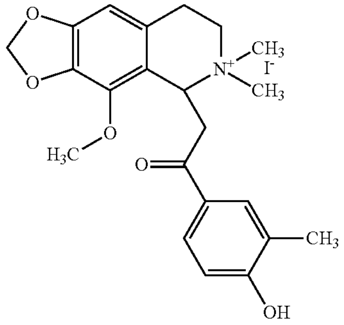 [SMILES: COc1c2c(cc3c1C(CC(=O)c1ccc(O)c(C)c1)[N+](C)(C)CC3)OCO2 ; [I-]] | B0002 |
| 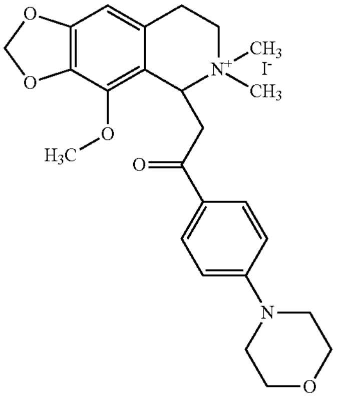 [SMILES: COc1c2c(cc3c1C(CC(=O)c1ccc(N4CCOCC4)cc1)[N+](C)(C)CC3)OCO2 ; [I-]] | B0004 |
| 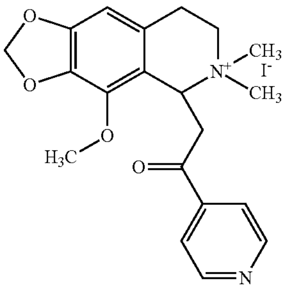 [SMILES: COc1c2c(cc3c1C(CC(=O)c1ccncc1)[N+](C)(C)CC3)OCO2 ; [I-]] | B0005 |
-continued
| Table of Series-B Compounds | |
|---|---|
| 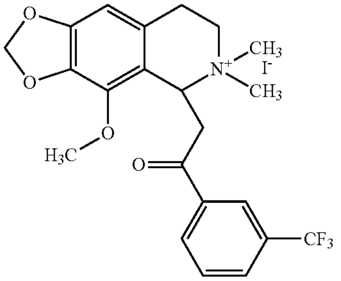 [SMILES: COc1c2c(cc3c1C(CC(=O)c1cccc(C(F)(F)F)c1)[N+](C)(C)CC3)OCO2 ; [I-]] | B0006 |
| 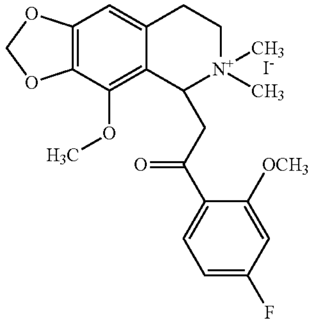 [SMILES: COc1cc(F)ccc1C(=O)CC1c2c(cc3c(c2OC)OCO3)CC[N+]1(C)C ; [I-]] | B0007 |
| 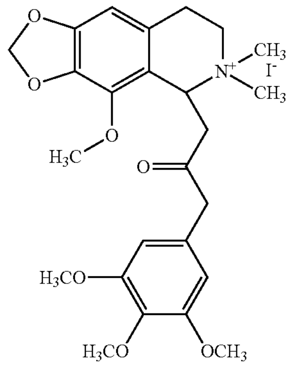 [SMILES: COc1cc(CC(=O)CC2c3c(cc4c(c3OC)OCO4)CC[N+]2(C)C)cc(OC)c1OC ; [I-]] | B0008 |
| 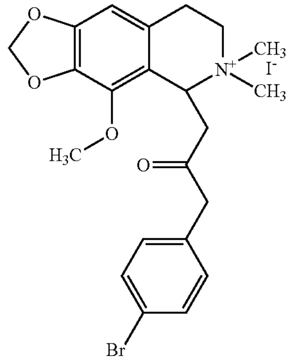 [SMILES: COc1c2c(cc3c1C(CC(=O)Cc1ccc(Br)cc1)[N+](C)(C)CC3)OCO2 ; [I-]] | B0011 |

Table of Series-B Compounds
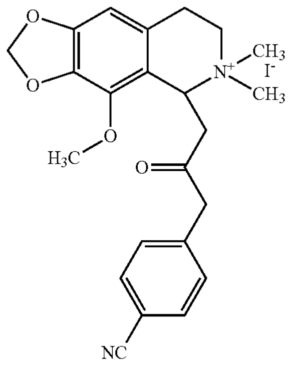 [SMILES: COc1c2c(cc3c1C(CC(=O)Cc1ccc(C#N)cc1)[N+](C)(C)CC3)OCO2 ; [I-]]
B0012
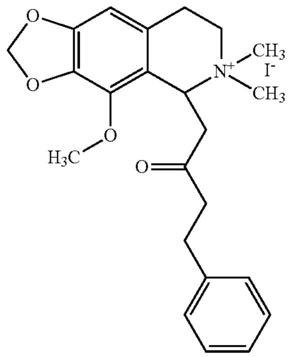 [SMILES: COc1c2c(cc3c1C(CC(=O)CCc1ccccc1)[N+](C)(C)CC3)OCO2 ; [I-]]
B0015
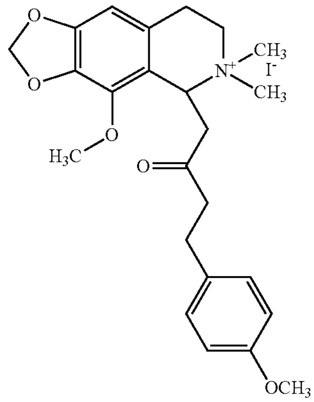 [SMILES: COc1ccc(CCC(=O)CC2c3c(cc4c(c3OC)OCO4)CC[N+]2(C)C)cc1 ; [I-]]
B0016
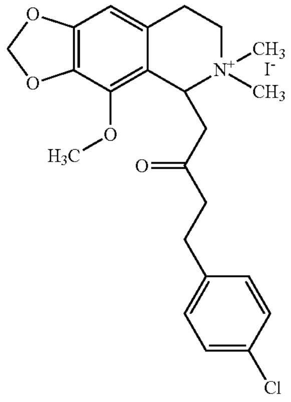 [SMILES: COc1c2c(cc3c1C(CC(=O)CCc1ccc(Cl)cc1)[N+](C)(C)CC3)OCO2 ; [I-]]
B0017
Table of Series-B Compounds
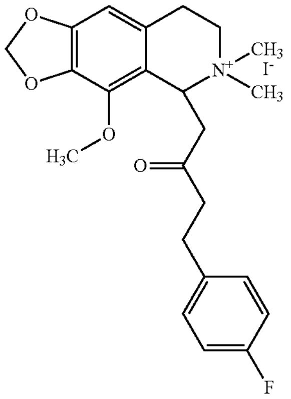 [SMILES: COc1c2c(cc3c1C(CC(=O)CCc1ccc(F)cc1)[N+](C)(C)CC3)OCO2 ; [I-]]
B0018
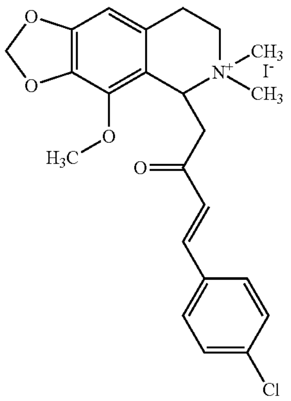
B0019
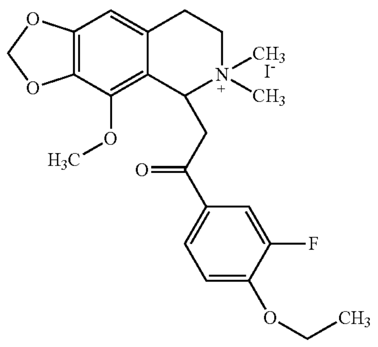
B0020
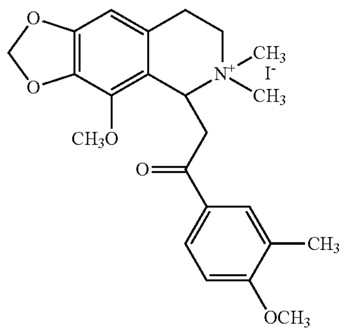
B0021

-continued
Table of Series-B Compounds
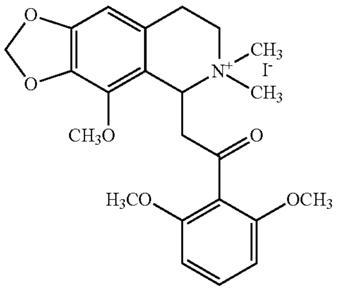
B0023
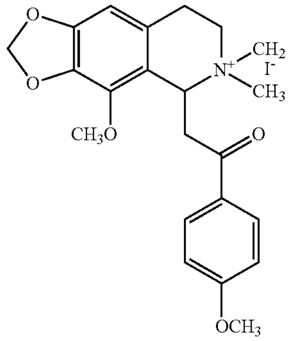
B0024
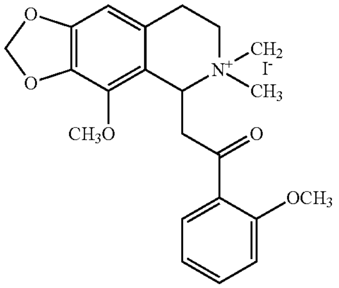
B0025
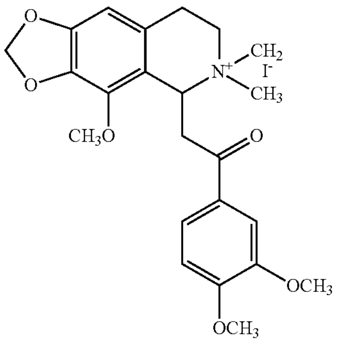
B0026
-continued
Table of Series-B Compounds
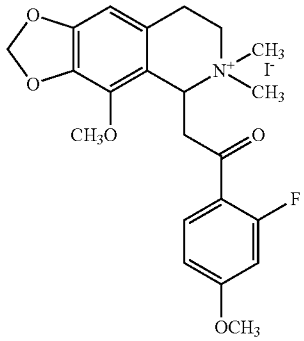
B0027
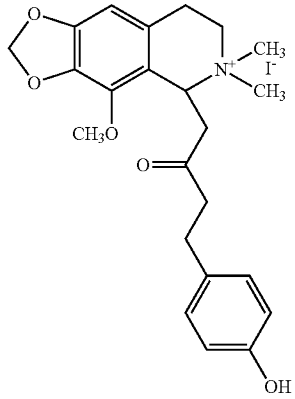
B0028
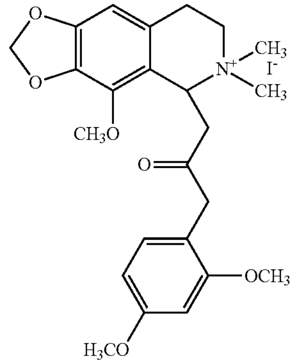
B0029
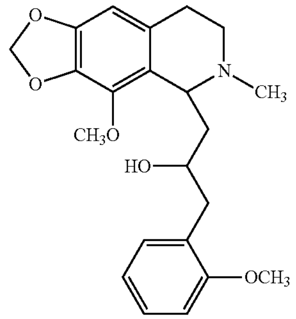
B0030

-continued
Table of Series-B Compounds
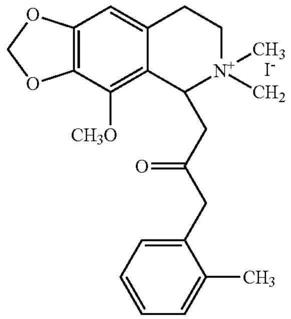
B0031
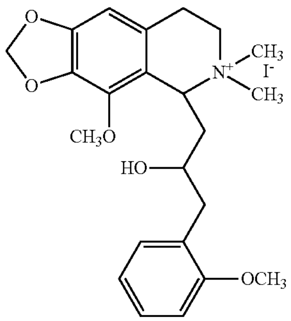
B0032
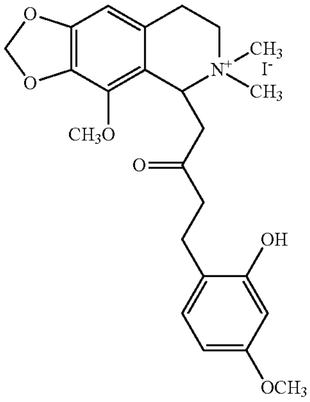
B0033
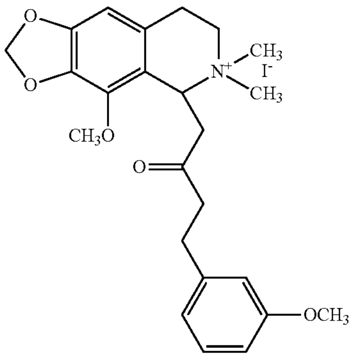
B0034
-continued
Table of Series-B Compounds
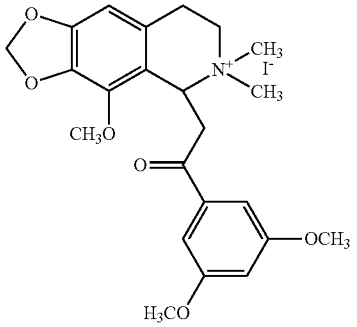
B0035
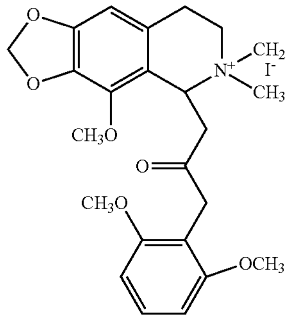
B0036
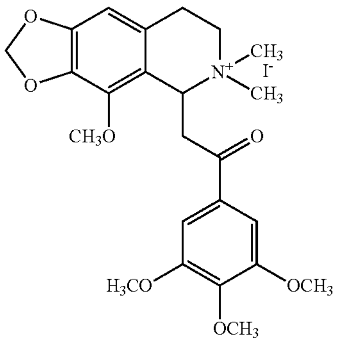
B0037
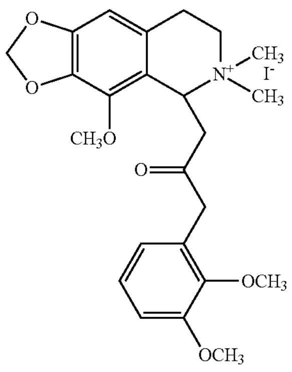
B0038

-continued
Table of Series-B Compounds
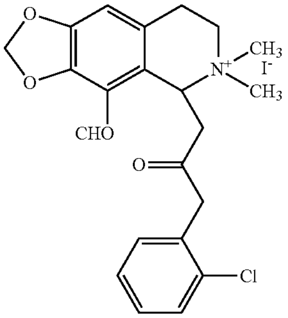 [SMILES: C[N+]1(C)CCc2cc3c(c(C=O)c2C1CC(=O)Cc1ccccc1Cl)OCO3 ; [I-]]
BOO39
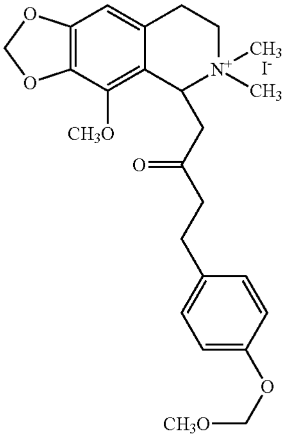
B0040
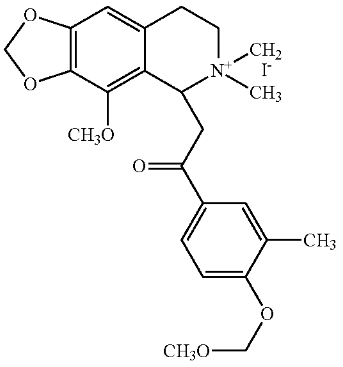
B0041
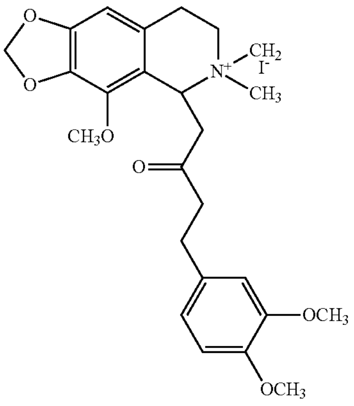
BOO42
-continued
Table of Series-B Compounds
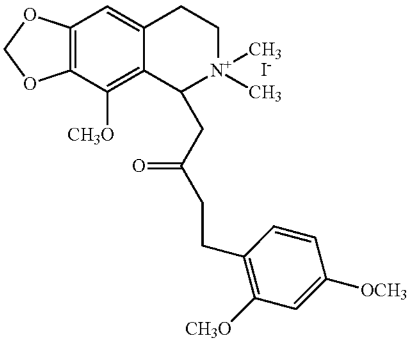
B0043
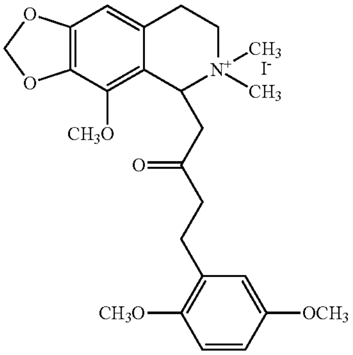
B0044
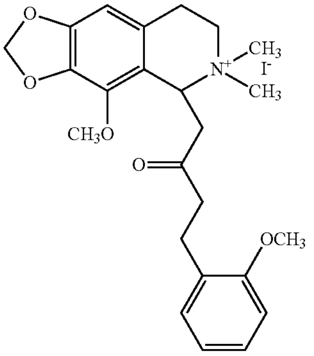
B0045
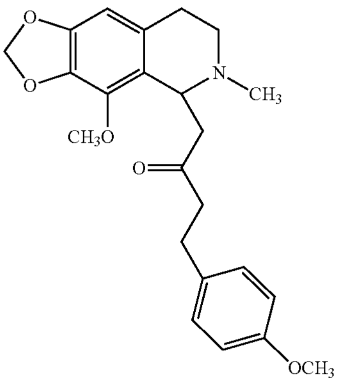
B0047

-continued
| Table of Series-B Compounds | |
|---|---|
| 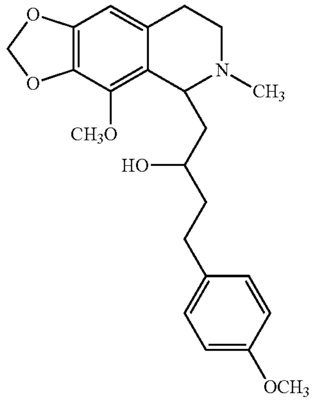 | B0048 |
| 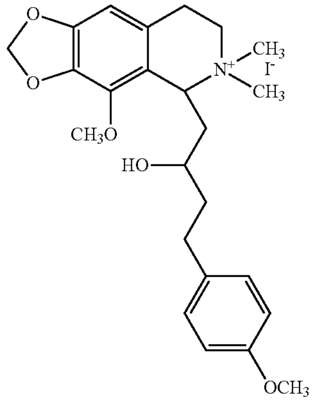 | B0049 |
| 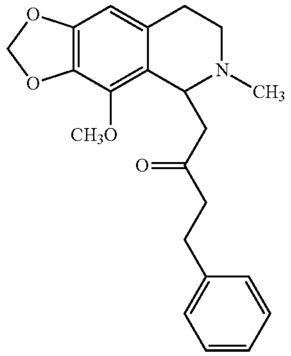 | B0050 |
| 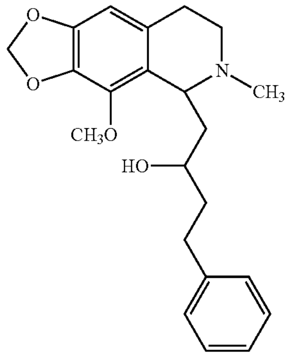 | B0051 |
-continued
| Table of Series-B Compounds | |
|---|---|
| 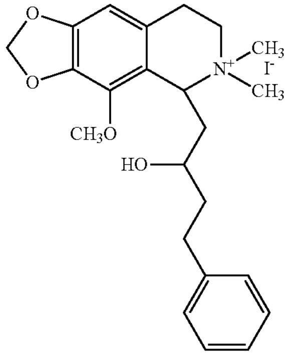 | B0052 |
| 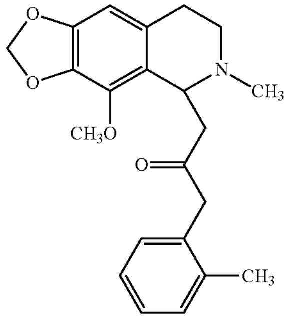 | B0053 |
| 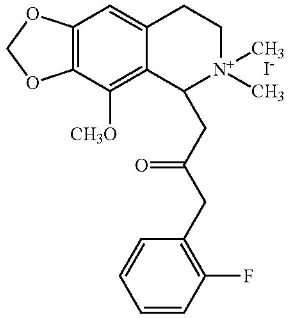 | B0055 |
| 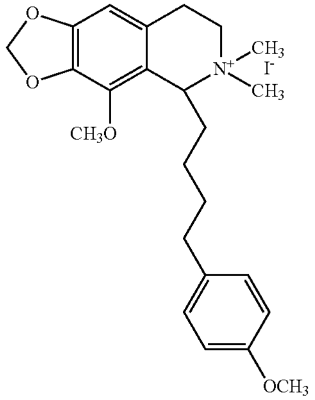 | B0056 |

-continued
Table of Series-B Compounds
B0057
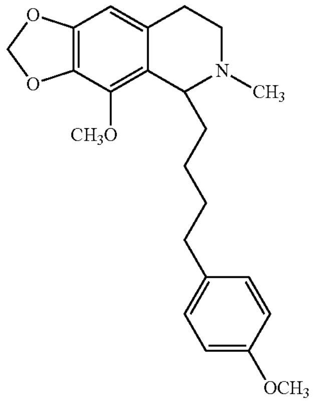
B0058
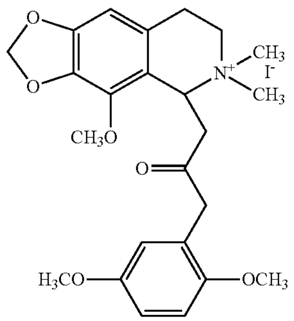
B0059
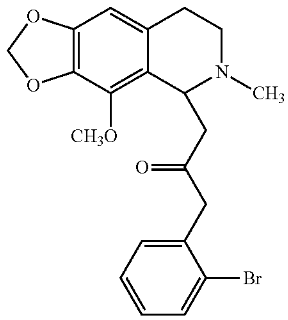
B0060
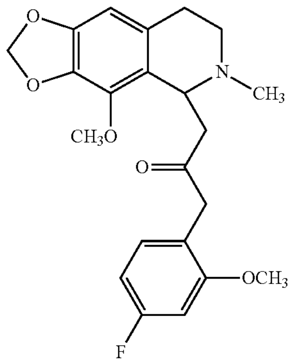
-continued
Table of Series-B Compounds
B0061
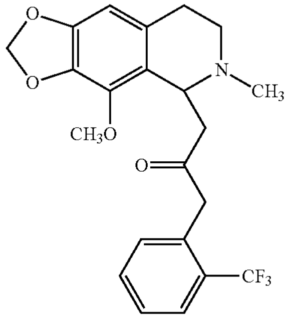
B0062
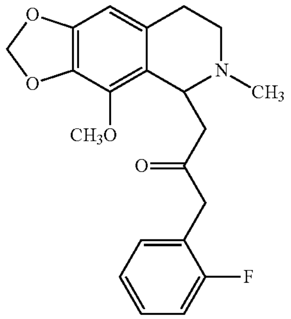
B0063
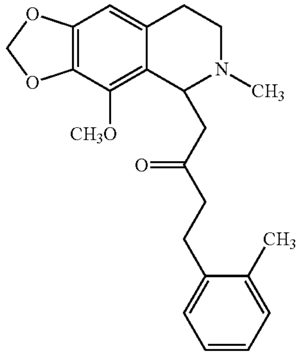
B0064
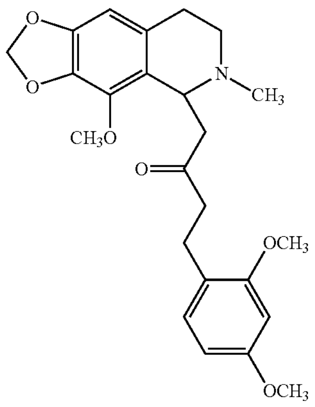

-continued

Table of Series-B Compounds

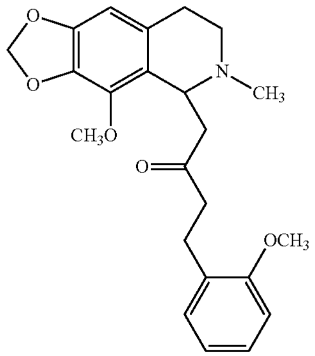

B0065

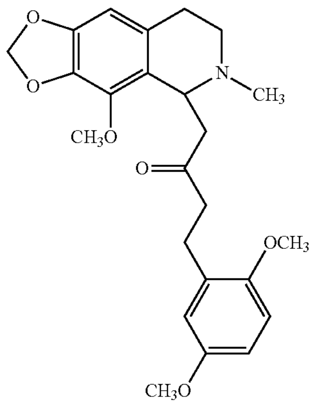

B0067

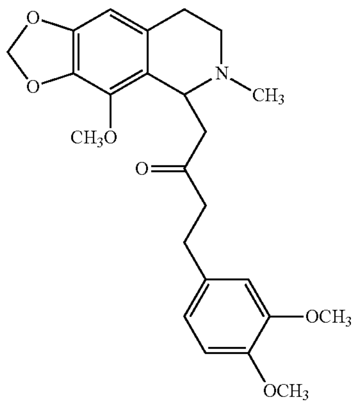

B0068

-continued

Table of Series-B Compounds

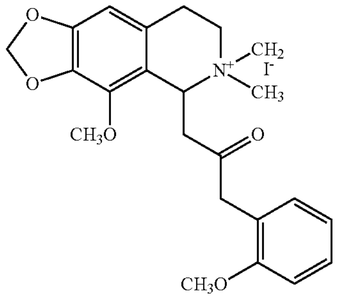

5009

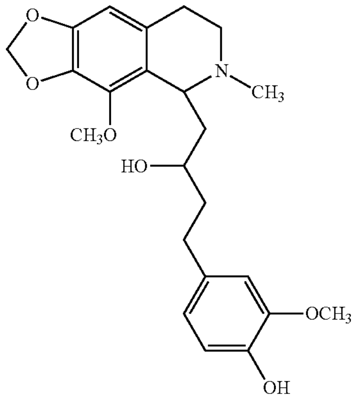

6810

An illustrative synthetic scheme is shown below for preparation of Series-C (both C-1 and C-2) compounds that contain various substituents and ring atoms. That scheme can be readily adapted for the preparation of compounds containing two carbonyl linkages, and also one carbonyl and one sulfonyl linkage in the opposite configurations from those shown. Ethanolamine or thioethanolamine can be replaced by ethylenediamine or N-methylethylene-diamine to prepare the corresponding dinitrogen compounds. Similar replacement with 2-aminoacetamide or an N-substituted acetamide or propionamide provides the corresponding aminoamido-containing ring system.

Scheme 3
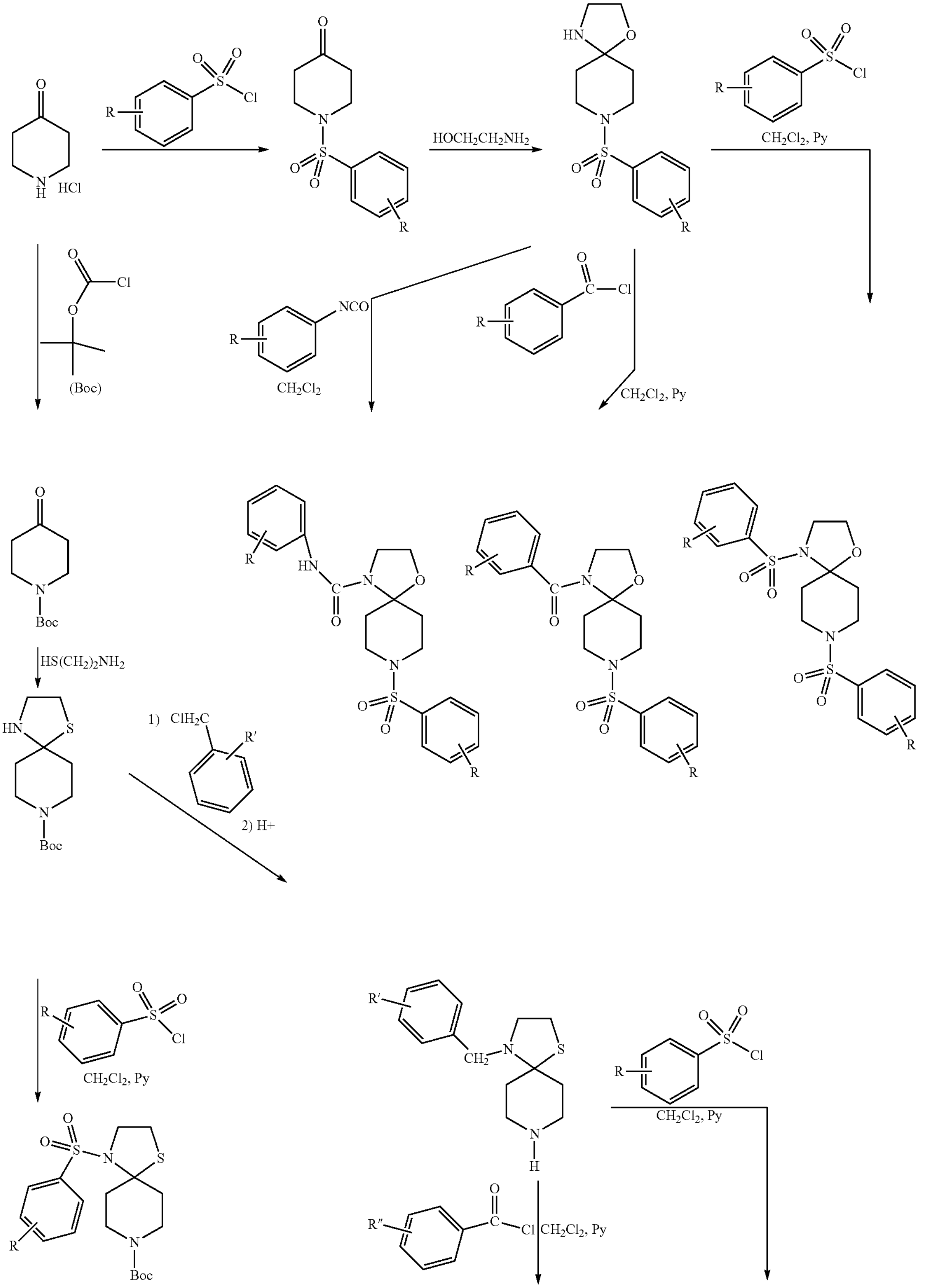

-continued
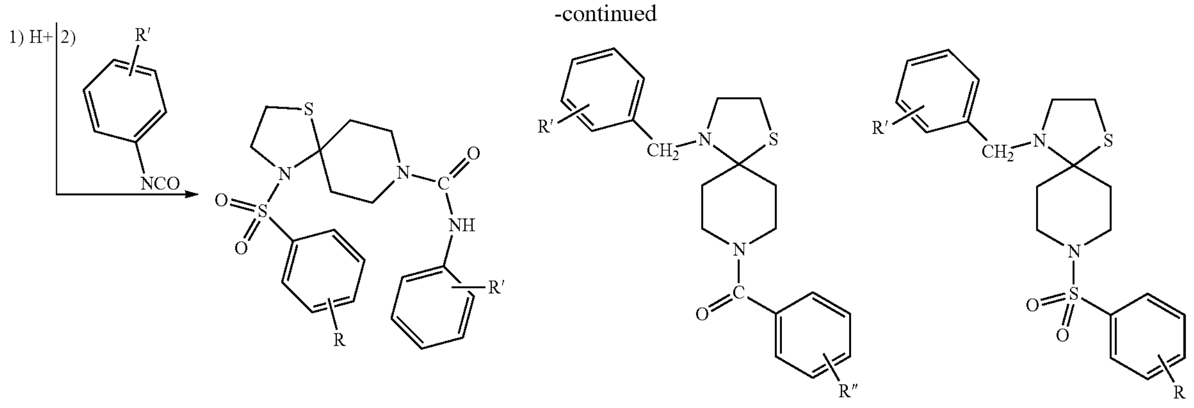
| Table of Series-C-1 Compounds | |
|---|---|
| 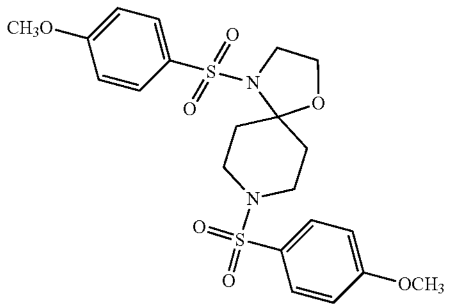 | 7866 |
| 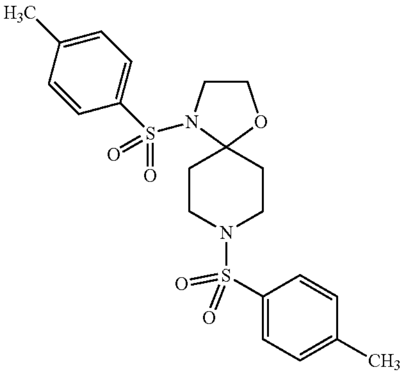 | C0001 |
| 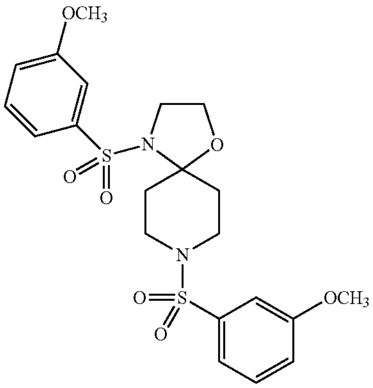 [SMILES: COc1cccc(S(=O)(=O)N2CCC3(CC2)OCCN3S(=O)(=O)c2cccc(OC)c2)c1] | C0002 |
-continued
| Table of Series-C-1 Compounds | |
|---|---|
| 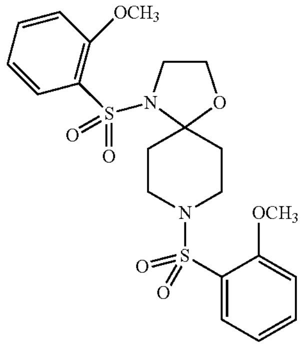 [SMILES: COc1ccccc1S(=O)(=O)N1CCC2(CC1)OCCN2S(=O)(=O)c1ccccc1OC] | C0003 |
| 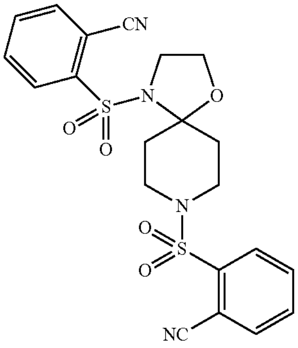 [SMILES: N#Cc1ccccc1S(=O)(=O)N1CCC2(CC1)OCCN2S(=O)(=O)c1ccccc1C#N] | C0004 |
| 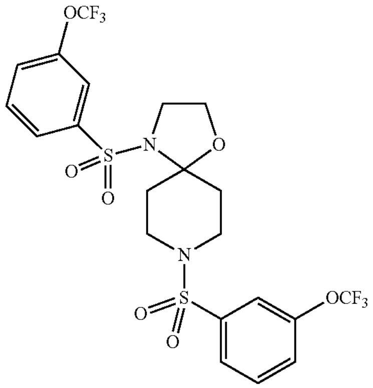 [SMILES: O=S(=O)(c1cccc(OC(F)(F)F)c1)N1CCC2(CC1)OCCN2S(=O)(=O)c1cccc(OC(F)(F)F)c1] | C0005 |

-continued
| Table of Series-C-1 Compounds |
|---|
| 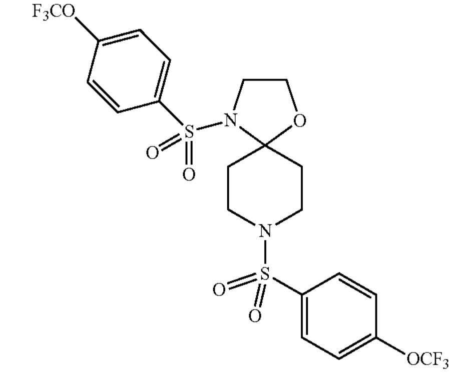 C0006 |
| 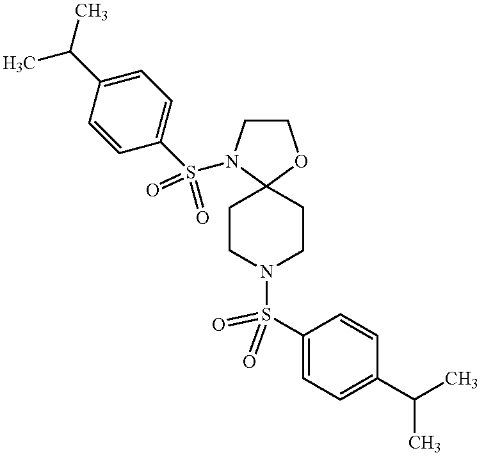 C0007 |
| 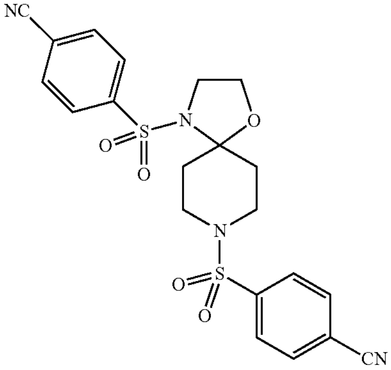 C0008 |
| 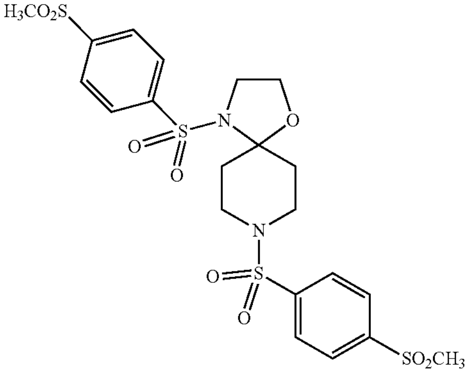 C0009 |
-continued
| Table of Series-C-1 Compounds |
|---|
| 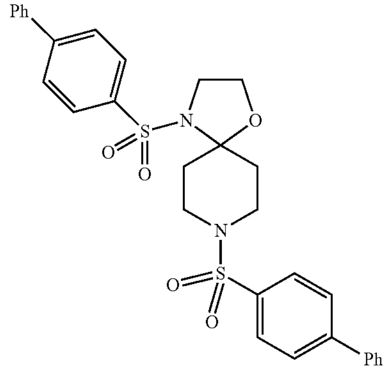 C0010 |
| 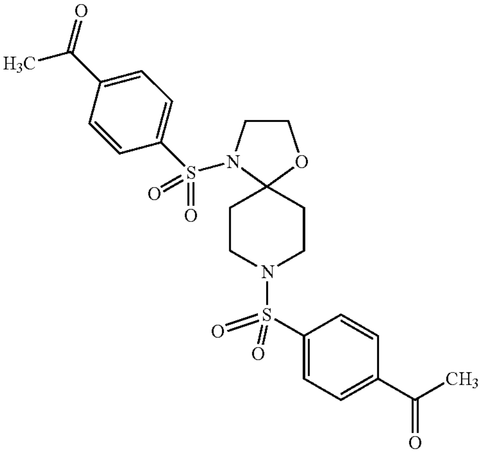 C0011 |
| 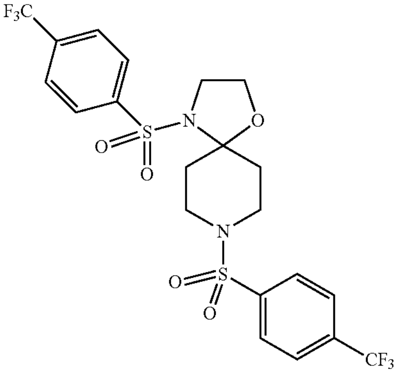 C0012 |
| 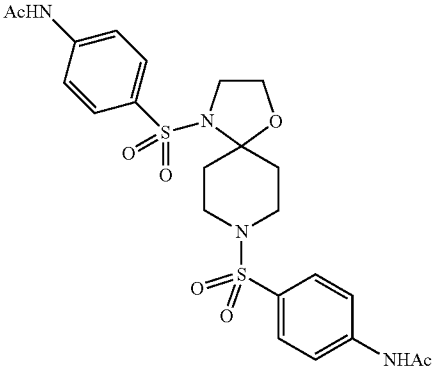 C0013 |

-continued
Table of Series-C-1 Compounds
C0014
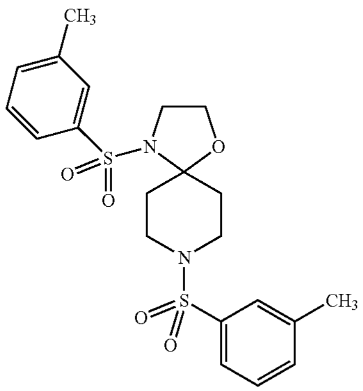 [SMILES: Cc1cccc(S(=O)(=O)N2CCC3(CC2)OCCN3S(=O)(=O)c2cccc(C)c2)c1]
C0015
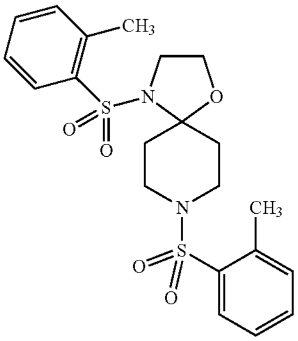 [SMILES: Cc1ccccc1S(=O)(=O)N1CCC2(CC1)OCCN2S(=O)(=O)c1ccccc1C]
C0016
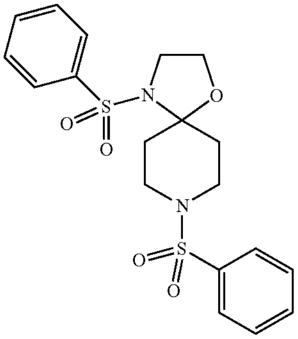 [SMILES: O=S(=O)(c1ccccc1)N1CCC2(CC1)OCCN2S(=O)(=O)c1ccccc1]
C0017
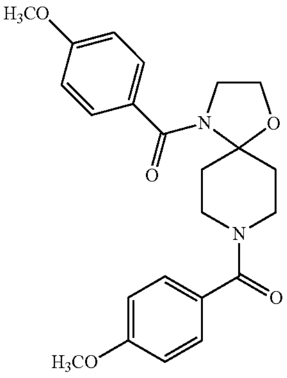 [SMILES: COc1ccc(C(=O)N2CCC3(CC2)OCCN3C(=O)c2ccc(OC)cc2)cc1]
-continued
Table of Series-C-1 Compounds
C0018
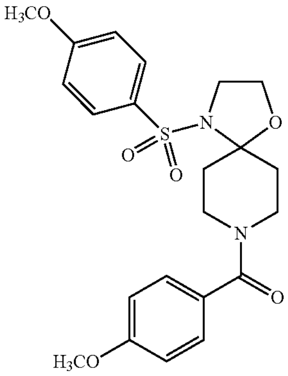 [SMILES: COc1ccc(C(=O)N2CCC3(CC2)OCCN3S(=O)(=O)c2ccc(OC)cc2)cc1]
C0019
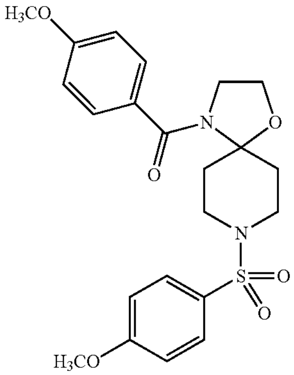 [SMILES: COc1ccc(C(=O)N2CCOC23CCN(S(=O)(=O)c2ccc(OC)cc2)CC3)cc1]
C0021
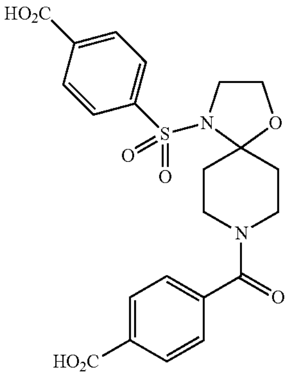 [SMILES: O=C(O)c1ccc(C(=O)N2CCC3(CC2)OCCN3S(=O)(=O)c2ccc(C(=O)O)cc2)cc1]
C0022
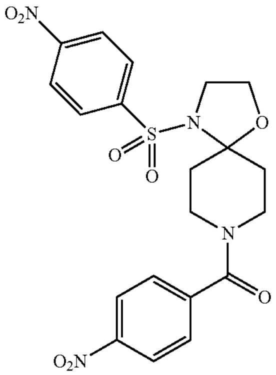

-continued
Table of Series-C-1 Compounds
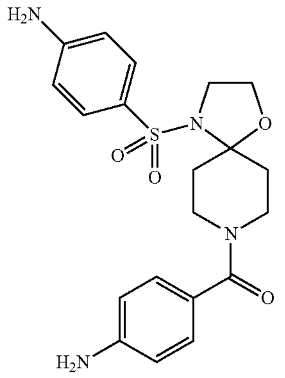 [SMILES: O=C(c1ccc([N+](=O)[O-])cc1)N1CCC2(CC1)OCCN2S(=O)(=O)c1ccc([N+](=O)[O-])cc1]
C0023
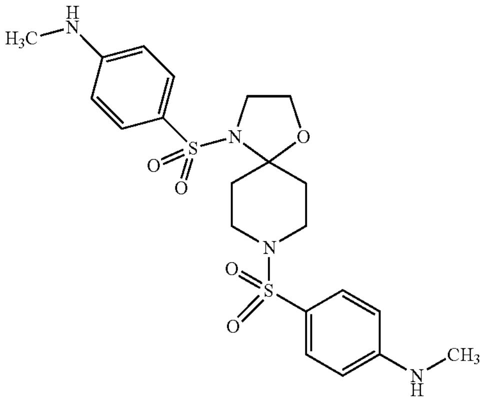
C0024
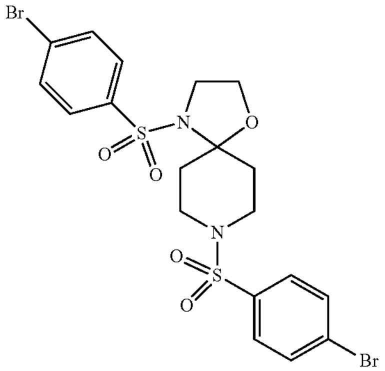 [SMILES: O=S(=O)(c1ccc(Br)cc1)N1CCC2(CC1)OCCN2S(=O)(=O)c1ccc(Br)cc1]
C0025
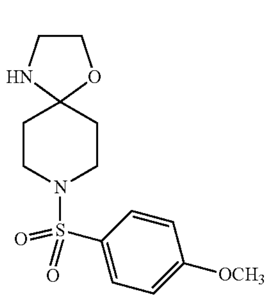 [SMILES: COc1ccc(S(=O)(=O)N2CCC3(CC2)NCCO3)cc1]
C0026
-continued
Table of Series-C-1 Compounds
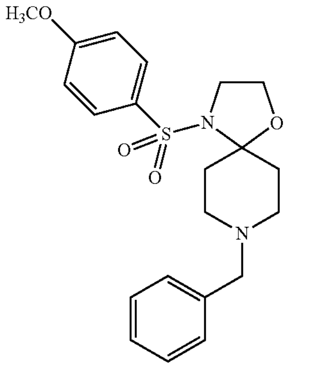 [SMILES: COc1ccc(S(=O)(=O)N2CCOC23CCN(Cc2ccccc2)CC3)cc1]
C0027-1
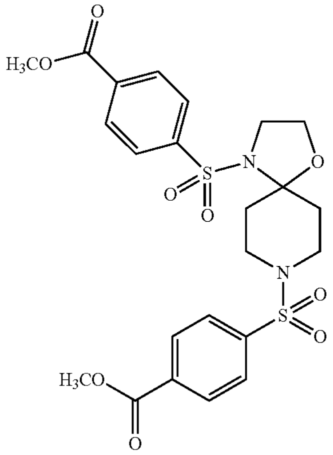 [SMILES: COC(=O)c1ccc(S(=O)(=O)N2CCC3(CC2)OCCN3S(=O)(=O)c2ccc(C(=O)OC)cc2)cc1]
C0028
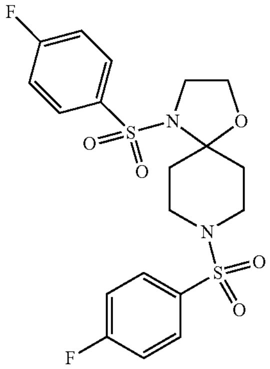 [SMILES: O=S(=O)(c1ccc(F)cc1)N1CCC2(CC1)OCCN2S(=O)(=O)c1ccc(F)cc1]
C0029
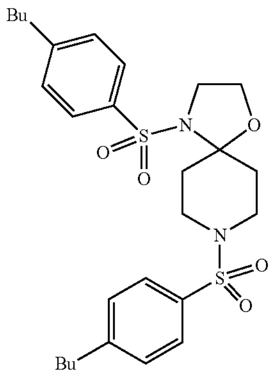
C0030

-continued
Table of Series-C-1 Compounds
C0031
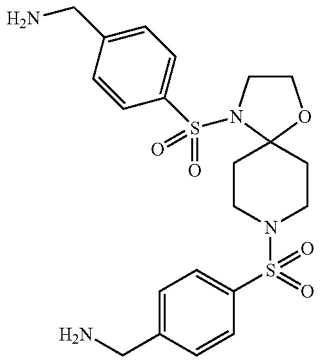 [SMILES: NCc1ccc(S(=O)(=O)N2CCC3(CC2)OCCN3S(=O)(=O)c2ccc(CN)cc2)cc1]
C0032
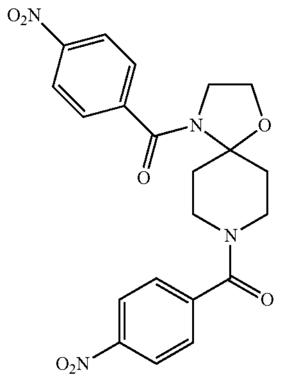 [SMILES: O=C(c1ccc([N+](=O)[O-])cc1)N1CCC2(CC1)OCCN2C(=O)c1ccc([N+](=O)[O-])cc1]
C0033
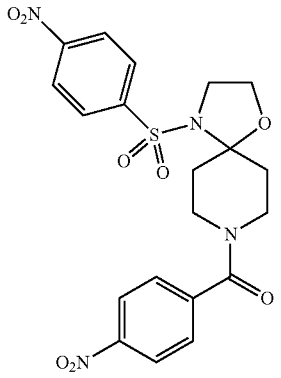 [SMILES: O=C(c1ccc([N+](=O)[O-])cc1)N1CCC2(CC1)OCCN2S(=O)(=O)c1ccc([N+](=O)[O-])cc1]
C0034
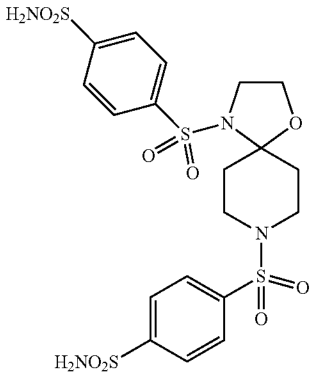 [SMILES: NS(=O)(=O)c1ccc(S(=O)(=O)N2CCC3(CC2)OCCN3S(=O)(=O)c2ccc(S(N)(=O)=O)cc2)cc1]
-continued
Table of Series-C-1 Compounds
C0034-3
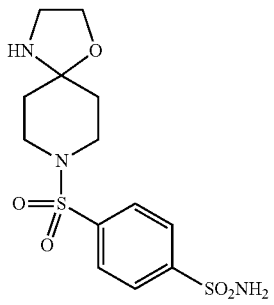 [SMILES: NS(=O)(=O)c1ccc(S(=O)(=O)N2CCC3(CC2)NCCO3)cc1]
C0037-2
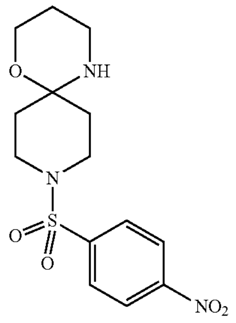 [SMILES: O=[N+]([O-])c1ccc(S(=O)(=O)N2CCC3(CC2)NCCCO3)cc1]
C0038
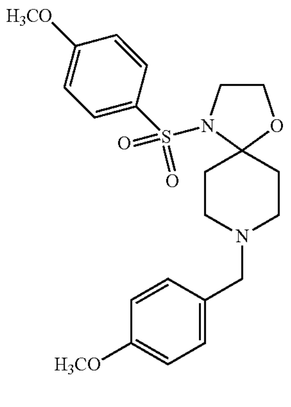 [SMILES: COc1ccc(CN2CCC3(CC2)OCCN3S(=O)(=O)c2ccc(OC)cc2)cc1]
C0040
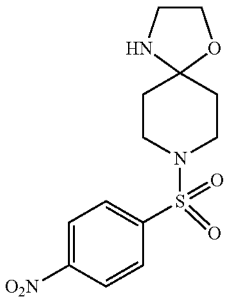 [SMILES: O=[N+]([O-])c1ccc(S(=O)(=O)N2CCC3(CC2)NCCO3)cc1]

-continued
Table of Series-C-1 Compounds
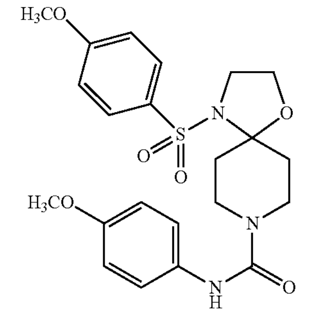 [SMILES: COc1ccc(NC(=O)N2CCC3(CC2)OCCN3S(=O)(=O)c2ccc(OC)cc2)cc1]
C0041
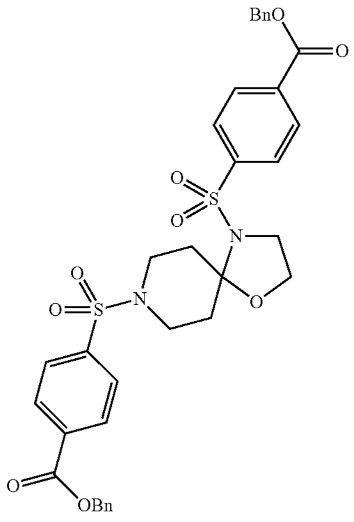 [SMILES: O=C(OCc1ccccc1)c1ccc(S(=O)(=O)N2CCC3(CC2)OCCN3S(=O)(=O)c2ccc(C(=O)OCc3ccccc3)cc2)cc1]
C0042
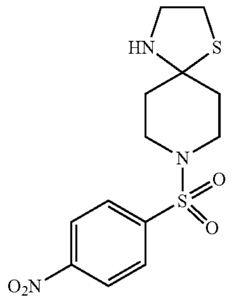 [SMILES: O=[N+]([O-])c1ccc(S(=O)(=O)N2CCC3(CC2)NCCS3)cc1]
C0044
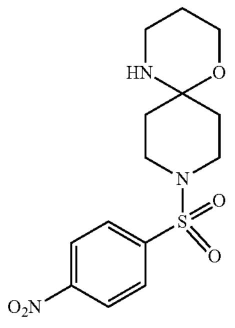 [SMILES: O=[N+]([O-])c1ccc(S(=O)(=O)N2CCC3(CC2)NCCCO3)cc1]
C0045
-continued
Table of Series-C-1 Compounds
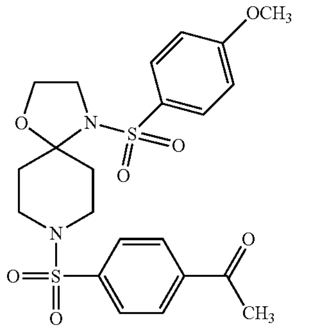 [SMILES: COc1ccc(S(=O)(=O)N2CCOC23CCN(S(=O)(=O)c2ccc(C(C)=O)cc2)CC3)cc1]
C0047
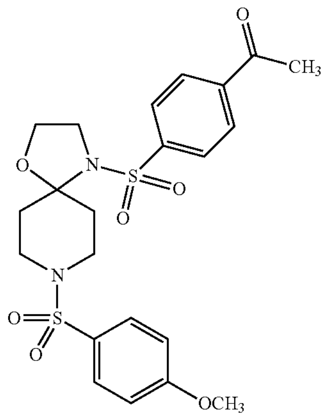 [SMILES: COc1ccc(S(=O)(=O)N2CCC3(CC2)OCCN3S(=O)(=O)c2ccc(C(C)=O)cc2)cc1]
C0048
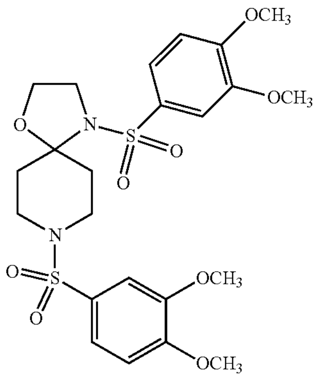 [SMILES: COc1ccc(S(=O)(=O)N2CCC3(CC2)OCCN3S(=O)(=O)c2ccc(OC)c(OC)c2)cc1OC]
C0049
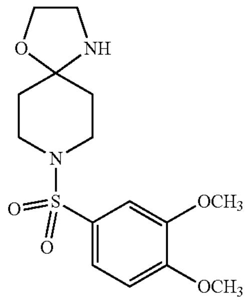 [SMILES: COc1ccc(S(=O)(=O)N2CCC3(CC2)NCCO3)cc1OC]
C0049-2

-continued
Table of Series-C-1 Compounds
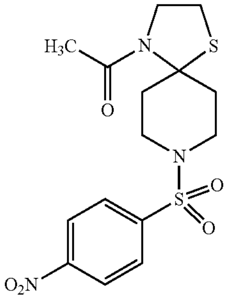 [SMILES: CC(=O)N1CCSC12CCN(S(=O)(=O)c1ccc([N+](=O)[O-])cc1)CC2]
C0050
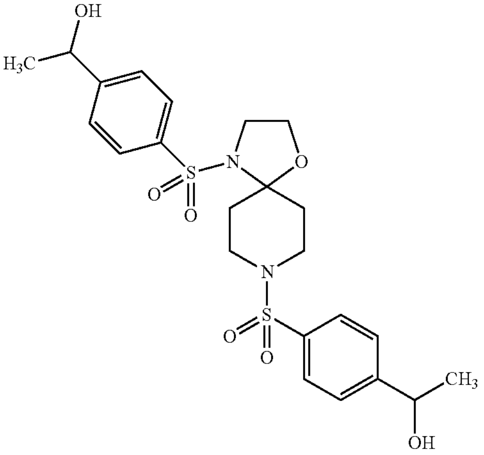 [SMILES: CC(O)c1ccc(S(=O)(=O)N2CCC3(CC2)OCCN3S(=O)(=O)c2ccc(C(C)O)cc2)cc1]
C0051
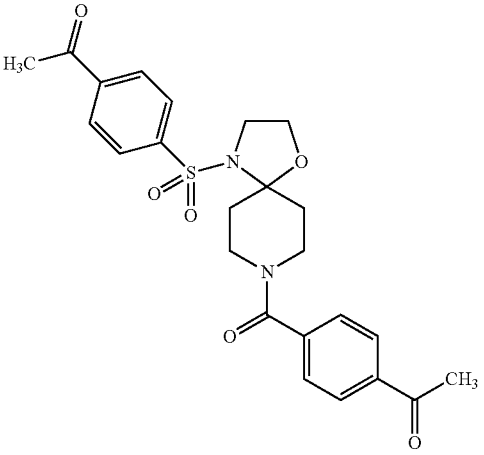 [SMILES: CC(=O)c1ccc(C(=O)N2CCC3(CC2)OCCN3S(=O)(=O)c2ccc(C(C)=O)cc2)cc1]
C0052
-continued
Table of Series-C-1 Compounds
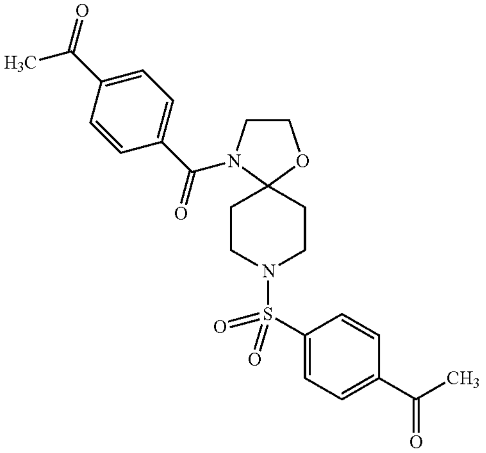 [SMILES: CC(=O)c1ccc(C(=O)N2CCOC23CCN(S(=O)(=O)c2ccc(C(C)=O)cc2)CC3)cc1]
C0053
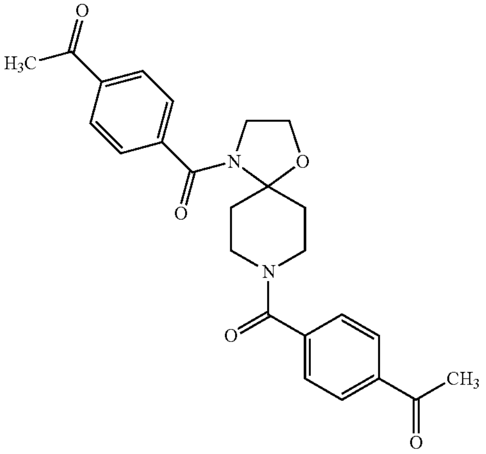 [SMILES: CC(=O)c1ccc(C(=O)N2CCC3(CC2)OCCN3C(=O)c2ccc(C(C)=O)cc2)cc1]
C0054
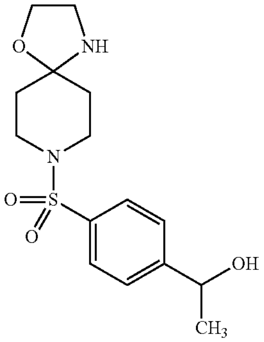 [SMILES: CC(O)c1ccc(S(=O)(=O)N2CCC3(CC2)NCCO3)cc1]
C0055-4
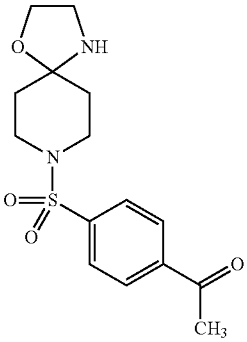 [SMILES: CC(=O)c1ccc(S(=O)(=O)N2CCC3(CC2)NCCO3)cc1]
C0055

-continued
| Table of Series-C-1 Compounds |
|---|
| 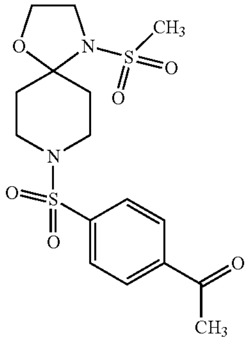 C0056 |
| 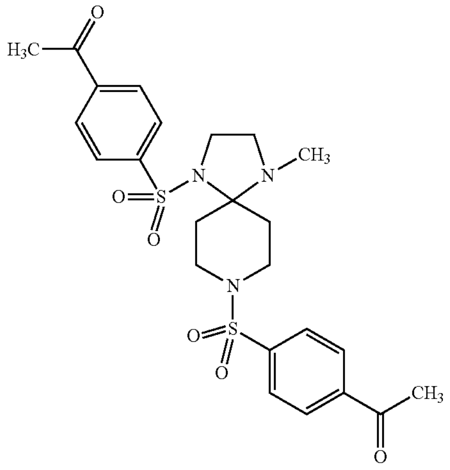 C0057 |
| 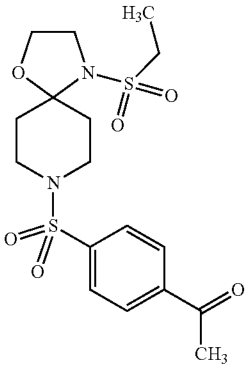 C0058 |
| 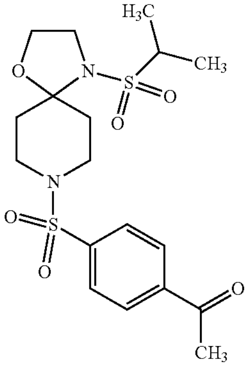 C0059 |
-continued
| Table of Series-C-1 Compounds |
|---|
| 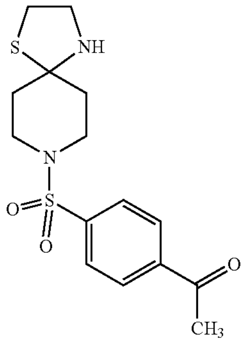 C0060 |
| 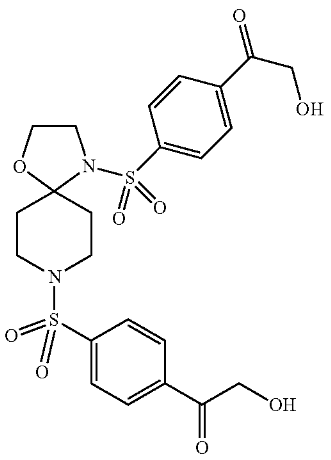 C0061 |
| 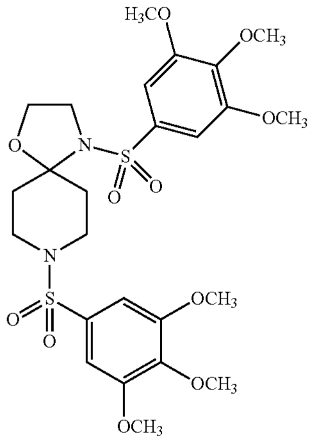 C0062 |

-continued
Table of Series-C-1 Compounds
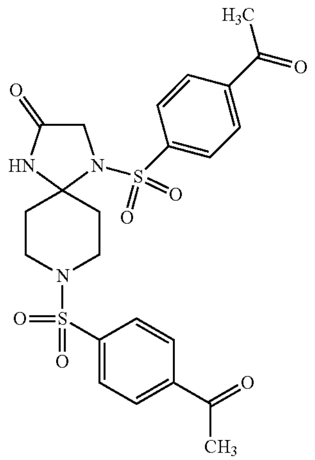 [SMILES: CC(=O)c1ccc(S(=O)(=O)N2CCC3(CC2)NC(=O)CN3S(=O)(=O)c2ccc(C(C)=O)cc2)cc1]
C0064
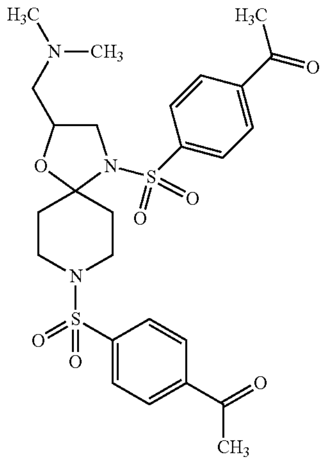 [SMILES: CC(=O)c1ccc(S(=O)(=O)N2CCC3(CC2)OC(CN(C)C)CN3S(=O)(=O)c2ccc(C(C)=O)cc2)cc1]
C0065
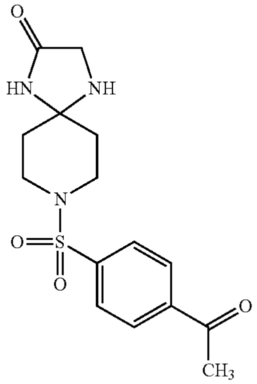 [SMILES: CC(=O)c1ccc(S(=O)(=O)N2CCC3(CC2)NCC(=O)N3)cc1]
C0066
-continued
Table of Series-C-1 Compounds
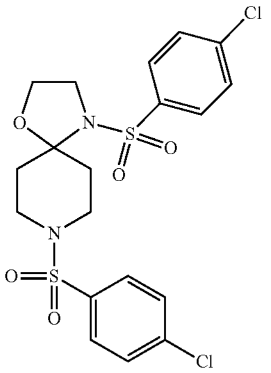 [SMILES: O=S(=O)(c1ccc(Cl)cc1)N1CCC2(CC1)OCCN2S(=O)(=O)c1ccc(Cl)cc1]
C0067
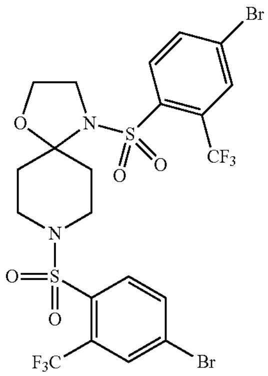 [SMILES: O=S(=O)(c1ccc(Br)cc1C(F)(F)F)N1CCC2(CC1)OCCN2S(=O)(=O)c1ccc(Br)cc1C(F)(F)F]
C0068
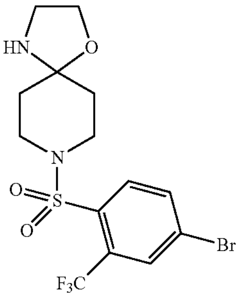 [SMILES: O=S(=O)(c1ccc(Br)cc1C(F)(F)F)N1CCC2(CC1)NCCO2]
C0068-2
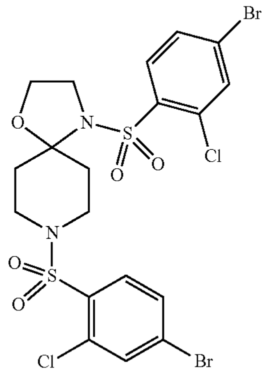 [SMILES: O=S(=O)(c1ccc(Br)cc1Cl)N1CCC2(CC1)OCCN2S(=O)(=O)c1ccc(Br)cc1Cl]
C0069

-continued
Table of Series-C-1 Compounds
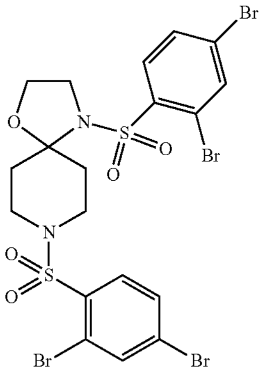 [SMILES: O=S(=O)(c1ccc(Br)cc1Br)N1CCC2(CC1)OCCN2S(=O)(=O)c1ccc(Br)cc1Br]
C0070
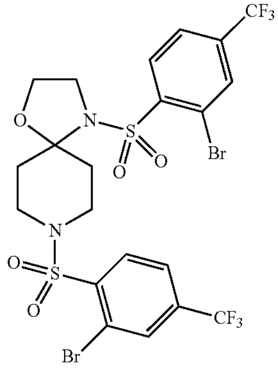 [SMILES: O=S(=O)(c1ccc(C(F)(F)F)cc1Br)N1CCC2(CC1)OCCN2S(=O)(=O)c1ccc(C(F)(F)F)cc1Br]
C0071
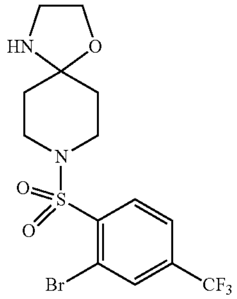 [SMILES: O=S(=O)(c1ccc(C(F)(F)F)cc1Br)N1CCC2(CC1)NCCO2]
C0071-2
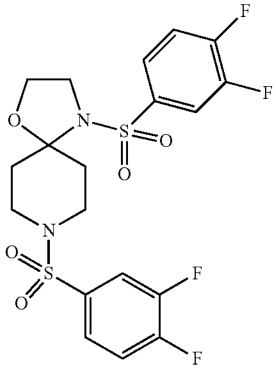 [SMILES: O=S(=O)(c1ccc(F)c(F)c1)N1CCC2(CC1)OCCN2S(=O)(=O)c1ccc(F)c(F)c1]
C0072
-continued
Table of Series-C-1 Compounds
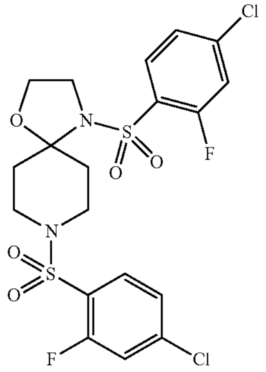 [SMILES: O=S(=O)(c1ccc(Cl)cc1F)N1CCC2(CC1)OCCN2S(=O)(=O)c1ccc(Cl)cc1F]
C0073
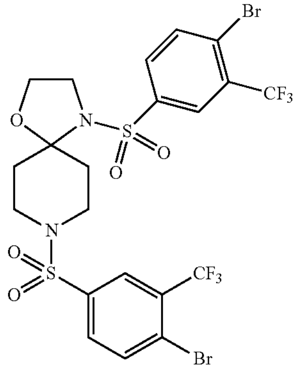 [SMILES: O=S(=O)(c1ccc(Br)c(C(F)(F)F)c1)N1CCC2(CC1)OCCN2S(=O)(=O)c1ccc(Br)c(C(F)(F)F)c1]
C0077
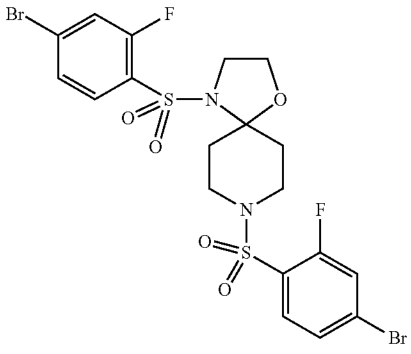 [SMILES: O=S(=O)(c1ccc(Br)cc1F)N1CCC2(CC1)OCCN2S(=O)(=O)c1ccc(Br)cc1F]
C0078
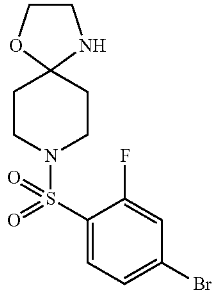 [SMILES: O=S(=O)(c1ccc(Br)cc1F)N1CCC2(CC1)NCCO2]
C0078-2

-continued
Table of Series-C-1 Compounds
C0080
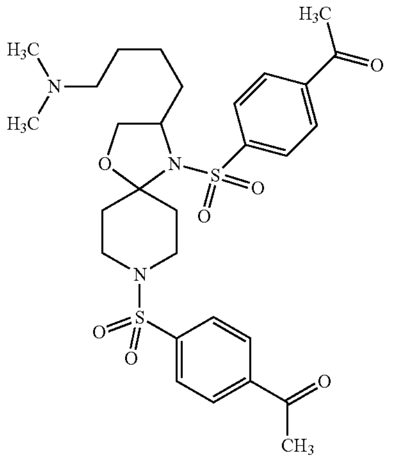 [SMILES: CC(=O)c1ccc(S(=O)(=O)N2CCC3(CC2)OCC(CCCCN(C)C)N3S(=O)(=O)c2ccc(C(C)=O)cc2)cc1]
C0082M
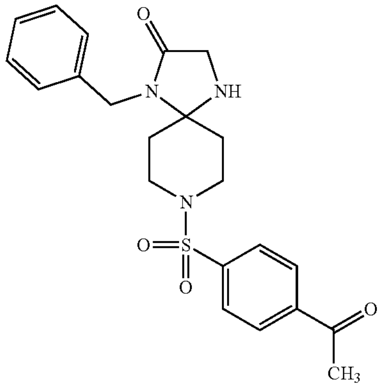 [SMILES: CC(=O)c1ccc(S(=O)(=O)N2CCC3(CC2)NCC(=O)N3Cc2ccccc2)cc1]
C0083M
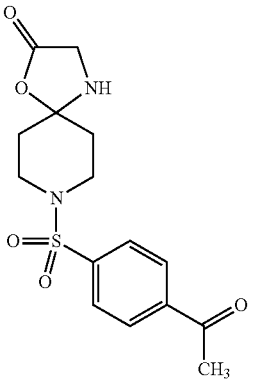 [SMILES: CC(=O)c1ccc(S(=O)(=O)N2CCC3(CC2)NCC(=O)O3)cc1]
-continued
Table of Series-C-1 Compounds
C0084M
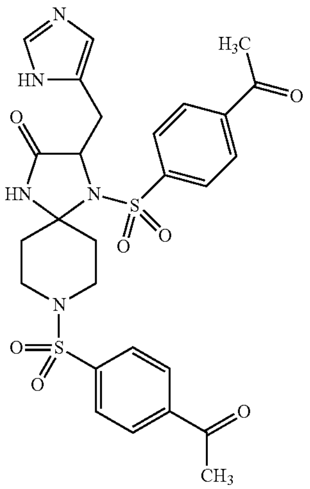 [SMILES: CC(=O)c1ccc(S(=O)(=O)N2CCC3(CC2)NC(=O)C(Cc2cnc[nH]2)N3S(=O)(=O)c2ccc(C(C)=O)cc2)cc1]
C0085M
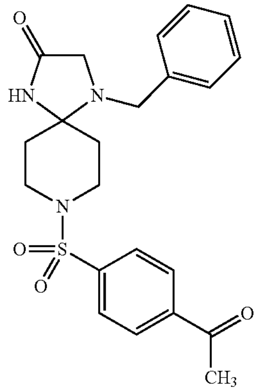 [SMILES: CC(=O)c1ccc(S(=O)(=O)N2CCC3(CC2)NC(=O)CN3Cc2ccccc2)cc1]
C0087M
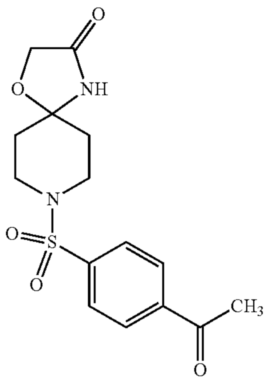 [SMILES: CC(=O)c1ccc(S(=O)(=O)N2CCC3(CC2)NC(=O)CO3)cc1]
C0136M (P5)
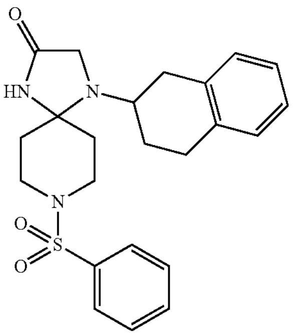 [SMILES: O=C1CN(C2CCc3ccccc3C2)C2(CCN(S(=O)(=O)c3ccccc3)CC2)N1]

-continued
Table of Series-C-1 Compounds
C0138M
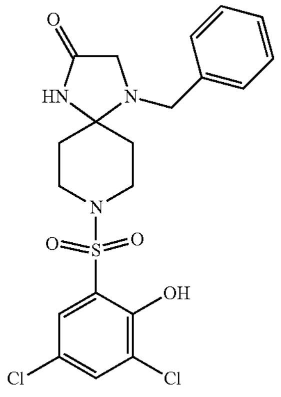 [SMILES: O=C1CN(Cc2ccccc2)C2(CCN(S(=O)(=O)c3cc(Cl)cc(Cl)c3O)CC2)N1]
C0139M
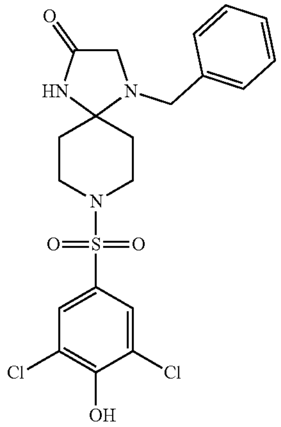 [SMILES: O=C1CN(Cc2ccccc2)C2(CCN(S(=O)(=O)c3cc(Cl)c(O)c(Cl)c3)CC2)N1]
C0140M
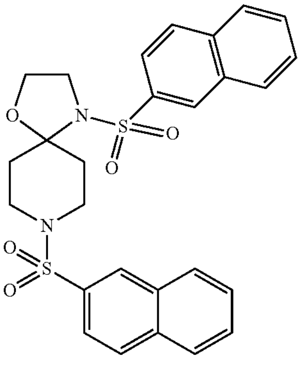 [SMILES: O=S(=O)(c1ccc2ccccc2c1)N1CCC2(CC1)OCCN2S(=O)(=O)c1ccc2ccccc2c1]
C0141M
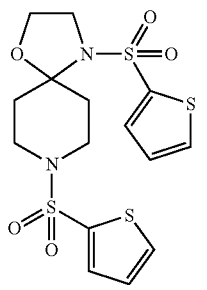 [SMILES: O=S(=O)(c1cccs1)N1CCC2(CC1)OCCN2S(=O)(=O)c1cccs1]
-continued
Table of Series-C-1 Compounds
C0141M-2
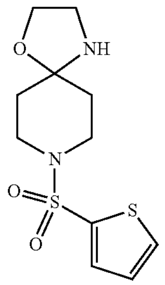 [SMILES: O=S(=O)(c1cccs1)N1CCC2(CC1)NCCO2]
C0142M
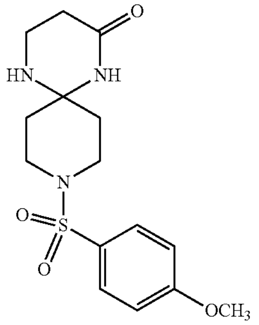 [SMILES: COc1ccc(S(=O)(=O)N2CCC3(CC2)NCCC(=O)N3)cc1]
C0143M-2
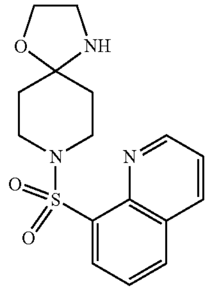 [SMILES: O=S(=O)(c1cccc2cccnc12)N1CCC2(CC1)NCCO2]
C0143M
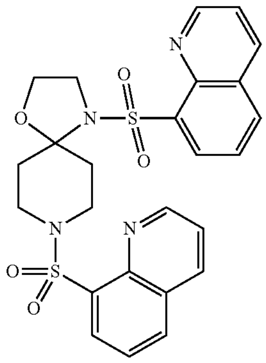 [SMILES: O=S(=O)(c1cccc2cccnc12)N1CCC2(CC1)OCCN2S(=O)(=O)c1cccc2cccnc12]
C0143M-2
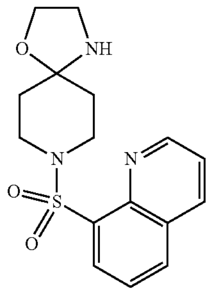 [SMILES: O=S(=O)(c1cccc2cccnc12)N1CCC2(CC1)NCCO2]

-continued
Table of Series-C-1 Compounds
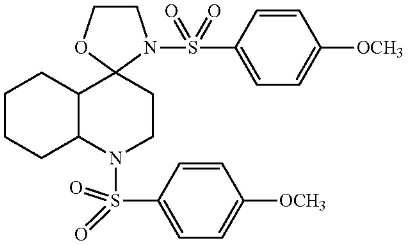 [SMILES: COc1ccc(S(=O)(=O)N2CCC3(OCCN3S(=O)(=O)c3ccc(OC)cc3)C3CCCCC32)cc1]
C0144M
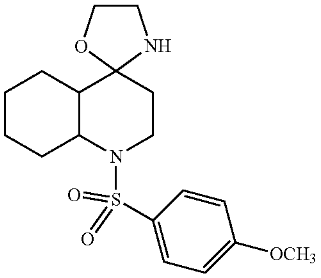 [SMILES: COc1ccc(S(=O)(=O)N2CCC3(NCCO3)C3CCCCC32)cc1]
C0144M-2
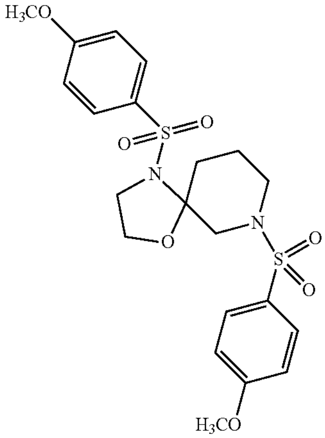 [SMILES: COc1ccc(S(=O)(=O)N2CCCC3(C2)OCCN3S(=O)(=O)c2ccc(OC)cc2)cc1]
C0145M
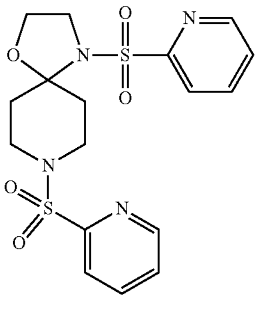 [SMILES: O=S(=O)(c1ccccn1)N1CCC2(CC1)OCCN2S(=O)(=O)c1ccccn1]
C0146M
-continued
Table of Series-C-1 Compounds
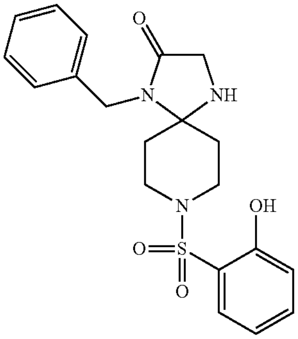 [SMILES: O=C1CNC2(CCN(S(=O)(=O)c3ccccc3O)CC2)N1Cc1ccccc1]
C0147M A2
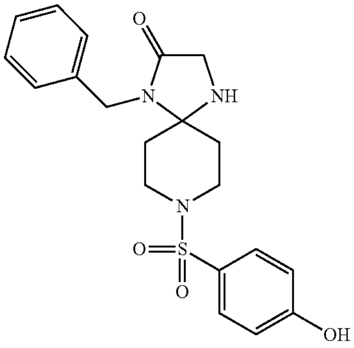 [SMILES: O=C1CNC2(CCN(S(=O)(=O)c3ccc(O)cc3)CC2)N1Cc1ccccc1]
C0148M
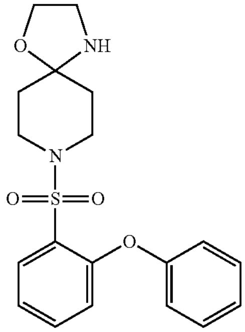 [SMILES: O=S(=O)(c1ccccc1Oc1ccccc1)N1CCC2(CC1)NCCO2]
C0149M-2
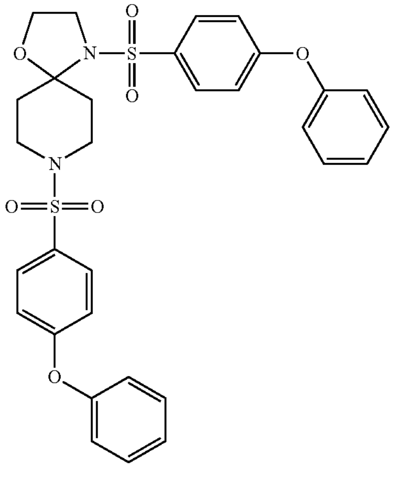 [SMILES: O=S(=O)(c1ccc(Oc2ccccc2)cc1)N1CCC2(CC1)OCCN2S(=O)(=O)c1ccc(Oc2ccccc2)cc1]
C0149M Table of Series-C-1 Compounds
C0150M
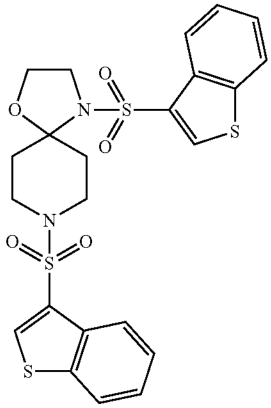 [SMILES: O=S(=O)(c1csc2ccccc12)N1CCC2(CC1)OCCN2S(=O)(=O)c1csc2ccccc12]
C0151M
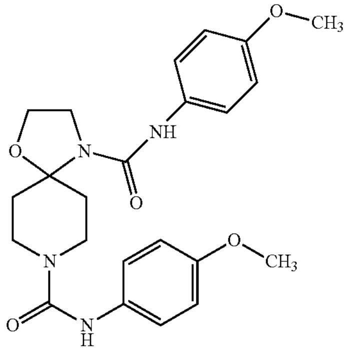 [SMILES: COc1ccc(NC(=O)N2CCC3(CC2)OCCN3C(=O)Nc2ccc(OC)cc2)cc1]
C0151M-2
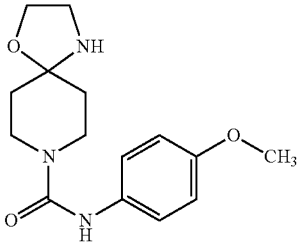 [SMILES: COc1ccc(NC(=O)N2CCC3(CC2)NCCO3)cc1]
C0152M-4
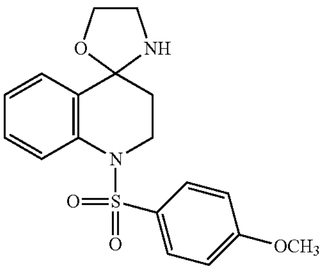 [SMILES: COc1ccc(S(=O)(=O)N2CCC3(NCCO3)c3ccccc32)cc1]
Table of Series C-2 Compounds
S-C0027
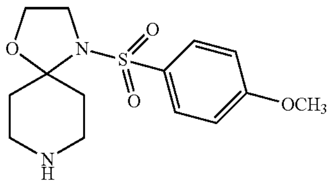 [SMILES: COc1ccc(S(=O)(=O)N2CCOC23CCNCC3)cc1]
Table of Series C-2 Compounds
C0027
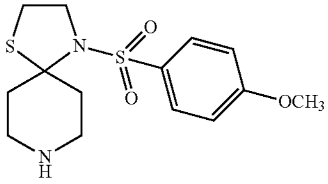 [SMILES: COc1ccc(S(=O)(=O)N2CCSC23CCNCC3)cc1]
C0043
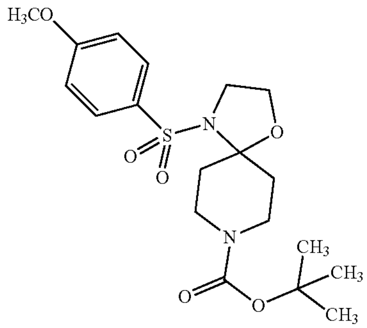 [SMILES: COc1ccc(S(=O)(=O)N2CCOC23CCN(C(=O)OC(C)(C)C)CC3)cc1]
C0046
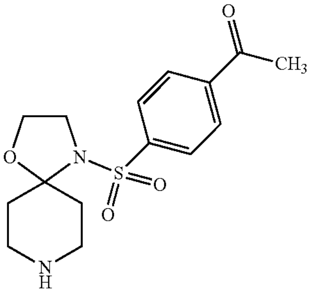 [SMILES: CC(=O)c1ccc(S(=O)(=O)N2CCOC23CCNCC3)cc1]
C0053-3
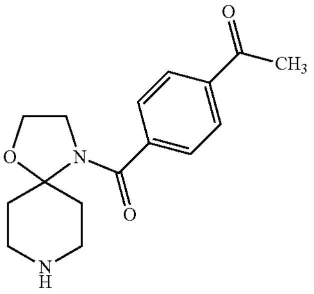 [SMILES: CC(=O)c1ccc(C(=O)N2CCOC23CCNCC3)cc1]
C0079M-7
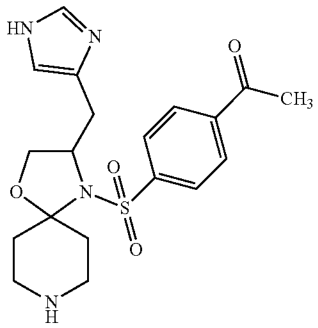 [SMILES: CC(=O)c1ccc(S(=O)(=O)N2C(Cc3c[nH]cn3)COC23CCNCC3)cc1]

-continued
Table of Series C-2 Compounds
C0080M-6
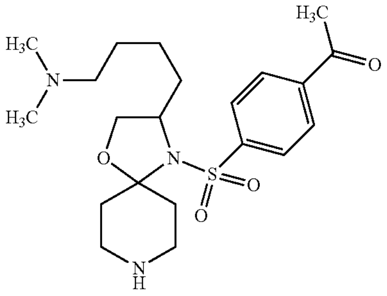 [SMILES: CC(=O)c1ccc(S(=O)(=O)N2C(CCCCN(C)C)COC23CCNCC3)cc1]
C0081M-7
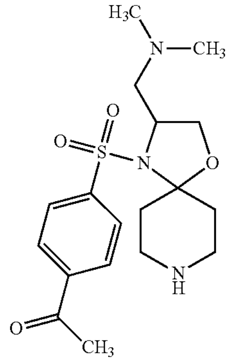 [SMILES: CC(=O)c1ccc(S(=O)(=O)N2C(CN(C)C)COC23CCNCC3)cc1]
C0086M
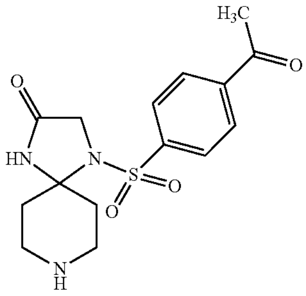 [SMILES: CC(=O)c1ccc(S(=O)(=O)N2CC(=O)NC23CCNCC3)cc1]
C0088M
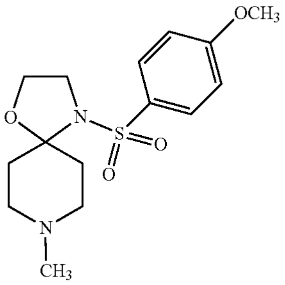 [SMILES: COc1ccc(S(=O)(=O)N2CCOC23CCN(C)CC3)cc1]
C0089M
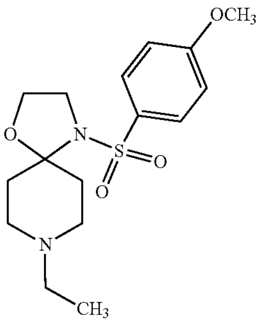 [SMILES: CCN1CCC2(CC1)OCCN2S(=O)(=O)c1ccc(OC)cc1]
-continued
Table of Series C-2 Compounds
C0090M
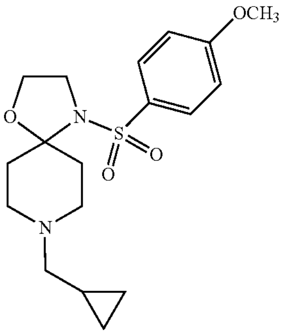 [SMILES: COc1ccc(S(=O)(=O)N2CCOC23CCN(CC2CC2)CC3)cc1]
C0091M
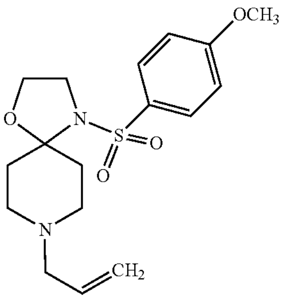 [SMILES: C=CCN1CCC2(CC1)OCCN2S(=O)(=O)c1ccc(OC)cc1]
C0092M
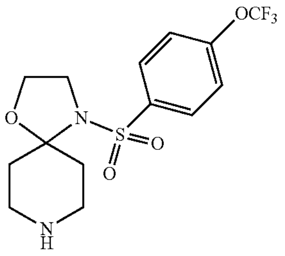 [SMILES: O=S(=O)(c1ccc(OC(F)(F)F)cc1)N1CCOC12CCNCC2]
C0093M
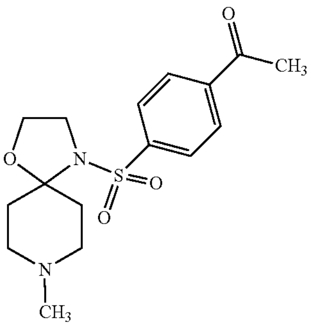 [SMILES: CC(=O)c1ccc(S(=O)(=O)N2CCOC23CCN(C)CC3)cc1]
C0094M
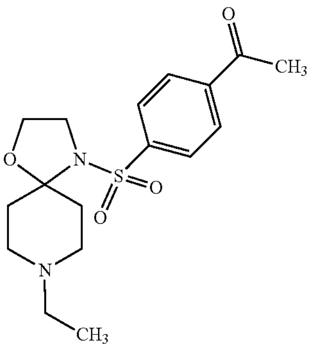 [SMILES: CCN1CCC2(CC1)OCCN2S(=O)(=O)c1ccc(C(C)=O)cc1]

-continued
Table of Series C-2 Compounds
C0095M
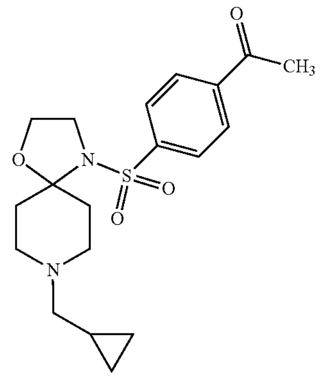 [SMILES: CC(=O)c1ccc(S(=O)(=O)N2CCOC23CCN(CC2CC2)CC3)cc1]
C0096M
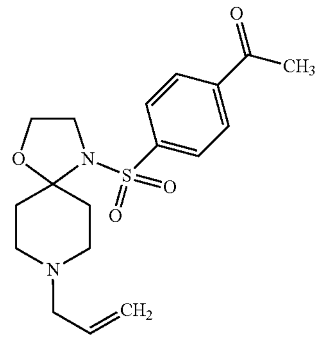 [SMILES: C=CCN1CCC2(CC1)OCCN2S(=O)(=O)c1ccc(C(C)=O)cc1]
C0097M
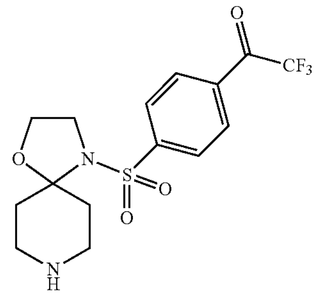 [SMILES: O=C(c1ccc(S(=O)(=O)N2CCOC23CCNCC3)cc1)C(F)(F)F]
C0099M
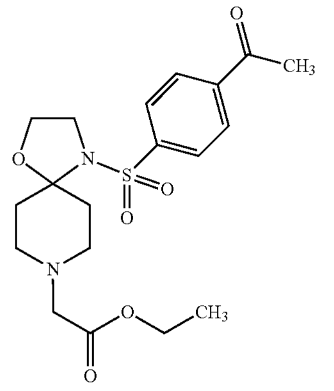 [SMILES: CCOC(=O)CN1CCC2(CC1)OCCN2S(=O)(=O)c1ccc(C(C)=O)cc1]
-continued
Table of Series C-2 Compounds
C0100M
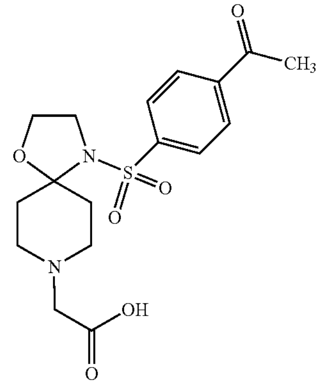 [SMILES: CC(=O)c1ccc(S(=O)(=O)N2CCOC23CCN(CC(=O)O)CC3)cc1]
C0101M
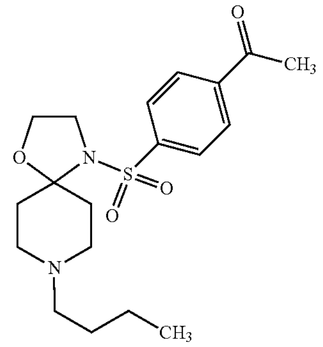 [SMILES: CCCCN1CCC2(CC1)OCCN2S(=O)(=O)c1ccc(C(C)=O)cc1]
C0102M
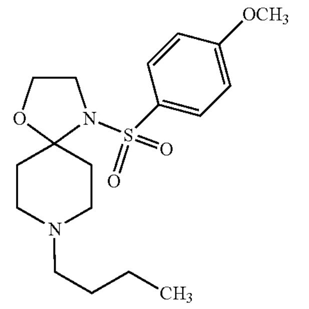 [SMILES: CCCCN1CCC2(CC1)OCCN2S(=O)(=O)c1ccc(OC)cc1]
C0104M
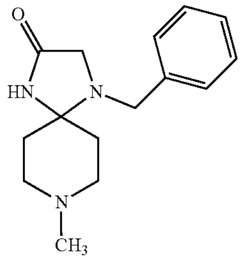 [SMILES: CN1CCC2(CC1)NC(=O)CN2Cc1ccccc1]
C0105M
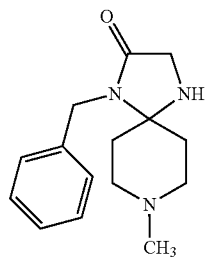 [SMILES: CN1CCC2(CC1)NCC(=O)N2Cc1ccccc1]

-continued
Table of Series C-2 Compounds
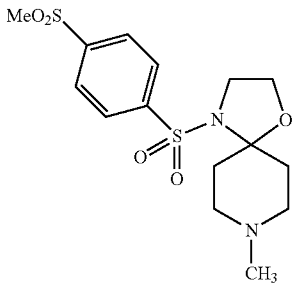 [SMILES: CN1CCC2(CC1)OCCN2S(=O)(=O)c1ccc(S(C)(=O)=O)cc1]
C0106 M
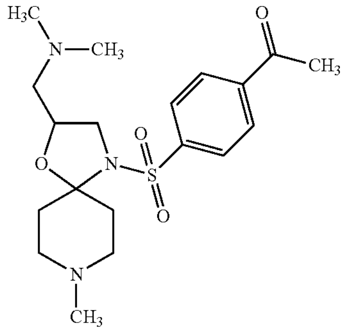 [SMILES: CC(=O)c1ccc(S(=O)(=O)N2CC(CN(C)C)OC23CCN(C)CC3)cc1]
C0108M
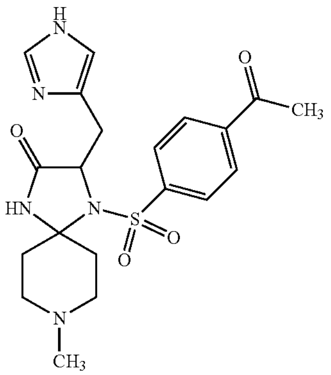 [SMILES: CC(=O)c1ccc(S(=O)(=O)N2C(Cc3c[nH]cn3)C(=O)NC23CCN(C)CC3)cc1]
C0109M
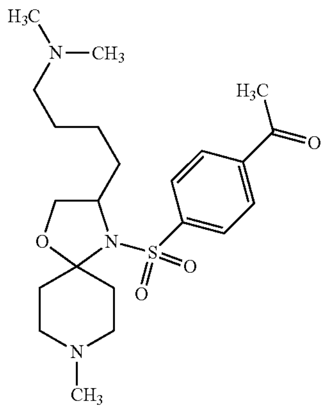 [SMILES: CC(=O)c1ccc(S(=O)(=O)N2C(CCCCN(C)C)COC23CCN(C)CC3)cc1]
C0111 M
-continued
Table of Series C-2 Compounds
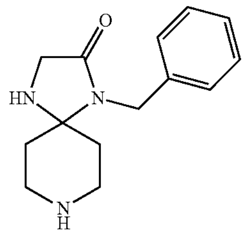 [SMILES: O=C1CNC2(CCNCC2)N1Cc1ccccc1]
C0114M
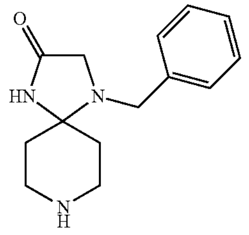 [SMILES: O=C1CN(Cc2ccccc2)C2(CCNCC2)N1]
C0115M
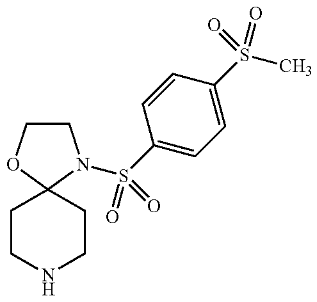 [SMILES: CS(=O)(=O)c1ccc(S(=O)(=O)N2CCOC23CCNCC3)cc1]
C0116M
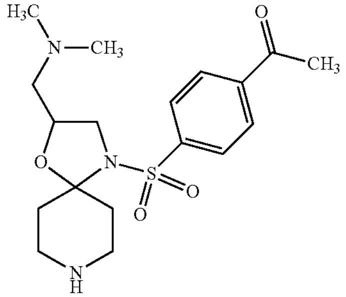 [SMILES: CC(=O)c1ccc(S(=O)(=O)N2CC(CN(C)C)OC23CCNCC3)cc1]
C0118M
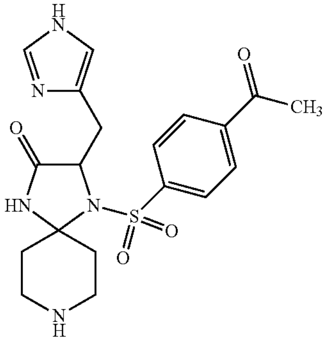 [SMILES: CC(=O)c1ccc(S(=O)(=O)N2C(Cc3c[nH]cn3)C(=O)NC23CCNCC3)cc1]
C0119M -continued
Table of Series C-2 Compounds
C0123M
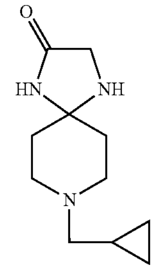
C0124M
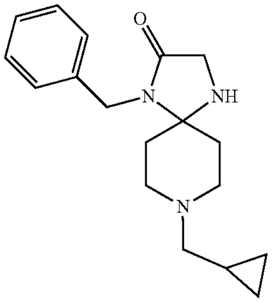 [SMILES: O=C1CNC2(CCN(CC3CC3)CC2)N1Cc1ccccc1]
C0125M
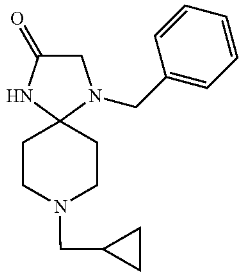 [SMILES: O=C1CN(Cc2ccccc2)C2(CCN(CC3CC3)CC2)N1]
C0126 M
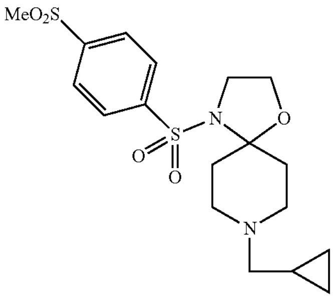 [SMILES: CS(=O)(=O)c1ccc(S(=O)(=O)N2CCOC23CCN(CC2CC2)CC3)cc1]
C0128M
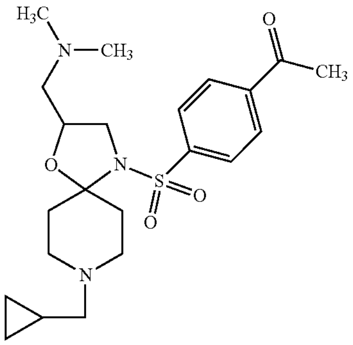 [SMILES: CC(=O)c1ccc(S(=O)(=O)N2CC(CN(C)C)OC23CCN(CC2CC2)CC3)cc1]
-continued
Table of Series C-2 Compounds
C0129M
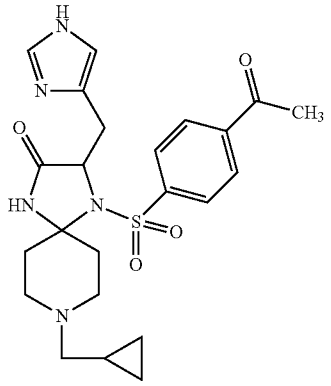 [SMILES: CC(=O)c1ccc(S(=O)(=O)N2C(Cc3c[nH]cn3)C(=O)NC23CCN(CC2CC2)CC3)cc1]
C0133M
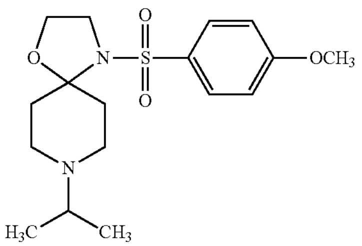 [SMILES: COc1ccc(S(=O)(=O)N2CCOC23CCN(C(C)C)CC3)cc1]
C0134M
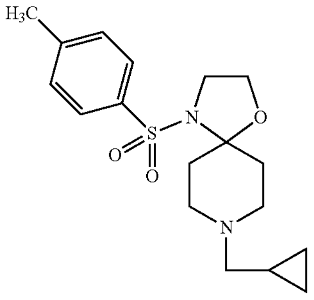 [SMILES: Cc1ccc(S(=O)(=O)N2CCOC23CCN(CC2CC2)CC3)cc1]
F-C0134
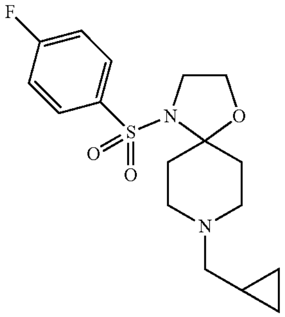 [SMILES: O=S(=O)(c1ccc(F)cc1)N1CCOC12CCN(CC1CC1)CC2]

-continued
Table of Series C-2 Compounds
C0135M
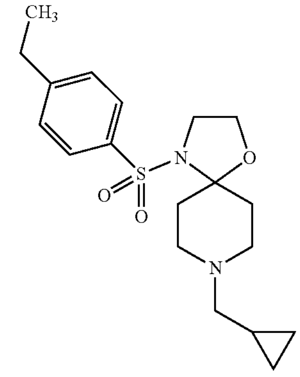 [SMILES: CCc1ccc(S(=O)(=O)N2CCOC23CCN(CC2CC2)CC3)cc1]
C0137M P7
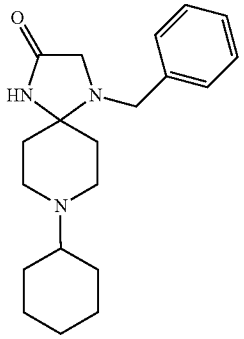 [SMILES: O=C1CN(Cc2ccccc2)C2(CCN(C3CCCCC3)CC2)N1]
C0145M-3
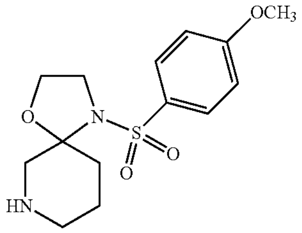 [SMILES: COc1ccc(S(=O)(=O)N2CCOC23CCCNC3)cc1]
C0153M-3
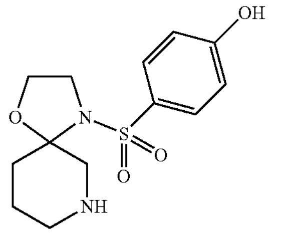 [SMILES: O=S(=O)(c1ccc(O)cc1)N1CCOC12CCCNC2]
Compound 4
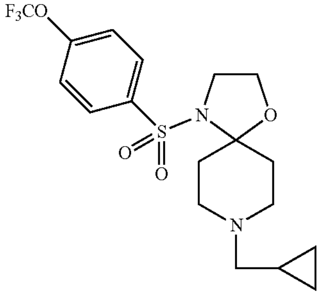 [SMILES: O=S(=O)(c1ccc(OC(F)(F)F)cc1)N1CCOC12CCN(CC1CC1)CC2]
-continued
Table of Series C-2 Compounds
Compound 9
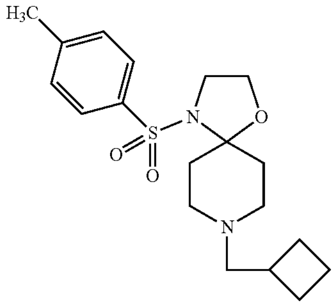 [SMILES: Cc1ccc(S(=O)(=O)N2CCOC23CCN(CC2CCC2)CC3)cc1]
Compound 10
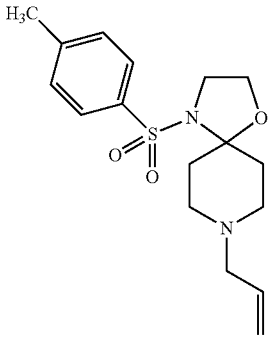 [SMILES: C=CCN1CCC2(CC1)OCCN2S(=O)(=O)c1ccc(C)cc1]
Table of Series D Compounds
Compound A
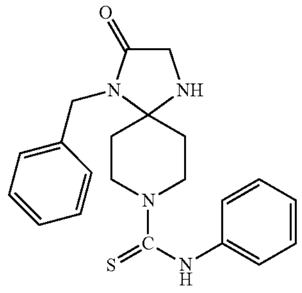 [SMILES: O=C1CNC2(CCN(C(=S)Nc3ccccc3)CC2)N1Cc1ccccc1]
Compound B
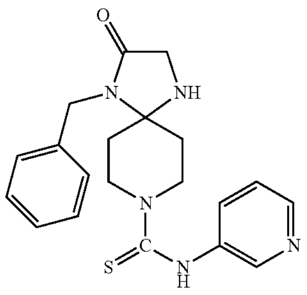 [SMILES: O=C1CNC2(CCN(C(=S)Nc3cccnc3)CC2)N1Cc1ccccc1]

-continued

| Table of Series D Compounds | |
|---|---|
| 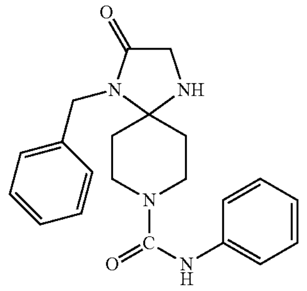 [SMILES: O=C(Nc1ccccc1)N1CCC2(CC1)NCC(=O)N2Cc1ccccc1] | Compound C |

Preparation of Series C-2 Compounds 4, 9 and 10

These three compounds were prepared via a common intermediate designated 9-2 herein that was prepared during the synthesis of Compound C0116M in application Ser. No. 12/561,091 (US Publication No. 20110105487 A1 dated May 5, 2011; WO 2010/051497), and referred to therein as Compound C0116M-1.

After preparation of Compound 9-2, the syntheses of Compounds 9 and 10 proceeded routinely by first adding the tosyl group in pyridine to the nitrogen of the five-membered ring, followed by removal of the t-BOC group with trifluoroacetic acid (TFA) in dichloromethane to form Compound 9-4 as shown below. Specifics of the syntheses are provided hereinafter.

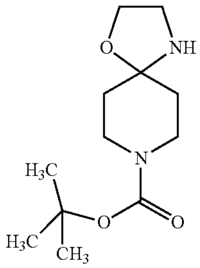

9-2

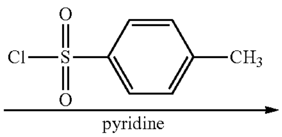

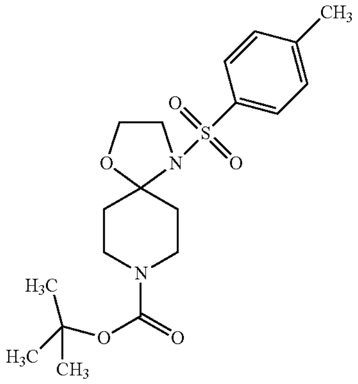

9-3

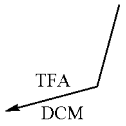

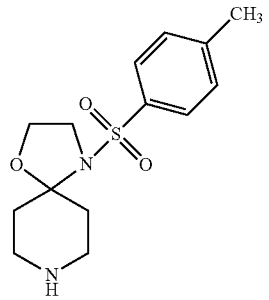

9-4

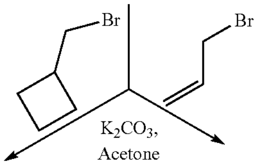

-continued

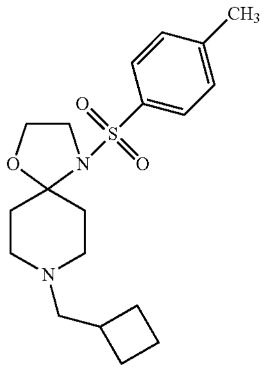

9

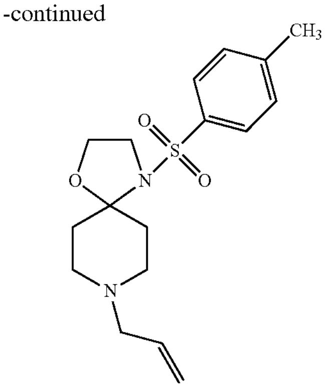

10

Compound 9-2 also served as the basis for preparation of Compound 4. Here, as shown below, 4-trifluoromethoxyphenyl sulfonylchloride was reacted in pyridine with the amine of the five-membered ring, and the t-BOC group removed in TFA/DCM as above to form Compound 4-1. The amine nitrogen of the six-membered ring of Compound 4-1 was then reacted with (bromomethyl)cyclopropane to form the N-alkylated product that is Compound 4.

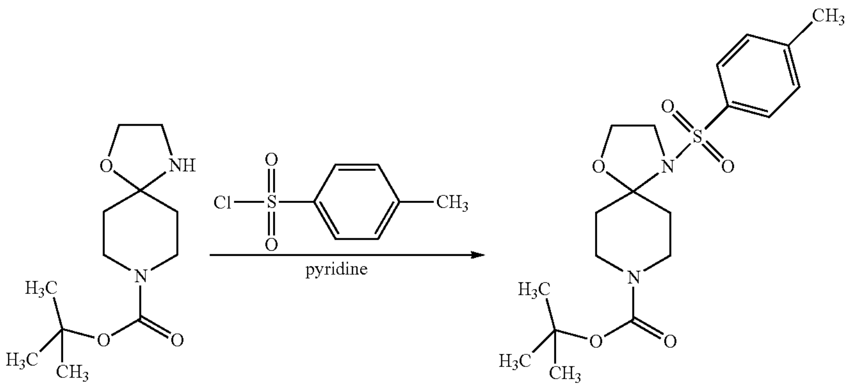

9-2

11

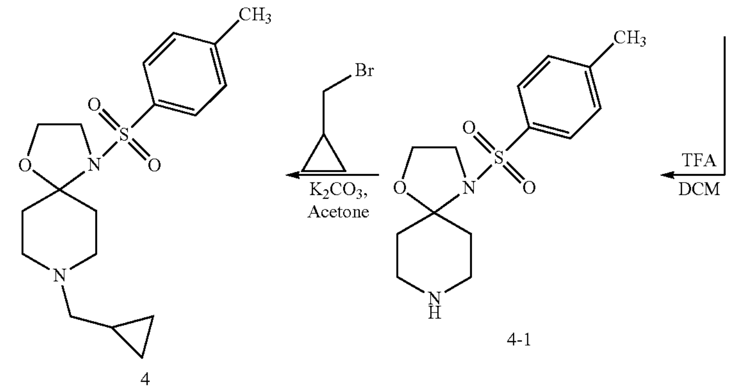

4-1

4

Preparation of Compound 9-2

To a solution of N-Boc-piperidin-4-one (50 g, 251 mmol) in ethanol (500 mL) was added 2-aminoethanol (46 g). The mixture was stirred at room temperature overnight (about 18 hours). Then the solvent was removed under reduced pressure. The residue was diluted with $CH_2C_2$ (DCM) and washed with saturated aqueous $Na_2CO_3$ (100 mL×6). The organic phase was dried over anhydrous $Na_2SO_4$, and concentrated to provide the product as a yellow oil (61 g, yield: 100%, confirmed by TLC).

Preparation of Compound 9-3

Toluenesulfonyl chloride (TsCl; 24.7 g, 130 mmol) was added to a solution of Compound 9-2 (31.2 g, 130 mmol) in pyridine (320 mL). The mixture was stirred overnight (about 18 hours) at room temperature. The reaction mixture was concentrated in vacuo to remove the pyridine and the residue was dissolved with DCM and washed with saturated $NaHCO_3$. The organic layer was dried over $Na_2SO_4$, concentrated and purified by column chromatography to provide the product as white solid (40 g, yield: 78%, confirmed by 1H NMR).

$^1$H NMR (400 MHz, $CDCl_3$): 7.74 (d, J=8.4 Hz, 2H); 7.31 (d, J=8.0 Hz, 2H); 4.13~4.03 (m, 4H); 3.56~3.50 (m, 2H); 2.89 (brs, 2H); 2.46 (s, 3H); 2.43~2.36 (m, 2H); 1.63 (brs, 2H); 1.47 (s, 9H).

Preparation of Compound 9-4

Trifluoroacetic acid ($CF_3COOH$; 60 mL) was added to a solution of Compound 9-3 (35.2 g, 88.7 mmol) in DCM (350 mL). The mixture was stirred at ice/water for 50 minutes. To the reaction mixture was added 200 mL of DCM, and the resulting composition washed with saturated $Na_2CO_3$. The organic layer was dried over $Na_2SO_4$, concentrated in vacuo to provide the crude product. The crude product was purified by column chromatography to provide the desired product as pale yellow oil (11.2 g, yield: 42%, confirmed by $^1$H NMR).

$^1$H NMR (400 MHz, $CDCl_3$): 7.75 (d, J=8.4 Hz, 2H); 7.29 (d, J=8.0 Hz, 2H); 3.95 (t, J=6.4 Hz, 2H); 3.75 (brs, 1H); 3.51~3.48 (t, J=5.6 Hz, 2H); 3.16~3.12 (dd, J=12.4, 4.0 Hz, 2H); 2.92~2.86 (td, J=12.8, 2.0 Hz, 2H); 2.48~2.44 (m, 2H); 2.41 (s, 3H); 1.65 (d, J=12.8 Hz, 2H).

Preparation of Compound 9

(Bromomethyl)cyclobutane (1.86 g, 12.5 mmol) was added to a mixture of Compound 9-4 (1.85 g, 6.25 mmol) and $K_2CO_3$ (3.39 g, 12.5 mmol) in acetone (40 mL), and the reaction mixture was stirred at reflux overnight (about 18 hours). After cooling, the mixture was filtered and concentrated, purified by chromatography with ethyl acetate (EA) to obtain crude product as pale yellow solid (1.6 g, yield: 70%, confirmed by LCMS, $^1$H NMR showed it was impure). The crude product was purified by further chromatography with EA to provide the desired product as white solid (1.15 g, yield: 50%, confirmed by LCMS and $^1$H NMR, HPLC: 99.3% @254 nm, 99.5 @214 nm).

$^1$H NMR (400 MHz, $CDCl_3$): 7.77 (d, J=8.0 Hz, 2H); 7.31 (d, J=8.0 Hz, 2H); 3.95 (t, J=6.0 Hz, 2H); 3.52 (t, J=6.4 Hz, 2H); 2.76~2.73 (d, J=10.0 Hz, 2H); 2.54~2.39 (m, 8H); 2.21~2.15 (t, J=11.6 Hz, 2H); 2.07~2.05 (m, 2H); 1.93~1.88 (m, 2H); 1.70~1.65 (m, 2H); 1.56~1.53 (d, J=12.4 Hz, 2H). MS (ESI) calcd for $C_{19}H_{28}N_2O_3S$ (m/z): 364.18, found: 365.1 $[M+1]^+$.

Preparation of Compound 10

To a mixture of Compound 9-4 (1.72 g, 5.8 mmol) and $K_2CO_3$ (1.6 g, 11.6 mmol) in acetone (30 mL) was added 3-bromoprop-1-ene (0.7 g, 5.8 mmol), and the reaction mixture was stirred at 40° C. for 2 hours. After cooling, the mixture was filtered and concentrated, purified by chromatography with EA to obtain the desired product as white solid (1.1 g, 56% yield, confirmed by LCMS and $^1$H NMR, HPLC: 98.8% @254 nm, 98.9 @214 nm).

$^1$H NMR (400 MHz, $CDCl_3$): 7.76~7.74 (d, J=8.0 Hz, 2H); 7.29~7.27 (d, J=8.0 Hz, 2H); 5.90~5.82 (m, 1H); 5.18~5.11 (m, 2H); 3.95~3.91 (t, J=6.0 Hz, 2H); 3.52~3.49 (t, J=6.0 Hz, 2H); 3.0~2.98 (d, J=6.4 Hz, 2H); 2.83~2.80 (dd, J=8.8, 2.4 Hz, 2H); 2.55~2.48 (td, J=13.2, 4.4 Hz, 2H); 2.41 (s, 3H); 2.19~2.14 (t, J=11.2 Hz, 2H); 1.58~1.55 (d, J=12.0 Hz, 2H). MS (ESI) calcd for $C_{17}H_{24}N_2O_3S$ (m/z): 336.45, found: 337.1 $[M+1]^+$.

Preparation of Compound 11

To a solution of Compound 9-2 (14.6 g, 60 mmol) in pyridine (150 mL) was added 4-(trifluoro-methoxy)benzene-1-sulfonyl chloride (15.7 g, 60 mmol). The mixture was stirred overnight (about 18 hours) at room temperature. The reaction mixture was concentrated in vacuo to remove the pyridine and the residue was dissolved with DCM, washed with saturated $NaHCO_3$. The organic layer was dried over $Na_2SO_4$, concentrated and purified by column chromatography to give product as white solid (20 g, yield: 71%, confirmed by 1H NMR and LCMS).

$^1$H NMR (400 MHz, $CDCl_3$): 7.92~7.90 (d, J=8.4 Hz, 2H); 7.35~7.32 (d, J=8.4 Hz, 2H); 4.13~3.97 (m, 4H); 3.51 (brs, 2H); 2.90 (brs, 2H); 2.45~2.35 (m, 2H); 1.58 (brs, 2H); 1.47 (s, 9H). MS (ESI) calcd for $C_{19}H_{25}F_3N_2O_6S$ (m/z): 466.14, found: 367.0 $[M+1]^+$.

Preparation of Compound 4-1

Trifluoroacetic acid ($CF_3COOH$; 20 mL) was added to a solution of Compound 11 (15 g, 32 mmol) in DCM (150 mL). The mixture was stirred at ice/water for 50 minutes. The reaction mixture was added to 200 mL of DCM, washed with saturated $Na_2CO_3$. The organic layer was dried over $Na_2SO_4$, concentrated in vacuo to provide the crude product. The crude product was purified by column chromatography to provide the desired product as pale yellow solid (5.9 g, yield: 50%, confirmed by $^1$H NMR).

$^1$H NMR (400 MHz, $CDCl_3$): 7.93~7.91 (d, J=8.4 Hz, 2H); 7.34~7.32 (d, J=8.0 Hz, 2H); 4.0~3.97 (t, J=5.6 Hz, 2H); 3.51~3.48 (t, J=6.0 Hz, 2H); 3.06~3.02 (dd, J=12.4, 4.0 Hz, 2H); 2.86~2.80 (t, J=13.2 Hz, 2H); 2.39~2.31 (td, J=12.8, 4.8 Hz, 2H); 2.48~2.44 (m, 2H); 1.64~1.62 (d, J=12.8 Hz, 2H).

Preparation of Compound 4

(Bromomethyl)cyclobutane (1.5 g, 4.1 mmol) was added to a mixture of Compound 4-1 (1.5 g, 4.1 mmol) and $K_2CO_3$ (1.13 g, 8.2 mmol) in acetone (15 mL), and the reaction mixture was stirred at reflux for 4 hours. After cooling, the mixture was filtered and concentrated, purified by chromatography with EA to provide the desired product as an off-white solid (1.05 g, yield: 61%, confirmed by LCMS and $^1$H NMR, HPLC: 96.9% @254 nm, 98.4 @214 nm).

$^1$H NMR (400 MHz, $CDCl_3$): 7.91~7.94 (d, J=8.8 Hz, 2H); 7.34~7.32 (d, J=8.0 Hz, 2H); 3.98~3.95 (t, J=6.0 Hz, 2H); 3.54~3.51 (t, J=6.4 Hz, 2H); 2.99~2.96 (dd, J=8.8, 2.0 Hz, 2H); 2.56~2.49 (td, J=12.8, 4.4 Hz, 2H); 2.26~2.17 (m, 4H); 1.60~1.57 (d, J=12.4 Hz, 2H); 0.87~0.84 (m, 1H); 0.52~0.48 (m, 2H); 0.10~0.07 (m, 2H). MS (ESI) calcd for $C_{18}H_{23}F_3N_2O_4S$ (m/z): 420.13, found: 421.1 $[M+1]^+$.

Preparation of Series D Compounds A, B and C

Compound A

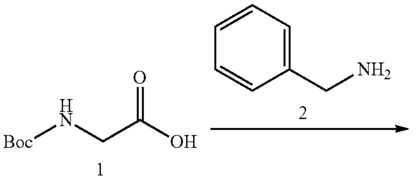

1

-continued

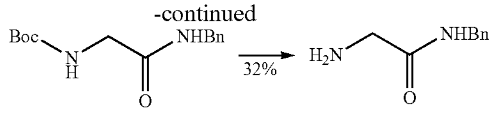

3 4

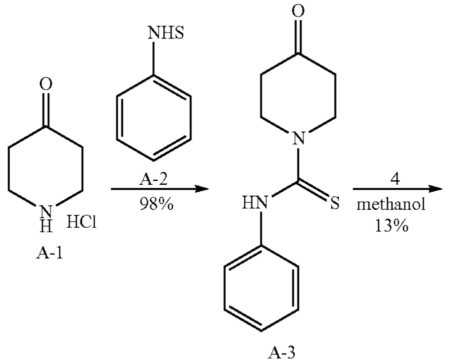

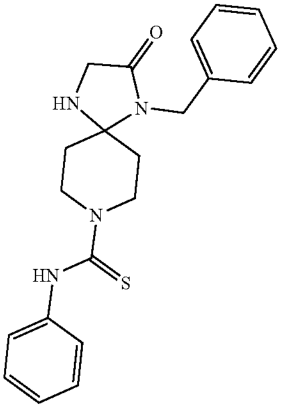

Compound A

Compound 4

To a solution of Compound 1 (10 g, 57 mmol) in THF (100 mL) was added 1,1'-carbonyldiimidazole (CDI) (11.1 g, 68.5 mmol) at room temperature, and the mixture was stirred for 30 minutes. Compound 2 (7.34 g, 68.5 mmol) was then added and stirred overnight (about 18 hours). The solvent was evaporated and the residue was dissolved in ethyl acetate (EA; 400 mL) to which was added 4M HCl/MeOH (50 mL), and the resulting admixture was stirred overnight (about 18 hours). The resulting white solid was filtered and suspended in EA, washed with aq·$NaHCO_3$ and concentrated to afford product as white solid (3.2 g, 34% yield, as confirmed by NMR).

1H-NMR (400 MHz, $CDCl_3$): 3.41 (s, 3H); 4.48 (d, J=6.0 Hz, 2H); 7.26~7.36 (m, 5H); 7.57 (br, s, 1H).

Compound A-3

A mixture of Compound A-1 (3.75 g, 24 mmol), A-2 (1.5 g, 11 mmol) and triethylamine (TEA) (4.5 g, 44.38 mmol) in dichloromethane (DCM) (50 mL) was stirred at room temperature overnight (about 18 hours). The reaction mixture was washed with water, dried over $Na_2SO_4$ and concentrated to afford product as white solid (2.55 g, 98% yield, confirmed by NMR).

1H-NMR (400 MHz, $CDCl_3$): 2.53 (t, J=6.4 Hz, 4H); 4.01 (t, J=6.4 Hz, 4H); 7.10~7.30 (m, 5H).

Compound A

A mixture of Compound A-3 (400 mg, 1.7 mmol) and Compound 4 (280 mg, 1.7 mmol) in methanol (60 mL) was heated to reflux overnight (about 18 hours) under argon. The mixture was concentrated and purified by pre-TLC to get product as pale white solid (84 mg, 13% yield, NMR and MS confirmed, 98% by HPLC).

1H-NMR (400 MHz, $CDCl_3$): 1.42 (d, J=12.4 Hz, 2H); 1.92 (dt, J=4.4, 13.2 Hz, 2H); 3.32 (dt, J=2.0, 12.8 Hz, 2H); 3.52 (s, 2H); 4.42 (s, 2H); 4.47 (s, 2H); 7.06 (t, J=7.6 Hz, 2H); 7.14 (t, J=7.6 Hz, 1H); 7.24~7.33 (m, 9H). MS (ESI) calcd for $C_{21}H_{24}N_4OS$ (m/z): 380.17, found: 381.2 $[M+1]^+$.

Compound B

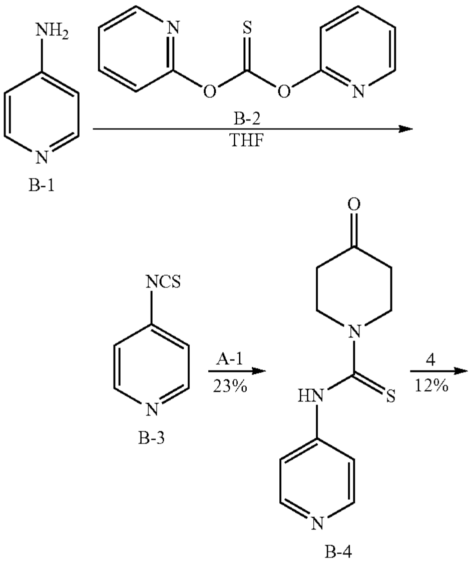

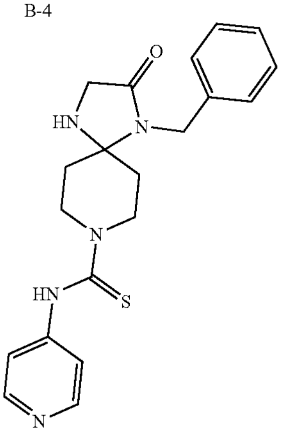

Compound B

Compound B-4

To a solution of pyridin-4-amine (400 mg, 4.25 mmol) in THF (35 mL) was added 60% NaH (340 mg, 8.5 mmol) in an ice bath, and the mixture was stirred for 1 hour. Compound B-2 (0.99 g, 4.25 mmol) was added and the mixture was permitted to gradually to reach room temperature and stirred for 3 hours. Compound A-1 (0.78 g, 5.1 mmol) and N,N-diisopropyl-ethylamine (DIEA; 1 mL) was added and the mixture was stirred at room temperature overnight (about 18 hours). Water was added and the resulting composition was extracted with EA, washed with brine, dried over $Na_2SO_4$, concentrated and purified by column chromatography to afford oil (0.23 g, 23% yield, NMR was not pure but the major component was title compound).

1H-NMR (400 MHz, $CDCl_3$): 2.66 (t, J=6.4 Hz, 4H); 4.12 (t, J=6.4 Hz, 4H); 7.11~7.12 (d, J=4.8 Hz, 2H); 8.50~8.52 (d, J=5.6 Hz, 2H).

Compound B

A solution of Compound B-4 (230 mg, 1.7 mmol) and Compound 4 (225 mg, 1.37 mmol) in methanol (25 mL) was heated to reflux overnight (about 18 hours) under argon. The mixture was concentrated and purified by pre-TLC to get product as yellow solid (45 mg, 12% yield, NMR and MS confirmed, 96% by HPLC).

1H-NMR (400 MHz, $CDCl_3$): 1.47 (d, J=13.2 Hz, 2H); 1.92~1.98 (m, 2H); 3.41 (t, J=13.2 Hz, 2H); 3.54 (s, 2H); 4.44 (s, 4H); 6.95 (d, J=4.4 Hz, 2H); 7.26~7.31 (m, 5H); 8.45 (d, J=4.0 Hz, 2H). MS (ESI) calcd for $C_{20}H_{23}N_5OS$ (m/z): 381.16, found: 382.4 $[M+1]^+$.

Compound C

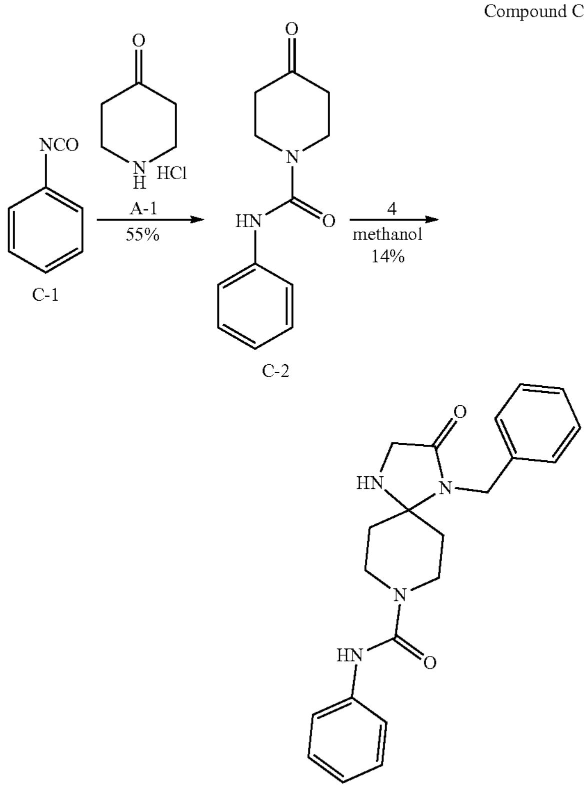

Compound C

Compound C-2

A mixture of Compound C-1 (1.0 g, 8.39 mmol), Compound A-I (2.83 g, 18.45 mmol) and potassium carbonate (4.64 g, 33.6 mmol) in DCM (50 mL) was stirred at ambient temperature for 18 hours. The mixture was washed with water, IN HCl (aqueous), dried over $Na_2SO_4$ and concentrated. The residue was purified by column chromatography (PE/EA:=3:1) to afford product as white solid (1.0 g, 55% yield, NMR confirmed the title compound).

1H-NMR (400 MHz, $CDCl_3$): 2.56 (t, J=6.4 Hz, 4H); 3.81 (t, J=6.4 Hz, 4H); 6.50 (brs, 1H); 7.07 (t, J=7.2 Hz, 4H); 7.28~7.37 (m, 4H).

Compound C

A mixture of Compound C-2 (400 mg, 1.84 mmol) and Compound 4 (400 mg, 2.44 mmol) in methanol (40 mL) was heated to reflux overnight (about 18 hours) under argon. The mixture was concentrated and purified by pre-TLC to provide the product as white solid (96 mg, 14% yield, NMR and MS confirmed, 98% by HPLC).

1H-NMR (400 MHz, $CDCl_3$): 1.45 (d, J=12.0 Hz, 2H); 1.85 (dt, J=4.4, 13.2 Hz, 2H); 3.19 (dt, J=2.0, 13.2 Hz, 2H);

3.55 (s, 2H); 3.96 (dt, J=13.6, 2.0 Hz, 2H); 4.44 (s, 2H); 6.29 (s, 1H); 7.02~7.06 (m, 1H); 7.22~7.33 (m, 10H); MS (ESI) calcd for $C_{21}H_{24}N_4O_2$ (m/z): 364.19, found: 365.2 $[M+1]^+$.

Example 1: FITC-NLX-based FLNA Screening Assay

A. Streptavidin-Coated 96-Well Plates

Streptavidin-coated 96-well plates (Reacti-Bind™ NeutrAvidin™ High binding capacity coated 96-well plate, Pierce-ENDOGEN) are washed three times with 200 μl of 50 mM Tris HCl, pH 7.4 according to the manufacturer's recommendation.

B. N-Biotinylated VAKGL Pentapeptide (Bn-VAKGL) (SEQ ID NO: 1)

Bn-VAKGL peptide (0.5 mg/plate) is dissolved in 50 μl DMSO and then added to 4450 μl of 50 mM Tris HCl, pH 7.4, containing 100 mM NaCl and protease inhibitors (binding medium) as well as 500 μl superblock in PBS (Pierce-ENDOGEN) [final concentration for DMSO: 1%].

C. Coupling of Bn-VAKGL Peptides to Streptavidin-Coated Plate

The washed streptavidin-coated plates are contacted with 5 μg/well of Bn-VAKGL (100 μl) for 1 hour (incubated) with constant shaking at 25° C. [50 μl of Bn-VAKGL peptide solution from B+50 μl binding medium, final concentration for DMSO: 0.5%]. At the end of the incubation, the plate is washed three times with 200 μl of ice-cold 50 mM Tris HCl, pH 7.4.

D. Binding of FITC-Tagged Naloxone [FITC-NLX] to VAKGL

Bn-VAKGL coated streptavidin plates are incubated with 10 nM fluorescein isothiocyanate-labeled naloxone (FITC-NLX; Invitrogen) in binding medium (50 mM Tris HCl, pH 7.4 containing 100 mM NaCl and protease inhibitors) for 30 minutes at 30° C. with constant shaking. The final assay volume is 100 μl. At the end of incubation, the plate is washed twice with 100 μl of ice-cold 50 mM Tris, pH 7.4. The signal, bound-FITC-NLX is detected using a DTX-880 multi-mode plate reader (Beckman).

E. Screening of Medicinal Chemistry Analogs

The compounds are first individually dissolved in 25% DMSO containing 50 mM Tris HCl, pH 7.4, to a final concentration of 1 mM (assisted by sonication when necessary) and then plated into 96-well compound plates. To screen the medicinal chemistry analogs (new compounds), each compound solution (1 μl) is added to the Bn-VAKGL coated streptavidin plate with 50 l/well of binding medium followed immediately with addition of 50 μl of FITC-NLX (total assay volume/well is 100 μl). The final screening concentration for each new compound is initially 1 μM.

Each screening plate includes vehicle control (total binding) as well as naloxone (NLX) and/or naltrexone (NTX) as positive controls. Compounds are tested in triplicate or quadruplicate. Percent inhibition of FITC-NLX binding for each compound is calculated [(Total FITC-NLX bound in vehicle-FITC-NLX bound with compound)/Total FITC-NLX bound in vehicle]×100%]. To assess the efficacies and potencies of the selected compounds, compounds that achieve approximately 60-70% inhibition at 1 μM are screened further at 1 and 0.1 μM concentrations.

The results of this screening assay are shown in the tables below.

FLNA Peptide Binding Assays

A-Series Compounds

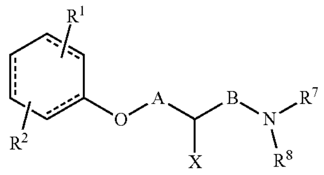

The $R^1$, $R^2$, $R^7$ and $R^8$, A, B and X groups are defined elsewhere herein.

| FLNA-binding Compound | Concentration of FLNA-binding Compound 0.01 μM | 0.1 μM | 1 μM |
|---|---|---|---|
| | Percent Binding Inhibition | | |
| Naloxone Control Average | 39.87% | 46.29% | 50.91% |
| 3333 | 40.4% | 48.5% | 54.2% |
| A0001 | 39.7% | 45.6% | 52.4% |
| A0002 | 38.7% | 43.7% | 49.9% |
| A0003 | 21.3% | 31.6% | 37.4% |
| A0004 | 40.0% | 43.7% | 47.6% |
| A0005 | 34.2% | 38.2% | 43.8% |
| A0006 | 37.9% | 43.5% | 47.5% |
| A0007 | 39.2% | 46.2% | 52.9% |
| A0008 | 34.5% | 33.5% | 39.8% |
| A0009 | 26.4% | 37.8% | 38.9% |
| A0010 | 36.0% | 36.5% | 39.0% |
| A0011 | 45.7% | 51.1% | 52.8% |
| A0012 | 39.7% | 49.6% | 54.4% |
| A0013 | 30.2% | 40.2% | 47.7% |
| A0014 | 33.8% | 39.7% | 44.7% |
| A0015 | 36.3% | 46.8% | 55.0% |
| A0017 | 29.8% | 38.6% | 44.0% |
| A0020 | 37.8% | 38.8% | 45.8% |
| A0021 | 36.8% | 43.4% | 49.5% |
| A0022 | 41.9% | 49.7% | 56.8% |
| A0025 | 39.0% | 49.8% | 53.2% |
| A0026 | 36.4% | 42.4% | 49.2% |
| A0028 | 39.5% | 43.8% | 50.5% |
| A0029 | 44.4% | 44.4% | 50.8% |
| A0030 | 35.6% | 44.4% | 48.9% |
| A0031 | 40.8% | 47.6% | 52.9% |
| A0032-1 | 35.6% | 43.9% | 50.0% |
| A0032 | 43.0% | 50.3% | 54.5% |
| A0033 | 46.4% | 51.8% | 56.5% |
| A0035 | 40.3% | 45.5% | 54.9% |
| A0036 | 45.6% | 50.1% | 54.4% |
| A0037 | 49.3% | 51.3% | 56.8% |
| A0038 | 46.4% | 52.3% | 56.6% |
| A0039 | 49.0% | 53.5% | 60.3% |
| A0040 | 45.0% | 50.4% | 56.3% |
| A0041 | 45.8% | 51.7% | 56.9% |
| A0042 | 47.2% | 48.3% | 55.8% |
| AOO43 | 46.4% | 48.9% | 51.8% |
| A0044 | 32.4% | 36.9% | 39.6% |
| A0045 | 28.1% | 35.0% | 37.8% |
| A0046 | 34.3% | 38.4% | 40.9% |
| A0047 | 40.9% | 42.9% | 44.5% |
| A0048 | 38.5% | 44.0% | 46.9% |
| A0049 | 46.2% | 49.4% | 49.3% |
| A0050 | 42.9% | 49.8% | 52.1% |
| A0051 | 45.9% | 45.4% | 52.1% |
| A0053 | 34.8% | 40.0% | 46.9% |
| A0054 | 28.7% | 35.8% | 41.4% |
| A0055 | 28.1% | 32.4% | 41.8% |
| A0056 | 34.4% | 40.9% | 41.3% |
| A0057 | 29.1% | 37.0% | 43.4% |
| A0058 | 28.9% | 36.6% | 42.1% |
| A0059 | 27.4% | 36.6% | 38.7% |

-continued

| FLNA-binding Compound | Concentration of FLNA-binding Compound 0.01 μM | 0.1 μM | 1 μM |
|---|---|---|---|
| | Percent Binding Inhibition | | |
| A0060 | 32.4% | 39.0% | 42.0% |
| A0061 | 27.5% | 38.9% | 42.8% |
| A0062 | — | — | — |
| A0063 | 21.2% | 31.0% | 38.8% |
| A0064 | 41.8% | 46.2% | 53.6% |
| A0065 | 38.7% | 50.0% | 50.8% |
| A0066 | 36.7% | 45.4% | 53.7% |
| A0067 | 32.7% | 39.1% | 44.3% |
| A0068 | 51.9% | 54.2% | 58.3% |
| A0069 | 32.0% | 40.4% | 46.1% |
| A0070 | 32.9% | 39.1% | 41.7% |
| A0071 | 44.7% | 46.8% | 53.9% |
| A0072 | 45.5% | 52.2% | 59.4% |
| A0073 | 47.3% | 54.8% | 59.7% |
| A0074 | — | — | — |
| A0075 | — | — | — |
| A0076 | 36.1% | 40.0% | 44.9% |
| A0077 | 41.1% | 48.7% | 49.4% |
| A0078 | 50.1% | 55.8% | 57.6% |
| Naloxone Control Average | 39.87% | 46.29% | 50.91% |

B-Series Compounds

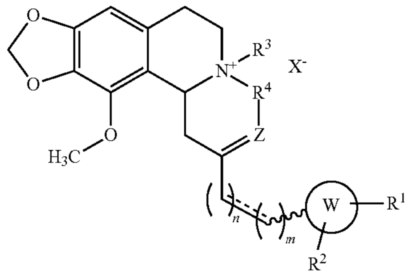

The $R^1$, $R^2$, $R^3$ and $R^4$, W, $X^-$ and Z groups, the dashed line, n and m are defined elsewhere herein.

| FLNA-binding Compound | Concentration of FLNA-binding Compound 0.01 μM | 0.1 μM | 1 μM |
|---|---|---|---|
| | Percent Binding Inhibition | | |
| Naloxone Control Average | 39.87% | 46.29% | 50.91% |
| 5009 | 42.5% | 47.3% | 54.3% |
| B0001 | 37.1% | 48.8% | 54.3% |
| B0002 | 40.2% | 46.4% | 55.0% |
| B0003 | 45.4% | 52.9% | 63.5% |
| B0004 | 38.9% | 50.0% | 54.8% |
| B0005 | 31.8% | 34.8% | 41.7% |
| B0006 | 45.1% | 53.5% | 61.3% |
| B0007 | 43.6% | 53.1% | 57.3% |
| B0008 | 35.5% | 40.3% | 52.8% |
| B0009 | 39.6% | 47.6% | 53.6% |
| B0010 | 39.4% | 43.4% | 50.3% |
| B0011 | 40.9% | 50.3% | 55.8% |
| B0012 | 39.4% | 46.9% | 51.7% |
| B0013 | 25.2% | 35.1% | 43.4% |
| B0014 | 25.7% | 30.9% | 37.8% |
| B0015 | 30.4% | 35.3% | 42.3% |
| B0016 | 27.1% | 33.7% | 41.9% |
| B0017 | 28.3% | 36.6% | 44.6% |
| B0018 | 37.2% | 43.7% | 47.6% |
| B0019 | 34.3% | 41.0% | 49.0% |
| B0020 | 38.1% | 45.5% | 50.6% |
| B0021 | 32.5% | 43.1% | 47.6% |

-continued

| FLNA-binding Compound | Concentration of FLNA-binding Compound 0.01 μM | 0.1 μM | 1 μM |
|---|---|---|---|
| | Percent Binding Inhibition | | |
| B0022 | 34.3% | 40.4% | 45.6% |
| B0023 | 28.5% | 37.8% | 46.4% |
| B0024 | 34.8% | 43.4% | 47.7% |
| B0025 | 41.7% | 49.4% | 56.6% |
| B0026 | 41.1% | 43.3% | 48.2% |
| B0027 | 40.2% | 46.7% | 49.8% |
| B0028 | 38.2% | 42.8% | 49.1% |
| B0029 | 33.4% | 42.9% | 50.2% |
| B0030 | 47.0% | 50.5% | 57.6% |
| B0031 | 36.2% | 44.2% | 50.5% |
| B0032 | 45.1% | 51.3% | 48.9% |
| B0033 | 42.1% | 46.8% | 49.4% |
| B0034 | 49.1% | 54.2% | 59.1% |
| B0035 | 45.4% | 44.7% | 51.0% |
| B0036 | 46.6% | 52.8% | 62.1% |
| B0037 | 47.4% | 53.0% | 52.4% |
| B0038 | 41.2% | 50.1% | 57.0% |
| B0039 | 43.3% | 45.7% | 50.9% |
| B0040 | 40.0% | 53.1% | 57.1% |
| B0041 | 44.0% | 46.8% | 52.8% |
| B0042 | 40.8% | 46.4% | 51.6% |
| B0043 | 30.8% | 39.2% | 46.8% |
| B0044 | 35.2% | 39.5% | 44.4% |
| B0045 | 63.2% | 68.2% | 73.9% |
| B0046 | 42.2% | 50.2% | 55.4% |
| B0047 | 30.7% | 37.6% | 47.1% |
| B0048 | 34.7% | 41.9% | 43.9% |
| B0049 | 32.2% | 40.1% | 47.1% |
| B0050 | 29.2% | 34.5% | 39.8% |
| B0051 | 29.9% | 35.7% | 43.7% |
| B0052 | 30.2% | 39.1% | 44.3% |
| B0053 | 33.1% | 37.3% | 47.6% |
| B0054 | 25.6% | 32.6% | 43.3% |
| B0055 | 63.2% | 68.2% | 73.9% |
| Naloxone Control Average | 39.87% | 46.29% | 50.91% |

C-Series-1 Compounds

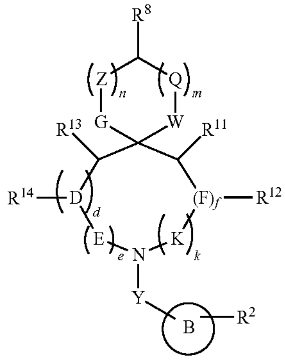

Each designation in the above formula is defined elsewhere herein.

| FLNA-binding Compound | Concentration of FLNA-binding Compound 0.01 μM | 0.1 μM | 1 μM |
|---|---|---|---|
| | Percent Binding Inhibition | | |
| Naloxone Control Average | 39.87% | 46.29% | 50.91% |
| 7866 | 38.5% | 47.9% | 53.4% |
| C0001 | 34.8% | 42.9% | 51.3% |
| C0002 | 38.4% | 45.6% | 42.8% |

-continued

| FLNA-binding Compound | Concentration of FLNA-binding Compound 0.01 μM | 0.1 μM | 1 μM |
|---|---|---|---|
| | Percent Binding Inhibition | | |
| C0003 | 38.3% | 45.3% | 48.8% |
| C0004 | 37.6% | 42.3% | 44.7% |
| C0005 | 35.2% | 44.5% | 51.5% |
| C0006 | 41.6% | 46.8% | 51.8% |
| C0007 | 40.5% | 46.3% | 48.9% |
| C0008 | 42.2% | 52.3% | 54.4% |
| C0009 | 41.7% | 49.0% | 53.9% |
| C0010 | 39.8% | 42.7% | 47.1% |
| C0011 | 37.6% | 41.4% | 46.0% |
| C0012 | 26.3% | 39.5% | 46.4% |
| C0013 | 39.6% | 42.4% | 49.1% |
| C0014 | 29.5% | 38.8% | 40.0% |
| C0015 | 31.2% | 40.6% | 45.5% |
| C0016 | 38.3% | 43.8% | 49.1% |
| C0017 | 28.9% | 35.4% | 40.7% |
| C0018 | 42.3% | 45.9% | 53.4% |
| C0019 | 30.1% | 38.2% | 43.6% |
| C0021 | 34.0% | 38.4% | 40.6% |
| C0022 | 34.5% | 37.6% | 43.9% |
| C0023 | 35.9% | 41.7% | 47.2% |
| C0024 | 37.9% | 46.4% | 50.4% |
| C0025 | 37.2% | 41.4% | 45.1% |
| C0028 | 32.2% | 36.6% | 43.3% |
| C0029 | 38.6% | 43.2% | 50.5% |
| C0030 | 37.4% | 45.4% | 56.0% |
| C0032 | 41.5% | 50.5% | 55.3% |
| C0033 | 43.9% | 48.4% | 51.3% |
| C0034 | 29.6% | 38.3% | 44.8% |
| C0038 | 31.7% | 36.0% | 43.5% |
| C0041 | 38.3% | 47.0% | 51.2% |
| C0042 | 42.4% | 49.7% | 56.1% |
| C0047 | 30.8% | 35.2% | 41.4% |
| C0048 | 28.5% | 38.9% | 45.9% |
| C0049 | 25.3% | 27.9% | 30.3% |
| C0051 | 27.0% | 30.4% | 36.4% |
| C0052 | 28.0% | 35.6% | 40.8% |
| C0053 | 28.9% | 33.8% | 39.3% |
| C0054 | 32.9% | 39.4% | 43.3% |
| C0057 | ND* | ND | ND |
| C0060 | 60.3% | 64.0% | 68.0% |
| C0061 | ND | ND | ND |
| C0062 | 39.5% | 49.5% | 48.0% |
| C0064 | 37.3% | 44.4% | 49.2% |
| C0065 | 37.1% | 44.0% | 47.0% |
| C0067 | 31.3% | 39.7% | 45.0% |
| C0068 | 53.7% | 58.6% | 62.2% |
| C0069 | ND | ND | ND |
| C0070 | 42.6% | 50.6% | 53.6% |
| C0071 | 39.1% | 49.6% | 55.2% |
| C0072 | 28.4% | 37.4% | 44.0% |
| C0073 | ND | ND | ND |
| C0077 | 45.7% | 47.7% | 51.0% |
| C0078 | 46.6% | 48.0% | 50.5% |
| C0080M | 46.8% | 53.3% | 54.6% |
| C0084M | 47.2% | 53.7% | 55.9% |
| C0085M | 45.7% | 53.7% | 60.7% |
| C0138M | 53.0% | 52.0% | 59.5% |
| C0139M | 48.9% | 53.1% | 61.6% |
| C0140M | 42.3% | 49.2% | 54.4% |
| C0141M | 33.1% | 39.0% | 46.9% |
| C0143M | 45.3% | 48.4% | 57.8% |
| C0144M | 46.4% | 50.7% | 55.7% |
| C0145M | 45.1% | 53.7% | 58.3% |
| C0148M | 46.2% | 52.0% | 57.0% |
| C0149M | 48.5% | 52.3% | 62.0% |
| C0150M | 47.3% | 51.8% | 61.4% |
| C0151M | 48.3% | 51.7% | 58.7% |
| C0152M | ND | ND | ND |
| C0154M | ND | ND | ND |
| Naloxone Control Average | 39.87% | 46.29% | 50.91% |

*ND = Not Done.

C-Series-2 Compounds

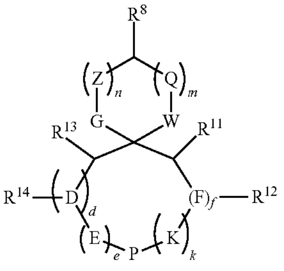

Each designation in the above formula is defined elsewhere herein.

| | Concentration of FLNA-binding Compound | | |
|---|---|---|---|
| FLNA-binding Compound | 0.01 µM | 0.1 µM<br>Percent Binding Inhibition | 1 µM |
| Naloxone Control Average | 39.87 | 46.29% | 50.91 |
| C0011 | 37.6% | 41.4% | 46.0% |
| C0026 | 42.3% | 44.8% | 49.0% |
| C0027 | 50.8% | 61.2% | 63.8% |
| S-C0027 | 39.1% | 46.5% | 53.6% |
| C0034-3 | 29.6% | 38.3% | 44.8% |
| C0037-2 | ND* | ND | ND |
| C0040 | 38.4% | 46.3% | 55.9% |
| C0043 | 43.9% | 51.3% | 58.0% |
| C0044 | 37.3% | 43.9% | 50.6% |
| C0045 | 39.1% | 48.9% | 53.7% |
| C0046 | 30.8% | 35.7% | 42.2% |
| C0050 | 26.7% | 34.5% | 36.4% |
| C0055 | 29.0% | 34.9% | 39.5% |
| C0056 | 33.7% | 38.9% | 41.4% |
| C0060 | 60.3% | 64.0% | 68.0% |
| C0086M | 37.9% | 48.1% | 53.4% |
| C0087M | 51.6% | 57.9% | 61.5% |
| C0088M | 40.1% | 52.4% | 56.1% |
| C0089M | 40.7% | 46.1% | 51.2% |
| C0090M | 42.5% | 52.5% | 55.8% |
| C0091M | 38.1% | 39.8% | 46.3% |
| C0093M | 44.8% | 49.9% | 53.5% |
| C0094M | 43.0% | 52.8% | 57.5% |
| C0095M | 40.1% | 46.6% | 50.5% |
| C0096M | 43.0% | 48.3% | 55.0% |
| C0099M | 46.9% | 53.3% | 56.0% |
| C0100M | 52.2% | 58.2% | 64.5% |
| C0101M | 50.5% | 56.4% | 59.0% |
| C0102M | 52.3% | 53.1% | 56.6% |
| C0104M | 51.4% | 54.1% | 55.2% |
| C0105M | 55.7% | 62.0% | 68.8% |
| C0106M | 45.8% | 55.6% | 58.9% |
| C0108M | 54.6% | 61.4% | 68.7% |
| C0114M | 57.1% | 63.2% | 66.7% |
| C0115M | 47.8% | 57.8% | 59.9% |
| C0116M | 53.9% | 60.0% | 62.9% |
| C0118M | 56.6% | 61.4% | 62.4% |
| C0119M | 41.6% | 55.5% | 60.0% |
| C0123M | 51.9% | 60.5% | 62.9% |
| C0124M | 47.7% | 52.2% | 58.7% |
| C0125M | 54.2% | 59.7% | 63.3% |
| C0126M | 50.7% | 55.4% | 67.3% |
| C0128M | 46.5% | 54.4% | 58.2% |
| C0133M | 47.8% | 54.9% | 58.5% |
| C0134M | 55.7% | 60.5% | 61.9% |
| F-C0134 | 37.4% | 45.7% | 53.1% |
| C0135M | 53.9% | 55.1% | 62.3% |
| C0136M(P5) | 46.7% | 55.2% | 58.2% |
| C0137M(P7) | 42.4% | 49.9% | 61.2% |
| C0142M | 35.1% | 39.4% | 56.0% |
| C0143M | 45.3% | 48.4% | 57.8% |
| C0148M | 46.2% | 52.0% | 57.0% |

-continued

| | Concentration of FLNA-binding Compound | | |
|---|---|---|---|
| FLNA-binding Compound | 0.01 µM | 0.1 µM<br>Percent Binding Inhibition | 1 µM |
| C0149M | 48.5% | 52.3% | 62.0% |
| C0150M | 47.3% | 51.8% | 61.4% |
| C0151M | 48.3% | 51.7% | 58.7% |
| C0152M-4 | ND | ND | ND |
| C0153M-3 | ND | ND | ND |
| Naloxone Control Average | 39.87% | 46.29% | 50.91% |

*ND = Not Done.

A preliminary study similar to that immediately above was carried out using Compounds 4, 9 and 10 and 100 nM of frozen-stored FITC-NLX rather than 10 nM FITC-NLX. The results of an average of two runs for this study are shown below.

| Compound | 0.1 nM | 1 nM | 10 nM | 100 nM | 1 µM |
|---|---|---|---|---|---|
| 4 | 18.8% | 21.3% | 17.9% | 28.8% | 42.9% |
| 9 | 22.5% | 24.8% | 27.7% | 35.3 | 49.6% |
| 10 | 27.5% | 27.3% | 26.6% | 27.3% | 34.5% |
| (+) NLX | 22.7% | 22.8% | 23.1% | 22.8% | 39.8% |

Example 2: MOR Agonist Activity Using GTPγS Binding Assay

To assess the mu opiate receptor (MOR) agonist activity of positive compounds from the FLNA screening, compounds were tested in a [$^{35}$S]GTPγS binding assay using striatal membranes. A previous study has shown that in striatal membranes, activation of MOR leads to an increase in [$^{35}$S]GTPγS binding to Gαo (Wang et al., 2005 *Neuroscience* 135:247-261). This assay measures a functional consequence of receptor occupancy at one of the earliest receptor-mediated events. The assay permits for traditional pharmacological parameters of potency, efficacy and antagonist affinity, with the advantage that agonist measures are not subjected to amplification or other modulation that may occur when analyzing parameters further downstream of the receptor.

Thus, striatal tissue was homogenized in 10 volumes of ice cold 25 mM HEPES buffer, pH 7.4, which contained 1 mM EGTA, 100 mM sucrose, 50 µg/ml leupeptin, 0.04 mM PMSF, 2 µg/ml soybean trypsin inhibitor and 0.2% 2-mercaptoethanol. The homogenates were centrifuged at 800×g for 5 minutes and the supernatants were centrifuged at 49,000×g for 20 minutes. The resulting pellets were suspended in 10 volume of reaction buffer, which contained 25 mM HEPES, pH 7.5, 100 mM NaCl, 50 µg/ml leupeptin, 2 µg/ml soybean trypsin inhibitor, 0.04 mM PMSF and 0.02% 2-mercaptomethanol.

The resultant striatal membrane preparation (200 g) was admixed and maintained (incubated) at 30° C. for 5 minutes in reaction buffer as above that additionally contained 1 mM $MgCl_2$ and 0.5 nM [$^{35}$S]GTPγS (0.1 µCi/assay, PerkinElmer Life and Analytical Sciences) in a total volume of 250 µl and continued for 5 minutes in the absence or presence of 0.1-10 µM of an assayed compound of interest. The reaction was terminated by dilution with 750 µl of ice-cold reaction buffer that contained 20 mM $MgCl_2$ and 1 mM EGTA and immediate centrifugation at 16,000×g for 5 minutes.

The resulting pellet was solubilized by sonicating for 10 seconds in 0.5 ml of immunoprecipitation buffer containing 0.5% digitonin, 0.2% sodium cholate and 0.5% NP-40. Normal rabbit serum (1 μl) was added to 1 ml of lysate and incubated at 25° C. for 30 minutes. Nonspecific immune complexes were removed by incubation with 25 μl of protein A/G-conjugated agarose beads at 25° C. for 30 minutes followed by centrifugation at 5,000×g at 4° C. for 5 minutes. The supernatant was divided and separately incubated at 25° C. for 30 minutes with antibodies raised against Gαo proteins (1:1,000 dilutions).

The immunocomplexes so formed were collected by incubation at 25° C. for 30 minutes with 40 μl of agarose-conjugated protein A/G beads and centrifugation at 5,000×g at 4° C. for 5 minutes. The pellet was washed and suspended in buffer containing 50 mM Tris-HCl, pH 8.0, and 1% NP-40. The radioactivity in the suspension was determined by liquid scintillation spectrometry. The specificity of MOR activation of [$^{35}$S]GTPγS binding to Gαo induced by a selective compound was defined by inclusion of 1 μM β-funaltrexamine (β-FNA; an alkylating derivative of naltrexone that is a selective MOR antagonist). DAMGO (1 or 10 μM) was used as a positive control.

The results of this study are shown in the Tables below.

FLNA-Binding Compound MOR Agonist Activity

| FLNA- | Concentration of FLNA-Binding Compound as Agonist | | | | | |
|---|---|---|---|---|---|---|
| Binding Compound | 0.1 μM | 1 μM | 1 μM + BFNA | % DAMGO (0.1 μm) | % DAMGO (1 μm) | % DAMGO + BFNA |
| A3333 | 170.7% | 328.3% | 65.9% | 88.9% | 101.0% | 136.7% |
| A0001 | 94.3% | 181.7% | 22.2% | 63.1% | 78.9% | 83.8% |
| A0002 | 155.6% | 199.4% | 6.5% | 104.1% | 86.6% | 24.5% |
| A0003 | 176.8% | 276.0% | 17.1% | 118.3% | 119.9% | 64.5% |
| A0004 | 97.4% | 144.2% | 86.0% | 55.2% | 55.6% | 130.9% |
| A0005 | 179.7% | 239.2% | 23.5% | 105.0% | 89.6% | 45.1% |
| A0006 | 170.0% | 190.9% | 18.2% | 113.8% | 82.9% | 68.7% |
| A0007 | 102.0% | 221.9% | 40.4% | 68.3% | 96.4% | 152.5% |
| A0008 | 163.8% | 235.0% | 133.9% | 109.6% | 102.1% | 505.3% |
| A0009 | 70.2% | 126.4% | 93.9% | 39.8% | 48.7% | 142.9% |
| A0010 | 277.2% | 319.0% | 190.3% | 161.9% | 119.5% | 365.3% |
| A0011 | 236.3% | 287.5% | 47.0% | 158.2% | 124.9% | 177.4% |
| A0012 | 149.3% | 185.7% | 122.4% | 99.9% | 80.7% | 461.9% |
| A0013 | 102.1% | 164.8% | 86.1% | 57.8% | 63.6% | 131.1% |
| A0014 | 147.0% | 174.9% | 140.8% | 83.2% | 67.5% | 214.3% |
| A0015 | 110.9% | 150.1% | 62.5% | 64.8% | 56.2% | 120.0% |
| A0017 | 161.9% | 246.0% | 65.2% | 96.9% | 100.4% | 187.9% |
| A0020 | 168.6% | 217.4% | 67.4% | 100.9% | 88.7% | 194.2% |
| A0021 | 133.3% | 275.3% | 12.1% | 79.8% | 112.4% | 34.9% |
| A0022 | 154.1% | 216.0% | 28.0% | 90.0% | 80.9% | 53.7% |
| A0025 | 58.6% | 138.7% | 52.2% | 33.2% | 54.5% | 198.5% |
| A0026 | 140.7% | 179.8% | 120.8% | 79.7% | 70.7% | 459.3% |
| A0028 | 143.6% | 187.7% | 116.7% | 81.3% | 73.8% | 443.7% |
| A0029 | 173.8% | 206.5% | 22.3% | 98.4% | 81.2% | 84.8% |
| A0030 | 133.4% | 287.8% | 165.2% | 75.5% | 113.2% | 628.1% |
| A0031 | 178.2% | 297.0% | 150.9% | 100.9% | 116.8% | 573.8% |
| A0032-1 | 187.4% | 324.5% | 224.5% | 95.5% | 117.6% | 303.8% |
| A0032 | 226.9% | 257.8% | 133.0% | 115.6% | 93.4% | 180.0% |
| A0033 | 155.8% | 254.6% | 118.2% | 79.4% | 92.2% | 159.9% |
| A0035 | 120.6% | 158.8% | 88.6% | 61.5% | 57.5% | 119.9% |
| A0036 | 144.1% | 167.5% | 63.2% | 73.4% | 60.7% | 85.5% |
| A0037 | 177.9% | 236.2% | 104.6% | 90.7% | 85.6% | 141.5% |
| A0038 | 176.7% | 234.5% | 107.0% | 90.1% | 85.0% | 144.8% |
| A0039 | 267.8% | 339.6% | 173.5% | 136.5% | 123.0% | 234.8% |
| A0040 | 46.1% | 149.0% | 16.7% | 23.5% | 54.0% | 22.6% |
| A0041 | 212.7% | 283.6% | 50.6% | 108.4% | 102.8% | 68.5% |
| A0042 | 147.5% | 233.1% | 89.5% | 75.2% | 84.5% | 121.1% |
| A0043 | 183.3% | 223.8% | 89.1% | 93.4% | 81.1% | 120.6% |
| A0044 | 176.2% | 209.1% | 134.7% | 89.8% | 75.8% | 182.3% |
| A0045 | 143.9% | 274.2% | 99.2% | 73.3% | 99.3% | 134.2% |
| A0046 | 257.5% | 354.1% | 140.0% | 131.2% | 128.3% | 189.4% |
| A0047 | 233.0% | 255.0% | 116.5% | 118.8% | 92.4% | 157.6% |
| A0048 | 233.7% | 302.9% | 167.2% | 119.1% | 109.7% | 226.3% |
| A0049 | 232.3% | 370.3% | 107.1% | 118.4% | 134.2% | 144.9% |
| A0050 | 151.0% | 189.3% | 81.0% | 77.0% | 68.6% | 109.6% |
| A0051 | 290.4% | 386.6% | 211.6% | 148.0% | 140.1% | 286.3% |
| A0053 | 78.5% | 118.2% | 15.1% | 46.5% | 47.5% | 46.2% |
| A0054 | 74.9% | 159.2% | 114.1% | 44.4% | 63.9% | 348.9% |
| A0055 | 89.8% | 195.2% | 33.5% | 53.2% | 78.4% | 102.4% |
| A0056 | 115.6% | 129.6% | 17.4% | 74.1% | 56.2% | 43.6% |
| A0057 | 124.2% | 192.1% | 44.8% | 79.6% | 83.3% | 112.3% |
| A0058 | 70.7% | 244.3% | 59.9% | 45.3% | 106.0% | 150.1% |
| A0059 | 99.2% | 129.9% | 85.7% | 63.5% | 56.4% | 214.8% |
| A0060 | 99.7% | 158.2% | 14.3% | 63.9% | 68.6% | 35.8% |
| A0061 | 110.3% | 197.1% | 10.7% | 70.7% | 85.5% | 26.8% |
| A0062 | ND | ND | ND | ND | ND | ND |
| A0063 | 122.8% | 245.8% | 310% | 78.7% | 106.6% | 77.7% |
| A0064 | 219.2% | 262.9% | 43.7% | 127.4% | 119.7% | 126.7% |
| A0065 | 197.6% | 266.8% | 44.9% | 126.6% | 115.7% | 112.5% |

-continued

| FLNA-Binding Compound | Concentration of FLNA-Binding Compound as Agonist 0.1 μM | 1 μM | 1 μM + BFNA | % DAMGO (0.1 μm) | % DAMGO (1 μm) | % DAMGO + BFNA |
|---|---|---|---|---|---|---|
| A0066 | 151.9% | 195.6% | 59.2% | 88.3% | 89.0% | 171.6% |
| A0067 | 170.8% | 254.4% | 33.9% | 99.2% | 115.8% | 98.3% |
| A0068 | 73.9% | 110.4% | 98.1% | 36.8% | 35.2% | 182.0% |
| A0069 | 122.7% | 244.2% | 29.5% | 71.3% | 111.2% | 85.5% |
| A0070 | 128.6% | 195.3% | 80.3% | 74.7% | 88.9% | 232.8% |
| A0071 | 225.7% | 310.9% | 239.4% | 128.2% | 122.9% | 1088.2% |
| A0072 | 254.3% | 305.1% | 171.8% | 126.8% | 97.2% | 318.7% |
| A0073 | 201.7% | 325.7% | 185.8% | 100.5% | 103.7% | 344.7% |
| A0074 | ND | ND | ND | ND | ND | ND |
| A0075 | ND | ND | ND | ND | ND | ND |
| A0076 | 79.8% | 172.6% | 41.2% | 46.4% | 78.6% | 119.4% |
| A0077 | 300.1% | 334.7% | 103.5% | 170.5% | 132.3% | 470.5% |
| A0078 | 250.5% | 289.9% | 147.8% | 124.9% | 92.3% | 274.2% |

Series B FLNA-Binding Compound MOR Agonist Activity

| FLNA-Binding Compound | Concentration of FLNA-Binding Compound as Agonist 0.1 μM | 1 μM | 1 μM + BFNA | % DAMGO (0.1 μM) | % DAMGO (1 μM) | % DAMGO + BFNA |
|---|---|---|---|---|---|---|
| 5009 | 128.5% | 270.4% | 87.5% | 66.9% | 83.2% | 181.5% |
| B0001 | 128.2% | 202.3% | 28.0% | 77.4% | 74.9% | 43.1% |
| B0002 | 165.7% | 219.0% | 101.4% | 100.0% | 81.1% | 156.0% |
| B0003 | 103.0% | 131.1% | 18.6% | 59.9% | 47.4% | 29.0% |
| B0004 | 170.3% | 231.7% | 72.0% | 102.8% | 85.8% | 110.8% |
| B0005 | 89.2% | 110.4% | 45.1% | 50.5% | 42.6% | 68.6% |
| B0006 | 77.0% | 131.3% | 18.6% | 44.8% | 47.5% | 29.0% |
| B0007 | 168.3% | 223.3% | 64.5% | 95.3% | 86.1% | 98.2% |
| B0008 | 148.3% | 264.1% | 46.0% | 84.0% | 101.9% | 70.0% |
| B0009 | 144.4% | 219.9% | 119.4% | 81.8% | 84.8% | 181.7% |
| B0010 | 132.9% | 184.4% | 152.0% | 75.3% | 71.1% | 231.4% |
| B0011 | 158.6% | 212.6% | 78.0% | 95.7% | 78.7% | 120.0% |
| B0012 | 167.4% | 212.0% | 145.1% | 97.8% | 79.4% | 278.5% |
| B0013 | 51.4% | 154.1% | 34.4% | 29.1% | 59.4% | 52.4% |
| B0014 | 166.6% | 250.5% | 44.3% | 98.5% | 93.7% | 67.1% |
| B0016 | 167.7% | 213.6% | 72.2% | 99.2% | 79.9% | 109.4% |
| B0017 | 99.6% | 122.0% | 49.6% | 58.9% | 45.6% | 75.2% |
| B0018 | 118.8% | 143.0% | 45.6% | 70.3% | 53.5% | 69.1% |
| B0019 | 101.0% | 256.5% | 81.4% | 59.7% | 96.0% | 123.3% |
| B0020 | 51.6% | 181.6% | 24.9% | 30.1% | 68.0% | 47.8% |
| B0021 | 126.9% | 256.4% | 42.9% | 75.9% | 104.7% | 123.6% |
| B0022 | 131.9% | 182.7% | 45.8% | 78.9% | 74.6% | 132.0% |
| B0023 | 166.1% | 245.3% | 28.4% | 99.4% | 100.1% | 81.8% |
| B0024 | 155.8% | 285.9% | 20.2% | 93.2% | 116.7% | 58.2% |
| B0025 | 159.6% | 234.6% | 137.7% | 96.3% | 86.8% | 211.8% |
| B0026 | 152.0% | 233.3% | 28.8% | 88.8% | 87.4% | 55.3% |
| B0027 | 140.9% | 266.9% | 21.6% | 82.3% | 100.0% | 41.5% |
| B0028 | 199.1% | 357.7% | 55.0% | 103.5% | 131.0% | 125.3% |
| B0029 | 171.9% | 210.3% | 17.6% | 89.4% | 77.0% | 40.1% |
| B0030 | 107.2% | 276.1% | 90.1% | 62.6% | 103.4% | 172.9% |
| B0031 | 210.8% | 272.0% | 28.8% | 109.6% | 99.6% | 65.6% |
| B0032 | 221.1% | 297.7% | 15.6% | 115.0% | 109.0% | 35.5% |
| B0033 | 149.3% | 188.9% | 41.9% | 77.6% | 69.2% | 95.4% |
| B0034 | 122.5% | 235.2% | 41.8% | 71.6% | 88.1% | 80.2% |
| B0035 | 188.0% | 248.7% | 74.2% | 109.8% | 93.2% | 142.4% |
| B0036 | 61.4% | 120.6% | 65.1% | 39.2% | 52.1% | 199.7% |
| B0037 | 119.8% | 186.0% | 106.2% | 76.5% | 80.4% | 325.8% |
| B0038 | 147.5% | 205.3% | 117.1% | 94.2% | 88.7% | 359.2% |
| B0039 | 171.8% | 290.5% | 78.3% | 100.4% | 108.8% | 150.3% |
| B0040 | 146.0% | 243.3% | 55.3% | 93.2% | 105.1% | 169.6% |
| B0041 | 61.6% | 109.3% | 41.9% | 39.3% | 47.2% | 128.5% |
| B0042 | 69.9% | 107.5% | 43.1% | 39.6% | 42.3% | 163.9% |
| B0043 | 74.8% | 248.1% | 166.4% | 42.4% | 97.6% | 632.7% |
| B0044 | 87.3% | 170.0% | 134.6% | 49.4% | 66.9% | 511.8% |
| B0045 | 129.3% | 193.1% | 83.8% | 82.6% | 83.4% | 257.1% |
| B0046 | 99.9% | 141.9% | 90.5% | 63.8% | 61.3% | 277.6% |
| B0047 | 187.8% | 235.6% | 68.4% | 106.3% | 92.6% | 260.1% |
| B0048 | 185.1% | 223.4% | 78.5% | 104.8% | 87.8% | 298.5% |
| B0049 | 181.6% | 364.0% | 133.2% | 102.8% | 143.1% | 506.5% |
| B0050 | 98.2% | 211.0% | 48.8% | 58.1% | 96.4% | 294.0% |

-continued

| FLNA- | Concentration of FLNA-Binding Compound as Agonist | | | | | |
|---|---|---|---|---|---|---|
| Binding Compound | 0.1 μM | 1 μM | 1 μM + BFNA | % DAMGO (0.1 μM) | % DAMGO (1 μM) | % DAMGO + BFNA |
| B0051 | 115.6% | 167.9% | 43.8% | 68.4% | 76.7% | 263.9% |
| B0052 | 98.2% | 151.7% | 40.9% | 58.1% | 69.3% | 246.4% |
| B0053 | 160.2% | 299.8% | 134.3% | 94.8% | 137.0% | 809.0% |
| B0054 | 157.8% | 186.7% | 111.0% | 93.4% | 85.3% | 668.7% |
| B0055 | 162.1% | 338.5% | 117.5% | 91.8% | 133.1% | 446.8% |
| B0056 | 174.7% | 288.8% | 41.8% | 98.9% | 113.6% | 158.9% |

Series C-i FLNA-Binding Compound MOR Agonist Activity

| FLNA- | Concentration of FLNA-Binding Compound as Agonist | | | | | |
|---|---|---|---|---|---|---|
| Binding Compound | 0.1 μM | 1 μM | 1 μM + BFNA | % DAMGO (0.1 μM) | % DAMGO (1 μM) | % DAMGO + BFNA |
| 7866 | 152.3% | 308.2% | 62.4% | 79.3% | 94.8% | 129.5% |
| C0001 | 129.3% | 184.3% | 33.9% | 75.2% | 66.6% | 52.9% |
| C0002 | 88.4% | 93.8% | 3.9% | 51.4% | 33.9% | 6.1% |
| C0003 | 162.3% | 215.9% | 107.7% | 91.9% | 83.3% | 163.9% |
| C0004 | 122.0% | 228.4% | 65.8% | 72.1% | 85.4% | 99.7% |
| C0005 | 180.4% | 227.2% | 166.4% | 105.4% | 85.1% | 319.4% |
| C0006 | 121.5% | 204.0% | 4.6% | 70.6% | 73.8% | 7.2% |
| C0007 | 79.1% | 195.0% | 10.9% | 46.0% | 70.5% | 17.0% |
| C0008 | 71.2% | 201.6% | 2.8% | 41.4% | 72.9% | 4.4% |
| C0009 | 146.3% | 256.2% | 26.4% | 85.1% | 92.6% | 41.2% |
| C0010 | 136.5% | 307.0% | 89.1% | 80.7% | 114.9% | 135.0% |
| C0011 | 217.0% | 305.0% | 19.0% | 126.8% | 114.3% | 36.5% |
| C0012 | 96.8% | 224.8% | 184.4% | 54.8% | 86.7% | 280.7% |
| C0013 | 156.6% | 301.2% | 39.6% | 91.0% | 108.9% | 61.8% |
| C0014 | 144.9% | 153.5% | 76.3% | 82.0% | 59.2% | 116.1% |
| C0015 | 138.7% | 204.7% | 126.8% | 78.5% | 78.9% | 193.0% |
| C0016 | 172.7% | 230.5% | 96.7% | 100.4% | 83.3% | 150.9% |
| C0017 | 153.8% | 284.5% | 94.1% | 87.1% | 109.7% | 143.2% |
| C0018 | 195.5% | 247.7% | 106.5% | 110.7% | 95.5% | 162.1% |
| C0019 | 104.4% | 176.6% | 52.8% | 59.1% | 68.1% | 80.4% |
| C0021 | 159.7% | 192.0% | 90.7% | 94.5% | 87.8% | 546.4% |
| C0022 | 194.3% | 328.7% | 13.4% | 113.5% | 123.2% | 25.7% |
| C0023 | 153.2% | 233.7% | 23.2% | 89.5% | 87.6% | 44.5% |
| C0024 | 178.4% | 229.6% | 59.3% | 92.8% | 84.1% | 135.1% |
| C0025 | 235.7% | 320.7% | 80.2% | 122.6% | 117.5% | 182.7% |
| C0028 | 93.9% | 132.4% | 78.4% | 55.6% | 60.5% | 472.3% |
| C0029 | 175.4% | 308.8% | 16.6% | 91.2% | 113.1% | 37.8% |
| C0030 | 150.3% | 226.8% | 95.0% | 96.0% | 98.0% | 291.4% |
| C0032 | 145.4% | 202.0% | 80.9% | 92.8% | 87.3% | 248.2% |
| C0033 | 134.5% | 186.4% | 76.6% | 85.9% | 80.6% | 235.0% |
| C0034 | 103.6% | 167.9% | 80.1% | 61.3% | 76.7% | 482.5% |
| C0041 | 186.1% | 244.4% | 95.5% | 110.1% | 111.7% | 575.3% |
| C0042 | 167.1% | 260.9% | 110.6% | 98.9% | 119.2% | 666.3% |
| C0047 | 142.2% | 206.1% | 80.1% | 98.1% | 88.5% | 182.0% |
| C0048 | 209.1% | 245.3% | 89.9% | 144.2% | 105.3% | 204.3% |
| C0049 | 106.6% | 210.0% | 81.0% | 73.5% | 90.1% | 184.1% |
| C0051 | 94.4% | 170.4% | 55.9% | 65.1% | 73.1% | 127.0% |
| C0052 | 108.4% | 162.8% | 42.7% | 74.8% | 69.9% | 97.0% |
| C0053 | 104.0% | 157.2% | 93.1% | 71.7% | 67.5% | 211.6% |
| C0054 | 68.2% | 127.0% | 43.5% | 47.0% | 54.5% | 98.9% |
| C0057 | ND* | ND | ND | ND | ND | ND |
| C0061 | ND | ND | ND | ND | ND | ND |
| C0062 | 127.8% | 310.5% | 59.8% | 81.9% | 134.7% | 149.9% |
| C0064 | 213.8% | 349.6% | 38.1% | 124.2% | 159.1% | 110.4% |
| C0065 | 198.3% | 279.5% | 47.7% | 127.0% | 121.3% | 119.5% |
| C0067 | 142.7% | 179.0% | 33.5% | 82.9% | 81.5% | 97.1% |
| C0068 | 107.2% | 263.1% | 165.9% | 53.4% | 83.8% | 307.8% |
| C0069 | ND | ND | ND | ND | ND | ND |
| C0070 | 165.6% | 210.8% | 114.2% | 96.2% | 95.9% | 331.0% |
| C0071 | 276.3% | 355.3% | 177.1% | 160.5% | 161.7% | 513.3% |
| C0072 | 172.7% | 259.1% | 67.1% | 100.3% | 117.9% | 194.5% |
| C0073 | ND | ND | ND | ND | ND | ND |
| C0077 | 192.7% | 265.4% | 136.7% | 109.5% | 104.9% | 621.4% |
| C0078 | 138.1% | 236.6% | 170.7% | 82.4% | 106.4% | 359.4% |
| C0080M | 187.9% | 205.4% | 167.1% | 112.1% | 92.4% | 351.8% |
| C0082M | 228.1% | 338.4% | 97.6% | 113.7% | 107.8% | 181.1% |

-continued

| FLNA- Binding Compound | Concentration of FLNA-Binding Compound as Agonist 0.1 μM | 1 μM | 1 μM + BFNA | % DAMGO (0.1 μM) | % DAMGO (1 μM) | % DAMGO + BFNA |
|---|---|---|---|---|---|---|
| C0084M | 163.1% | 255.5% | 133.2% | 97.3% | 114.9% | 280.4% |
| C0085M | 211.6% | 246.2% | 43.7% | 105.5% | 78.4% | 112.6% |
| C0138M | 126.9% | 183.9% | 51.5% | 86.3% | 90.9% | 131.0% |
| C0139M | 156.1% | 206.6% | 51.0% | 106.2% | 102.2% | 129.8% |
| C0140M | 126.1% | 215.4% | 83.0% | 85.8% | 106.5% | 211.2% |
| C0141M | 161.5% | 213.9% | 47.9% | 109.9% | 105.8% | 121.9% |
| C0143M | 81.0 | 193.3 | 86.5 | 47.1% | 59.3% | 94.7% |
| C0144M | 186.3 | 295.9 | 125.9 | 108.3% | 90.8% | 137.9% |
| C0145M | 193.0 | 289.2 | 87.0 | 112.2% | 88.7% | 95.3% |
| C0146M | ND | ND | ND | ND | ND | ND |
| C0147M A2 | ND | ND | ND | ND | ND | ND |
| C0148M A2 | 181.3 | 360.6 | 87.6 | 105.4% | 110.6% | 95.9% |
| C0149M | 209.8 | 406.7 | 93.4 | 122.0% | 124.8% | 102.3% |
| C0150M | 167.1 | 423.1 | 93.4 | 97.2% | 129.8% | 173.2% |
| C0151M | 346.8 | 397.6 | 212.8 | 201.6% | 122.0% | 233.1% |
| C0152M | ND | ND | ND | ND | ND | ND |
| DAMGO Average | 168.5% | 266.1% | 53.2% | ND | ND | ND |

*ND = Not Done.

Series C-2 FLNA-Binding Compound MOR Agonist Activity

| FLNA- Binding Compound | Concentration of FLNA-Binding Compound as Agonist 0.1 μM | 1 μM | 1 μM + BFNA | % DAMGO (0.1 μM) | % DAMGO (1 μM) | % DAMGO + BFNA |
|---|---|---|---|---|---|---|
| C0011 | 217.0% | 305.0% | 19.0% | 126.8% | 114.3% | 36.5% |
| C0026 | 207.2% | 288.4% | 21.2% | 107.7% | 105.6% | 48.3% |
| C0027 | 233.2% | 313.9% | 72.2% | 121.3% | 115.0% | 164.5% |
| S-C0027 | 156.2% | 286.8% | 56.2% | 74.2% | 84.4% | 98.1% |
| C0034-3 | ND* | ND | ND | ND | ND | ND |
| C0037-2 | ND | ND | ND | ND | ND | ND |
| C0040 | 145.8% | 308.3% | 90.4% | 93.1% | 133.2% | 277.3% |
| C0043 | 175.4% | 242.6% | 83.3% | 103.8% | 110.9% | 501.8% |
| C0044 | 173.7% | 280.1% | 59.1% | 102.8% | 128.0% | 356.0% |
| C0045 | 149.2% | 238.8% | 105.3% | 88.3% | 109.1% | 634.3% |
| C0046 | 286.2% | 492.9% | 156.8% | 197.4% | 211.5% | 356.4% |
| C0050 | 110.3% | 127.6% | 59.0% | 76.1% | 54.8% | 134.1% |
| C0055 | ND | ND | ND | ND | ND | ND |
| C0056 | 98.6% | 193.4% | 86.3% | 68.0% | 83.0% | 196.1% |
| C0060 | 166.5% | 218.9% | 143.9% | 114.8% | 93.9% | 327.0% |
| C0086M | 206.8% | 265.3% | 152.3% | 117.5% | 104.9% | 692.3% |
| C0087M | 262.8% | 329.6% | 142.5% | 138.9% | 132.8% | 293.8% |
| C0088M | 276.3% | 355.3% | 177.1% | 160.5% | 161.7% | 513.3% |
| C0089M | 234.5% | 295.3% | 81.9% | 136.3% | 134.4% | 237.4% |
| C0090M | 237.0% | 341.0% | 41.0% | 137.7% | 155.2% | 118.8% |
| C0091M | 207.9% | 274.4% | 80.8% | 118.1% | 108.5% | 367.3% |
| C0093M | 140.0% | 211.8% | 44.0% | 81.3% | 96.4% | 127.5% |
| C0094M | 172.5% | 263.5% | 115.3% | 100.2% | 119.9% | 334.2% |
| C0095M | 189.1% | 224.6% | 107.7% | 107.4% | 88.8% | 489.5% |
| C0096M | 186.4% | 328.9% | 127.1% | 105.9% | 130.0% | 577.7% |
| C0099M | 157.2% | 195.7% | 114.7% | 93.8% | 88.0% | 241.5% |
| C0100M | 173.6% | 245.9% | 195.6% | 103.6% | 110.6% | 411.8% |
| C0101M | 138.2% | 274.3% | 174.8% | 82.5% | 123.4% | 368.0% |
| C0102M | 131.8% | 272.0% | 150.4% | 78.6% | 122.4% | 316.6% |
| C0104M | 188.2% | 238.9% | 143.8% | 99.5% | 96.3% | 296.5% |
| C0105M | 198.1% | 220.3% | 73.1% | 104.7% | 88.8% | 150.7% |
| C0106M | 171.8% | 240.7% | 117.2% | 102.5% | 108.3% | 246.7% |
| C0108M | 205.6% | 258.5% | 76.9% | 108.7% | 104.1% | 158.6% |
| C0114M | 114.0% | 144.3% | 35.9% | 77.6% | 71.4% | 91.3% |
| C0115M | 177.2% | 226.8% | 118.4% | 105.7% | 102.0% | 249.3% |
| C0116M | 258.4% | 302.8% | 152.0% | 136.6% | 122.0% | 313.4% |
| C0118M | 166.2% | 261.5% | 79.2% | 87.8% | 105.4% | 163.3% |
| C0119M | 105.7% | 167.8% | 35.1% | 71.9% | 83.0% | 89.3% |
| C0124M | 252.0% | 305.1% | 61.4% | 133.2% | 122.9% | 126.6% |
| C0125M | 168.6% | 195.2% | 159.7% | 89.1% | 78.6% | 329.3% |
| C0126M | 181.8% | 265.3% | 108.5% | 108.5% | 119.3% | 228.4% |
| C0128M | 197.8% | 286.0% | 63.9% | 104.5% | 115.2% | 131.8% |
| C0133M | 139.4% | 214.8% | 72.4% | 83.2% | 96.6% | 152.4% |

-continued

| FLNA- | Concentration of FLNA-Binding Compound as Agonist | | | | | |
|---|---|---|---|---|---|---|
| Binding Compound | 0.1 μM | 1 μM | 1 μM + BFNA | % DAMGO (0.1 μM) | % DAMGO (1 μM) | % DAMGO + BFNA |
| C0134M | 158.5% | 207.3% | 46.6% | 94.6% | 93.3% | 98.1% |
| F-00134 | 290.6% | 378.9% | 66.6% | 138.1% | 111.4% | 116.2% |
| C0135M | 161.3% | 310.1% | 113.3% | 85.3% | 124.9% | 233.6% |
| C0136M (P5) | 176.8% | 237.3% | 74.5% | 93.4% | 95.6% | 153.6% |
| C0137M (P7) | 180.8% | 193.8% | 55.8% | 95.6% | 78.1% | 115.1% |
| C0142M | 143.7% | 192.5% | 98.7% | 97.8% | 95.2% | 251.1% |
| C0143M | 81.0% | 193.3% | 86.5% | 47.1% | 59.3% | 94.7 |
| C0144M-21 | 86.3% | 295.9% | 125.9% | 108.3% | 90.8% | 137.9% |
| C0145M-31 | 93.0% | 289.2% | 87.0% | 112.2% | 88.7% | 95.3% |
| C0149M-22 | 09.8% | 406.7% | 93.4% | 122.0% | 124.8% | 102.3% |
| C0150M-21 | 67.1% | 423.1% | 158.1% | 97.2% | 129.8% | 173.2% |
| C0151M-23 | 46.8% | 397.6% | 212.8% | 201.6% | 122.0% | 233.1% |
| C0152M-2 | ND | ND | ND | ND | ND | ND |
| C0153M-3 | ND | ND | ND | ND | ND | ND |
| DAMGO Average | 168.5% | 266.1% | 53.2% | ND | ND | ND |

*ND = Not Done.

A preliminary study similar to that immediately above was carried out using Compounds 4, 9 and 10 and resynthesized Compound C0134M and DAMGO. The results of an average of two runs for this study are shown below.

| | Concentration of FLNA-Binding Compound as Agonist | | |
|---|---|---|---|
| Compound | 0.1 μM | 1 μM | 1 μM + βNFA |
| 4 | 133.9% | 165.2% | 49.5% |
| 9 | 156.6% | 197.2% | 56.6% |
| 10 | 163.1% | 191.8% | 60.4% |
| C0134M | 150.7% | 224.0% | 53.2% |
| DAMGO | 144.7% | 233.4% | 56.8% |

The above results indicate that Compounds 9 and 10 not only bind well to FLNA, but are also MOR agonists, whereas Compound 4 bound well to FLNA, but was not as potent a MOR agonist as were the other two compounds. The newly synthesized Compound C0134M exhibited similar MOR agonist activity to that shown previously.

Materials and Methods

An in vitro study was conducted under the direction of Hoau-Yan Wang, Ph.D. by the Dept. of Physiology, Pharmacology & Neuroscience, CUNY Medical School, 138th Street and Convent Avenue, New York, NY 10031, to assess the top two filamin A (FLNA)-binding compounds, C0105 and C0114 for the ability to block amyloid $beta_{42}$ ($Aβ_{42}$)-induced FLNA-α7 nicotinic acetylcholine receptor (α7nAChR) association and tau phosphorylation, indicating the potential to treat Alzheimer's disease.

Animals

Adult Sprague Dawley rats (2 months old) were used for organotypic frontocortical slice cultures. Rats were maintained on a 12-hour light/dark cycle with food and water. All animal procedures comply with the National Institutes of Health Guide for Care Use of Laboratory Animals and were approved by the City College of New York Animal Care and Use Committee.

Organotypic Frontocortical Slice Cultures

Rat brain slice organotypic culture methods were modified from those published previously. [Adamchik et al., *Brain Res Brain Res Protoc* 5:153-158 (2000).]FCX slices (20 μM thickness) were transferred to sterile, porous Millicell-CM inserts (0.4 m). Each culture insert unit contained two brain slices and was placed into individual wells of a 12-well culture tray in 2 ml medium: 50% MEM with Earl's salts, 2 mM L-glutamine, 25% Earl's balanced salt solution, 6.5 g/l D-glucose, 20% fetal bovine serum (FBS), 5% horse serum, 25 mM HEPES buffer, pH 7.2, and 50 mg/ml streptomycin and 50 mg/ml penicillin. Cultures were kept in an incubator for 2 days at 36° C. in 5% $CO_2$ to minimize the impact of injury from slice preparation.

On the day of experiment, medium was removed, the brain slices rinsed and incubated in 0.1% FBS-containing medium for 4 hr at 36° C. in 5% $CO_2$. Brain slices were then cultured with 100 nM $Aβ_{42}$ and/or 0.1, 1 nM compound C0105 or compound C0114 in fresh 0.1% FBS-containing medium for 16 hours. Brain slices (6 slices for each experiment) were washed with ice-cold Krebs-Ringer and used to assess α7nAChR-FLNA complex level and phosphorylated tau ($pS^{202}$-, $pT^{231}$- and $pT^{181}$-tau). Brain slices were also used to determine the α7nAChR and NMDAR activity by the level of calcium influx through each of these two channels and the level of cell death using voltage-gated calcium channel mediated calcium influx.

For immunohistochemistry, additional slices were removed and fixed in 4% paraformaldehyde in PBS at 4° C. The effect of C0105 and C0114 on intraneuronal $Aβ_{42}$ accumulation was determined by the $Aβ_{42}$ immunostaining level.

Brain Synaptosome Preparation

Brain synaptosomes (P2 fraction) were prepared from FCX slice cultures. Following methods described previously, [Wang et al., *J Biol Chem* 278:31547-31553 (2003)] FCX was solubilized immediately after removal from cultures to obtain synaptosomes. The synaptosomes were washed twice and suspended in 2 ml of ice-cold Kreb's-Ringer (K—R): 25 mM HEPES, pH 7.4; 118 mM NaCl, 4.8 mM KCl, 25 mM $NaHCO_3$, 1.3 mM $CaCl_2$), 1.2 mM $MgSO_4$, 1.2 mM $KH_2PO_4$, 10 mM glucose, 100 μM ascorbic acid, mixture of protease and protein phosphatase inhibitors (Roche Diagnostics) that had been aerated for 10 minutes with 95% $O_2$/5% $CO_2$. The protein concentration was determined using the Bradford method (Bio-Rad).

In Vitro Studies Using Organotypic FCX Tissues

To assess the effect of compounds C0105 and C0114 on $A\beta_{42}$-induced $\alpha$7nAChR-FLNA interaction and tau phosphorylation ($pS^{202}$-, $pT^{231}$- and $pT^{181}$-tau) levels, rat frontal cortical slice culture system was used. Rat brain FCX were chopped coronally into 200 m slices using a Mcllwain chopper (Brinkman Instruments) and suspended in 10 ml of ice-cold oxygenated K—R.

The rat brain slice organotypic culture was performed as described previously. [Wang et al., *Biol Psychiatry* 67, 522-530 (2010).]Rat FCX slices were transferred to sterile, porous 0.4 μm Millicell-CM insert, 2 slices per insert per well containing 2 ml medium: 50% MEM with Earl's salts, 2 mM L-glutamine, 25% Earl's balanced salt solution, 6.5 g/l D-glucose, 20% fetal bovine serum (FBS), 5% horse serum, 25 mM HEPES buffer, pH 7.2, and 50 mg/ml streptomycin and 50 mg/ml penicillin. Cultures were kept in an incubator for 2 days at 36° C. in 5% $CO_2$.

On the day of study, medium was removed, the brain slices rinsed and incubated in 0.1% FBS-containing medium for 4 hours at 36° C. in 5% $CO_2$. Brain slices were then cultured with 0. μM $A\beta_{42}$ together with 0.1, 1 or 10 nM Compound C0105 or 1 or 10 nM C0114 in fresh 0.1% FBS-containing medium for 16 hours. The brain slices were then removed and washed with ice-cold PBS three times and either processed for functional assays described below or fixed in ice-cold 4% paraformaldehyde PBS at 4° C. for determination of intraneuronal $A\beta_{42}$ aggregate and NFT levels by immunohistochemical method.

1) FLNA Association with $\alpha$7nAChR and Other Receptors

The level of FLNA-associated $\alpha$7nAChRs was determined using a co-immunoprecipitation/Western blotting method as described previously. [Wang et al., *Biol Psychiatry* 67:522-530 (2010); Wang et al., *PLoS One* 3:e1554 (2008); Wang et al., *J Neurosci* 35:10961-10973 (2009)] Briefly, brain slice extract (200 g) was incubated with 1 g anti-FLNA immobilized on protein A agarose beads at 4° C. overnight (about 18 hours) with constant end-over-end rotation. The anti-FLNA immunocomplexes were obtained by centrifugation, and then washed and dissociated using antigen elution buffer. Following neutralization with 1.5M Tris, pH 8.8, the resultant FLNA-associated protein complexes were solubilized by boiling for 5 minutes in SDS-containing sample preparation buffer. The levels of FLNA-associated $\alpha$7nAChR, TLR4, IR and MOR were assessed by Western blotting using specific antibodies directed against the respective proteins and the blot stripped and re-probed for FLNA for immunoprecipitation/loading control.

2) Tau Phosphorylation

Using an established method, [Wang et al., *J Biol Chem* 278:31547-31553 (2003); Wang et al., *Biol Psychiatry* 67:522-530 (2010)]tau proteins were immunoprecipitated with immobilized anti-tau (SC-65865), which does not discriminate between phosphorylation states. The levels of phosphorylated tau (pSer202tau, pThr231tau and pThr181tau) as well as total tau precipitated (loading controls) are assessed by Western blotting using specific antibodies directed against each of the phosphoepitopes and the anti-tau, respectively.

3) Functional Assessment of $\alpha$7nAChR and NMDAR

The effect of Compounds C0105 and C0114 on $\alpha$7nAChR and NMDAR function was assessed in organotypic FCX slice cultures treated with vehicle, 0.1 μM $A\beta_{42}$ or 0.1 μM $A\beta_{42+0.1}$-10 nM C0105 or 1-10 nM C0114. Synaptosomes prepared from rat FCX slices (6 slices/assay) were washed twice in ice-cold K—R, centrifuged and re-suspended in 0.5 ml K—R.

NMDAR and $\alpha$7nAChR mediated $^{45}Ca^{2+}$ influx was measured as described previously. [Wang et al., *Biol Psychiatry* 67:522-530 (2010).]Synaptosomes (50 g) were incubated at 37° C. for 5 minutes in oxygenated 0.3 mM $Mg^{2+}$ K—R containing 5 μM $^{45}Ca^{2+}$ (10 Ci/mmol, PerkinElmer) followed by incubation with vehicle, 0.1-10 μM NMDA/1 μM glycine or 0.1-10 μM PNU282987 (a potent and selective agonist for the $\alpha$7 subtype of neural nicotinic acetylcholine receptors) for 5 minutes. The reaction was terminated by 1 ml ice-cold 0.5 mM EGTA-containing $Ca^{2+}$-free K—R and centrifugation. After two washes, synaptosomal $^{45}Ca^{2+}$ contents were assessed using scintillation spectrometry.

The background $^{45}Ca^{2+}$ was estimated using hypotonically lysed synaptosomes. The absolute $Ca^{2+}$ influx was calculated by subtracting background $^{45}Ca^{2+}$ count. The percent increase in $Ca^{2+}$ influx was calculated as % [(drug-treated−vehicle)/vehicle].

4) Cell Death Measured by $K^+$-Evoked $Ca^{+2}$ Influx

Because the level of voltage-gated $Ca^{2+}$ channel activity is indicative of the integrity of the cells, the effect of compounds C0105 and C0114 on $A\beta_{42}$-induced cell death was assessed in organotypic FCX slice cultures treated with vehicle, 0. μM $A\beta_{42}$ or 0.1 μM $A\beta_{42}$+0.1-10 nM compound C0105 or 1-10 nM compound C0114 using $K^+$-depolarization mediated $Ca^{2+}$ influx. Synaptosomes prepared from rat FCX slices (6 slices/assay) were washed twice in ice-cold K—R, centrifuged and re-suspended in 0.5 ml K—R. The level of voltage-gated $Ca^{2+}$ channel mediated $^{45}Ca^{2+}$ influx was measured as described previously. [Wang et al., *Biol Psychiatry* 67:522-530 (2010).]

Synaptosomes (50 g) were incubated at 37° C. for 5 minutes in oxygenated 0.3 mM $Mg^{2+}$ K—R containing 5 μM $^{45}Ca^{2+}$ (10 Ci/mmol, PerkinElmer) followed by incubation with vehicle or 65 mM $K^+$ (made with isomolar replacement of $Na^+$) for 1 minute. The reaction was terminated by 1 ml ice-cold 0.5 mM EGTA-containing $Ca^{2+}$-free K—R and centrifugation. After two washes, synaptosomal $^{45}Ca^{2+}$ contents were assessed using scintillation spectrometry. The background $^{45}Ca^{2+}$ was estimated using hypotonically lysed synaptosomes. The absolute $Ca^{2+}$ influx was calculated by subtracting background $^{45}Ca^{2+}$ count. The percent increase in $Ca^{2+}$ influx was calculated as % [(drug-treated−vehicle)/vehicle].

5) Measuring Levels of Signaling Molecules Associated with NMDAR or IR after Receptor Stimulation NMDAR signaling and their interaction with synaptic anchoring protein, PSD-95, were compared in brain slices from organotypic culture FCX treated with vehicle, 0.1 μM $A\beta_{42}$ and 0. μM $A\beta_{42}$+0.1-10 nM of compound C0105 or 1 and 10 nM of compound C0114 for 16 hours. NMDAR activation and signaling was initiated by incubation of 6 slices with either 0.3 mM $Mg^{2+}$ containing KR (LMKR; basal) or LMKR containing 10 μM NMDA and 1 μM glycine at 37° C. for 30 minutes.

The incubation mixture was aerated with 95% $O_2$/5% $CO_2$ every 10 minutes for 1 minute during the stimulation. Ligand stimulation was terminated by the addition of 1 ml of ice-cold $Ca^{2+}$-free K—R containing mixture of protein phosphatase inhibitors, 0.5 mM EGTA and 0.1 mM EDTA. Brain slices were harvested by a brief centrifugation and were homogenized in 0.25 ml of ice-cold immunoprecipitation buffer. The homogenates were centrifuged at 1000×g for 5 minutes (4° C.) and the supernatant (post-mitochondrial fraction) was sonicated for 10 seconds on ice.

The proteins were solubilized in 0.5% digitonin, 0.2% sodium cholate and 0.5% NP-40 for 60 minutes at 4° C. with end-over-end rotation. The resultant lysates were cleared by centrifugation at 50,000×g for 5 minutes and diluted with 0.75 ml of immunoprecipitation buffer. Protein concentrations were measured by Bradford method (Bio-Rad).

To determine the association of NMDARs with PSD-95, as well as NMDAR signaling, the levels of NMDAR subunits, PSD-95 and NMDAR-associated signaling molecules were measured in anti-NR1 immunoprecipitates. In these studies, brain slice lysates (100 g) were immunoprecipitated overnight at 4° C. with 2 g of immobilized anti-NR1 onto covalently conjugated protein A-agarose beads (Pierce-ENDOGEN). Anti-NR1 immunoprecipitates were incubated with 75 μl antigen elution buffer (Pierce-ENDOGEN) and 2% SDS for 2 minutes on ice, centrifuged to remove antibody-protein A-agarose complexes and neutralized immediately with 10 μl 1.5 M Tris buffer, pH 8.8 followed by addition of 65 μl 2×PAGE sample buffer and boiled for 5 minutes.

Seventy-five μ of the obtained eluates (50%) were size fractionated on 7.5% SDS-PAGE. Proteins were transferred to nitrocellulose membrane and the levels of various NMDA receptor subunits, PSD-95, signaling proteins were measured using Western blotting with antibodies for PSD-95, nNOS, phospholipase C-71, 7PKC, $pY^{402}$PyK2, $pY^{416}$Src or phosphotyrosine. The blots were stripped and re-probed with anti-NR1 to assess the immunoprecipitation efficiency and loading.

IR activation and signaling was initiated by incubation of 6 slices that were further chopped horizontally into 100 m (100 m×200 m×3 mm) with either KR (basal) or KR containing 1 nM insulin at 37° C. for 30 minutes. The incubation mixture was aerated with 95% $O_2$/5% $CO_2$ every 10 minutes for 1 minute during the stimulation. Ligand stimulation was terminated by the addition of 1 ml of ice-cold $Ca^{2+}$-free K—R containing mixture of protein phosphatase inhibitors, 0.5 mM EGTA and 0.1 mM EDTA. Brain slices were harvested by a brief centrifugation and were homogenized in 0.25 ml of ice-cold immunoprecipitation buffer. The homogenates were centrifuged at 1000×g for 5 minutes (4° C.) and the supernatant (post-mitochondrial fraction) was sonicated for 10 seconds on ice. The proteins were solubilized in 0.5% digitonin, 0.2% sodium cholate and 0.5% NP-40 for 60 minutes at 4° C. with end-over-end rotation. The resultant lysates were then cleared by centrifugation at 50,000×g for 5 minutes and diluted with 0.75 ml of immunoprecipitation buffer. Protein concentrations were measured by Bradford method (Bio-Rad).

To determine the IR activation and signaling, the levels of $pY^{1150/1151}$IRβ and the level of IR signal transducer, IRS-1 were measured in anti-IR immunoprecipitates. In these experiments, brain slice lysates (100 μg) were immunoprecipitated overnight (about 18 hours) at 4° C. with 2 μg of immobilized anti-IRβ onto covalently conjugated protein A-agarose beads (Pierce-ENDOGEN).

Anti-IRβ immunoprecipitates were incubated with 75 μl antigen elution buffer (Pierce-ENDOGEN) and 2% SDS for 2 min on ice, centrifuged to remove antibody-protein A-agarose complexes and neutralized immediately with 10 μl 1.5 M Tris buffer, pH8.8 followed by addition of 65 μl 2×PAGE sample buffer and boiled for 5 minutes. Seventy-five μ of the obtained eluates (50%) were then size fractionated on 7.5% SDS-PAGE. Proteins were transferred to nitrocellulose membrane and the levels of $pY^{1150/1151}$IRβ and IRS-1 proteins were measured using Western blotting with antibodies for $pY^{1150/1151}$IRβ and IRS-1. The blots were stripped and re-probed with anti-IRβ to assess the immunoprecipitation efficiency and loading.

6) Immunohistochemical Studies

Quantitative immunohistochemistry on consecutive 5-μm sections containing PFCX and entorhinal cortex/HP were used to determine the levels of A42 aggregates/plaques and neurofibrillary pathology (NFT and paired helical filament [PHF]immunoreactivity) using single labeling immunohistochemistry as described previously. [Wang et al., *Biol Psychiatry* 67:522-530 (2010); D'Andrea et al., Histopathology 38:120-134 (2001); Nagele et al., *Neuroscience* 110: 199-211 (2002).]One section was immunostained with anti-NFT or —PHF. The next (consecutive) section (often containing the same neuron) was immunostained with anti-$Aβ_{42}$ antibodies to measure relative levels of accumulated $Aβ_{42}$ peptide in neurons. The relative $Aβ_{42}$ accumulation rate/extent were compared among different cell types in sections from cultured FCX slices and icv $Aβ_{42}$-infused mouse brains using a computer-assisted image analysis as described previously [Wang et al. *J Biol Chem* 275:5626-5632 (2000)].

Brain slices were fixed at 4° C. in 0.15 M phosphate-buffered 10% formalin, pH 7.4 for 2 weeks, paraffin embedded, serially sectioned at 5 m, and processed for brightfield immunohistochemistry as described previously [Wang et al., *J Biol Chem* 275:5626-5632 (2000)]. The $Aβ_{42}$ immunoreactivity was absent when pre-absorbing anti-$Aβ_{42}$ with $Aβ_{42}$ but not $Aβ_{42-1}$. Specimens were examined using a Nikon FXA microscope with a Princeton Instruments CCD camera and recorded digitally.

Relative intensities of the NFT/PHF and $Aβ_{42}$ immunoreactivity were measured and compared among similar and different cell types using Image Pro Plus and Metamorph software as described previously [D'Andrea et al., *Histopathology* 38:120-134 (2001)]. The correlations between the amount of NFT/PHF immunoreactivity and $Aβ_{42}$-positive material accumulated within mature neurons were also determined.

In Vivo Studies

An in vivo study was conducted under the direction of Hoau-Yan Wang, $P_h$.D. by the Dept. of Physiology, Pharmacology & Neuroscience, CUNY Medical School, 138th Street and Convent Avenue, New York, NY 10031, in an amyloid $beta_{42}$ ($Aβ_{42}$) infusion model of Alzheimer's disease for the ability 1) to block $Aβ_{42}$-induced FLNA association with α7 nicotinic acetylcholine receptor (α7nAChR) and toll-like receptor 4 (TLR4), 2) tau phosphorylation, and 3) $Aβ_{42}$-α7nAChR association indicating the potential to treat Alzheimer's disease.

ICV $Aβ_{42}$ Infusion Mouse Model

Mice

Eight-week-old male and female E129 mice (30-35 g), progeny of the breeding pairs from Taconic (Germantown, New York) were used in the intracerebroventricular (ICV) $Aβ_{42}$ study. Mice were maintained on a 12-hour light/dark cycle with food and water. All animal procedures comply with the National Institutes of Health *Guide for Care Use of Laboratory Animals and were approved by the City College of New York Animal Care and Use Committee.*

Intracerebroventricular $Aβ_{42}$ Administration and Compound Treatment

Mice anesthetized with 30 mg/kg sodium pentobarbital intraperitoneally were placed in a mouse stereotaxic surgery apparatus as described by Wang et al., *Biol Psychiatry* 67:522-530 (2010). Mice receiving 7-day continuous ICV $Aβ_{42}$ infusion were implanted with a minipump for mice (Alzet) that delivers 0.1 l/hr through a surgical glue-secured cannula placed in the left ventricle at the following coordinates: [anterior-posterior from bregma, 3.0 mm; lateral, 1.0 mm; horizontal, 3.0 mm]. The $A\beta_{42}$ (0.2 nmol/l) was dissolved in 10% DMSO containing 50 mM Tris, pH 9.0, to prevent aggregation. Each mouse received 4.8 nmol $A\beta_{42}$ daily for 7 days. Control mice received 7-day ICV infusion of vehicle.

To assess the effect of in vivo Compound C0105 on $A\beta_{42}$-elicited effects, mice received 10 mg/kg of Compound C0105 by intraperitoneal (i.p.) injection daily for 2 weeks starting on the day of surgery (day 1: 2 hours after recovery from surgery, day 2-14 twice daily: between 10-11 a.m. and 3-4 p.m.). Twenty-four hours after the last injection, FCX and hippocampus from one half brain was solubilized for assessment of α7nAChR-FLNA complex level and phosphorylated tau ($pS^{202}$-, $pT^{231}$- and $pT^{181}$-tau) using published methods [Wang et al., *Biol Psychiatry* 67:522-530 (2010)].

Whether the compounds has an effect on levels of $A\beta_{42}$-α7nAChR coupling was assessed because dissociating $A\beta_{42}$ from α7nAChRs is beneficial in reducing AD pathologies. [Wang et al., *Biol Psychiatry* 67:522-530 (2010); Wang et al., *J Neurosci* 35:10961-10973 (2009).] In addition, prefrontal cortex (PFCX) is used to determine the level of synaptic activity using α7nAChR and NMDAR activity as the guide. The other brain halves were immersion-fixed in cold 0.15 M phosphate-buffered 10% formalin, pH 7.4, and processed for immunohistochemical determinations of intraneuronal $A\beta_{42}$ aggregates/plaques and NFTs as well as morphological integrity.

Brain Synaptosome Preparation

Brain synaptosomes (P2 fraction) were prepared from prefrontal cortex and hippocampus of treated mice sacrificed by rapid decapitation. Following methods described previously [Wang et al., *J Biol Chem* 278:31547-31553 (2003)], tissue was solubilized immediately after harvesting to obtain synaptosomes. The synaptosomes were washed twice and suspended in 2 ml of ice-cold Kreb's-Ringer (K—R): 25 mM HEPES, pH 7.4; 118 mM NaCl, 4.8 mM KCl, 25 mM $NaHCO_3$, 1.3 mM $CaCl_2$), 1.2 mM $MgSO_4$, 1.2 mM $KH_2PO_4$, 10 mM glucose, 10 μM ascorbic acid, mixture of protease and protein phosphatase inhibitors (Roche Diagnostics) that had been aerated for 10 minutes with 95% $O_2$/5% $CO_2$. The protein concentration was determined using the Bradford method (Bio-Rad).

Ex Vivo Assessments of Tissues from Treated Mice

Using synaptosomes prepared from prefrontal cortex or hippocampi of mice receiving continuous ICV infusions of vehicle or $A\beta_{42}$ and twice daily i.p. injections of Compound C0105 or vehicle, these studies assessed the effect of Compound C0105 on $A\beta_{42}$-induced α7nAChR-FLNA interaction, tau phosphorylation ($pS^{202}$-, $pT^{231}$- and $pT^{181}$-tau) levels, $A\beta_{42}$-(α7nAChR interaction and signaling impairments.

1) α7nAChR-FLNA/TLR4 Interaction

The level of FLNA-associated α7nAChRs and TLR4s were determined using a co-immunoprecipitation/Western blotting method as described previously [Wang et al., *Biol Psychiatry* 67:522-530 (2010); Wang et al., *J Neurosci* 35:10961-10973 (2009); and Wang et al., *PLoS One* 3:e1554 (2008)]. Briefly, synaptosomal extracts (200 g) prepared from prefrontal cortex or hippocampus from treated mice were incubated with 1 g anti-FLNA immobilized on protein A agarose beads at 4° C. overnight (about 18 hours) with constant end-over-end rotation. The anti-FLNA immunocomplexes were obtained by centrifugation, washed and dissociated using antigen elution buffer. Following neutralization with 1.5M Tris, pH 8.8, the resultant FLNA-associated protein complexes were solubilized by boiling for 5 minutes in SDS-containing sample preparation buffer. The levels of FLNA-associated α7nAChRs and TLR4s were assessed by Western blotting and the blot stripped and re-probed for FLNA for immunoprecipitation/loading control.

To assess the effect of elevated $A\beta_{42}$ and Compound C0105 treatment on FLNA and α7nAChR expression, FLNA and (α7nAChR levels were measured in the tissue extract by Western blotting with β-actin as the loading control.

2) Tau Phosphorylation

Using established methods [Wang et al., *Biol Psychiatry* 67:522-530 (2010); and Wang et al., *J Biol Chem* 278:31547-31553 (2003)], tau proteins were immunoprecipitated with immobilized anti-tau (SC-65865), which does not discriminate between phosphorylation states. The levels of phosphorylated tau (pSer202tau, pThr231tau and pThr181tau) as well as total tau precipitated (loading controls) were assessed by Western blotting using specific antibodies directed against each of the phosphoepitopes and the anti-tau, respectively.

3) $A\beta_{42}$-α7nAChR Interaction

The level of $A\beta_{42}$-α7nAChR complexes were measured in synaptosomes from prefrontal cortex and hippocampus of treated mice using an established method [Wang et al., *Biol Psychiatry* 67:522-530 (2010); and Wang et al., *J Biol Chem* 278:31547-31553 (2003)]. Briefly, $A\beta_{42}$-α7nAChR complexes were immunoprecipitated with immobilized anti-$A\beta_{42}$ and the (α7nAChR contents were measured by Western blotting. Anti-actin was added to immunoprecipitation and the β-actin level in the immunoprecipitates served as immunoprecipitation/loading control.

4) Functional Assessment of α7nAChR and NMDAR

The effect of Compound C0105 on α7nAChR and NMDAR function was assessed in mice infused with $A\beta_{42}$ or vehicle. Synaptosomes prepared from prefrontal cortex or hippocampus were washed twice in ice-cold K—R, centrifuged and re-suspended in 0.5 ml K—R.

NMDAR and α7nAChR mediated $^{45}Ca^{2+}$ influx was measured as described previously [Wang et al., *Biol Psychiatry* 67:522-530 (2010)]. Synaptosomes (50 g) were incubated at 37° C. for 5 minutes in oxygenated 0.3 mM $Mg^{2+}$ K—R containing 5 M $^{45}Ca^{2+}$ (10 Ci/mmol, PerkinElmer) followed by incubation with vehicle, 0.1-10 μM NMDA/1 μM glycine or 0.1-10 μM PNU282987 for 5 minutes. The reaction was terminated by admixture of 1 ml ice-cold 0.5 mM EGTA-containing $Ca^{2+}$-free K—R and centrifugation.

After two washes, synaptosomal $^{45}Ca^{2+}$ contents were assessed using scintillation spectrometry. The background $^{45}Ca^{2+}$ was estimated using hypotonically lysed synaptosomes. The absolute $Ca^{2+}$ influx was calculated by subtracting background $^{45}Ca^{2+}$ count. The percent increase in $Ca^{2+}$ influx was calculated as % [(drug-treated−vehicle)/vehicle].

5) Cell Death Measured by $K^+$-Evoked $Ca^{+2}$ Influx

Because the level of voltage-gated $Ca^{2+}$ channel activity is indicative of the integrity of the cells, the effect of Compound C0105 on $A\beta_{42}$-induced cell death was assessed in treated mice using $K^+$-depolarization mediated $Ca^{2+}$ influx. Synaptosomes prepared from prefrontal cortex were washed twice in ice-cold K—R, centrifuged and re-suspended in 0.5 ml K—R.

The level of voltage-gated $Ca^{2+}$ channel mediated $^{45}Ca^{2+}$ influx was measured as described previously [Wang et al., *Biol Psychiatry* 67:522-530 (2010)]. Synaptosomes (50 g)

were incubated at 37° C. for 5 minutes in oxygenated 0.3 mM $Mg^{2+}$ K—R containing 5 μM $^{45}Ca^{2+}$ (10 Ci/mmol, PerkinElmer) followed by incubation with vehicle or 65 mM $K^+$ (made with isomolar replacement of $Na^+$) for 1 minute. The reaction was terminated by admixture of 1 ml ice-cold 0.5 mM EGTA-containing $Ca^{2+}$-free K—R and centrifugation.

After two washes, synaptosomal $^{45}Ca^{2+}$ content was assessed using scintillation spectrometry. The background $^{45}Ca^{2+}$ was estimated using hypotonically lysed synaptosomes. The absolute $Ca^{2+}$ influx was calculated by subtracting background $^{45}Ca^{2+}$ count. The percent increase in $Ca^{2+}$ influx was calculated as % [(drug-treated−vehicle)/vehicle].

6) Measuring Levels of Signaling Molecules Associated with NMDAR or IR after Receptor Stimulation NMDAR signaling and their interaction with synaptic anchoring protein, PSD-95 were compared in synaptosomes from treated mice. NMDAR activation and signaling was initiated by incubation of 6 slices with either 0.3 mM $Mg^{2+}$ containing KR (LMKR; basal) or LMKR containing 10 μM NMDA and 1 μM glycine at 37° C. for 30 minutes.

The incubation mixture was aerated with 95% $O_2$/5% $CO_2$ every 10 min for 1 minute during the stimulation. Ligand stimulation was terminated by the addition of 1 ml of ice-cold $Ca^{2+}$-free K—R containing mixture of protein phosphatase inhibitors, 0.5 mM EGTA and 0.1 mM EDTA. After harvesting, tissues were briefly centrifuged and homogenized in 0.25 ml of ice-cold immunoprecipitation buffer. The homogenates were centrifuged at 1000×g for 5 minutes (4° C.) and the supernatant (post-mitochondrial fraction) was sonicated for 10 seconds on ice.

The proteins were solubilized in 0.5% digitonin, 0.2% sodium cholate and 0.5% NP-40 for 60 minutes at 4° C. with end-over-end rotation. The resultant lysates were cleared by centrifugation at 50,000×g for 5 minutes and diluted with 0.75 ml of immunoprecipitation buffer. Protein concentrations were measured by Bradford method (Bio-Rad).

To determine the NMDARs association with PSD-95 as well as NMDAR signaling, the levels of NMDAR subunits, PSD-95 and NMDAR-associated signaling molecules were measured in anti-NR1 immunoprecipitates. In these studies, brain tissue lysates (100 g) were immunoprecipitated overnight (about 18 hours) at 4° C. with 2 g of immobilized anti-NR1 onto covalently conjugated protein A-agarose beads (Pierce-ENDOGEN). Anti-NR1 immunoprecipitates were incubated with 75 μl antigen elution buffer (Pierce-ENDOGEN) and 2% SDS for 2 minutes on ice, centrifuged to remove antibody-protein A-agarose complexes and neutralized immediately with 10 μl 1.5 M Tris buffer, pH 8.8 followed by addition of 65 μl 2×PAGE sample buffer and boiled for 5 minutes. Seventy-five μ of the obtained eluates (50%) were size fractionated on 7.5% SDS-PAGE. Proteins were transferred to a nitrocellulose membrane and the levels of various NMDA receptor subunits, PSD-95, signaling proteins were measured using Western blotting with antibodies for PSD-95, nNOS, phospholipase C-71, 7PKC, $pY^{402}$PyK2, $pY^{416}$Src or phosphotyrosine. The blots were stripped and re-probed with anti-NR1 to assess the immunoprecipitation efficiency and loading.

IR activation and signaling was initiated by incubation of tissue with either K—R (basal) or K—R containing 1 nM insulin at 37° C. for 30 minutes. The incubation mixture was aerated with 95% $O_2$/5% $CO_2$ every 10 minutes for 1 minute during the stimulation. Ligand stimulation was terminated by the addition of 1 ml of ice-cold $Ca^{2+}$-free K—R containing mixture of protein phosphatase inhibitors, 0.5 mM EGTA and 0.1 mM EDTA.

Tissues were briefly centrifuged and homogenized in 0.25 ml of ice-cold immunoprecipitation buffer. The homogenates were centrifuged at 1000×g for 5 minutes (4° C.) and the supernatant (post-mitochondrial fraction) was sonicated for 10 seconds on ice. The proteins were solubilized in 0.5% digitonin, 0.2% sodium cholate and 0.5% NP-40 for 60 minutes at 4° C. with end-over-end rotation. The resultant lysates were then cleared by centrifugation at 50,000×g for 5 minutes and diluted with 0.75 ml of immunoprecipitation buffer. Protein concentrations were measured by Bradford method (Bio-Rad).

To determine the IR activation and signaling, the levels of $pY^{1150/1151}$IRβ and the level of IR signal transducer, IRS-1 were measured in anti-IR immunoprecipitates. In these studies, brain tissue lysates (100 g) were immunoprecipitated overnight (about 18 hours) at 4° C. with 2 g of immobilized anti-IRβ onto covalently conjugated protein A-agarose beads (Pierce-ENDOGEN).

Anti-IRβ immunoprecipitates were incubated with 75 μl antigen elution buffer (Pierce-ENDOGEN) and 2% SDS for 2 minutes on ice, centrifuged to remove antibody-protein A-agarose complexes and neutralized immediately with 10 μl 1.5 M Tris buffer, pH 8.8 followed by addition of 65 μl 2×PAGE sample buffer and boiled for 5 minutes.

Seventy-five μ of the obtained eluates (50%) were then size fractionated on 7.5% SDS-PAGE. Proteins were transferred to nitrocellulose membrane and the levels of $pY^{1150/1151}$IRβ and IRS-1 proteins were measured using Western blotting with antibodies for $pY^{1150/1151}$IRβ and IRS-1. The blots were stripped and re-probed with anti-IRβ to assess the immunoprecipitation efficiency and loading.

7) Assessment of Cytokine Levels

Parietal cortices (about 10 mg) derived from (1) vehicle-treated sham, (2) compound C0105 treated sham, (3) vehicle-treated ICV $Aβ_{42}$, and (4) compound C0105 treated ICV $Aβ_{42}$ mice were first thawed slowly (−80° C. to −20° C. to −4° C.), homogenized in 100 μl of ice-cold homogenization medium (25 mM HEPES, pH 7.5; 50 mM NaCl, mixture of protease and protein phosphatase inhibitors) by sonication and then solubilized with 0.5% polyoxyethylene (40) nonyl phenyl ether (NP-40), 0.2% Na cholate and 0.5% digitonin at 4° C. for 1 hour with end-over-end shaking. Following centrifugation, the resultant lysate was then dilute with 500 μl (total volume 600 μl) and used as the source of cytokines.

To determine the levels of cytokines in these tissues, 0.5 μg/well biotinylated mouse monoclonal anti-TNF-α, anti-IL-6 and anti-IL-IP were coated onto streptavidin-coated plates (Reacti-Bind™ NeutrAvidin™ High binding capacity coated 96-well plate; Thermo Scientific Pierce Protein Research Products; Rockford, IL). Plates were washed 3 times with ice-cold 50 mM Tris HCl (pH 7.4) and incubated at 30° C. with 100 μl of lysate derived from the above mentioned tissues for 1 hour.

Plates were washed 3 times with ice-cold 50 mM Tris HCl (pH 7.4) and incubated at 30° C. with 0.5 μg/well unconjugated rabbit anti-TNF-α, anti-IL-6 and anti-IL-1β for 1 hour. After two washes with 50 mM Tris HCl (pH 7.4), each well was incubated in 0.5 μg/well FITC-conjugated anti-rabbit IgG (human and mouse absorbed) for 1 hour at 30° C. Plates were washed twice with 200 μl ice-cold Tris HCl, pH 7.4 and the residual FITC signals were determined by multimode plate reader, DTX880 (Beckman). Each lysate was surveyed twice.

8) Immunohistochemical Studies

Quantitative immunohistochemistry on consecutive 5-μm sections containing prefrontal cortex and entorhinal cortex/ hippocampus was used to determine the levels of $A\beta_{42}$ aggregates/plaques and neurofibrillary pathology (NFT and paired helical filament [PHF]immunoreactivity) using single labeling immunohistochemistry as described previously [[Wang et al., *Biol Psychiatry* 67:522-530 (2010)]; D'Andrea et al., *Histopathology* 38:120-134 (2001); and Nagele et al., *Neuroscience* 110:199-211 (2002)]. One section was immunostained with anti-NFT or —PHF. The next (consecutive) section (often containing the same neuron) was immunostained with anti-$A\beta_{42}$ antibodies to measure relative levels of accumulated $A\beta_{42}$ peptide in neurons. The relative $A\beta_{42}$ accumulation extents were compared among different cell types using a computer-assisted image analysis as described previously [Wang et al., *J Biol Chem* 275:5626-5632 (2000)].

Brain tissues were fixed at 4° C. in 0.15 M phosphate-buffered 10% formalin, pH 7.4 for 2 weeks, paraffin embedded, serially sectioned at 5 m, and processed for brightfield immunohistochemistry as described. The $A\beta_{42}$ immunoreactivity was absent when pre-absorbing anti-$A\beta_{42}$ with $A\beta_{42}$ but not $A\beta_{42-1}$. Specimens were examined using a Nikon FXA microscope with a Princeton Instruments CCD camera and recorded digitally.

Relative intensities of the NFT/PHF and $A\beta_{42}$ immunoreactivity were measured and compared among similar and different cell types using Image-Pro® Plus (MediaCybernetics, Inc.; Bethesda, MD) and Metamorph® software (Molecular Devices, Inc.; Sunnyvale, CA) as described previously [D'Andrea et al., *Histopathology* 38:120-134 (2001)]. The correlations between the amount of NFT/PHF immunoreactivity and $A\beta_{42}$-positive material accumulated within mature neurons were also determined.

Postmortem Tissue

This study protocol conformed to the Declaration of Helsinki: Ethical Principles for Biomedical Research Involving Human Beings (the $4^{th}$ amendment) as reflected in a prior approval by the City College of New York and City University of New York Medical School human research committee. The participants had a uniform clinical evaluation that included a medical history, complete neurological examination, cognitive testing including Mini-Mental state examination and other cognitive tests on episodic memory, semantic memory and language, working memory, perceptual speed, and visuospatial ability as well as psychiatric rating. Based on this information, subjects received AD diagnoses based on NINCDS-ADRDA criteria [Mckhann et al., *Neurology* 34, 939-944 (1984)].

Postmortem brain tissues (frontal cortex=FCX) from patients with clinically diagnosed sporadic AD and control tissues from normal, age-matched, neurologically normal individuals were obtained from the Harvard Brain Tissue Resource Center (HBTRC, Belmont, MA) and UCLA Brain Tissue Resource Center (UBTRC, Los Angeles, CA). Both HBTRC and UBTRC are supported in part by Public Health Service grants from the National Institute of Health. The postmortem time intervals for collecting these brains were 13 hours (mean postmortem intervals for collection of AD and control brain samples were 6.0±0.9 hours and 5.8±0.8 hours, respectively).

Diagnostic neuropathological examination was conducted on fixed sections stained with hematoxylin and eosin stain and with modified Bielschowsky silver staining [Yamamoto et al., *Neuropathol Appl Neurobiol* 12, 3-9 (1986)] to establish any disease diagnosis according to the criteria defined by the National Institute on Aging and the Reagan Institute Working Group on Diagnostic Criteria for the Neuropathological Assessment of AD [Hyman et al., *J Neuropathol Exp Neurol* 56, 1095-1097 (1997)] and brain tissue from age-matched controls was similarly screened. The presence of both neuritic (amyloid) plaques and neurofibrillary tangles in all AD brains was confirmed by Nissl and Bielschowsky staining as well as characterized immunohisto-chemically with anti-$A\beta_{42}$ and -NFT staining in frontal and entorhinal cortex as well as hippocampus as described previously ([Wang et al., *J Neurochem* 75, 1155-1161 (2000)].

Control tissues exhibited no gross and minimal, localized microscopic neuropathology of AD (0-3 neuritic plaques/10× field and 0-6 NFTs/10× field in hippocampus). One gram blocks of FCX were dissected using a band saw from fresh frozen coronal brain sections maintained at −80° C. These blocks were derived from Brodmann areas 10 and/or 46. All postmortem tissues were identified by an anonymous identification number, and studies were performed as a best matched pair without knowledge of clinical information.

The Assessment of Test Compound Effects on $A\beta_{42}$ Affinity for α7nAChRs

To determine the compound effect on $A\beta_{42}$ affinity for the α7nAChRs, 200 g of synaptosomes prepared from control subjects were biotinylated. The biotinylated synaptosomes were lysed by brief sonication in hypertonic solutions and used as the tissue source to determine $A\beta_{42}$ affinity for the α7nAChRs in the presence and absence of Compound C0105.

In Vitro Treatment of Brain Slices for the Assessment of Test Compound on α7nAChR-FLNA, TLR4-FLNA and $A\beta_{42}$-α7nAChR Associations, $Ca^{2+}$ Influx, NMDAR and IR Signaling Postmortem frontal cortex tissues were gradually thawed (from −80° C. to −20° C.) and were sliced using a chilled McIlwain tissue chopper (200 m×200 m×3 mm). Approximately 20 mg of the brain slices were suspended in 1 ml of ice-cold oxygenated Kreb's-Ringer solution (K—R), containing 25 mM HEPES, pH 7.4, 118 mM NaCl, 4.8 mM KCl, 1.3 mM $CaCl_2$), 1.2 mM $KH_2PO_4$, 1.2 mM $MgSO_4$, 25 mM $NaHCO_3$, 10 mM glucose, 10 μM ascorbic acid, 50 μg/ml leupeptin, 0.2 mM PMSF, 25 μg/ml pepstatin A, and 0.01 U/ml soybean trypsin inhibitor and centrifuged briefly. Following two additional washes with 1 ml of ice-cold K—R, brain slices were suspended in 1 ml of K—R.

To determine whether exposure to exogenous $A\beta_{42}$ increases α7nAChR-FLNA, TLR4-FLNA and $A\beta_{42}$-α7nAChR association and causes $A\beta_{42}$-induced α7nAChR and N-methyl-D-aspartate receptor (NMDAR) dysfunction, approximately 20 mg of frontal cortical slices from control subjects were incubated with 0. μM of $A\beta_{42}$ at 37° C. for 1 hour. To test the effects of C0105 on $A\beta_{42}$-incubated control and native AD tissues, Compound C0105 (0.1 and 1 nM) was added 10 minutes following 0. μM $A\beta_{42}$. Incubation continued for 1 hour in the dark to minimize light destruction of the test agents. The incubation mixture in a total incubation volume of 0.5 ml was aerated with 95% $O_2$/5% $CO_2$ every 15 minutes for 1 minute during the incubation. Reaction was terminated by the addition of 1.5 ml of ice-cold $Ca^{2+}$-free K—R. Tissue slices were harvested by a brief centrifugation and used as the tissue sources for various assays.

To assess the effects of various α7nAChR agents on α7nAChR-FLNA linkages, about 20 mg of FCX from control subjects was incubated with 1 mM nicotine, PNU282987, α-bungarotoxin, methyllycaconitine, galantamine, memantine, and $A\beta_{40}$ along with 0.1 μM $A\beta_{42}$. Incubation continued for 1 hour in the dark. The incubation mixture in a total incubation volume of 0.5 ml was aerated for 1 minute every 15 minutes with 95% $O_2$/5% $CO_2$. The reaction was terminated by the addition of 1.5 ml of ice-cold $Ca^{2+}$-free K—R, and slices were collected by a brief centrifugation.

Separately, the compound effect on α7nAChR-FLNA, TLR4-FLNA and $A\beta_{42}$-α7nAChR complex levels were determined after incubation with 0.1 and 1 nM compounds in matching Krebs-Ringer and $A\beta_{42}$-incubated synaptosomes from control subjects and Krebs-Ringer incubated Alzheimer's disease patients. The levels of α7nAChR-FLNA, TLR4-FLNA and $A\beta_{42}$-α7nAChR complexes in the obtained synaptosomes were measured by co-immunoprecipitation method as described below that has been published [Wang et al., *J Neurosci* 35, 10961-10973 (2009)].

Assessment of α7nAChR-FLNA, TLR4-FLNA and $A\beta_{42}$-α7nAChR Association by Co-Immunoprecipitation Two-hundred μg of synaptosomes are pelleted by centrifugation and then solubilized by brief sonication in 250 μl of immunoprecipitation buffer (25 mM HEPES, pH 7.5; 200 mM NaCl, 1 mM EDTA, 50 μg/ml leupeptin, 10 μg/ml aprotinin, 2 μg/ml soybean trypsin inhibitor, 0.04 mM PMSF, 5 mM NaF, 1 mM sodium vanadate, 0.5 mM β-glycerophosphate and 0.1% 2-mercaptoethanol containing 0.5% digitonin, 0.2% sodium cholate and 0.5% NP-40 and incubated at 4° C. with end-to-end shaking for 1 hour. Following dilution with 750 μl of ice-cold immunoprecipitation buffer and centrifugation (4° C.) to remove insoluble debris, the α7nAChR-/LR4-FLNA and $A\beta_{42}$-α7nAChR complexes in the lysate are isolated by immunoprecipitation with 16 hours of incubation at 4° C. with immobilized rabbit anti-FLNA (1 μg)- and anti-$A\beta_{42}$ antibodies (1 μg)-protein A-conjugated agarose beads, respectively.

The resultant immunocomplexes were pelleted by centrifugation at 4° C. After three washes with 1 ml of ice-cold phosphate-buffered saline (PBS) (pH 7.2) and centrifugation, the isolated α7nAChR-/TLR4-FLNA and $A\beta_{42}$-α7nAChR complexes are solubilized by boiling for 5 minutes in 100 μl of SDS-PAGE sample preparation buffer (62.5 mM Tris-HCl, pH 6.8; 10% glycerol, 2% SDS; 5% 2-mercaptoethanol, 0.1% bromophenol blue). The content of α7nAChRs in 50% of the obtained anti-$A\beta_{42}$ immunoprecipitate was determined by Western blotting with monoclonal anti-α7nAChR antibodies. In the assay for determining $A\beta_{42}$-α7nAChR complex level, immobilized rabbit anti-actin (0.5 g)-protein A-conjugated agarose were added together with anti-$A\beta_{42}$ in the co-immunoprecipitation process.

The content of β-actin in resultant immunoprecipitates is then analyzed by immunoblotting using monoclonal anti-β-actin to illustrate even immunoprecipitation efficiency and loading. In the assay for determining α7nAChR-/TLR4-FLNA complex levels, the blots obtained are stripped and re-probed with monoclonal anti-FLNA for assessing immunoprecipitation efficiency and loading.

Assessment of $Ca^{2+}$ Influx in Synaptosomes as a Functional Measurement of the Compounds NMDAR-, α7nAChR- and voltage-gated calcium channel-mediated [$^{45}Ca^{2+}$ ]influx were studied using synaptosomes prepared from postmortem frontal cortical slices from control and AD subjects. In brief, brain synaptosomes (100 g for postmortem study) were incubated at 37° C. for 5 minutes in oxygenated 0.3 mM $Mg^{2+}$ K—R (low $Mg^{2+}$ K—R, LMKR) containing 5 μM $^{45}Ca^{2+}$ (10 Ci/mmol) followed by incubation with vehicle, 0.1-10 μM PNU 282987, a specific α7nAChR agonist, or 0.1-10 μM NMDA+1 μM glycine for 5 minutes or 65 mM $K^+$ (made with isomolar replacement of $Na^+$) for 1 minute in a total incubation volume of 0.5 ml. The reaction was terminated by addition of 0.5 ml ice-cold $Ca^{2+}$-free K—R containing 0.5 mM EGTA and centrifugation at 4° C. After two additional washes, $^{45}Ca^{2+}$ contents in synaptosomes were assessed using scintillation spectrometry (Beckman). The background $^{45}Ca^{2+}$ was estimated using hypotonically lysed synaptosomes. The absolute $Ca^{2+}$ influx was calculated by subtracting the background $^{45}Ca^{2+}$ count. The percent increase in $Ca^{2+}$ influx was calculated as % [(drug-treated−vehicle)/vehicle].

NMDAR Signaling and Association with PSD-95

NMDAR signaling and their interaction with synaptic anchoring protein, PSD-95 were compared in K—R and Compound C0105 (1 nM)-exposed frontal cortical slices from control and AD subjects. NMDAR activation and signaling were initiated by incubation of approximately 10 mg of in vitro treated brain slices with either LMKR (basal) or LMKR containing 10 μM NMDA and 1 μM glycine at 37° C. for 30 minutes. The incubation mixture was aerated with 95% $O_2$/5% $CO_2$ every 10 minutes for 1 minute during the stimulation. Ligand stimulation was terminated by the addition of 1 ml of ice-cold $Ca^{2+}$-free K—R containing 0.5 mM EGTA and 0.1 mM EDTA.

Brain slices were harvested by a brief centrifugation and were homogenized in 0.25 ml of ice-cold immunoprecipitation buffer. The homogenates were centrifuged at 1000×g for 5 minutes (4° C.) and the supernatant (post-mitochondrial fraction) is sonicated for 10 seconds on ice. The proteins are solubilized in 0.5% digitonin, 0.2% sodium cholate and 0.5% NP-40 for 60 minutes at 4° C. with end-over-end rotation. The resultant lysates are then cleared by centrifugation at 50,000×g for 5 minutes and diluted with 0.75 ml of immunoprecipitation buffer. Protein concentrations are measured by Bradford method (Bio-Rad).

To determine the NMDAR signaling and the NMDAR complexes association with PSD-95 [also known as Disks large homolog 4 (DLH4)], the levels of NMDAR subunits, PSD-95 and NMDAR-associated signaling molecules were measured in anti-NR1 immunoprecipitates. Two $NR^1$ and two $NR^2$ protein subunits form the heterotetramer NMDA receptor.

In these studies, brain slice lysates (200 g) were immunoprecipitated overnight (about 18 hours) at 4° C. with 2 g of immobilized anti-NR1 onto covalently conjugated protein A-agarose beads (Pierce-ENDOGEN). Anti-NR1 immunoprecipitates were incubated with 75 μl antigen elution buffer (Pierce-ENDOGEN) and 2% SDS for 2 minutes on ice, centrifuged to remove antibody-protein A-agarose complexes and neutralized immediately with 10 μl 1.5 M Tris buffer, pH 8.8, followed by addition of 65 μl 2×PAGE sample buffer and boiled for 5 minutes. Seventy-five μ of the obtained eluates (50%) were then size fractionated on 7.5% SDS-PAGE. Proteins were transferred to nitrocellulose membrane and the levels of various NMDA receptor subunits, PSD-95, signaling proteins were measured using Western blotting with antibodies for NR1, PSD-95, nNOS, phospholipase C-71, 7PKC, $pY^{402}$PyK2, $pY^{416}$Src or phosphotyrosine. The blots were stripped and re-probed with anti-NR1 or -NR2A/—NR2B to assess the loading as appropriate.

IR Activation and Signaling

IR signaling was compared in K—R and compound C0105-exposed frontal cortical slices from control and AD subjects. IR activation and signaling were initiated by incubation of approximately 10 mg of in vitro treated brain slices with either KR (basal) or KR containing 1 nM insulin at 37° C. for 30 minutes. The incubation mixture was aerated with 95% $O_2$/5% $CO_2$ every 10 minutes for 1 minute during the stimulation. Ligand stimulation was terminated by the addition of 1 ml of ice-cold $Ca^{2+}$-free K—R containing 0.5 mM EGTA and 0.1 mM EDTA. Brain slices were harvested by a brief centrifugation and were homogenized in 0.25 ml of ice-cold immunoprecipitation buffer. The homogenates were centrifuged at 1000×g for 5 minutes (4° C.) and the supernatant (post-mitochondrial fraction) is sonicated for 10 seconds on ice. The proteins are solubilized in 0.5% digitonin, 0.2% sodium cholate and 0.5% NP-40 for 60 minutes at 4° C. with end-over-end rotation. The resultant lysates are then cleared by centrifugation at 50,000×g for 5 minutes and diluted with 0.75 ml of immunoprecipitation buffer. Protein concentrations are measured by Bradford method (Bio-Rad).

To determine the IR signaling, the levels of $pY^{1150/1151}$- and $pY^{972}$-IRs as well as insulin receptor substrate (IRS)-1 recruited to IR were measured in anti-IRβ immunoprecipitates. In these studies, brain slice lysates (200 g) were immunoprecipitated overnight (about 18 hours) at 4° C. with 2 μg of immobilized anti-IRβ onto covalently conjugated protein A-agarose beads (Pierce-ENDOGEN). Anti-IR immunoprecipitates were incubated with 75 μl antigen elution buffer (Pierce-ENDOGEN) and 2% SDS for 2 minutes on ice, centrifuged to remove antibody-protein A-agarose complexes and neutralized immediately with 10 μl 1.5 M Tris buffer, pH 8.8 followed by addition of 65 μl 2×PAGE sample buffer and boiled for 5 minutes. Seventy-five μ of the obtained eluates (50%) were then size fractionated on 7.5% SDS-PAGE. Proteins were transferred to nitrocellulose membrane and the levels of activated IR ($pY^{1150/1151}$ and $pY^{972}$) and IRS-1 recruited were measured using Western blotting with antibodies for $pY^{1150/1151}$-IRβ, $pY^{972}$-IRβ or IRS-1. The blots were stripped and re-probed with anti-IR to assess the loading as appropriate.

Western Blot Analysis

Solubilized immunoprecipitates derived from co-immunoprecipitation assays were separated by either 7.5 or 10% SDS-PAGE and then electrophoretically transferred to nitrocellulose membranes. The membranes were washed with PBS and blocked overnight (about 18 hours) at 4° C. with 10% milk in PBS with 0.1% Tween®-20 (PBST). Following three 5-minute washes with 0.1% PBST, the membranes were incubated at room temperature for 2 hours with antibody of choice at 1:500-1:1,000 dilutions. After three 2-minute washes in 0.1% PBST, membranes were incubated for 1 hour with anti-species IgG-HRP (1:5,000 dilution) and washed with 0.1% PBST three times, 2-minutes each. Immunoreactivity was visualized by reacting with chemiluminescent reagent (Pierce-ENDOGEN) for exactly 5 minutes and immediately exposing to X-ray film. Specific bands were quantified by densitometric scanning (GS-800 calibrated densitometer, Bio-Rad Laboratories).

Assessment of LPS-Induced Tau Phosphorylation Using Postmortem Human Frontal Cortical Slices Hippocampi from non-demented control subjects were chopped into coronal slices (100 μm thickness) using a McIlwain tissue chopper (Brinkman Instruments) as previously described [Wang et al., *J Neurosci,* 29:10961-10973 (2009)]. The slices are carefully separated in 10 ml of oxygenated ice-cold dissection medium with two pairs of fine forceps and gentle shaking.

To determine whether Compound C0105 can reduce LPS- and $A\beta_{42}$-induced tau phosphorylation, approximately 20 mg of human hippocampal slices were incubated at 37° C. for 1 hour with 1 or 10 g LPS or 0.1 μM $A\beta_{42}$ in oxygenated Kreb's-Ringer (25 mM HEPES, pH 7.4; 118 mM NaCl, 4.8 mM KCl, 25 mM $NaHCO_3$, 1.3 mM $CaCl_2$), 1.2 mM $MgSO_4$, 1.2 mM $KH_2PO_4$, 10 mM glucose, 100 μM ascorbic acid, 50 μg/ml leupeptin, 10 g/ml aprotinin, 2 μg/ml soybean trypsin inhibitor, 0.04 mM PMSF and mixture of protein phosphatase inhibitors) with or without 1 nM Compound C0105 (total incubation volume is 500 μl). The reaction mixture was aerated with 95% $O_2$/5% $CO_2$ for 1 minute every 10 minutes. The reaction was terminated by diluting with 1.5 ml of ice-cold 1 mM EDTA-containing $Ca^{2+}$-free Kreb's-Ringer and centrifuged for 10 minutes at 15,000×g (4° C.).

After removal of the supernatant, the slices were homogenized to prepare post-mitochondrial (P2) fraction. The obtained P2 fraction was solubilized in 500 μl of immunoprecipitation buffer (25 mM HEPES, pH7.5; 200 mM NaCl, 1 mM EDTA, 0.02% 2-mercaptoethanol, 50 μg/ml leupeptin, 10 μg/ml aprotinin, 2 μg/ml soybean trypsin inhibitor, 0.04 mM PMSF and mixture of protein phosphatase inhibitors) containing 0.5% digitonin, 0.2% sodium cholate and 0.5% NP-40. Following dilution with 1.5 ml of ice-cold immunoprecipitation buffer and centrifugation (4° C.) to remove insoluble debris, the total tau proteins in the tissue lysate were purified by immunoprecipitation with incubating with immobilized anti-tau antibodies (1 μg) for 16 hours at 4° C. as previously described [Wang et al., *J Biol Chem,* 278:31547-31553 (2003); Wang et al., *Biol Psychiatry,* 67:522-530 (2010)].

The anti-tau immunocomplexes were enriched by incubation with 50 μl of protein A/G-conjugated agarose beads at 4° C. and centrifugation. The purified tau proteins were washed three times with ice-cold phosphate-buffered saline (pH 7.2) and then solubilized by boiling for 5 minutes in 150 μl of SDS-PAGE sample preparation buffer (62.5 mM Tris-HCl, pH6.8; 10% glycerol, 2% SDS; 5% 2-mercaptoethanol, 0.1% bromophenol blue). The content of phosphorylated serine202-tau, threonine231-tau and threonine181-tau in 50 μl of solubilized anti-tau immunoprecipitate was separated on 8-16% SDS-PAGE, electrophorectically transferred to nitrocellulose membrane and determined by Western blots with specific antibodies directed against pSerine202-tau (AT-8), pThreonine231-tau (AT-180) and pThreonine181-tau (AT270), respectively.

To ensure equal amounts of tau precipitated by anti-tau antibodies are loaded onto SDS-PAGE, the total tau content in the anti-tau immunoprecipitate was determined by Western blot using anti-tau antibody (Tau-5) that does not discriminate between phosphorylated and non-phosphorylated tau.

Figure 47B:
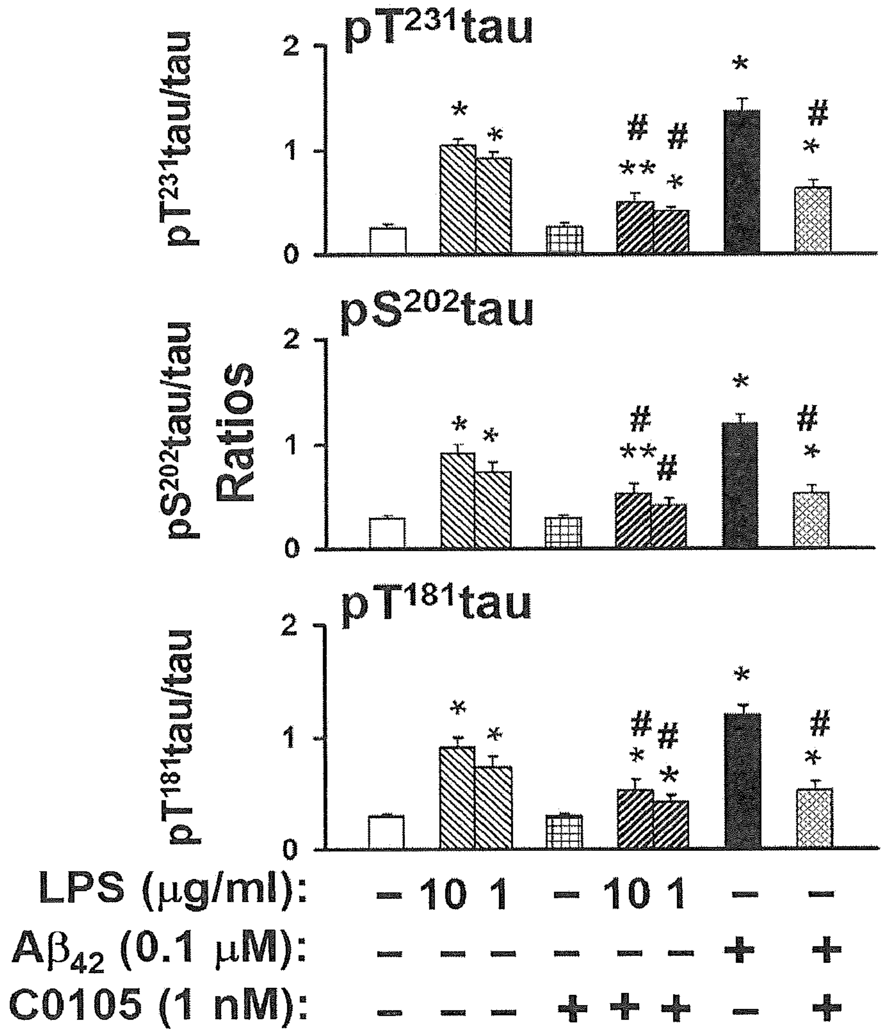
Figure 47C:
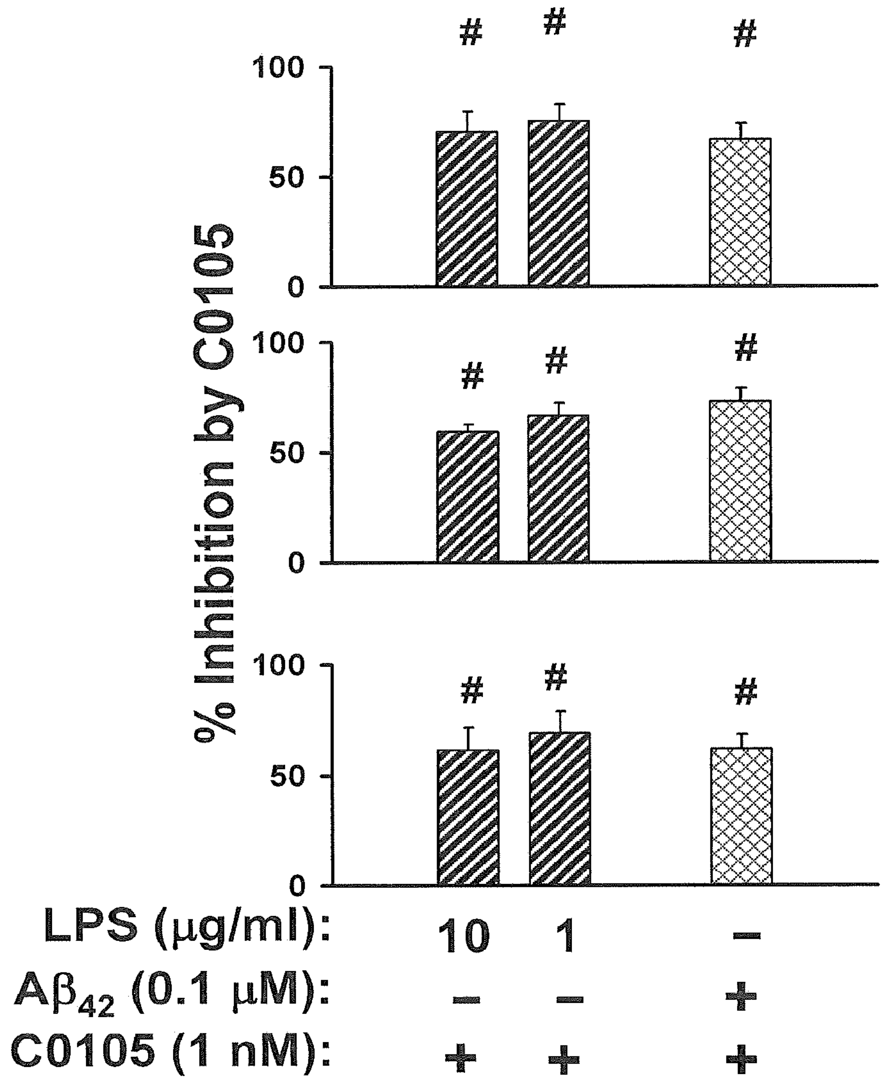

These results are illustrated in FIGS. 47A, 47B and 47C.

Effects on Release of Pro-Inflammatory Cytokines (IL-1β, IL-6 and TNFα) Induced from Primary Human Astrocytes by Contact with $A\beta_{42}$ and LPS Human astrocytes express both the TLR4 and TLR2 cell surface receptors. $A\beta_{42}$ and LPS each bind to and activate the TLR4 signaling pathway resulting in the release of pro-inflammatory cytokines such as IL-1p, IL-6 and TNFα, as is shown in previous studies discussed herein, as well as in the studies shown in FIGS. 48A and 48B.

Experimental Design:

A primary astrocyte culture was prepared according to the provider (Lonza). The adherent astrocytes were trypsinized by 0.25% trypsin-EDTA, then collected and sub-cultured in 12-well plate (1.2 ml/well). When the cells were 80-85% confluent, cells were treated in an incubator under 5% $CO_2$ with 100 fM, 10 pM or 1 nM Compound C0105 immediately followed by the addition of $A\beta_{42}$ (0. μM) and LPS (1 μg/ml); i.e., simultaneously adding the insulting ligand and Compound C0105 to the cells. Vehicle groups were treated with 0.1% DMSO only. Incubation continued for 24 hours post addition. Culture medium was used as the blank (non-treat) and the levels of cytokines, TNF-α, IL-6 and IL-1β in 200 μl of culture medium were determined. Each well was sampled once.

To determine the effect of Compound C0105 on cytokine release from human astrocytes, 0.5 μg/well biotinated mouse monoclonal anti-TNF-α, -IL-6 and -IL-1β were coated onto streptavidin-coated plates (Reacti-Bind™ NeutrAvidin™ High binding capacity coated 96-well plates). Plates were washed 3 times with ice-cold 50 mM Tris HCl (pH 7.4) and incubated at 30° C. with 200 μl medium derived from the above mentioned conditions. Plates were washed 3 times with ice-cold 50 mM Tris HCl (pH 7.4) and incubated at 30° C. with 0.5 μg/well un-conjugated rabbit anti-TNF-α, -IL-6 and -IL-1β for 1 hour. After three 1 minute washes with 50 mM Tris HCl (pH 7.4), each well was incubated in 0.25 μg/well FITC-conjugated anti-rabbit IgG (human and mouse absorbed) for 1 hour at 30° C. Plates were washed twice with 200 μl ice-cold Tris HCl, pH 7.4 and the residual FITC signals were determined by multimode plate reader, DTX880 (Beckman).

Figures 48, 48A:
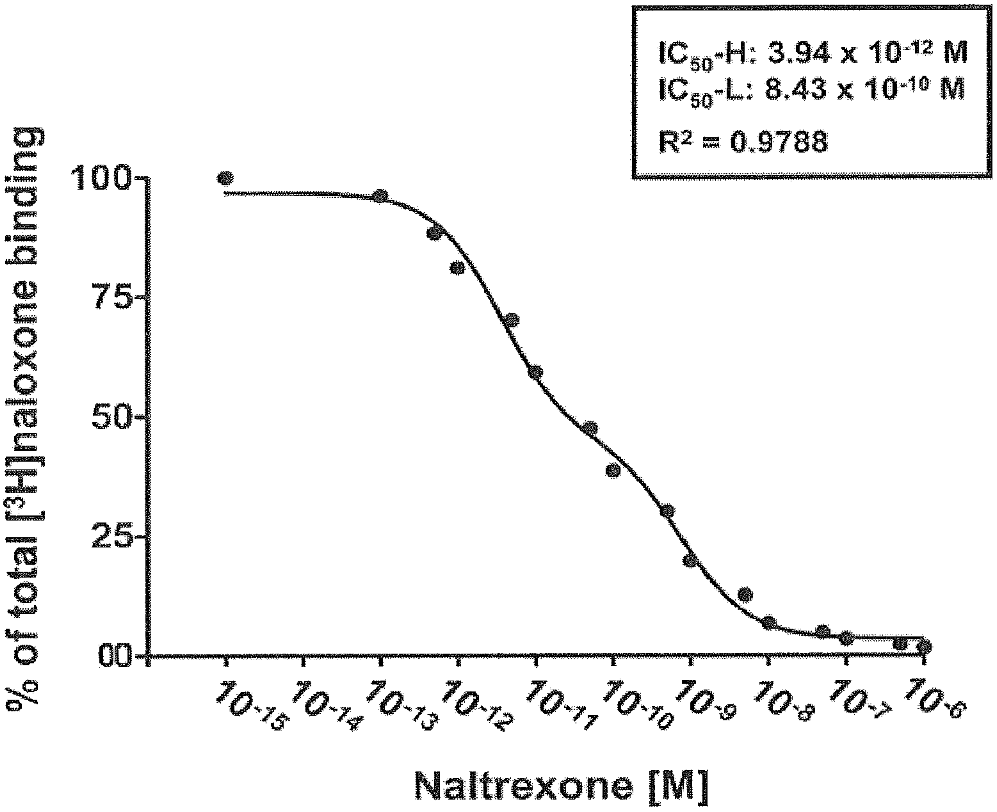
FIG. 48, in four parts as FIGS. 48A, 48B, 48C and 48D, are graphs showing competition curves that illustrate the binding of radio-labeled naloxone [$^3$H]NLX in the presence of naltrexone (NTX) or illustrative Compound C0105 to the filamin A (FLNA) or the filamin A (FLNA) pentamer of SEQ ID NO. 1 as reported in Wang et al., *PLoS One.* 3(2): e1554 (2008).
FIG. 48A illustrates [$^3$H]NLX binding to FLNA in the membranes of A7 cells in the presence of indicated amounts of naltrexone (NTX) and is taken from Wang et al., *PLoS One.* 3(2): e1554 (2008), FIG. 3.
Figure 48B:
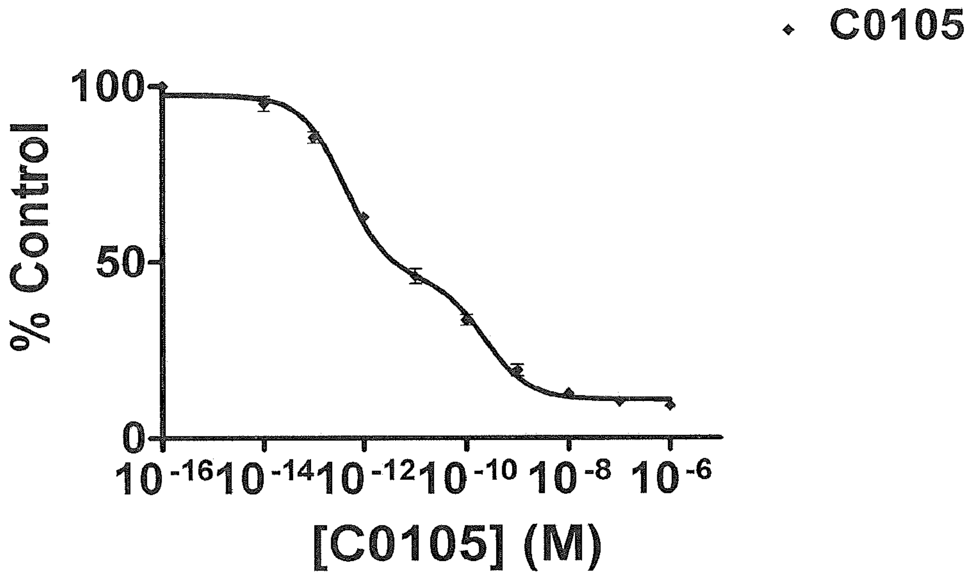
FIG. 48B illustrates binding of [$^3$H]NLX to FLNA in the membranes of A7 cells in the presence of indicated amounts of Compound C0105.
Figure 48C:
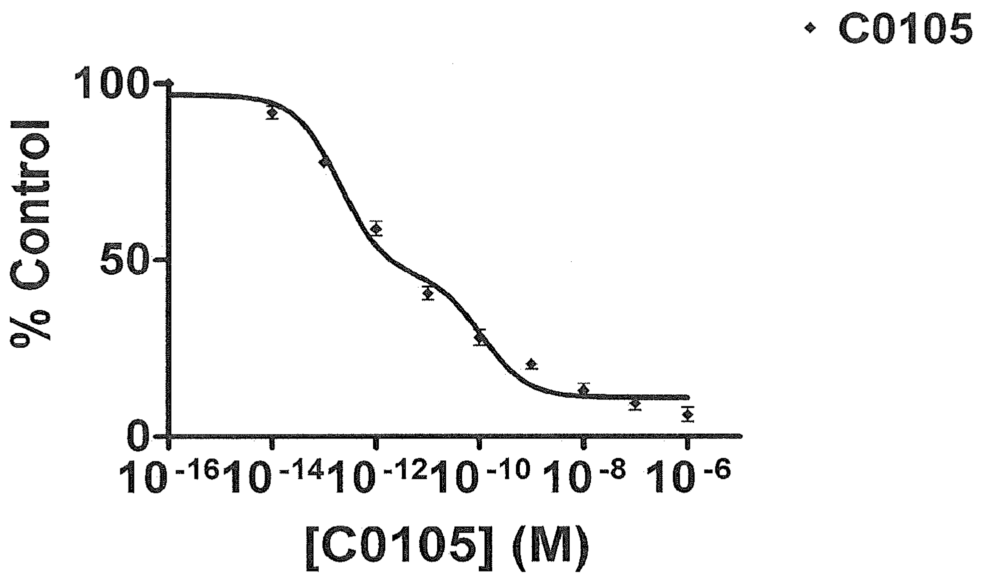
FIG. 48C. illustrates binding of [$^3$H]NLX in the presence of indicated amounts of Compound C0105 to FLNA in the membranes of SK-N-MC cells.
Figure 48D:
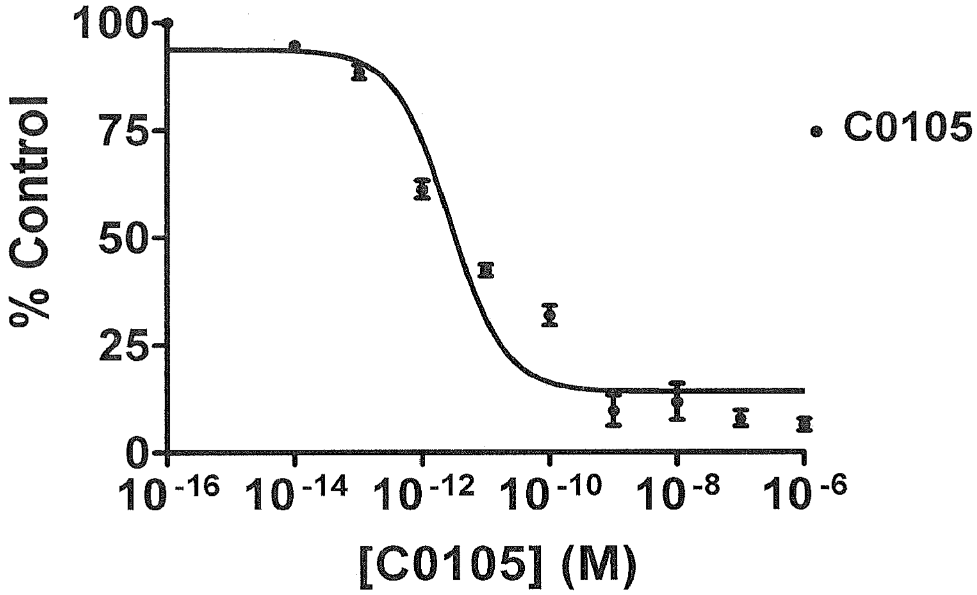
FIG. 48D illustrates binding of [$^3$H]NLX to the FLNA pentamer of SEQ ID NO. 1 in the presence of indicated amounts of Compound C0105.

The results of these studies are shown in FIG. 48 for $A\beta_{42}$ and LPS. As can be seen, Compound C0105 inhibited release of each of the assayed cytokines by about 75 to about 95 percent for each of the three cytokines and each of the four ligands. Statistical analysis by one-way ANOVA: $p<0.01$; $p^*<0.01$ compared to vehicle treated group for each insult.

FLNA Affinity Binding Studies

A series of binding studies using various compounds as ligand and FLNA or the FLNA pentamer of SEQ ID NO:1 as the receptor. These studies were carried out in a generally similar manner using a competition (displacement) curve for the inhibition of [$^3$H]NLX binding by in the presence of the ligand, and the results are shown in FIG. 16. Specifics of each study are set out below.

The competition (displacement) curve (FIG. 48A) for the inhibition of [$^3$H]NLX binding by naltrexone to membranes from FLNA-expressing A7 (human melanocytic; ATCC CRL-2500) cells that are free of most receptors and particularly mu shows two affinity states with $IC_{50\text{-}H}$ (high) of 3.94 picomolar and $IC_{50\text{-}L}$ (low) of 834 picomolar. A nonlinear curve-fit analysis was performed using a competition equation that assumed two saturable sites for the naltrexone curve comprising of 16 concentrations ranging from 0.1 pM to 1 mM. Data are derived from six studies each using a different set of A7 cells.

Figures 16B, 16C:
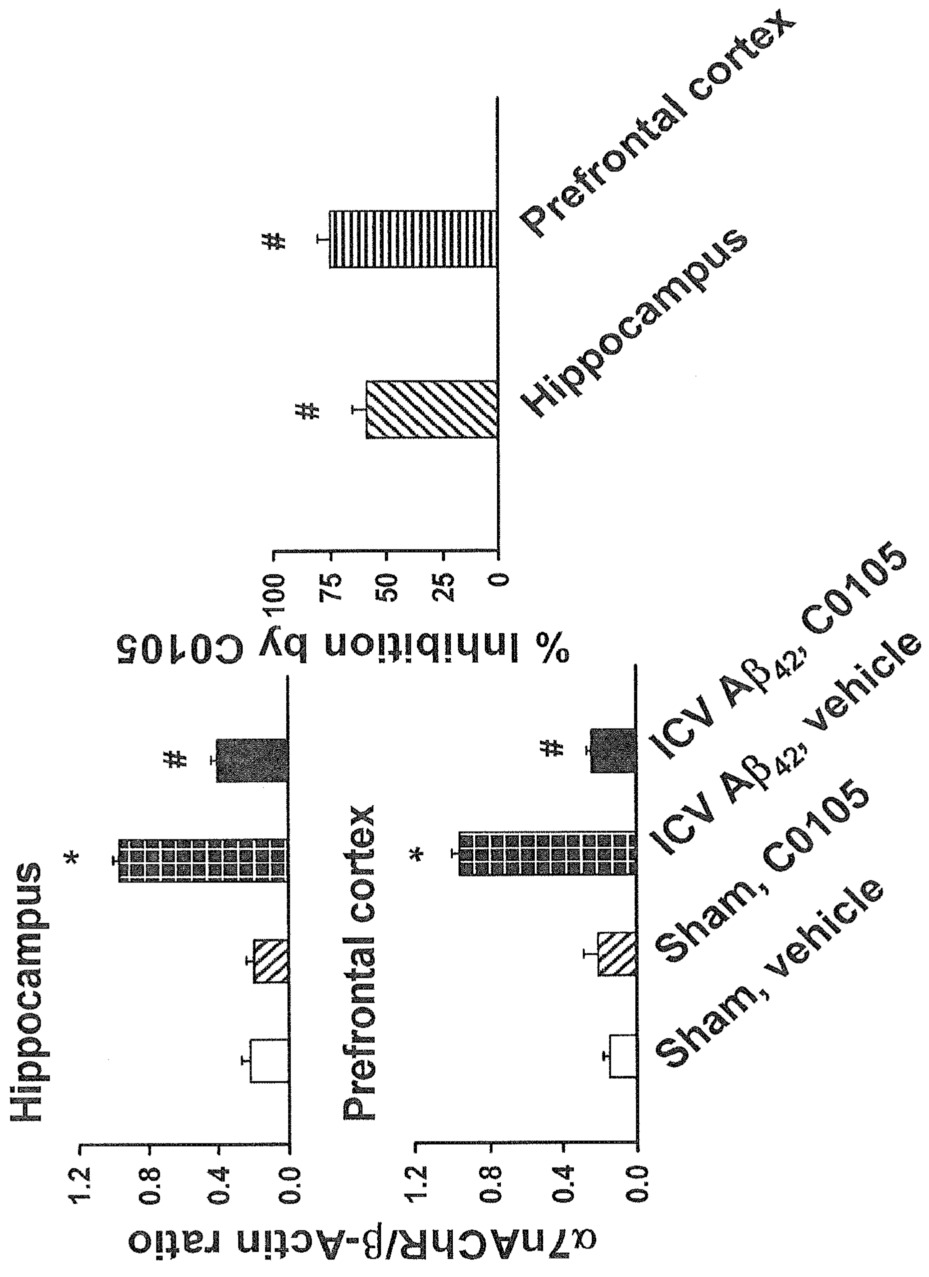

The binding affinity of Compound C0105 for FLNA was similarly determined (FIG. 16B). Briefly, 100 mg of A7 cell membranes were incubated with 0.5 nM [$^3$H]NLX in the presence of 0.01 nM-1 mM Compound C0105 at 30° C. for 60 minutes in 250 ml of the binding medium (50 mM Tris-HCl, pH 7.5; 100 mM NaCl; and protease and protein phosphatase inhibitors). Nonspecific binding was defined by 1 mM NTX. Reactions were terminated by rapid filtration through 3% BSA-treated glass microfiber binder free grade B (GF/B) membranes under vacuum. Filters were washed twice with 5 ml ice-cold binding medium, and [$^3$H]NLX retained on the filters was measured by liquid scintillation spectrometry. The data obtained were analyzed using the GraphPad Software, Inc. (San Diego, CA) Prism program. Here, an $IC_{50\text{-}H}$ of 0.43 picomolar and $IC_{50\text{-}L}$ of 226 picomolar were determined. N=4.

The binding affinity of Compound C0105 for FLNA was similarly determined (FIG. 16C). Briefly, 200 mg of SK-N-MC (human neuroepithelioma; ATCC HTB-10) cell membranes that contain with both α7nAChR and mu-opioid receptors were incubated with 0.5 nM [$^3$H]NLX in the presence of 1 mM DAMGO and 0.01 nM-1 mM Compound C0105 at 30° C. for 60 minutes in 250 ml of the binding medium (50 mM Tris-HCl, pH 7.5; 100 mM NaCl; and protease and protein phosphatase inhibitors). Nonspecific binding was defined by 1 mM NTX. Reactions were terminated by rapid filtration through 3% BSA-treated GF/B membranes under vacuum. Filters were washed twice with 5 ml ice-cold binding medium, and [$^3$H]NLX retained on the filters was measured by liquid scintillation spectrometry. The data obtained were analyzed using the GraphPad Software, Inc. (San Diego, CA) Prism program. Here, an $IC_{50\text{-}H}$ of 0.201 picomolar and $IC_{50\text{-}L}$ of 111 picomolar were determined. N=4.

The binding affinity of Compound C0105 for the VAKGL peptide was also determined by a displacement assay (FIG. 16D). Briefly, 10 mg of N-terminal biotinylated VAKGL (SEQ ID NO:1) peptide (Bn-VAKGL) was incubated with 0.5 nM [$^3$H]NLX in the presence of 0.01 nM-1 mM Compound C0105 at 30° C. for 60 minutes in 250 ml of the binding medium (50 mM Tris-HCl, pH 7.5; 100 mM NaCl; and protease and protein phosphatase inhibitors). Nonspecific binding was defined by 1 mM NTX. The reaction was terminated by addition of 1 ml of ice-cold binding medium. The [$^3$H]NLX-bound Bn-VAKGL was trapped by incubation with 20 ml NeutrAvidin®-agarose (Thermo), followed by centrifugation. Following two 1.5 ml washes with PBS, the bound [$^3$H]NLX was determined using scintillation spectrometry. The data obtained were analyzed using the GraphPad Software, Inc. (San Diego, CA) Prism program. Here, a single $IC_{50}$ value was obtained, as was expected for the 5-mer peptide of SEQ ID NO:1, and its value was 2.76 picomolar. N=4.

The data obtained in these studies illustrate the similar affinities exhibited between naloxone and illustrative Compound C0105 for FLNA. These data also illustrate the similarity in binding activity as a receptor shown between the intact FLNA molecule and the 5-mer FLNA peptide of SEQ ID NO:1, and thereby validate the use of that 5-mer peptide as a surrogate for the complete molecule in the assays carried out herein.

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. A method of inhibiting hyperphosphorylation of a tau protein in a patient, wherein the method comprises administering a compound of the structure:

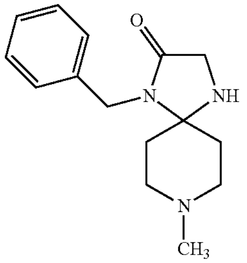

or

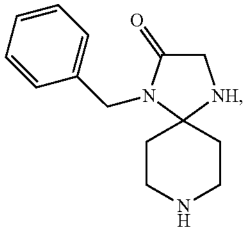

or a pharmaceutically acceptable salt and/or solvate thereof to the patient.

2. The method of claim 1, wherein the patient has a phosphorylated tau protein at $S^{202}$, $T^{231}$, or $T^{181}$.

3. The method of claim 1, wherein the method inhibits the hyperphosphorylation of a tau proteins at $S^{202}$, $T^{231}$, or $T^{181}$.

4. The method of claim 2, wherein the method reduces the level of phosphorylation at $S^{202}$, $T^{231}$, or $T^{181}$ by at least 50%.

5. The method of claim 1, wherein the patient has a tau-containing neurofibrillary tangle (NFT).

6. The method of claim 1, wherein the method reduces formation of a tau-containing neurofibrillary tangle (NFT) in the patient's brain.

7. The method of claim 1, wherein the patient has a neuritic plaque.

8. The method of claim 1, wherein the method reduces formation of a neuritic plaque in the patient's brain.

9. The method of claim 1, wherein the compound is:

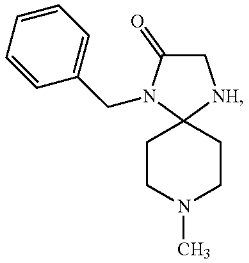 [SMILES: CN1CCC2(CC1)NCC(=O)N2Cc1ccccc1]

or pharmaceutically acceptable salt and/or solvate thereof.

10. The method of claim 1, wherein the compound is:

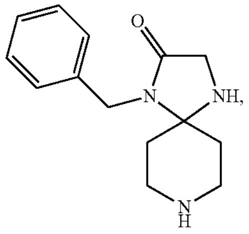

or pharmaceutically acceptable salt and/or solvate thereof.

11. The method of claim 1, wherein the compound is not a salt or solvate.

12. The method of claim 1, wherein the compound is a pharmaceutically acceptable salt.

13. The method of claim 1, wherein the compound is a pharmaceutically acceptable solvate.

14. The method of claim 1, wherein the compound is administered orally.

15. The method of claim 1, wherein the compound is administered daily.

16. The method of claim 1, wherein the compound is administered once or twice daily.

17. A method of inhibiting Aβ-induced α7nAChR-mediated signaling in a patient, wherein the method comprises administering a compound of the structure:

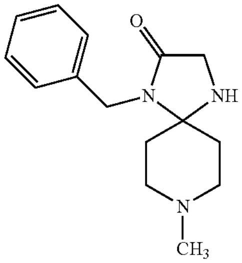

or

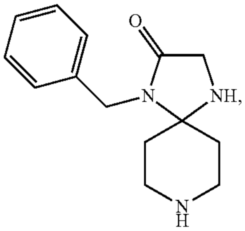

, or a pharmaceutically acceptable salt and/or solvate thereof to the patient.

18. The method of claim 17, wherein the patient has a phosphorylated tau protein at $S^{202}$, $T^{231}$, or $T^{181}$.

19. A method of inhibiting interaction of Aβ with α7nAChR in a patient, wherein the method comprises administering a compound of the structure:

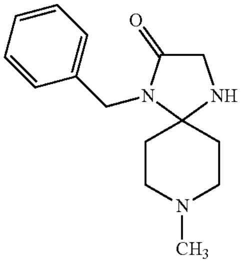

or

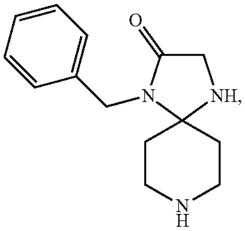 [SMILES: O=C1CNC2(CCNCC2)N1Cc1ccccc1]

, or a pharmaceutically acceptable salt and/or solvate thereof to the patient.

20. The method of claim 19, wherein the patient has a phosphorylated tau protein at $S^{202}$, $T^{231}$, or $T^{181}$.

* * * * *